(12) United States Patent
D'Souza et al.

(10) Patent No.: US 8,944,061 B2
(45) Date of Patent: Feb. 3, 2015

(54) CUSHION TO FRAME ASSEMBLY MECHANISM

(71) Applicant: ResMed Limited, Bella Vista (AU)

(72) Inventors: Errol Savio Alex D'Souza, Hornsby Heights (AU); Aaron Samuel Davidson, Mona Vale (AU); Matthew Eves, Manly Vale (AU); Robin Garth Hitchcok, Normanhurst (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 13/834,189

(22) Filed: Mar. 15, 2013

(65) Prior Publication Data

US 2013/0213402 A1    Aug. 22, 2013

Related U.S. Application Data

(63) Continuation of application No. 11/989,137, filed as application No. PCT/AU2006/000035 on Jan. 12, 2006, now Pat. No. 8,397,728.

(60) Provisional application No. 60/726,265, filed on Oct. 14, 2005, provisional application No. 60/734,746, filed on Nov. 9, 2005.

(51) Int. Cl.
*A61M 16/06*    (2006.01)

(52) U.S. Cl.
CPC ........... *A61M 16/0683* (2013.01); *A61M 16/06* (2013.01); *A61M 16/0616* (2014.02); *A61M 16/0638* (2014.02)
USPC ............. 128/206.24; 128/206.21; 128/206.28

(58) Field of Classification Search
CPC ........... A61M 16/06; A61M 16/0605; A61M 16/0633; A61M 16/0683; A61M 2016/0661
USPC .......................... 128/206.21, 206.24, 206.28; D24/110.1, 110.4, 110.5
See application file for complete search history.

(56) References Cited

U.S. PATENT DOCUMENTS

| | | |
|---|---|---|
| 364,394 A | 6/1887 | Bright |
| 428,592 A | 5/1890 | Chapman |
| 443,191 A | 12/1890 | Illing |
| 781,516 A | 1/1905 | Guthrie, Jr. |
| 812,706 A | 2/1906 | Warbasse |

(Continued)

FOREIGN PATENT DOCUMENTS

| | | |
|---|---|---|
| AU | 91/77110 | 11/1991 |
| AU | 94/64816 | 12/1994 |

(Continued)

OTHER PUBLICATIONS

U.S. Appl. No. 13/870,678, filed Apr. 2013, Kwok et al.

(Continued)

*Primary Examiner* — Laura Bouchelle
(74) *Attorney, Agent, or Firm* — Nixon & Vanderhye P.C.

(57) ABSTRACT

A full-face mask assembly includes a frame, a cushion provided to the frame, the cushion adapted to form a seal around the patent's nose and mouth and a skeleton frame to maintain the cushion to the frame, the skeleton frame including at least one of an upper support member adapted to support a forehead support, lower headgear clip receptacles adapted to be engaged with clips provided to straps of a headgear assembly, and an annular elbow connection seal adapted to engage an inlet conduit.

91 Claims, 99 Drawing Sheets

(56) References Cited

U.S. PATENT DOCUMENTS

| | | |
|---|---|---|
| 1,081,745 A | 12/1913 | Johnston et al. |
| 1,125,542 A | 1/1915 | Humphries |
| 1,176,886 A | 3/1916 | Ermold |
| 1,192,186 A | 7/1916 | Greene |
| 1,206,045 A | 11/1916 | Smith |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,502,450 A | 7/1924 | Wood |
| 1,610,793 A | 12/1926 | Kaufman |
| 1,632,449 A | 6/1927 | McKesson |
| 1,653,572 A | 12/1927 | Jackson |
| 1,710,160 A | 4/1929 | Gibbs |
| 1,837,591 A | 12/1931 | Shindel |
| 1,873,160 A | 8/1932 | Sturtevant |
| 1,926,027 A | 9/1933 | Biggs |
| 2,011,733 A | 8/1935 | Shindel |
| 2,104,016 A | 1/1938 | Biggs |
| 2,123,353 A | 7/1938 | Catt |
| 2,127,136 A | 8/1938 | Pobirs |
| 2,130,555 A | 9/1938 | Malcom |
| 2,133,699 A | 10/1938 | Heidbrink |
| 2,149,067 A | 2/1939 | Otero |
| 2,166,164 A | 7/1939 | Lehmberg |
| 2,245,658 A | 6/1941 | Erickson |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,353,643 A | 7/1944 | Bulbulian |
| 2,371,965 A | 3/1945 | Lehmberg |
| 2,376,871 A | 5/1945 | Fink |
| 2,382,364 A | 8/1945 | Yant |
| 2,415,846 A | 2/1947 | Randall |
| 2,428,451 A | 10/1947 | Emerson |
| 2,433,565 A | 12/1947 | Korman |
| 2,438,058 A | 3/1948 | Kincheloe |
| 2,473,518 A | 6/1949 | Garrard et al. |
| D156,060 S | 11/1949 | Wade |
| D161,337 S | 12/1950 | Hill |
| 2,540,567 A | 2/1951 | Bennett |
| 2,578,621 A | 12/1951 | Yant |
| 2,590,006 A | 3/1952 | Gordon |
| 2,625,155 A | 1/1953 | Engelder |
| 2,641,253 A | 6/1953 | Engelder |
| 2,693,178 A | 11/1954 | Gilroy |
| 2,706,983 A | 4/1955 | Matheson et al. |
| 2,749,910 A | 6/1956 | Faulconer, Jr. |
| RE24,193 E | 8/1956 | Emerson |
| 2,820,651 A | 1/1958 | Phillips |
| 2,837,090 A | 6/1958 | Bloom et al. |
| 2,868,196 A | 1/1959 | Stampe |
| 2,875,757 A | 3/1959 | Galleher, Jr. |
| 2,875,759 A | 3/1959 | Galleher, Jr. |
| 2,881,444 A | 4/1959 | Fresh et al. |
| 2,882,895 A | 4/1959 | Galeazzi |
| 2,902,033 A | 9/1959 | Galleher, Jr. |
| 2,917,045 A | 12/1959 | Schildknecht et al. |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher, Jr. |
| 3,042,035 A | 7/1962 | Coanda |
| 3,117,574 A | 1/1964 | Replogle |
| 3,182,659 A | 5/1965 | Blount |
| 3,189,027 A | 6/1965 | Bartlett, Jr. |
| 3,193,624 A | 7/1965 | Webb et al. |
| 3,238,943 A | 3/1966 | Holley |
| 3,288,138 A | 11/1966 | Sachs |
| 3,315,672 A | 4/1967 | Cunningham et al. |
| 3,315,674 A | 4/1967 | Bloom et al. |
| 3,330,273 A | 7/1967 | Bennett |
| 3,330,274 A | 7/1967 | Bennett |
| 3,362,420 A | 1/1968 | Blackburn et al. |
| 3,363,833 A | 1/1968 | Laerdal |
| 3,545,436 A | 12/1970 | Holloway |
| 3,556,122 A | 1/1971 | Laerdal |
| 3,580,051 A | 5/1971 | Blevins |
| 3,670,726 A | 6/1972 | Mahon et al. |
| 3,682,171 A | 8/1972 | Dali et al. |
| 3,700,000 A | 10/1972 | Hesse et al. |
| 3,720,235 A | 3/1973 | Schrock |
| 3,725,953 A | 4/1973 | Johnson et al. |
| 3,739,774 A | 6/1973 | Gregory |
| 3,750,333 A | 8/1973 | Vance |
| 3,752,157 A | 8/1973 | Malmin |
| 3,754,552 A | 8/1973 | King |
| 3,796,216 A | 3/1974 | Schwarz |
| 3,799,164 A | 3/1974 | Rollins |
| D231,803 S | 6/1974 | Huddy |
| 3,830,230 A | 8/1974 | Chester |
| 3,861,385 A | 1/1975 | Carden |
| 3,902,486 A | 9/1975 | Guichard |
| 3,905,361 A | 9/1975 | Hewson et al. |
| 3,910,261 A | 10/1975 | Ragsdale et al. |
| 3,938,614 A | 2/1976 | Ahs |
| 3,972,321 A | 8/1976 | Proctor |
| 3,978,854 A | 9/1976 | Mills, Jr. |
| 4,006,744 A | 2/1977 | Steer |
| 4,062,357 A | 12/1977 | Laerdal |
| 4,069,516 A | 1/1978 | Watkins, Jr. |
| 4,077,404 A | 3/1978 | Elam |
| D248,497 S | 7/1978 | Slosek |
| D250,131 S | 10/1978 | Lewis et al. |
| 4,120,302 A | 10/1978 | Ziegler |
| 4,142,527 A | 3/1979 | Garcia |
| 4,153,051 A | 5/1979 | Shippert |
| 4,156,426 A | 5/1979 | Gold |
| 4,167,185 A | 9/1979 | Lewis |
| 4,201,205 A | 5/1980 | Bartholomew |
| 4,226,234 A | 10/1980 | Gunderson |
| 4,231,363 A | 11/1980 | Grimes |
| 4,233,972 A | 11/1980 | Hauff et al. |
| 4,239,038 A | 12/1980 | Holmes |
| 4,245,632 A | 1/1981 | Houston |
| 4,248,218 A | 2/1981 | Fischer |
| 4,263,908 A | 4/1981 | Mizerak |
| 4,264,743 A | 4/1981 | Maruyama et al. |
| 4,265,239 A | 5/1981 | Fischer, Jr. et al. |
| 4,266,540 A | 5/1981 | Panzik et al. |
| 4,267,845 A | 5/1981 | Robertson, Jr. et al. |
| 4,273,124 A | 6/1981 | Zimmerman |
| D262,322 S | 12/1981 | Mizerak |
| 4,304,229 A | 12/1981 | Curtin |
| 4,312,359 A | 1/1982 | Olson |
| 4,328,797 A | 5/1982 | Rollins et al. |
| 4,337,767 A | 7/1982 | Yahata |
| 4,347,205 A | 8/1982 | Stewart |
| 4,354,488 A | 10/1982 | Bartos |
| 4,367,735 A | 1/1983 | Dali |
| 4,367,816 A | 1/1983 | Wilkes |
| 4,369,284 A | 1/1983 | Chen |
| 4,402,316 A | 9/1983 | Gadberry |
| 4,406,283 A | 9/1983 | Bir |
| 4,412,537 A | 11/1983 | Tiger |
| 4,414,973 A | 11/1983 | Matheson et al. |
| 4,417,575 A | 11/1983 | Hilton et al. |
| 4,422,456 A | 12/1983 | Teip |
| 4,446,576 A | 5/1984 | Hisataka |
| 4,449,526 A | 5/1984 | Elam |
| 4,454,880 A | 6/1984 | Muto et al. |
| 4,454,881 A | 6/1984 | Huber et al. |
| 4,455,675 A | 6/1984 | Bose et al. |
| 4,458,679 A | 7/1984 | Ward |
| 4,467,799 A | 8/1984 | Steinberg |
| 4,493,614 A | 1/1985 | Chu et al. |
| 4,522,639 A | 6/1985 | Ansite et al. |
| 4,548,200 A | 10/1985 | Wapner |
| 4,549,542 A | 10/1985 | Chien |
| 4,558,710 A | 12/1985 | Eichler |
| 4,572,323 A | 2/1986 | Randall |
| 4,579,113 A | 4/1986 | McReadie et al. |
| 4,587,967 A | 5/1986 | Chu et al. |

(56) References Cited

U.S. PATENT DOCUMENTS

| | | |
|---|---|---|
| 4,593,688 A | 6/1986 | Payton |
| 4,601,465 A | 7/1986 | Roy |
| D285,496 S | 9/1986 | Berman |
| 4,616,647 A | 10/1986 | McCreadie |
| 4,617,637 A | 10/1986 | Chu et al. |
| 4,622,964 A | 11/1986 | Flynn |
| 4,630,604 A | 12/1986 | Montesi |
| 4,641,645 A | 2/1987 | Tayebi |
| 4,641,647 A | 2/1987 | Behan |
| D289,238 S | 4/1987 | Arthur, Jr. |
| 4,655,213 A | 4/1987 | Rapoport et al. |
| 4,657,010 A | 4/1987 | Wright |
| 4,660,555 A | 4/1987 | Payton |
| 4,665,570 A | 5/1987 | Davis |
| 4,671,267 A | 6/1987 | Stout |
| 4,671,271 A | 6/1987 | Bishop et al. |
| 4,674,134 A | 6/1987 | Lundin |
| 4,676,241 A | 6/1987 | Webb et al. |
| 4,677,975 A | 7/1987 | Edgar et al. |
| 4,677,977 A | 7/1987 | Wilcox |
| 4,686,977 A | 8/1987 | Cosma |
| 4,699,139 A | 10/1987 | Marshall et al. |
| 4,706,664 A | 11/1987 | Snook et al. |
| 4,707,863 A | 11/1987 | McNeal |
| 4,711,636 A | 12/1987 | Bierman |
| 4,713,844 A | 12/1987 | Westgate |
| H397 H | 1/1988 | Stark |
| D293,613 S | 1/1988 | Wingler |
| 4,739,755 A | 4/1988 | White et al. |
| 4,753,233 A | 6/1988 | Grimes |
| 4,767,411 A | 8/1988 | Edmunds |
| 4,770,169 A | 9/1988 | Schmoegner et al. |
| 4,772,760 A | 9/1988 | Graham |
| 4,774,941 A | 10/1988 | Cook |
| 4,774,946 A | 10/1988 | Ackerman et al. |
| 4,782,832 A | 11/1988 | Trimble et al. |
| 4,790,829 A | 12/1988 | Bowden et al. |
| 4,799,477 A | 1/1989 | Lewis |
| 4,802,857 A | 2/1989 | Laughlin |
| 4,803,981 A | 2/1989 | Vickery |
| 4,807,617 A | 2/1989 | Nesti |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,827,924 A | 5/1989 | Japuntich |
| 4,830,138 A | 5/1989 | Palmaer et al. |
| 4,832,017 A | 5/1989 | Schnoor |
| 4,838,878 A | 6/1989 | Kalt et al. |
| 4,841,953 A | 6/1989 | Dodrill |
| 4,848,334 A | 7/1989 | Bellm |
| 4,848,366 A | 7/1989 | Aita et al. |
| 4,850,346 A | 7/1989 | Michel et al. |
| 4,856,118 A | 8/1989 | Sapiejewski |
| D304,384 S | 10/1989 | Derobert |
| 4,886,058 A | 12/1989 | Brostrom et al. |
| 4,899,740 A | 2/1990 | Napolitano |
| 4,905,683 A | 3/1990 | Cronjaeger |
| 4,907,584 A | 3/1990 | McGinnis |
| 4,910,806 A | 3/1990 | Baker et al. |
| 4,914,957 A | 4/1990 | Dougherty |
| 4,915,105 A | 4/1990 | Lee |
| 4,915,106 A | 4/1990 | Aulgur et al. |
| 4,919,128 A | 4/1990 | Kopala et al. |
| 4,919,654 A | 4/1990 | Kalt |
| 4,938,210 A | 7/1990 | Shene |
| 4,938,212 A | 7/1990 | Snook et al. |
| 4,941,476 A | 7/1990 | Fisher |
| 4,944,310 A | 7/1990 | Sullivan |
| 4,945,907 A | 8/1990 | Tayebi |
| 4,947,860 A | 8/1990 | Fisher |
| D310,431 S | 9/1990 | Bellm |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| D313,277 S | 12/1990 | Haining |
| 4,976,698 A | 12/1990 | Stokley |
| 4,986,269 A | 1/1991 | Hakkinen |
| 4,989,271 A | 2/1991 | Sapiejewski et al. |
| 4,989,596 A | 2/1991 | Macris et al. |
| 4,989,599 A | 2/1991 | Carter |
| 4,996,983 A | 3/1991 | AmRhein |
| 5,000,173 A | 3/1991 | Zalkin et al. |
| 5,003,631 A | 4/1991 | Richardson |
| 5,003,633 A | 4/1991 | Itoh |
| 5,005,568 A | 4/1991 | Loescher et al. |
| 5,005,571 A | 4/1991 | Dietz |
| 5,018,519 A | 5/1991 | Brown |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,027,809 A | 7/1991 | Robinson |
| 5,038,772 A | 8/1991 | Kolbe et al. |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,491 A | 9/1991 | Derrick |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| 5,080,092 A | 1/1992 | Tenna |
| D323,908 S | 2/1992 | Hollister et al. |
| 5,093,940 A | 3/1992 | Nishiyama |
| 5,109,839 A | 5/1992 | Blasdell et al. |
| 5,109,840 A | 5/1992 | Daleiden |
| 5,113,857 A | 5/1992 | Dickerman et al. |
| 5,117,818 A | 6/1992 | Palfy |
| 5,121,745 A | 6/1992 | Israel |
| 5,121,746 A | 6/1992 | Sikora |
| 5,123,677 A | 6/1992 | Kreczko et al. |
| 5,127,397 A | 7/1992 | Kohnke |
| 5,133,347 A | 7/1992 | Huennebeck |
| 5,137,017 A | 8/1992 | Salter |
| 5,138,722 A | 8/1992 | Urella et al. |
| 5,140,980 A | 8/1992 | Haughey et al. |
| 5,140,982 A | 8/1992 | Bauman |
| 5,146,914 A | 9/1992 | Sturrock |
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer et al. |
| 5,188,101 A | 2/1993 | Tumolo |
| D334,633 S | 4/1993 | Rudolph |
| 5,199,424 A | 4/1993 | Sullivan et al. |
| D335,322 S | 5/1993 | Jones |
| 5,207,665 A | 5/1993 | Davis et al. |
| 5,220,699 A | 6/1993 | Farris |
| 5,222,478 A | 6/1993 | Scarberry et al. |
| 5,231,983 A | 8/1993 | Matson et al. |
| 5,233,978 A | 8/1993 | Callaway |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,279,289 A | 1/1994 | Kirk |
| 5,280,784 A | 1/1994 | Kohler |
| 5,291,880 A | 3/1994 | Almovist et al. |
| 5,299,448 A | 4/1994 | Maryyanek |
| 5,299,579 A | 4/1994 | Gedeon et al. |
| 5,299,599 A | 4/1994 | Farmer et al. |
| 5,301,689 A | 4/1994 | Wennerholm |
| 5,304,146 A | 4/1994 | Johnson et al. |
| 5,311,862 A | 5/1994 | Blasdell et al. |
| 5,322,057 A | 6/1994 | Raabe et al. |

(56) References Cited

U.S. PATENT DOCUMENTS

| | | |
|---|---|---|
| 5,322,059 A | 6/1994 | Walther |
| 5,331,691 A | 7/1994 | Runckel |
| D349,586 S | 8/1994 | Handke |
| 5,334,646 A | 8/1994 | Chen |
| 5,335,656 A | 8/1994 | Bowe et al. |
| 5,343,878 A | 9/1994 | Scarberry et al. |
| 5,349,949 A | 9/1994 | Schegerin |
| 5,353,789 A | 10/1994 | Schlobohm |
| 5,355,878 A | 10/1994 | Griffiths et al. |
| 5,355,893 A | 10/1994 | Mick et al. |
| 5,357,945 A | 10/1994 | Messina |
| 5,357,951 A | 10/1994 | Ratner |
| 5,364,367 A | 11/1994 | Banks et al. |
| 5,372,130 A | 12/1994 | Stern et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,388,571 A | 2/1995 | Roberts et al. |
| 5,390,373 A | 2/1995 | Flory |
| 5,391,248 A | 2/1995 | Brain |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,400,781 A | 3/1995 | Davenport |
| 5,404,871 A | 4/1995 | Goodman et al. |
| 5,411,021 A | 5/1995 | Gdulla et al. |
| 5,419,317 A | 5/1995 | Blasdell et al. |
| 5,419,318 A | 5/1995 | Tayebi |
| 5,425,359 A | 6/1995 | Liou |
| 5,429,126 A | 7/1995 | Bracken |
| 5,429,683 A | 7/1995 | Le Mitouard |
| 5,431,158 A | 7/1995 | Tirotta |
| 5,437,267 A | 8/1995 | Weinstein et al. |
| 5,438,981 A | 8/1995 | Starr et al. |
| 5,441,046 A | 8/1995 | Starr et al. |
| D362,061 S | 9/1995 | McGinnis et al. |
| 5,462,528 A | 10/1995 | Roewer |
| 5,477,852 A | 12/1995 | Landis et al. |
| 5,479,920 A | 1/1996 | Piper et al. |
| 5,481,763 A | 1/1996 | Brostrom et al. |
| 5,485,837 A | 1/1996 | Soles Bee et al. |
| 5,488,948 A | 2/1996 | Dubruille et al. |
| 5,492,116 A | 2/1996 | Scarberry et al. |
| 5,501,214 A | 3/1996 | Sabo |
| 5,503,147 A | 4/1996 | Bertheau |
| 5,509,404 A | 4/1996 | Lloyd et al. |
| 5,509,409 A | 4/1996 | Weatherholt |
| 5,511,541 A | 4/1996 | Dearstine |
| 5,513,634 A | 5/1996 | Jackson |
| 5,513,635 A | 5/1996 | Bedi |
| 5,517,986 A | 5/1996 | Starr et al. |
| 5,522,382 A | 6/1996 | Sullivan et al. |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,568,946 A | 10/1996 | Jackowski |
| 5,570,682 A | 11/1996 | Johnson |
| 5,570,684 A | 11/1996 | Behr |
| 5,570,689 A | 11/1996 | Starr et al. |
| 5,575,278 A | 11/1996 | Bonhomme et al. |
| D377,089 S | 12/1996 | Starr et al. |
| 5,592,937 A | 1/1997 | Freund |
| 5,592,938 A | 1/1997 | Scarberry et al. |
| 5,608,647 A | 3/1997 | Rubsamen et al. |
| 5,617,849 A | 4/1997 | Springett et al. |
| 5,623,923 A | 4/1997 | Bertheau et al. |
| 5,642,726 A | 7/1997 | Owens et al. |
| 5,642,730 A | 7/1997 | Baran |
| 5,645,054 A | 7/1997 | Cotner et al. |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,653,228 A | 8/1997 | Byrd |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,171 A | 8/1997 | Kimm et al. |
| 5,660,174 A | 8/1997 | Jacobelli |
| 5,662,101 A | 9/1997 | Ogden et al. |
| 5,666,946 A | 9/1997 | Langenback |
| 5,676,133 A | 10/1997 | Hickle et al. |
| D385,960 S | 11/1997 | Rudolph |
| 5,682,881 A | 11/1997 | Winthrop et al. |
| 5,685,296 A | 11/1997 | Zdrojkowski et al. |
| 5,687,715 A | 11/1997 | Landis et al. |
| D389,238 S | 1/1998 | Kirk, III et al. |
| 5,704,345 A | 1/1998 | Berthon-Jones |
| 5,707,342 A | 1/1998 | Tanaka |
| 5,709,204 A | 1/1998 | Lester |
| 5,715,814 A | 2/1998 | Ebers |
| 5,724,964 A | 3/1998 | Brunson et al. |
| 5,724,965 A | 3/1998 | Handke et al. |
| 5,735,272 A | 4/1998 | Dillon et al. |
| 5,740,795 A | 4/1998 | Brydon |
| 5,740,799 A | 4/1998 | Nielson |
| 5,746,201 A | 5/1998 | Kidd |
| 5,752,509 A | 5/1998 | Lachmann et al. |
| 5,752,511 A | 5/1998 | Simmons et al. |
| 5,778,872 A | 7/1998 | Fukunaga et al. |
| 5,782,774 A | 7/1998 | Shmulewitz |
| 5,794,615 A | 8/1998 | Estes |
| 5,794,617 A | 8/1998 | Brunell et al. |
| 5,794,619 A | 8/1998 | Edeiman et al. |
| D398,987 S | 9/1998 | Cotner et al. |
| 5,807,341 A | 9/1998 | Heim |
| 5,813,423 A | 9/1998 | Kirchgeorg |
| 5,832,918 A | 11/1998 | Pantino |
| D402,755 S | 12/1998 | Kwok |
| 5,842,469 A | 12/1998 | Rapp et al. |
| RE36,165 E | 3/1999 | Behr |
| 5,884,624 A | 3/1999 | Barnett et al. |
| 5,887,587 A | 3/1999 | Groenke |
| 5,896,857 A | 4/1999 | Hely et al. |
| 5,906,203 A | 5/1999 | Klockseth et al. |
| 5,909,732 A | 6/1999 | Diesel et al. |
| 5,918,598 A | 7/1999 | Belfer et al. |
| 5,921,239 A | 7/1999 | McCall et al. |
| D412,745 S | 8/1999 | Scheu |
| 5,935,136 A | 8/1999 | Hulse et al. |
| 5,937,445 A | 8/1999 | Ravo et al. |
| 5,937,851 A | 8/1999 | Serowski et al. |
| 5,954,049 A | 9/1999 | Foley et al. |
| 5,964,485 A | 10/1999 | Hame et al. |
| 5,966,745 A | 10/1999 | Schwartz et al. |
| 5,970,975 A | 10/1999 | Estes et al. |
| 5,975,079 A | 11/1999 | Hellings et al. |
| 6,003,511 A | 12/1999 | Fukunaga et al. |
| 6,006,748 A | 12/1999 | Hollis |
| D419,658 S | 1/2000 | Matchett et al. |
| 6,016,804 A | 1/2000 | Gleason et al. |
| D421,298 S | 2/2000 | Kenyon et al. |
| 6,019,101 A | 2/2000 | Cotner et al. |
| 6,026,811 A | 2/2000 | Settle |
| 6,029,660 A | 2/2000 | Calluaud et al. |
| 6,029,665 A | 2/2000 | Berthon-Jones |
| 6,039,044 A | 3/2000 | Sullivan |
| D423,096 S | 4/2000 | Kwok |
| 6,044,844 A | 4/2000 | Kwok et al. |
| 6,062,221 A | 5/2000 | Brostrom et al. |
| 6,082,360 A | 7/2000 | Rudolph et al. |
| 6,086,118 A | 7/2000 | McNaughton et al. |

(56) References Cited

U.S. PATENT DOCUMENTS

| | | | |
|---|---|---|---|
| 6,091,973 A | 7/2000 | Colla et al. |
| D428,987 S | 8/2000 | Kwok |
| 6,095,996 A | 8/2000 | Steer et al. |
| 6,098,205 A | 8/2000 | Schwartz et al. |
| 6,102,040 A | 8/2000 | Tayebi et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,155,253 A | 12/2000 | Gamberini |
| 6,192,886 B1 | 2/2001 | Rudolph |
| 6,193,914 B1 | 2/2001 | Harrison |
| D439,326 S | 3/2001 | Hecker et al. |
| 6,196,223 B1 | 3/2001 | Belfer et al. |
| 6,211,263 B1 | 4/2001 | Cinelli et al. |
| 6,213,125 B1 | 4/2001 | Reese et al. |
| 6,231,548 B1 | 5/2001 | Bassett |
| D443,355 S | 6/2001 | Gunaratnam et al. |
| 6,241,930 B1 | 6/2001 | Harrison |
| 6,257,237 B1 | 7/2001 | Suzuki |
| 6,257,626 B1 | 7/2001 | Campau |
| 6,258,066 B1 | 7/2001 | Urich |
| 6,279,573 B1 | 8/2001 | Johnson et al. |
| 6,295,366 B1 | 9/2001 | Baller et al. |
| 6,328,031 B1 | 12/2001 | Tischer et al. |
| 6,328,038 B1 | 12/2001 | Kessler et al. |
| 6,340,024 B1 | 1/2002 | Brookman et al. |
| 6,341,606 B1 | 1/2002 | Bordewick et al. |
| 6,345,618 B1 | 2/2002 | Hayek |
| 6,347,631 B1 | 2/2002 | Hansen et al. |
| 6,357,440 B1 | 3/2002 | Hansen et al. |
| 6,357,441 B1 | 3/2002 | Kwok et al. |
| 6,358,279 B1 | 3/2002 | Tahi et al. |
| 6,371,110 B1 | 4/2002 | Peterson et al. |
| 6,374,826 B1 | 4/2002 | Gunaratnam et al. |
| 6,388,640 B1 | 5/2002 | Chigira et al. |
| 6,397,847 B1 | 6/2002 | Scarberry et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,418,928 B1 | 7/2002 | Bordewick et al. |
| 6,419,660 B1 | 7/2002 | Russo |
| 6,422,238 B1 | 7/2002 | Lithgow |
| 6,423,036 B1 | 7/2002 | Van Huzen |
| 6,425,395 B1 | 7/2002 | Brewer et al. |
| 6,427,694 B1 | 8/2002 | Hecker et al. |
| 6,431,172 B1 | 8/2002 | Bordewick |
| 6,434,796 B1 | 8/2002 | Speirs |
| 6,439,230 B1 | 8/2002 | Gunaratnam et al. |
| 6,439,234 B1 | 8/2002 | Curti et al. |
| 6,448,303 B1 | 9/2002 | Paul |
| 6,463,931 B1 | 10/2002 | Kwok et al. |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| D468,823 S | 1/2003 | Smart |
| 6,513,526 B2 | 2/2003 | Kwok et al. |
| 6,520,182 B1 | 2/2003 | Gunaratnam |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,557,556 B2 | 5/2003 | Kwok et al. |
| 6,561,188 B1 | 5/2003 | Ellis |
| 6,561,190 B1 | 5/2003 | Kwok |
| 6,561,191 B1 | 5/2003 | Kwok |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,615,830 B1 | 9/2003 | Serowski et al. |
| 6,615,832 B1 | 9/2003 | Chen |
| 6,626,177 B1 | 9/2003 | Ziaee |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,663 B2 | 11/2003 | Barnett et al. |
| D484,237 S | 12/2003 | Lang et al. |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,261 B2 | 1/2004 | Lithgow |
| 6,679,265 B2 | 1/2004 | Strickland et al. |
| 6,691,707 B1 | 2/2004 | Gunaratnam et al. |
| 6,691,708 B2 | 2/2004 | Kwok et al. |
| 6,701,535 B2 | 3/2004 | Dobbie et al. |
| 6,701,926 B2 | 3/2004 | Olsen et al. |
| 6,701,927 B2 | 3/2004 | Kwok et al. |
| 6,710,099 B2 | 3/2004 | Cinelli et al. |
| 6,712,072 B1 | 3/2004 | Lang |
| 6,729,333 B2 | 5/2004 | Barnett et al. |
| D492,992 S | 7/2004 | Guney et al. |
| D493,521 S | 7/2004 | Guney |
| 6,766,800 B2 | 7/2004 | Chu et al. |
| 6,766,817 B2 | 7/2004 | da Silva |
| 6,772,760 B2 | 8/2004 | Frater et al. |
| 6,776,162 B2 | 8/2004 | Wood |
| 6,776,163 B2 | 8/2004 | Dougill et al. |
| 6,789,543 B2 | 9/2004 | Cannon |
| 6,796,308 B2 | 9/2004 | Gunaratnam et al. |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,851,425 B2 | 2/2005 | Jaffre et al. |
| 6,851,428 B2 | 2/2005 | Dennis |
| 6,851,429 B2 | 2/2005 | Bishop |
| 6,860,269 B2 | 3/2005 | Kwok et al. |
| 6,860,270 B2 | 3/2005 | Sniadich |
| 6,871,649 B2 | 3/2005 | Kwok et al. |
| 6,892,729 B2 | 5/2005 | Smith et al. |
| 6,895,965 B2 | 5/2005 | Scarberry et al. |
| 6,907,882 B2 | 6/2005 | Ging et al. |
| 6,914,091 B2 | 7/2005 | Donald et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,959,710 B2 | 11/2005 | Barnett et al. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,000,614 B2 | 2/2006 | Lang et al. |
| 7,007,696 B2 | 3/2006 | Palkon et al. |
| 7,011,090 B2 | 3/2006 | Drew et al. |
| 7,018,362 B2 | 3/2006 | Bierman et al. |
| 7,021,311 B2 * | 4/2006 | Gunaratnam et al. ... 128/206.24 |
| 7,040,321 B2 | 5/2006 | Goebel |
| 7,047,972 B2 | 5/2006 | Ging et al. |
| 7,052,127 B2 | 5/2006 | Harrison |
| 7,059,326 B2 | 6/2006 | Heidmann et al. |
| 7,066,586 B2 | 6/2006 | da Silva |
| 7,069,932 B2 | 7/2006 | Eaton et al. |
| 7,076,282 B2 | 7/2006 | Munro et al. |
| 7,076,822 B2 | 7/2006 | Pearce |

(56) References Cited

U.S. PATENT DOCUMENTS

| | | |
|---|---|---|
| 7,080,645 B2 | 7/2006 | Genger et al. |
| 7,093,599 B2 | 8/2006 | Chen |
| 7,100,610 B2 | 9/2006 | Biener et al. |
| 7,101,359 B2 | 9/2006 | Kline et al. |
| 7,107,989 B2 | 9/2006 | Frater et al. |
| 7,114,497 B2 | 10/2006 | Aylsworth et al. |
| 7,146,976 B2 | 12/2006 | McKown |
| 7,152,599 B2 | 12/2006 | Thomas |
| 7,152,601 B2 | 12/2006 | Barakat et al. |
| 7,441,618 B2 | 12/2006 | Lubke et al. |
| 7,178,525 B2 | 2/2007 | Matula, Jr. et al. |
| 7,185,652 B2 | 3/2007 | Gunaratnam et al. |
| 7,191,781 B2 | 3/2007 | Wood |
| 7,207,328 B1 | 4/2007 | Altemus |
| 7,207,335 B2 | 4/2007 | Kwok et al. |
| 7,210,481 B1 | 5/2007 | Lovell et al. |
| 7,216,647 B2 | 5/2007 | Lang et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,308,895 B2 | 12/2007 | Wixey et al. |
| 7,318,437 B2 | 1/2008 | Gunaratnam et al. |
| 7,318,439 B2 | 1/2008 | Raje et al. |
| 7,320,323 B2 | 1/2008 | Lang et al. |
| 7,341,060 B2 | 3/2008 | Ging et al. |
| 7,353,826 B2 | 4/2008 | Sleeper et al. |
| 7,461,656 B2 | 12/2008 | Gunaratnam et al. |
| 7,470,256 B2 | 12/2008 | Lampropoulos et al. |
| 7,481,220 B2 | 1/2009 | Meyer et al. |
| 7,487,772 B2 | 2/2009 | Ging et al. |
| 7,503,327 B2 | 3/2009 | Gunaratnam |
| 7,509,958 B2 | 3/2009 | Amarasinghe et al. |
| 7,520,869 B2 | 4/2009 | Lampropoulos et al. |
| 7,523,754 B2 | 4/2009 | Lithgow et al. |
| 7,562,658 B2 | 7/2009 | Madaus et al. |
| 7,614,400 B2 | 11/2009 | Lithgow et al. |
| 7,614,401 B2 | 11/2009 | Thompson |
| 7,621,274 B2 | 11/2009 | Sprinkle et al. |
| 7,624,735 B2 | 12/2009 | Ho et al. |
| 7,640,934 B2 | 1/2010 | Zollinger et al. |
| 7,654,263 B2 | 2/2010 | Lang et al. |
| 7,658,189 B2 | 2/2010 | Davidson et al. |
| 7,665,464 B2 | 2/2010 | Kopacko et al. |
| D614,762 S | 4/2010 | Lang et al. |
| 7,699,808 B2 | 4/2010 | Marrs et al. |
| 7,703,457 B2 | 4/2010 | Barnett et al. |
| 7,708,017 B2 | 5/2010 | Davidson |
| 7,743,767 B2 | 6/2010 | Ging et al. |
| 7,762,259 B2 | 7/2010 | Gunaratnam |
| 7,775,209 B2 | 8/2010 | Biener et al. |
| 7,779,832 B1 | 8/2010 | Ho |
| 7,798,144 B2 | 9/2010 | Kwok et al. |
| 7,814,911 B2 | 10/2010 | Bordewick et al. |
| 7,819,119 B2 | 10/2010 | Ho |
| 7,827,990 B1 | 11/2010 | Melidis et al. |
| 7,841,345 B2 | 11/2010 | Guney et al. |
| 7,856,980 B2 | 12/2010 | Lang et al. |
| 7,856,982 B2 | 12/2010 | Matula, Jr. et al. |
| 7,861,715 B2 | 1/2011 | Jones et al. |
| 7,874,293 B2 | 1/2011 | Gunaratnam et al. |
| 7,878,199 B2 | 2/2011 | Ging et al. |
| 7,900,631 B2 | 3/2011 | Persson |
| 7,900,635 B2 | 3/2011 | Gunaratnam et al. |
| 7,931,024 B2 | 4/2011 | Ho et al. |
| 7,958,893 B2 | 6/2011 | Lithgow et al. |
| 7,967,013 B2 | 6/2011 | Ging et al. |
| 7,967,014 B2 | 6/2011 | Heidmann et al. |
| 7,971,590 B2 | 7/2011 | Frater et al. |
| 7,992,559 B2 | 8/2011 | Lang et al. |
| 7,997,267 B2 | 8/2011 | Ging et al. |
| D645,961 S | 9/2011 | Biener et al. |
| 8,042,538 B2 | 10/2011 | Ging et al. |
| 8,042,541 B2 | 10/2011 | Amarasinghe et al. |
| 8,042,542 B2 | 10/2011 | Ging et al. |
| 8,042,546 B2 | 10/2011 | Gunaratnam et al. |
| 8,051,850 B2 | 11/2011 | Kwok et al. |
| 8,091,553 B2 | 1/2012 | Bordewick et al. |
| 8,096,301 B2 | 1/2012 | Smith et al. |
| 8,136,524 B2 | 3/2012 | Ging et al. |
| 8,136,525 B2 | 3/2012 | Lubke et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,297,283 B2 | 10/2012 | Hitchcock et al. |
| 8,397,728 B2 | 3/2013 | D'Souza et al. |
| 8,479,738 B2 | 7/2013 | Lang et al. |
| 8,496,004 B2 | 7/2013 | Lang et al. |
| 8,746,250 B2 | 6/2014 | Biener et al. |
| 2001/0020474 A1 | 9/2001 | Hecker et al. |
| 2002/0020416 A1 | 2/2002 | Namey |
| 2002/0029780 A1 | 3/2002 | Frater et al. |
| 2002/0046755 A1 | 4/2002 | DeVoss |
| 2002/0066452 A1 | 6/2002 | Kessler et al. |
| 2002/0069872 A1 | 6/2002 | Gradon et al. |
| 2002/0108613 A1* | 8/2002 | Gunaratnam et al. ... 128/205.25 |
| 2002/0124849 A1 | 9/2002 | Billette de Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2003/0019495 A1 | 1/2003 | Palkon et al. |
| 2003/0062048 A1 | 4/2003 | Gradon et al. |
| 2003/0089373 A1 | 5/2003 | Gradon et al. |
| 2003/0168063 A1 | 9/2003 | Gambone et al. |
| 2003/0196656 A1 | 10/2003 | Moore et al. |
| 2003/0196658 A1 | 10/2003 | Ging et al. |
| 2004/0025883 A1 | 2/2004 | Eaton et al. |
| 2004/0094157 A1 | 5/2004 | Dantanarayana et al. |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0112385 A1 | 6/2004 | Drew et al. |
| 2004/0118406 A1 | 6/2004 | Lithgow et al. |
| 2004/0127856 A1 | 7/2004 | Johnson |
| 2004/0177850 A1* | 9/2004 | Gradon et al. ........... 128/206.21 |
| 2004/0182398 A1 | 9/2004 | Sprinkle et al. |
| 2004/0211428 A1 | 10/2004 | Jones |
| 2004/0226566 A1 | 11/2004 | Gunaratnam et al. |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0098183 A1 | 5/2005 | Nash et al. |
| 2005/0150495 A1 | 7/2005 | Rittner et al. |
| 2005/0155604 A1 | 7/2005 | Ging et al. |
| 2005/0211252 A1 | 9/2005 | Lang et al. |
| 2005/0241644 A1 | 11/2005 | Gunaratnam et al. |
| 2006/0076017 A1 | 4/2006 | Walker et al. |
| 2006/0118117 A1 | 6/2006 | Berthon-Jones et al. |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0213520 A1 | 9/2006 | Frater et al. |
| 2006/0219246 A1 | 10/2006 | Dennis |
| 2006/0254593 A1 | 11/2006 | Chang |
| 2006/0260614 A1 | 11/2006 | Biener et al. |
| 2006/0272646 A1 | 12/2006 | Ho et al. |
| 2006/0283461 A1 | 12/2006 | Lubke et al. |
| 2007/0044804 A1 | 3/2007 | Matula, Jr. et al. |
| 2007/0137653 A1 | 6/2007 | Wood |
| 2007/0144525 A1 | 6/2007 | Davidson et al. |
| 2007/0215161 A1 | 9/2007 | Frater et al. |
| 2007/0221226 A1 | 9/2007 | Hansen et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110464 A1 | 5/2008 | Davidson et al. |

(56) References Cited

U.S. PATENT DOCUMENTS

| | | |
|---|---|---|
| 2008/0110469 A1 | 5/2008 | Weinberg |
| 2008/0178875 A1 | 7/2008 | Henry |
| 2008/0178886 A1 | 7/2008 | Lieberman et al. |
| 2008/0200880 A1 | 8/2008 | Kyvik et al. |
| 2008/0257354 A1 | 10/2008 | Davidson et al. |
| 2008/0302365 A1 | 12/2008 | Cohen et al. |
| 2008/0314389 A1 | 12/2008 | Thomas et al. |
| 2009/0044808 A1 | 2/2009 | Guney et al. |
| 2009/0050156 A1 | 2/2009 | Ng et al. |
| 2009/0126739 A1 | 5/2009 | Ng et al. |
| 2009/0139526 A1 | 6/2009 | Melidis et al. |
| 2009/0139527 A1 | 6/2009 | Ng et al. |
| 2009/0173343 A1 | 7/2009 | Omura et al. |
| 2009/0217929 A1 | 9/2009 | Kwok et al. |
| 2009/0223518 A1 | 9/2009 | Kwok et al. |
| 2009/0223521 A1 | 9/2009 | Howard et al. |
| 2010/0000534 A1 | 1/2010 | Kooij et al. |
| 2010/0000543 A1 | 1/2010 | Berthon-Jones et al. |
| 2010/0018534 A1 | 1/2010 | Veliss et al. |
| 2010/0089401 A1 | 4/2010 | Lang et al. |
| 2010/0108072 A1 | 5/2010 | D'Souza et al. |
| 2010/0132717 A1 | 6/2010 | Davidson et al. |
| 2010/0192955 A1 | 8/2010 | Biener et al. |
| 2010/0282265 A1 | 11/2010 | Melidis et al. |
| 2010/0300447 A1 | 12/2010 | Biener et al. |
| 2011/0030692 A1 | 2/2011 | Jones et al. |
| 2011/0056497 A1 | 3/2011 | Scheiner et al. |
| 2011/0220110 A1 | 9/2011 | Frater et al. |
| 2011/0220114 A1 | 9/2011 | Lithgow et al. |
| 2011/0226254 A1 | 9/2011 | Lang et al. |
| 2011/0259337 A1 | 10/2011 | Hitchcock et al. |
| 2012/0138063 A1 | 6/2012 | Eves et al. |
| 2012/0174928 A1 | 7/2012 | Raje et al. |
| 2012/0266886 A1 | 10/2012 | Davidson et al. |
| 2013/0037033 A1 | 2/2013 | Hitchcock et al. |
| 2013/0081628 A1 | 4/2013 | Davidson et al. |
| 2013/0081629 A1 | 4/2013 | Davidson et al. |
| 2013/0081630 A1 | 4/2013 | Davidson et al. |
| 2013/0081631 A1 | 4/2013 | Davidson et al. |
| 2013/0081632 A1 | 4/2013 | Davidson et al. |
| 2013/0086795 A1 | 4/2013 | Davidson et al. |
| 2013/0086796 A1 | 4/2013 | Davidson et al. |
| 2013/0087147 A1 | 4/2013 | Davidson et al. |
| 2013/0087148 A1 | 4/2013 | Davidson et al. |
| 2013/0087149 A1 | 4/2013 | Davidson et al. |
| 2013/0092168 A1 | 4/2013 | Davidson et al. |
| 2013/0092170 A1 | 4/2013 | Davidson et al. |

FOREIGN PATENT DOCUMENTS

| | | |
|---|---|---|
| AU | 95/16178 | 7/1995 |
| AU | 94/59430 | 10/1995 |
| AU | 95/32914 | 2/1996 |
| AU | 96/51130 | 10/1996 |
| AU | 97/41018 | 4/1998 |
| AU | 98/89312 | 1/1999 |
| AU | 2005100738 | 11/2005 |
| CA | 618807 | 4/1961 |
| CA | 623129 | 7/1961 |
| CA | 1039144 | 9/1978 |
| CN | 1219883 | 6/1999 |
| CN | 2464353 | 12/2001 |
| CN | 1735439 | 2/2006 |
| DE | 185 017 | 5/1907 |
| DE | 284 800 | 11/1913 |
| DE | 459 104 | 4/1928 |
| DE | 701 690 | 1/1941 |
| DE | 30 11 900 | 10/1980 |
| DE | 146 688 | 1/1981 |
| DE | 30 15 279 | 10/1981 |
| DE | 31 49 449 | 10/1982 |
| DE | 159 396 | 3/1983 |
| DE | 33 45 067 | 6/1984 |
| DE | 37 07 952 | 3/1987 |
| DE | 35 37 507 | 4/1987 |
| DE | 35 39 073 | 5/1987 |
| DE | 37 19 009 | 12/1988 |
| DE | 39 27 038 | 2/1991 |
| DE | 40 04 157 | 4/1991 |
| DE | 42 12 259 | 1/1993 |
| DE | 42 33 448 | 4/1993 |
| DE | 43 43 205 | 6/1995 |
| DE | 195 48 380 | 7/1996 |
| DE | 196 03 949 | 8/1997 |
| DE | 297 15 718 | 10/1997 |
| DE | 197 35 359 | 1/1998 |
| DE | 297 23 101 | 7/1998 |
| DE | 197 03 526 | 8/1998 |
| DE | 298 10 846 | 8/1998 |
| DE | 198 17 332 | 1/1999 |
| DE | 198 07 961 | 8/1999 |
| DE | 198 08 105 | 9/1999 |
| DE | 198 40 760 | 3/2000 |
| DE | 200 05 346 | 5/2000 |
| DE | 299 23 141 | 5/2000 |
| DE | 200 17 940 | 2/2001 |
| DE | 199 44 242 | 3/2001 |
| DE | 199 54 517 | 6/2001 |
| DE | 100 02 571 | 7/2001 |
| DE | 199 62 515 | 7/2001 |
| DE | 100 45 183 | 5/2002 |
| DE | 100 45 183 A1 | 5/2002 |
| DE | 102 13 905 | 10/2002 |
| DE | 10 2004 055 433 | 11/2004 |
| DE | 103 31 837 | 1/2005 |
| DE | 20 2004 018 108 | 2/2005 |
| DE | 103 38 169 | 3/2005 |
| DE | 10 2004 037 344 A1 | 3/2006 |
| EP | 0 054 154 | 6/1982 |
| EP | 0 252 052 | 1/1988 |
| EP | 0 264 772 | 4/1988 |
| EP | 0 288 937 | 11/1988 |
| EP | 0 334 555 | 9/1989 |
| EP | 0 386 605 | 9/1990 |
| EP | 0 427 474 | 5/1991 |
| EP | 0 462 701 | 12/1991 |
| EP | 0 466 960 | 1/1992 |
| EP | 0 303 090 B1 | 4/1992 |
| EP | 0 549 299 | 6/1993 |
| EP | 0 602 424 | 6/1994 |
| EP | 0 608 684 | 8/1994 |
| EP | 0 658 356 | 6/1995 |
| EP | 0 697 225 | 2/1996 |
| EP | 0 178 925 A2 | 4/1996 |
| EP | 0 747 078 | 12/1996 |
| EP | 0 776 679 | 6/1997 |
| EP | 0 821 978 | 2/1998 |
| EP | 0 853 962 | 7/1998 |
| EP | 1 027 905 A2 | 8/2000 |
| EP | 1 057 494 A2 | 12/2000 |
| EP | 1 099 452 | 5/2001 |
| EP | 1 118 346 | 7/2001 |
| EP | 1 163 923 | 12/2001 |
| EP | 1 205 205 | 5/2002 |
| EP | 1 258 266 | 11/2002 |
| EP | 1 334 742 | 8/2003 |
| EP | 1 356 841 | 10/2003 |
| EP | 1 356 843 | 10/2003 |
| EP | 1 360 971 | 11/2003 |
| EP | 1 481 702 | 12/2004 |
| EP | 2 471 566 | 7/2012 |
| EP | 2 471 567 | 7/2012 |
| FR | 780018 | 4/1935 |
| FR | 2 574 657 | 6/1986 |
| FR | 2 658 725 | 8/1991 |
| FR | 2 720 280 | 12/1995 |
| FR | 2 749 176 | 12/1997 |
| FR | 2 823 122 | 10/2002 |
| GB | 532 214 | 1/1941 |
| GB | 649 689 | 1/1951 |

(56) References Cited

FOREIGN PATENT DOCUMENTS

| | | |
|---|---|---|
| GB | 823 887 | 11/1959 |
| GB | 880 942 | 10/1961 |
| GB | 1 395 391 | 5/1975 |
| GB | 1 467 828 | 3/1977 |
| GB | 2 145 335 | 3/1985 |
| GB | 2 147 506 | 5/1985 |
| GB | 2 164 569 | 3/1986 |
| GB | 2 176 404 | 12/1986 |
| GB | 2 186 801 | 8/1987 |
| GB | 2 267 648 | 12/1993 |
| GB | 2 368 533 | 5/2002 |
| GB | 2 385 533 | 5/2003 |
| JP | S39-13991 | 7/1964 |
| JP | S51-142793 | 11/1976 |
| JP | H03-007173 | 1/1991 |
| JP | H09-216240 | 8/1997 |
| JP | H11-000397 | 1/1999 |
| JP | H11-104256 | 4/1999 |
| JP | H11-508159 | 7/1999 |
| JP | 2000-279520 | 10/2000 |
| JP | 2000-325481 | 11/2000 |
| JP | 2000-515784 | 11/2000 |
| JP | 2002-028240 | 4/2002 |
| JP | 2002-543943 | 12/2002 |
| JP | 2003-175106 | 6/2003 |
| JP | 2003-535657 | 12/2003 |
| JP | 2004-000570 | 1/2004 |
| JP | 2005-337371 | 12/2005 |
| JP | 3802872 | 7/2006 |
| JP | 2008-501438 | 1/2008 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20392 | 11/1992 |
| WO | WO 92/20395 | 11/1992 |
| WO | WO 93/01854 | 2/1993 |
| WO | WO 93/24169 | 12/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/28207 | 9/1996 |
| WO | WO 96/39206 | 12/1996 |
| WO | WO 97/00092 A1 | 1/1997 |
| WO | WO 97/07847 | 3/1997 |
| WO | WO 97/09090 | 3/1997 |
| WO | WO 97/41911 | 11/1997 |
| WO | WO 98/03145 | 1/1998 |
| WO | WO 98/04310 | 2/1998 |
| WO | WO 98/11930 | 3/1998 |
| WO | WO 98/12965 | 4/1998 |
| WO | WO 98/18514 | 5/1998 |
| WO | WO 98/23305 | 6/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 99/16327 | 4/1999 |
| WO | WO 99/25410 | 5/1999 |
| WO | WO 99/43375 | 9/1999 |
| WO | WO 99/58181 | 11/1999 |
| WO | WO 99/61088 | 12/1999 |
| WO | WO 99/65554 | 12/1999 |
| WO | WO 00/20072 | 4/2000 |
| WO | WO 00/21600 | 4/2000 |
| WO | WO 00/35525 | 6/2000 |
| WO | WO 00/38772 | 7/2000 |
| WO | WO 00/50121 | 8/2000 |
| WO | WO 00/57942 | 10/2000 |
| WO | WO 00/69521 A1 | 11/2000 |
| WO | WO 00/72905 | 12/2000 |
| WO | WO 00/74758 | 12/2000 |
| WO | WO 00/76568 | 12/2000 |
| WO | WO 00/78381 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 02/11804 A2 | 2/2002 |
| WO | WO 02/32491 | 4/2002 |
| WO | WO 02/38221 | 5/2002 |
| WO | WO 02/45784 | 6/2002 |
| WO | WO 03/005931 | 1/2003 |
| WO | WO 03/059427 | 7/2003 |
| WO | WO 03/082406 | 10/2003 |
| WO | WO 03/090827 | 11/2003 |
| WO | WO 03/105921 | 12/2003 |
| WO | WO 2004/007010 | 1/2004 |
| WO | WO 2004/022144 | 3/2004 |
| WO | WO 2004/022145 | 3/2004 |
| WO | WO 2004/022146 | 3/2004 |
| WO | WO 2004/022147 | 3/2004 |
| WO | WO 2004/041342 | 5/2004 |
| WO | WO 2004/073778 | 9/2004 |
| WO | WO 2004/078228 | 9/2004 |
| WO | WO 2004/078230 | 9/2004 |
| WO | WO 2004/096332 | 11/2004 |
| WO | WO 2005/002656 | 1/2005 |
| WO | WO 2005/018523 | 3/2005 |
| WO | WO 2005/021075 | 3/2005 |
| WO | WO 2005/028010 | 3/2005 |
| WO | WO 2005/053781 | 6/2005 |
| WO | WO 2005/063326 | 7/2005 |
| WO | WO 2005/063328 | 7/2005 |
| WO | WO 2005/086943 | 9/2005 |
| WO | WO 2005/094928 | 10/2005 |
| WO | WO 2005/099801 | 10/2005 |
| WO | WO 2005/110220 | 11/2005 |
| WO | WO 2005/118040 | 12/2005 |
| WO | WO 2005/123166 | 12/2005 |
| WO | WO 2006/000046 | 1/2006 |
| WO | WO 2006/014630 | 2/2006 |
| WO | WO 2006/015772 A1 | 2/2006 |
| WO | WO 2006/052653 | 5/2006 |
| WO | WO 2006/069345 | 6/2006 |
| WO | WO 2006/069415 | 7/2006 |
| WO | WO 2006/074513 | 7/2006 |
| WO | WO 2006/074515 | 7/2006 |
| WO | WO 2006/074516 | 7/2006 |
| WO | WO 2006/099658 | 9/2006 |
| WO | WO 2006/102707 | 10/2006 |
| WO | WO 2006/130903 | 12/2006 |
| WO | WO 2006/138416 | 12/2006 |
| WO | WO 2007/009182 | 1/2007 |
| WO | WO 2007/041751 | 4/2007 |
| WO | WO 2007/041786 | 4/2007 |
| WO | WO 2007/045008 | 4/2007 |
| WO | WO 2007/048174 | 5/2007 |
| WO | WO 2007/053878 | 5/2007 |
| WO | WO 2007/143772 | 12/2007 |
| WO | WO 2007/143792 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/026627 | 3/2009 |
| WO | WO 2009/052560 | 4/2009 |
| WO | WO 2009/062265 | 5/2009 |
| WO | WO 2009/108994 | 9/2009 |
| WO | WO 2009/108995 | 9/2009 |
| WO | WO 2009/109004 | 9/2009 |
| WO | WO 2010/028425 | 3/2010 |
| WO | WO 2010/066004 | 6/2010 |

(56) References Cited

FOREIGN PATENT DOCUMENTS

| WO | WO 2011/060479 | 5/2011 |
|---|---|---|
| WO | WO 2013/057647 | 4/2013 |
| WO | WO 2013/061260 | 5/2013 |

OTHER PUBLICATIONS

Adam J. Singer MD et al. "The Cyanoacrylate Topical Skin Adhesives," American Journal of Emergency Medicine, vol. 26, 2008, pp. 490-496.
Nellcor Puritan Bennett, "There are a Lot of Noses Out There," dated 1995, pp. 1-12.
New Zealand Appln. No. 2003275762—Examiner's Report No. 3, dated Nov. 18, 2009.
New Zealand Appln. No. 539836—Examination Report, dated Aug. 25, 2005.
New Zealand Appln. No. 564877—Examination Report, dated Dec. 2, 2009.
New Zealand Appln. No. 567375—Examination Report, dated Nov. 17, 2009.
New Zealand Appln. No. 587344—Examination Report, dated Jan. 19, 2012.
New Zealand Appln. No. 587344—Examination Report, dated Aug. 3, 2012.
New Zealand Appln. No. 587820—Examination Report, dated Sep. 13, 2010.
New Zealand Appln. No. 597552—Examination Report, dated Jan. 19, 2012.
New Zealand Appln. No. 597689—Examination Report, dated Jan. 25, 2012.
New Zealand Appln. No. 607032—Examination Report, dated Feb. 18, 2013.
PCT/AU2003/001163—International Search Report, dated Nov. 4, 2003.
PCT/AU2003/001471—International Search Report, dated Feb. 12, 2004.
PCT/AU2004/000563—International Search Report, dated Jun. 23, 2004.
PCT/AU2004/001760—International Search Report, dated Jan. 12, 2005.
PCT/AU2004/001760—International Preliminary Report on Patentability, dated Jul. 3, 2006.
PCT/AU2004/001813—International Search Report, dated Mar. 7, 2005.
PCT/AU2004/001813—International Preliminary Report on Patentability, dated Jul. 3, 2006.
PCT/AU2004/001832—International Search Report, dated Mar. 24, 2005.
PCT/AU2004/001832—International Preliminary Report on Patentability, dated Jul. 3, 2006.
PCT/AU2005/000803—International Search Report, dated Jun. 30, 2005.
PCT/AU2005/000850—International Search Report, dated Aug. 12, 2005.
PCT/AU2005/000850—International Preliminary Report on Patentability, dated Dec. 20, 2006.
PCT/AU2006/000032—International Search Report, dated May 15, 2006.
PCT/AU2006/000032—International Preliminary Report on Patentability, dated Jul. 17, 2007.
PCT/AU2006/000770—International Search Report, dated Aug. 3, 2006.
PCT/AU2006/001570—International Search Report, dated Jan. 5, 2007.
PCT/AU2007/001051—International Search Report, dated Nov. 5, 2007.
PCT/AU2007/001052—International Search Report, dated Oct. 9, 2007.
PCT/AU2007/001456—International Search Report, dated Dec. 12, 2007.
PCT/AU2007/001936—International Search Report, dated Mar. 4, 2008.
PCT/AU2009/000240—International Search Report, dated May 21, 2009.
PCT/AU2009/000241—International Search Report, dated May 18, 2009.
PCT/AU2009/000262—International Search Report, dated Jun. 9, 2009.
PCT/AU2009/001102—International Search Report, dated Dec. 11, 2009.
Australian Appln. No. 2005253641—Examiner's First Report, dated Apr. 20, 2010.
Australian Appln. No. 2005253641—Examiner's Report, dated Aug. 18, 2011.
Australian Appln. No. 2006206040—Examination Report, dated Jun. 27, 2012.
Australian Appln. No. 2009221630—Examination Report, dated Mar. 21, 2013.
Australian Appln. No. 2010251884—Examination Report, dated Jul. 27, 2012.
Chinese Appln. No. 200480011911.9—Office Action (w/English translation), dated Jun. 24, 2010.
Chinese Appln. No. 200580020203.6—Office Action (w/English translation), dated Jun. 1, 2010.
Chinese Appln. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200680002169.4—Office Action (w/English translation), dated Mar. 23, 2010.
Chinese Appln. No. 200680002169.4—Third Office Action (w/English translation), dated Nov. 11, 2010.
Chinese Appln. No. 200810109270.0—Office Action (w/English translation), dated Oct. 19, 2011.
Chinese Appln. No. 200810109270.0—Office Action (w/English translation), dated Jun. 27, 2012.
Chinese Appln. No. 200910223650.1—Office Action (w/English translation), dated Mar. 29, 2012.
Chinese Appln. No. 200980116004.3—Office Action (w/English translation), dated Dec. 24, 2012.
Chinese Appln. No. 201010000226.3—Office Action (w/English translation), dated Apr. 26, 2012.
Chinese Appln. No. 201010517066.X—Office Action (w/English translation), dated Nov. 10, 2011.
ComfortLite™, Respironics, http://comfortlite.respironics.com, before applicants' filing date.
ComfortLite™ 2, Respironics, http://comfortlite2.respironics.com, before applicants' filing date.
"Ear Loop Face Mask", before applicants' filing date.
European Appln. No. EP 01944732.5—Office Action, dated Nov. 27, 2009.
European Appln. No. EP 02714190.2—Search Report, dated Jul. 11, 2006.
European Appln. No. EP 03793493.2—Supplementary Search Report, dated Dec. 2, 2009.
European Appln. No. EP 03793493.2—Office Action, dated Mar. 18, 2011.
European Appln. No. EP 03810331.3—Supplementary Search Report, dated Dec. 18, 2009.
European Appln. No. EP 04730413.4—Supplementary Search Report, dated Sep. 29, 2009.
European Appln. No. EP 04802114.1—Supplementary Search Report, dated May 7, 2009.
European Appln. No. EP 04802133.1—Supplementary Search Report, dated Sep. 8, 2009.
European Appln. No. EP 04802133.1—Office Action, dated Dec. 22, 2009.
European Appln. No. EP 05746824.1—Supplementary Search Report, dated Dec. 17, 2009.
European Appln. No. EP 05749447.8—Supplementary Search Report, dated Dec. 8, 2009.

(56) References Cited

OTHER PUBLICATIONS

European Appln. No. EP 06704287.9—Supplementary Search Report, dated Oct. 6, 2009.
European Appln. No. EP 06704287.9—Office Action, dated Jul. 18, 2011.
European Appln. No. EP 07784697.0—Search Report, dated Jul. 27, 2009.
European Appln. No. EP 07845378.4—Search Report, dated Dec. 1, 2009.
European Appln. No. EP 08154854.7—Extended Search Report, dated Nov. 27, 2008.
European Appln. No. EP 08154854.7—Examination Report, dated Jul. 1, 2011.
European Appln. No. EP 08161249.1—Extended Search Report, dated Mar. 19, 2009.
European Appln .No. EP 08161868.8—Search Report, dated Sep. 23, 2008.
European Appln .No. EP 09003544.5—Search Report, dated Jun. 2, 2009.
European Appln. No. EP 09161984.1—Extended Search Report, dated Sep. 3, 2009.
European Appln. No. EP 09178736.6—Search Report, dated Apr. 19, 2010.
European Appln. No. EP 10181516.5—Search Report, dated Jun. 13, 2012.
European Appln. No. EP 10182015.7—Search Report, dated Jun. 15, 2012.
European Appln. No. EP 11174401.7—Search Report, dated Oct. 20, 2011.
European Appln. No. EP 11174407.4—Extended Search Report, dated Oct. 20, 2011.
European Appln. No. EP 12154923.2—Extended Search Report, dated Jun. 1, 2012.
European Appln. No. EP 12154926.5—Extended Search Report, dated Jun. 6, 2012.
European Appln. No. EP 12165749.8—Extended Search Report, dated Oct. 10, 2012.
European Appln. No. EP 12165751.4—Extended Search Report, dated Oct. 8, 2012.
Fisher and Paykel Col.—Product Family—http://www.fphcare.com/osa/products.asp/, before applicants' filing date.
German Patent No. 101 51 984—Decision from Opposition hearing by Weinmann (w/English translation), dated Dec. 6, 2007.
Hans Rudolph, Inc.—Mask Products—http://www.rudolphkc.com/products.php?category=MASKS, before applicants' filing date.
"If You Hate CPAP! You Need CPAP Pro®," www.cpappro.com, before applicants' filing date.
Japanese Appln. No. 2003-537718—Office Action (w/English translation), dated Oct. 7, 2008.
Japanese Appln. No. 2003-559587—Office Action (w/English translation), dated Mar. 17, 2009.
Japanese Appln. No. 2005-004072—Office Action (w/English translation), dated Sep. 24, 2009.
Japanese Appln. No. 2005-337371—Reasons for Rejection (w/English translation), dated Feb. 22, 2011.
Japanese Appln. No. 2005-337371—Final Office Action (w/English translation), dated Jan. 31, 2012.
Japanese Appln. No. 2006-504029—Office Action (w/English translation), dated Nov. 10, 2009.
Japanese Appln. No. 2006-545843—Notice of Reasons for Rejection (w/English translation), dated Jun. 7, 2011.
Japanese Appln. No. 2007-515732—Office Action (w/English translation), dated Aug. 24, 2010.
Japanese Appln. No. 2007-515732—Office Action (w/English translation), dated Aug. 16, 2011.
Japanese Appln. No. 2007-515732—Office Action (w/English translation), dated Jun. 12, 2012.
Japanese Appln. No. 2007-550636—Office Action (w/English translation), dated Mar. 18, 2011.
Japanese Appln. No. 2007-550636—Office Action (w/English translation), dated Mar. 21, 2012.
Japanese Appln. No. 2007-550636—Notice of Allowance, dated Jul. 10, 2012.
Japanese Appln. No. 2009-140433—Office Action (w/English translation), dated Aug. 20, 2011.
Japanese Appln. No. 2009-140433—Notice of Allowance, dated Sep. 4, 2012.
Japanese Appln. No. 2010-195597—Office Action (w/English translation), dated Jun. 12, 2012.
Japanese Appln. No. 2010-214485—Office Action (w/English translation), dated Jun. 12, 2012.
Japanese Appln. No. 2010-268127—Notice of Reasons for Rejection (w/English translation), dated Jul. 10, 2012.
Japanese Appln. No. 2010-548986—Notice of Reasons for Rejection (w/English translation), dated Apr. 16, 2013.
Japanese Appln. No. 2011-038110—Office Action (w/English translation), dated Aug. 14, 2012.
Japanese Appln. No. S52-164619—English translation of Figure 1, Dec. 1977.
Joel W. Beam, "Tissue Adhesives for Simple Traumatic Lacerations," Journal of Athletic Training, 2008, vol. 43, No. 2, pp. 222-224.
JP 11-000397A Machine Translation, provided by the Japanese Patent Office, Jan. 6, 2009, full document.
Laurent Brochard, "Pressure Support Ventilation," Chapter 9, Part IV—Conventional Methods of Ventilator Support, pp. 239-257, 1994.
Mask 1 Photographs, Respironics Inc., Reusable Full Mask (small) Part #452033 Lot #951108, before applicants' filing date.
Mask 2 Photographs, Puritan—Bennett, Adam Curcuit, Shell Part #231700, Swivel Part #616329-00, Pillows (medium) Part #616324, before applicants' filing date.
Mask 3 Photographs, DeVilbiss Healthcare Inc., Devilbiss Seal-Ring and CPAP Mask Kit (medium), Part #73510-669, before applicants' filing date.
Mask 4 Photographs, Respironics Inc., Monarch Mini Mask with Pressure Port, Part #572004, Monarch Headgear, Part #572011, before applicants' filing date.
Mask 5 Photographs, Healthdyne Technologies, Nasal CPAP Mask (medium narrow), Part #702510, before applicants' filing date.
Mask 6 Photographs, Healthdyne Technologies, Soft Series Nasal CPAP Mask, Part #702020, before applicants' filing date.
Mask 7 Photographs, DeVilbiss Healthcare Inc., Small Mask and Seal Rings, Part #73510-668, before applicants' filing date.
Mask 8 Photographs, Respironics Inc., Reusable Contour Mask (medium), Part #302180, before applicants' filing date.
Mask 9 Photographs, Healthdyne Technologies, Healthdyne Large Headgear, before applicants' filing date.
Mask 10 Photographs, Respironics Inc., Soft Cap (medium), Part #302142, before applicants' filing date.
Mask 11 Photographs, Weinmann: Hamburg, Nasalmaskensystem mit Schalldämpfer (medium), Part #WN 23105, before applicants' filing date.
Mask 12 Photographs, Life Care, before applicants' filing date.
Mask 13 Photographs, Healthdyne Technologies, before applicants' filing date.
Mark 14 Photographs, King System, before applicants' filing date.
Mask 15 Photographs, Respironics Inc., Pediatric Mask, before applicants' filing date.
Mask 16 Photographs, Hans Rudolph Inc., Hans Rudolph Silicone Rubber Face Mask/8900, before applicants' filing date.
McPherson et al., "Respiratory Therapy Equipment," Chapter 8, Third Edition, Introduction to Ventilators, pp. 230-253, 1985.
Merriam-Webster Online Dictionary definition of moveable from the 14th century, before applicants' filing date.
PCT/AU2009/001144—International Search Report, dated Dec. 8, 2009.
PCT/AU2010/000657—International Search Report, dated Sep. 9, 2010.
9 photographs of Weinmann mask, WM 23122, 1991.
Photograph of Weinmann mask, acquired prior to 1998.
4 additional photographs of Weinmann mask, currently considered before applicants' filing date.

(56) References Cited

OTHER PUBLICATIONS

Product Brochure for ResMed "Sullivan® Mirage™—The Mirage is Real. A Perfect Fit—First Time," © 1997 ResMed Limited, 4 pages.
Product Brochure for ResMed "Sullivan® Mirage™—The Mirage is Real. A Perfect Fit—First Time," © 1998 ResMed Limited, 4 pages.
ResCare, "Introducing The Sullivan Bubble Mask System—Series 3," 4 pages, currently considered before Applicant's filing date.
ResCare, "The Sullivan—APD 2 Nasal CPAP System," 10 pages, currently considered before Applicant's filing date.
ResCare, "The Sullivan Mask System," 2 pages, currently considered before Applicant's filing date.
ResCare, "Sullivan Nasal CPAP Products—Mask Systems Handbook," Sep. 1993.
ResMed, "Mask Frames," retrieved from www.resmed.com/maskframes/mask.htm, 2 pages, captured Jan. 4, 1997.
ResMed, "Modular Mask Components," retrieved from http://www.resmed.com/products/standards.htm, 3 pages, captured Dec. 15, 2000.
ResMed, "Nasal Cushions," retrieved from www.resmed.com/cushions/cushions.htm, captured Jan. 4, 1997.
ResMed, "ResMed Origins," pp. 1-64, currently considered before Applicant's filing date.
ResMed, "Sullivan Comfort Bi-level System Operating Manual," dated 2000, pp. 1-26.
ResMed Co.—Mask Products—http://resmed.com/portal/site/ResMedUS/index.jsp?, before applicants' filing date.
ResMed Ltd., "Improving patient compliance with The ResMed Range of Mask Systems The Ultimate Interface for CPAP treatment," before applicants' filing date, 4 pages.
Respironics Co.—Mask Family—http://masksfamily.respironics.com/, before Applicant's filing date.
Snapp Nasal Interface, Tiara Medical Systems, Inc.—http://tiaramed.com/asp_shops/shopdisplayproducts.asp?id=109&cat=SNAPP%2A+Nasal+Interface, before applicants' filing date.
"Somnomask" brochure, 1999 along with various invoices relating to the "Somnomask".
Somnotron CPAP—Great WM 2300 Instruction Manual, Weinmann Hamburg, 1991, 11 pages.
Subbu Venkatraman et al., "Review Skin Adhesives and Skin Adhesion 1. Transdermal Drug Delivery Systems," Biomaterials, vol. 19, 1998, pp. 1119-1136.
The ResMed Range of Mask Systems, product brochure, Nov. 1995, 4 pages.
Unsolicited email from Elson Silva, PhD, dated Mar. 28, 2008, "Requesting IDS of US 6,766,817 for patents on fluids moving on porosity by Unsaturated Hydraulic Flow," (email provided in both HTML and plain text format).
U.S. Appl. No. 12/083,779—Office Action including PTO-892 listings, dated Feb. 17, 2012.
U.S. Appl. No. 12/083,779—Office Action including PTO-892 listings, dated Sep. 28, 2012.
U.S. Appl. No. 13/745,077—Office Action including PTO-892 listings, dated Apr. 10, 2013.
U.S. Appl. No. 13/747,701—Office Action including PTO-892 listings, dated Apr. 8, 2013.
U.S. Appl. No. 13/747,772—Office Action including PTO-892 listings, dated Apr. 2013.
U.S. Appl. No. 60/424,686, filed Nov. 8, 2002 (expired).
U.S. Appl. No. 60/483,622, filed Jul. 1, 2003 (expired).
U.S. Appl. No. 60/533,214, filed Dec. 31, 2003 (expired).
U.S. Appl. No. 60/634,802, filed Dec. 10, 2004 (expired).
U.S. Appl. No. 60/643,121, filed Jan. 12, 2005 (expired).
U.S. Appl. No. 60/645,672, filed Jan. 21, 2005 (expired).
U.S. Appl. No. 60/795,615, filed Apr. 28, 2006 (expired).
U.S. Appl. No. 60/833,841, filed Jul. 28, 2006 (expired).
U.S. Appl. No. 60/835,442, filed Aug. 4, 2006 (expired).
U.S. Appl. No. 60/852,649, filed Oct. 19, 2006 (expired).
U.S. Appl. No. 60/874,968, filed Dec. 15, 2006 (expired).
U.S. Appl. No. 60/907,856, filed Apr. 19, 2007 (expired).
U.S. Appl. No. 60/924,241, filed May 4, 2007 (expired).
U.S. Appl. No. 60/929,393, filed Jun. 25, 2007 (expired).
U.S. Appl. No. 60/935,179, filed Jul. 30, 2007 (expired).
U.S. Appl. No. 60/935,336, filed Aug. 8, 2007 (expired).
U.S. Appl. No. 60/996,160, filed Nov. 5, 2007 (expired).
U.S. Appl. No. 61/006,409, filed Jan. 11, 2008 (expired).
U.S. Appl. No. 61/064,818, filed Mar. 28, 2008 (expired).
U.S. Appl. No. 61/071,512, filed May 2, 2008 (expired).
U.S. Appl. No. 61/213,326, filed May 29, 2009 (expired).
U.S. Appl. No. 61/222,711, filed Jul. 2, 2009 (expired).
U.S. Appl. No. 61/263,175, filed Nov. 20, 2009 (expired).
U.S. Appl. No. 61/272,162, filed Aug. 25, 2009 (expired).
U.S. Appl. No. 61/272,250, filed Sep. 4, 2009 (expired).
Webster's New World Dictionary, Third College Edition 1988, definition for engaged and flexible, before applicants' filing date.
Webster's Third New International Dictionary, 1993, Dictionary definition for adjustable, bendable, and mild steel, before applicants' filing date.
ComfortLite™, Respironics, http://comfortlite.respironics.com, admitted prior art.
ComfortLite™ 2, Respironics, http://comfortlite2.respironics.com, admitted prior art.
"Ear Loop Face Mask", admitted prior art.
Fisher and Paykel Col.—Product Family—http://www.fphcare.com/osa/products.asp/, admitted prior art.
Hans Rudolph, Inc.—Mask Products—http://www.rudolphkc.com/products.php?category=MASKS, admitted prior art.
"If You Hate CPAP! You Need CPAP Pro®," www.cpappro.com, admitted prior art.
Mask 1 Photographs, Respironics Inc., Reusable Full Mask (small) Part #452033 Lot #951108, admitted prior art.
Mask 2 Photographs, Puritan—Bennett, Adam Curcuit, Shell Part #231700, Swivel Part #616329-00, Pillows (medium) Part #616324, admitted prior art.
Mask 3 Photographs, DeVilbiss Healthcare Inc., Devilbiss Seal-Ring and CPAP Mask Kit (medium), Part #73510-669, admitted prior art.
Mask 4 Photographs, Respironics Inc., Monarch Mini Mask with Pressure Port, Part #572004, Monarch Headgear, Part #572011, admitted prior art.
Mask 5 Photographs, Healthdyne Technologies, Nasal CPAP Mask (medium narrow), Part #702510, admitted prior art.
Mask 6 Photographs, Healthdyne Technologies, Soft Series Nasal CPAP Mask Part #702020, admitted prior art.
Mask 7 Photographs, DeVilbiss Healthcare Inc., Small Mask and Seal Rings, Part #73510-668, admitted prior art.
Mask 8 Photographs, Respironics Inc., Reusable Contour Mask (medium), Part #302180, admitted prior art.
Mask 9 Photographs, Healthdyne Technologies, Healthdyne Large Headgear, admitted prior art.
Mask 10 Photographs, Respironics Inc., Soft Cap (medium), Part #302142, admitted prior art.
Mask 11 Photographs, Weinmann: Hamburg, Nasalmaskensystem mit Schalldampfer (medium), Part #WN 23105, admitted prior art.
Mask 12 Photographs, Life Care, admitted prior art.
Mask 13 Photographs, Healthdyne Technologies, admitted prior art.
Mark 14 Photographs, King System, admitted prior art.
Mask 15 Photographs, Respironics Inc., Pediatric Mask, admitted prior art.
Mask 16 Photographs, Hans Rudolph Inc., Hans Rudolph Silicone Rubber Face Mask/8900, admitted prior art.
Merriam-Webster Online Dictionary definition of moveable from the 14th century, admitted prior art.
4 additional photographs of Weinmann mask, admitted prior art.
ResCare, "Introducing The Sullivan Bubble Mask System—Series 3," 4 pages, admitted prior art.
ResCare, "The Sullivan—APD 2 Nasal CPAP System," 10 pages, admitted prior art.
ResCare, "The Sullivan Mask System," 2 pages, admitted prior art.
ResMed, "ResMed Origins," pp. 1-64, admitted prior art.
ResMed Co.—Mask Products—http://resmed.com/portal/site/ResMedUS/index.jsp?, admitted prior art.

(56) References Cited

OTHER PUBLICATIONS

ResMed Ltd., "Improving patient compliance with The ResMed Range of Mask Systems The Ultimate Interface for CPAP treatment," admitted prior art, 4 pages.
Respironics Co.—Mask Family—http://masksfamily.respironics.com/, admitted prior art.
Snapp Nasal Interface, Tiara Medical Systems, Inc.—http://tiaramed.com/asp_shops/shopdisplayproducts.asp?id=109&cat=SNAPP%2A+Nasal+Interface, admitted prior art.
Webster's New World Dictionary, Third College Edition 1988, definition for engaged and flexible, admitted prior art.
Webster's Third New International Dictionary, 1993, Dictionary definition for adjustable, bendable, and mild steel, admitted prior art.

* cited by examiner

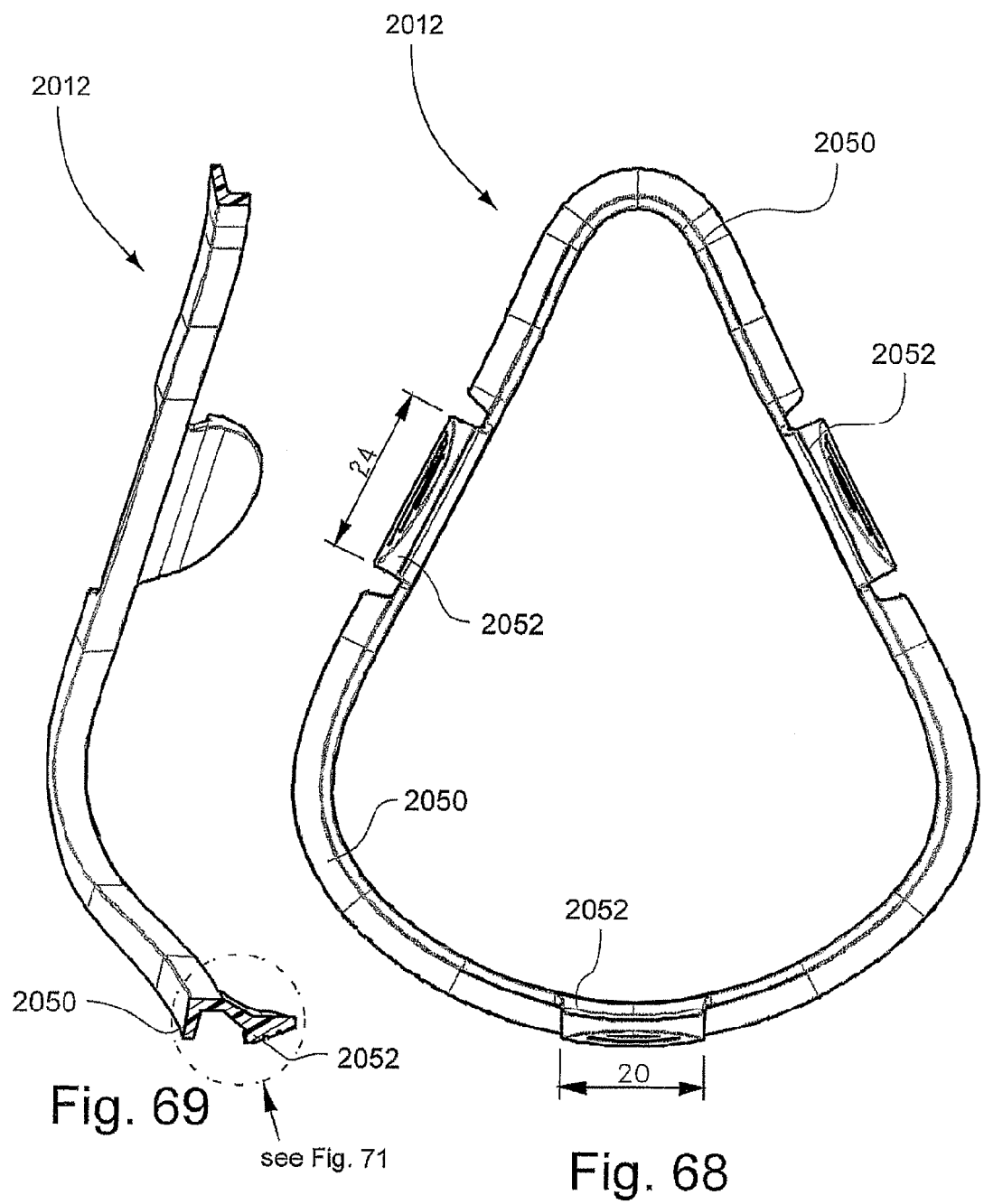

CUSHION TO FRAME ASSEMBLY MECHANISM

CROSS-REFERENCE TO APPLICATIONS

This application is a continuation of U.S. patent application Ser. No. 11/989,137, filed Jan. 22, 2008, allowed, which is the U.S. national phase of International Application No. PCT/AU2006/000035, filed Jan. 12, 2006, which claims the benefit of U.S. Provisional Application Nos. 60/726,265, filed Oct. 14, 2005, and 60/734,746, filed Nov. 9, 2005, each of which is incorporated herein by reference in its entirety.

FIELD OF THE INVENTION

The present invention relates to a method and apparatus for assembling a patient interface for use in treatment of sleep disordered breathing (SDB) such as obstructive sleep apnea (OSA). In particular, the present invention relates to a method and apparatus for securing a face-contacting portion of a patient interface, such as a cushion, to a frame or shell of the patient interface.

BACKGROUND OF THE INVENTION

Patient interfaces, such as a mask assembly, for use with blowers and flow generators in the treatment of sleep disordered breathing (SDB) typically include a soft-patient contacting portion, such as a cushion, and a rigid shell or frame. In use, the patient interface is held in a sealing position by headgear so as to enable a supply of air at positive pressure to be delivered to the patient's airways. When the cushion and frame are manufactured from different materials, they need to be held together in some way. It is also generally desirable that the patient interface be cleanable, for example, allowing a person to wash a mask between uses. While some semi-permanent assembly methods are available, they generally leave small gaps and crevices that can accumulate dirt and be difficult to clean. Hence, it is generally desirable that the frame and cushion include a mechanism that enables both assembly and disassembly. It is also desirable that there be a seal between the frame and cushion to reduce or eliminate leaks from the assembly in use. Since many patients lack dexterity, a good design is simple and easy to use for patients.

A number of cushion to frame assembly mechanisms are known. For example, see U.S. Pat. No. 6,412,487 to Gunaratnam, et al. and U.S. Pat. No. 6,823,869 to Raje et al. Also see ResMed's MIRAGE®, ULTRA MIRAGE®, ACTIVA®, and VISTA® masks.

A problem with existing assembly mechanisms includes difficulty with alignment and assembly, e.g., both putting the cushion onto the frame and putting the cushion clip into the sub-assembly. Another problem with existing assembly mechanisms includes difficulty with adhesive, e.g., gluing, that does not allow disassembly for cleaning. Yet another problem with existing assembly mechanisms includes over-moided parts that can still have points of ingress that cannot be easily cleaned, e.g., see Respironics' ComfortCurve mask. Still another problem with existing assembly mechanisms includes interference methods that can be difficult to use on large frames, e.g. full-face mask, and can have misalignment issues.

Thus, there is a need for an improved assembly mechanism that does not suffer from at least one of the above-mentioned drawbacks.

SUMMARY OF THE INVENTION

One aspect of the invention relates to a cushion to frame assembly mechanism structured to facilitate assembly and provide a compliant seal between the cushion and the frame.

Another aspect of the invention relates to a cushion to frame assembly mechanism that includes an angled lip or flap provided to the cushion interior wall that forms a seal against the frame.

Another aspect of the invention relates to a cushion to frame assembly mechanism that is integrated with the frame mating geometry.

Another aspect of the invention relates to a cushion to frame assembly mechanism that includes an overall wedge, taper, or angle in the slot of the frame that receives the cushion.

Another aspect of the invention relates to a cushion to frame assembly mechanism that includes a cushion clip.

Another aspect of the invention relates to a full-face mask assembly including a frame and a cushion provided to the frame. The cushion is adapted to form a seal around the patient's nose and mouth. A flexible lip is provided to an interior wall of the cushion. The flexible lip is adapted to engage the frame to provide a seal in use.

Another aspect of the invention relates to a full-face mask assembly including a frame and a cushion provided to the frame. The cushion is adapted to form a seal around the patient's nose and mouth. The frame includes a retaining recess that is adapted to receive a retaining portion provided to the cushion. The retaining recess has an angled configuration with respect to the frame.

Another aspect of the invention relates to a full-face mask assembly including a frame, a cushion provided to the frame, and a clip to maintain the cushion to the frame. The cushion is adapted to form a seal around the patient's nose and mouth.

Another aspect of the invention relates to a full-face mask assembly including a frame, a cushion provided to the frame, and a skeleton frame to maintain the cushion to the frame. The cushion is adapted to form a seal around the patient's nose and mouth. The skeleton frame includes at least one of an upper support member adapted to support a forehead support, lower headgear clip receptacles adapted to be engaged with clips provided to straps of a headgear assembly, and an annular elbow connection seal adapted to engage an inlet conduit.

Yet another aspect of the invention relates to a full-face mask assembly including a frame and a cushion provided to the frame. The cushion is adapted to form a seal around the patient's nose and mouth. The cushion includes hooks or tabs integrally formed therewith that are adapted to interlock with locking features integrally formed with the frame.

Yet another aspect of the invention relates to a full-face mask assembly including a frame and a cushion provided to the frame. The cushion is adapted to form a seal around the patient's nose and mouth. The frame includes outer and inner walls that define a retaining recess adapted to receive therein a retaining portion provided to the cushion. The retaining portion includes a flexible lip to engage the inner wall and provide a seal in use. The retaining portion includes a space behind the flexible lip to provide the flexible lip with a range of movement.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 67-71 are various views of the cushion clip of the mask assembly shown in FIG. 52 and showing exemplary dimensions of an embodiment;

DETAILED DESCRIPTION OF ILLUSTRATED EMBODIMENTS

The following includes descriptions of mask assemblies including cushion to frame assembly mechanisms according to several illustrated embodiments of the present invention. In each of the illustrated embodiments, the mask assembly includes a cushion that is adapted to be removably connected to a frame via a cushion to frame assembly mechanism.

The cushion to frame assembly mechanism provides an interface between the cushion and frame to facilitate assembly and disassembly. In addition, the cushion to frame assembly mechanism may be structured to provide a compliant seal between the cushion and frame and reduce or eliminate the risk of leakage.

In the illustrated embodiment, the cushion and frame form a part of a full-face mask. Specifically, the cushion provides a seal around the patient's nose and mouth to enable the delivery of breathable gas to the patient's nose and mouth. However, aspects of the present invention may be applicable to other breathing arrangements, e.g., a nasal mask, a mouth mask, etc. Also, each illustrated embodiment includes features that may be used with and/or in the other illustrated embodiments, as would be apparent to those of ordinary skill in the art.

1. First Embodiment of Cushion to Frame Assembly Mechanism

Figure 1:
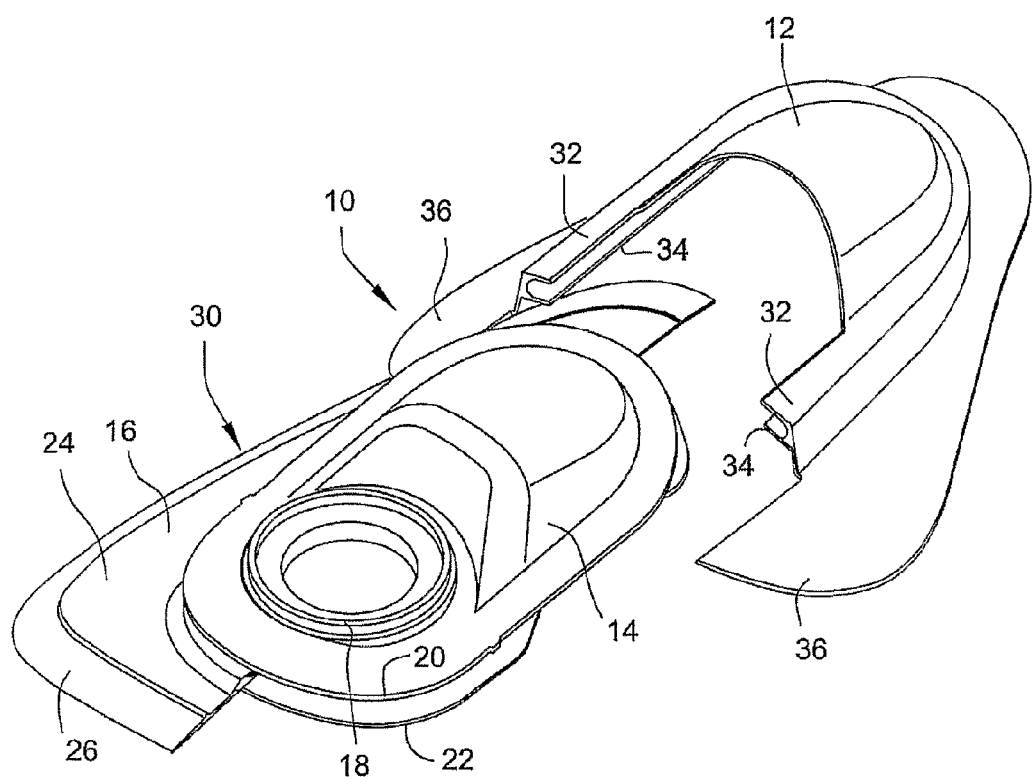
FIG. 1 is a top perspective view of a mask assembly including a, cushion to frame assembly mechanism according to an embodiment of the present invention, the mask assembly in a pre-assembled condition.
Figure 2:
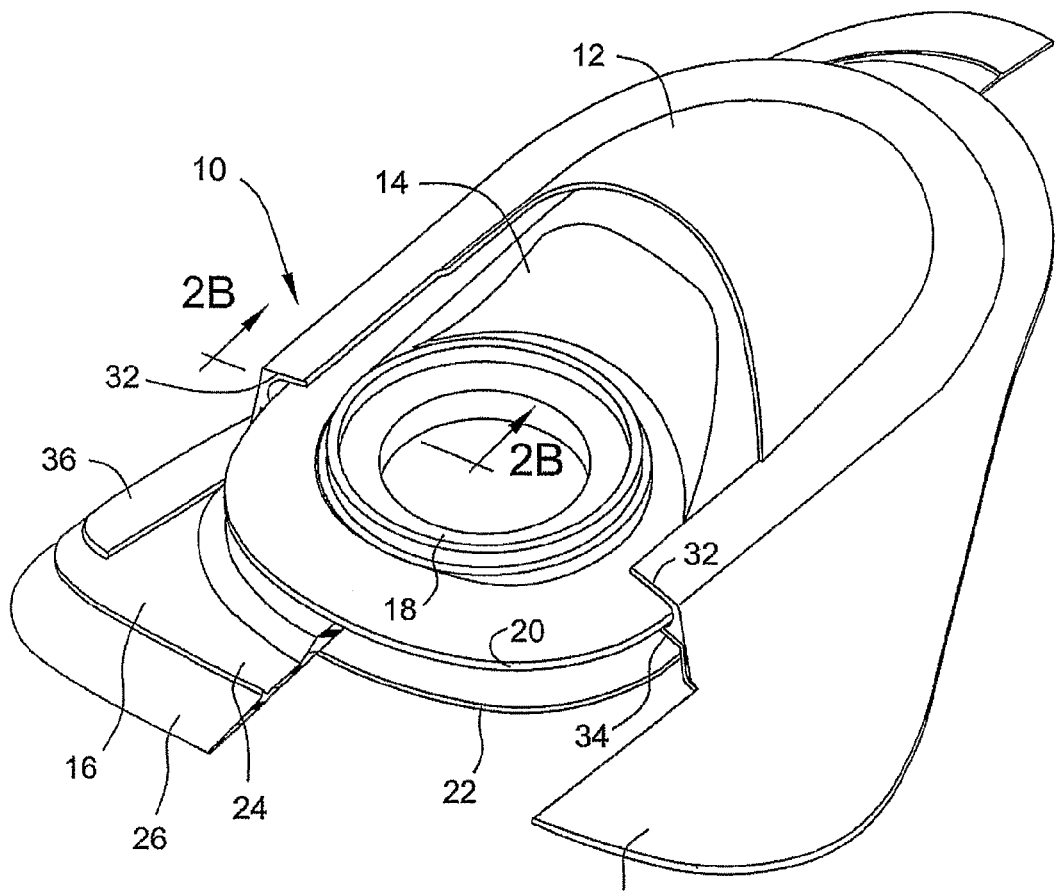
FIG. 2 is a top perspective view of the mask assembly shown in FIG. 1, the mask assembly in an assembled condition.
Figure 2B:
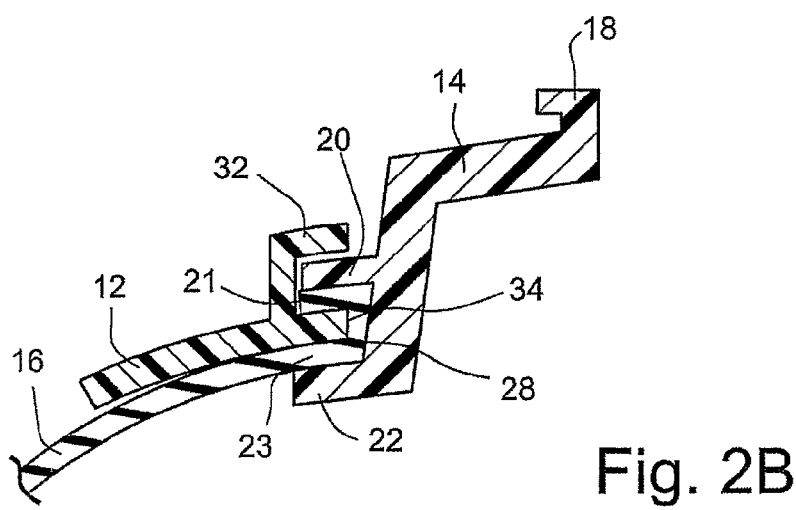
FIG. 2B is a cross-sectional view through line 2B-2B in FIG. 2.

FIGS. 1 2, and 2B illustrate a mask assembly 10 including a cushion to frame assembly mechanism according to an embodiment of the present invention. In the illustrated embodiment, the cushion to frame assembly mechanism includes a slide-on frame clip 12 that is adapted to removably connect the frame 14 to the cushion 16.

Specifically, the frame 14 includes a main body that provides an opening 18 for communicating with an inlet conduit. At least a portion of the frame perimeter includes spaced apart upper and lower retaining wall portions 20, 22. The cushion 16 (only half being shown) includes a cushion wall 24 and a face-contacting portion 26, e.g., membrane. The cushion wall 24 includes a central opening with upper and lower walls 21, 23 that define an inner edge 28 (see FIG. 2B). As shown in FIG. 1, the frame 14 is received within the central opening of the cushion 16 so that the inner edge 28 of the cushion 16 is received between the upper and lower retaining wall portions 20, 22 of the frame 14. This partially secures the cushion 16 to the frame 14 to provide a cushion/frame sub-assembly 30. A slide-on frame clip 12 is engaged with the sub-assembly 30 to maintain engagement between the frame 14 and cushion 16.

As illustrated, the frame clip 12 has a U-shaped configuration that provides upper and lower retaining wall portions 32, 34. The frame clip 12 is slid onto the sub-assembly 30 such that the upper and lower retaining wall portions 32, 34 straddle the upper wall portion 20 of the frame 14. In addition, the lower wall portion 34 of the frame clip 12 sandwiches the U-shaped recess formed by the upper and lower walls 21, 23 of the inner edge 28 of the cushion 16 against the corresponding U-shaped configuration formed by the upper wall portion 20 and lower wall portion 22 of the frame 14 (see FIG. 2B). This arrangement provides a compressive force into the cushion 16 (in the direction of the arrow shown in FIG. 2B). Further, as shown in FIG. 2, the frame clip 12 provides support wings 36 that support the cushion wall 24 in use.

In an embodiment, the frame 14 and frame clip 12 may be constructed of polycarbonate and the cushion 16 may be constructed of liquid silicone rubber (LSR). However, other suitable materials may be used.

In an embodiment, the frame 14 could potentially be overmolded with cushion 16, thereby negating the need for frame clip 12.

2. Second Embodiment of Cushion to Frame Assembly Mechanism

Figure 3:
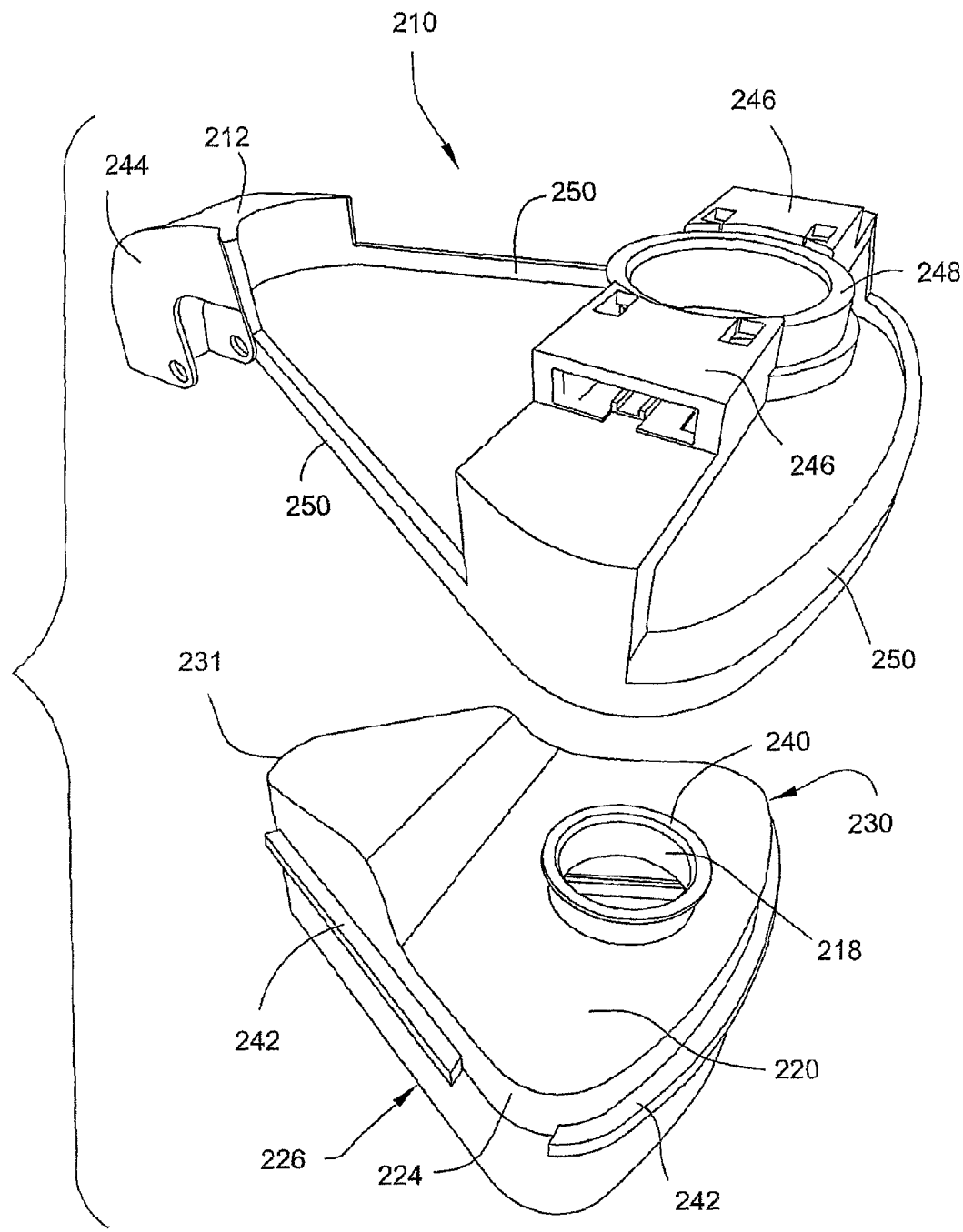
FIG. 3 is a top perspective view of a mask assembly including a cushion to frame assembly mechanism according to another embodiment of the present invention, the mask assembly in a pre-assembled condition.
Figure 4:
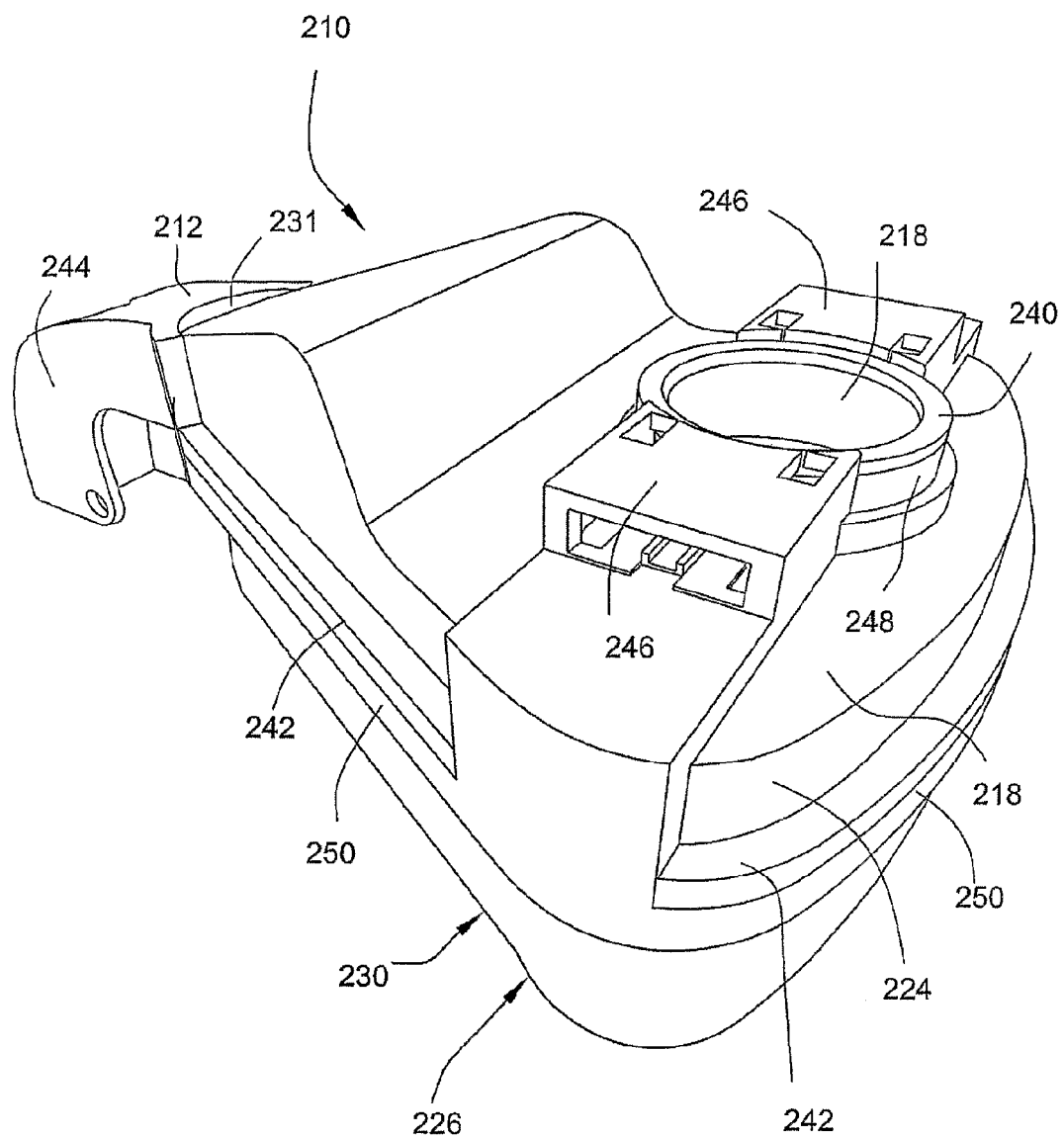
FIG. 4 is a top perspective view of the mask assembly shown in FIG. 3, the mask assembly in an assembled condition.

FIGS. 3 and 4 illustrate a mask assembly 210 including a cushion to frame assembly mechanism according to another embodiment of the present invention. In the illustrated embodiment, the cushion to frame assembly mechanism includes a skeleton frame 212 that is adapted to removably interlock with a cushion/frame sub-assembly 230.

Specifically, a frame and a cushion are integrally molded in one-piece to provide a cushion/frame sub-assembly 230. In an embodiment, the cushion/frame sub-assembly 230 may be constructed of liquid silicone rubber (LSR). However, other suitable materials may be used.

The cushion/frame sub-assembly 230 includes an upper wall 220 that provides an opening 218 for communicating with an inlet conduit. An annular wall 240 surrounds the opening 218. A side wall 224 extends from the upper wall 220 and leads to a face contacting portion 226. In an embodiment, the face contacting portion 226 has a double wall construction, e.g., membrane and underlying support cushion. The side wall 224 includes elongated protrusions 242 that extend around the perimeter of the cushion/frame sub-assembly 230. In the illustrated embodiment, the side wall 224 includes three spaced apart elongated protrusions 242 (only two being visible). However, the side wall 224 may include one continuous protrusion, or any suitable number of spaced apart protrusions.

The skeleton frame 212 includes an upper support member 244 adapted to support a forehead support, lower headgear clip receptacles 246 adapted to be engaged with clips provided to straps of a headgear assembly (not shown), and an annular elbow connection seal 248 adapted to engage an inlet conduit, e.g., elbow. The upper support member 244 and clip receptacles 246 are interconnected via elongated frame members 250. In the illustrated embodiment, the skeleton frame 212 is formed of plastic and has an integral one-piece construction.

As shown in FIG. 4, the skeleton frame 212 is engaged with the cushion/frame sub-assembly 230 such that the annular elbow connection seal 248 interlocks with the annular wall 240 of the cushion/frame sub-assembly 230, the upper support member 244 interlocks or is frictionally engaged with a top portion 231 of the cushion/frame sub-assembly 230, and the elongated frame members 250 interlock with respective protrusions 242 provided around the perimeter of the cushion/frame sub-assembly 230. The skeleton frame 212 adds rigidity to the cushion/frame sub-assembly 230 and provides attachment points for a forehead support, a headgear assembly, and an inlet conduit.

Figure 5:
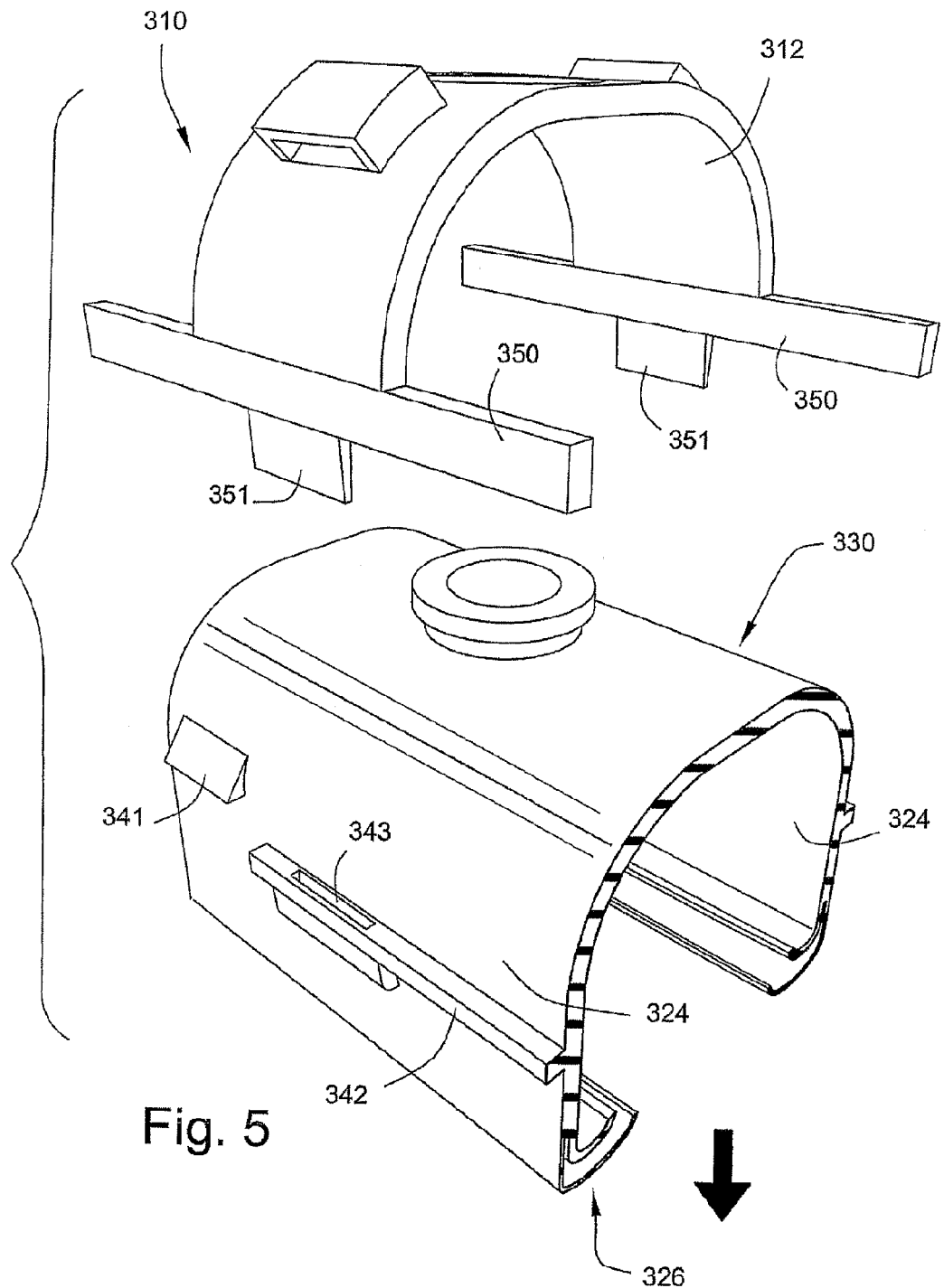
FIG. 5 is a top perspective view of a mask assembly including a cushion to frame assembly mechanism according to another embodiment of the present invention, the mask assembly in a pre-assembled condition.

FIG. 5 illustrates a mask assembly 310 including a cushion to frame assembly mechanism according to another embodiment of the present invention. Similar to the above embodiment, the cushion to frame assembly mechanism includes a skeleton frame 312 that is adapted to removably interlock with a one-piece integrally molded cushion/frame sub-assembly 330.

As illustrated, each side wall 324 of the cushion/frame sub-assembly 330 includes a protrusion 341 and an elongated extension 342 that provides a slot 343. The skeleton frame 312 includes elongated frame members 350 that each include a tab 351. The skeleton frame 312 is engaged with the cushion/frame sub-assembly 330 such that the tabs 351 are received within respective slots 343 of the cushion/frame sub-assembly 330, and the elongated frame members 350 interlock with respective protrusions 341 provided on the perimeter of the cushion/frame sub-assembly 330. When interlocked, the tabs 351 provide support to the face contacting portion 326, e.g., membrane and underlying support cushion, of the cushion 316.

Also, the skeleton frame 312 and/or cushion/frame sub-assembly 330 is designed such that the tool core is along a single line of draw (indicated by the arrow).

In an embodiment, the cushion/frame sub-assembly 230, 330 could potentially be over-molded with the skeleton frame 212, 312.

3. Third Embodiment of Cushion to Frame Assembly Mechanism

Figure 6:
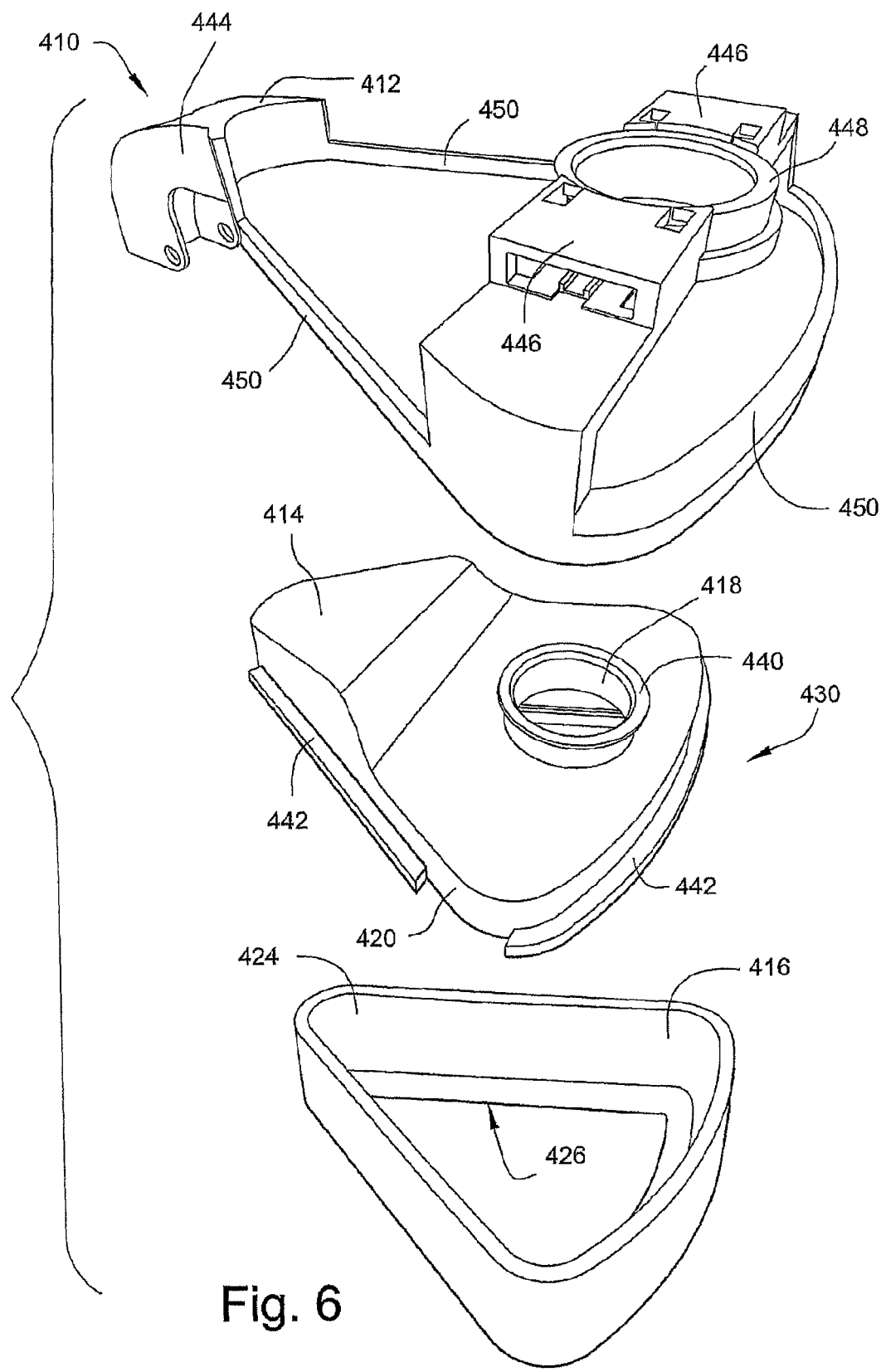
FIG. 6 is a top perspective view of a mask assembly including a cushion to frame assembly mechanism according to another embodiment of the present invention, the mask assembly in a pre-assembled condition.
Figure 7:
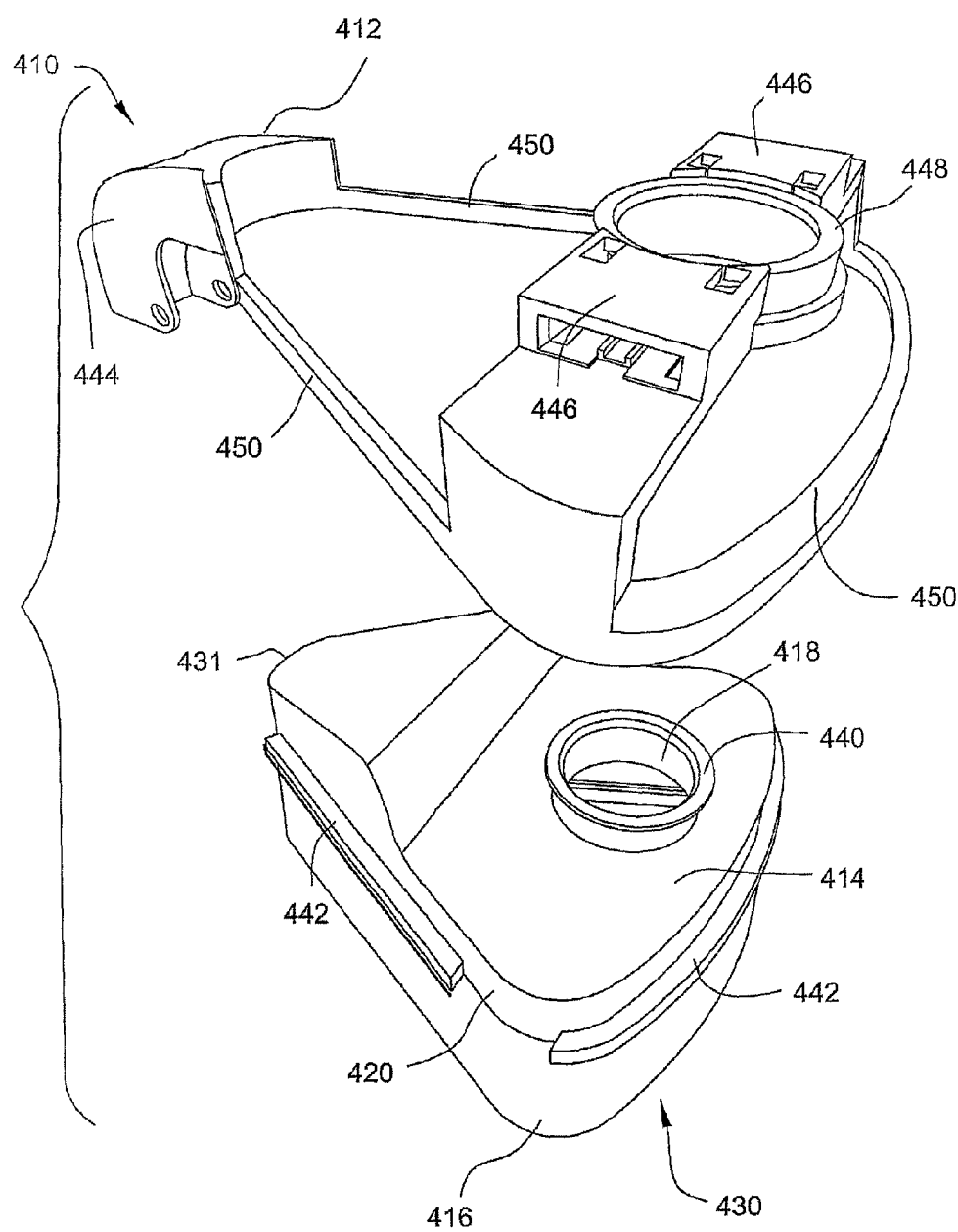
FIG. 7 is a top perspective view of the mask assembly shown in FIG. 6, the mask assembly in a partial assembled condition.
Figure 8:
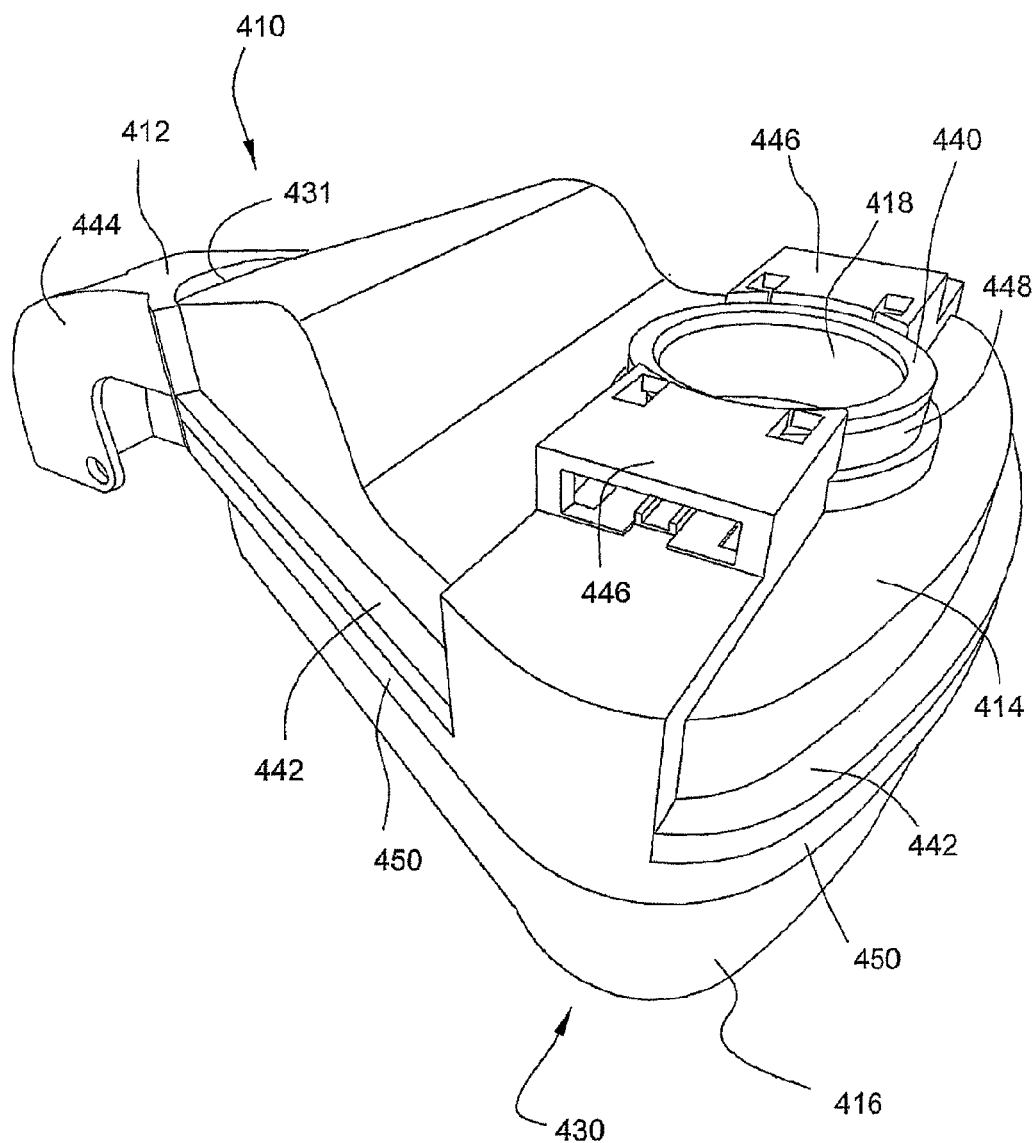
FIG. 8 is a top perspective view of the mask assembly shown in FIG. 6, the mask assembly in an assembled condition.

FIGS. 6-8 illustrate a mask assembly 410 including a cushion to frame assembly mechanism according to another embodiment of the present invention. In the illustrated embodiment, the cushion to frame assembly mechanism includes a skeleton frame 412 that is adapted to removably interlock with a cushion/frame sub-assembly 430.

Specifically, a frame 414 and a cushion 416 are formed separately from one another and then interlocked to provide a cushion/frame sub-assembly 430. As shown in FIG. 6, the cushion 416 includes a side wall 424 and a face contacting portion 426 extending from the side wall 424. In an embodiment, the face contacting portion 426 has a double wall construction, e.g., membrane and underlying support cushion. Also, in an embodiment, the cushion 416 is constructed of liquid silicone rubber (LSR). However, other suitable materials may be used.

The frame 414 includes an upper wall that provides an opening 418 for communicating with an inlet conduit. An annular wall 440 surrounds the opening 418. A side wall 420 extends from the upper wall and includes elongated protrusions 442 that extend around the perimeter thereof. In the illustrated embodiment, the side wall 420 includes three spaced apart elongated protrusions 442 (only two being visible). However, the side wall 420 may include one continuous protrusion, or any suitable number of spaced apart protrusions. In an embodiment, the frame 414 is constructed of polycarbonate.

As shown in FIG. 7, the cushion 416 is interlocked with the frame 414 to provide the cushion/frame sub-assembly 430. The cushion 416 may be interlocked with the frame 414 in any suitable manner, e.g., mechanical interlock, etc.

As best shown in FIGS. 6 and 7, the skeleton frame 412 includes an upper support member 444 adapted to support a forehead support, lower headgear clip receptacles 446 adapted to be engaged with clips provided to straps of a headgear assembly (not shown), and an annular elbow connection seal 448 adapted to engage an inlet conduit, e.g., elbow. The upper support member 444 and clip receptacles 446 are interconnected via elongated frame members 450. In the illustrated embodiment, the skeleton frame 412 is formed of plastic and has, an integral one-piece construction.

As shown in FIG. 8, the skeleton frame 412 is engaged with the cushion/frame sub-assembly 430 such that the annular elbow connection seal 448 interlocks with the annular wall 440 of the cushion/frame sub-assembly 430, the upper support member 444 interlocks with a top portion 431 of the cushion/frame sub-assembly 430, and the elongated frame members 450 interlock with respective protrusions 442 provided around the perimeter of the cushion/frame sub-assembly 430. The skeleton frame 412 adds rigidity to the cushion/frame sub-assembly 430 and provides attachment points for a forehead support, a headgear assembly, and an inlet conduit.

Figure 9:
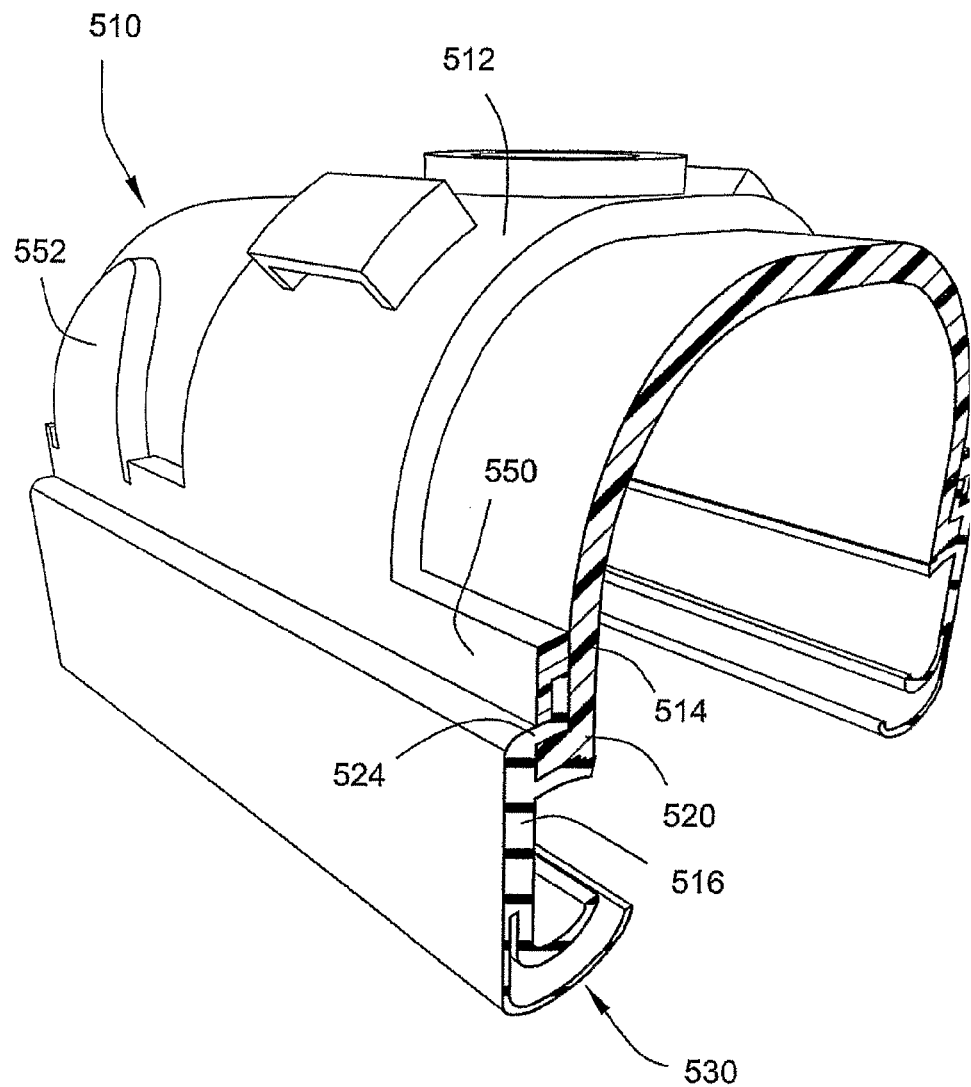
FIG. 9 is a side perspective view of a mask assembly including a cushion to frame assembly mechanism according to another embodiment of the present invention, the mask assembly in an assembled condition.

FIG. 9 illustrates a mask assembly 510 including a cushion to frame assembly mechanism according to another embodiment of the present invention. Similar to the above embodiment, the cushion to frame assembly mechanism includes a skeleton frame 512 that is adapted to removably interlock with a separately formed and interlocked cushion/frame sub-assembly 530.

The skeleton frame 512 is interlocked with the cushion/frame sub-assembly 530 via snap-fit clips 552. As illustrated, when the skeleton frame 512 is interlocked with the cushion/frame sub-assembly 530, the elongated frame members 550 of the skeleton frame 512 trap the cushion 516 to the frame 514. That is, the skeleton frame 512 and the frame side wall 520 sandwich the cushion side wall 524 to secure the cushion 516 to the frame 514.

In an embodiment, the frame 414 could potentially be over-molded with the cushion 416. Also, the cushion/frame sub-assembly 430, 530 could potentially be over-molded with the skeleton frame 412, 512.

4. Fourth Embodiment of Cushion to Frame Assembly Mechanism

Figure 10:
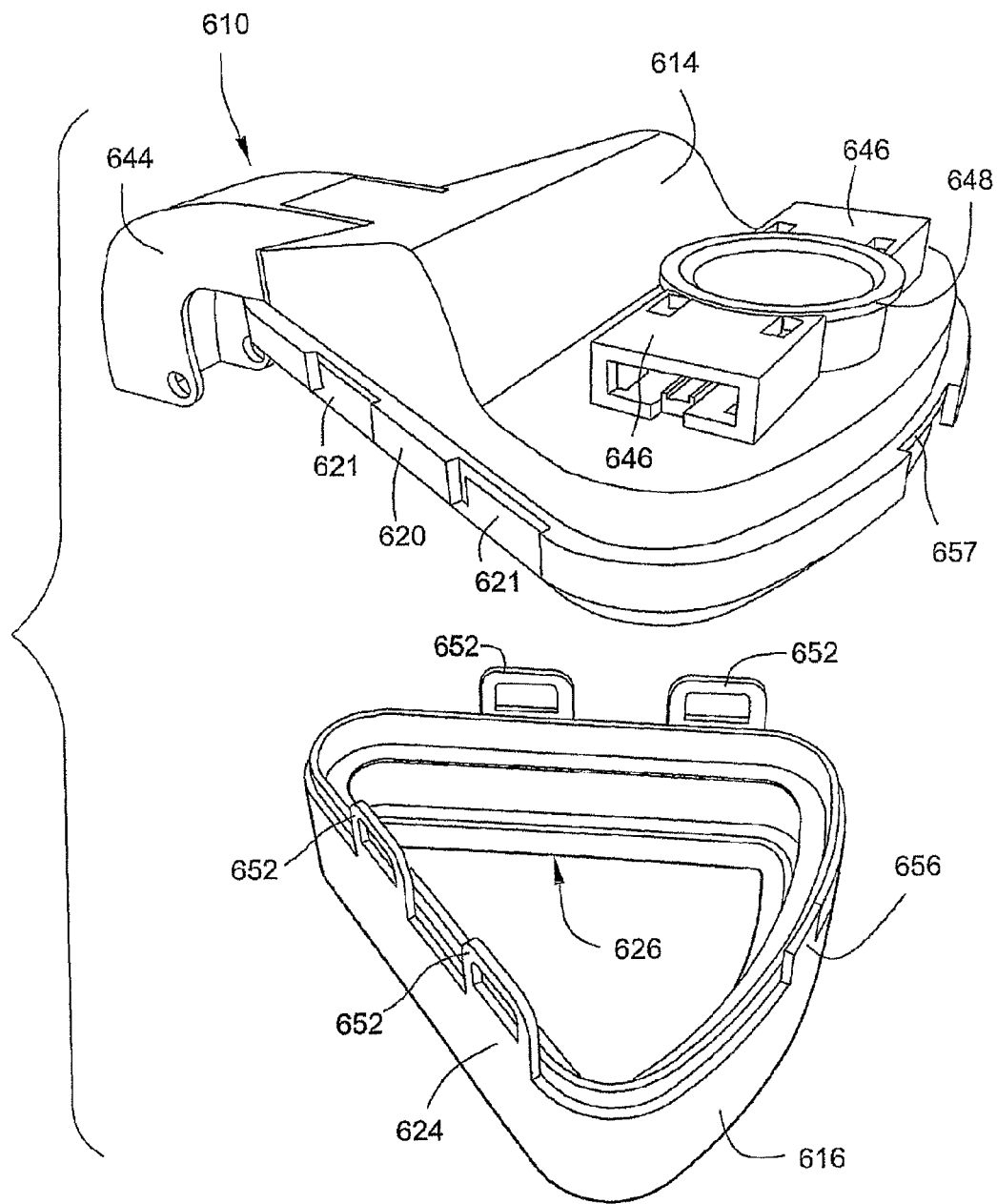
FIG. 10 is a top perspective view of a mask assembly including a cushion to frame assembly mechanism according to another embodiment of the present invention, the mask assembly in a pre-assembled condition.
Figure 11:
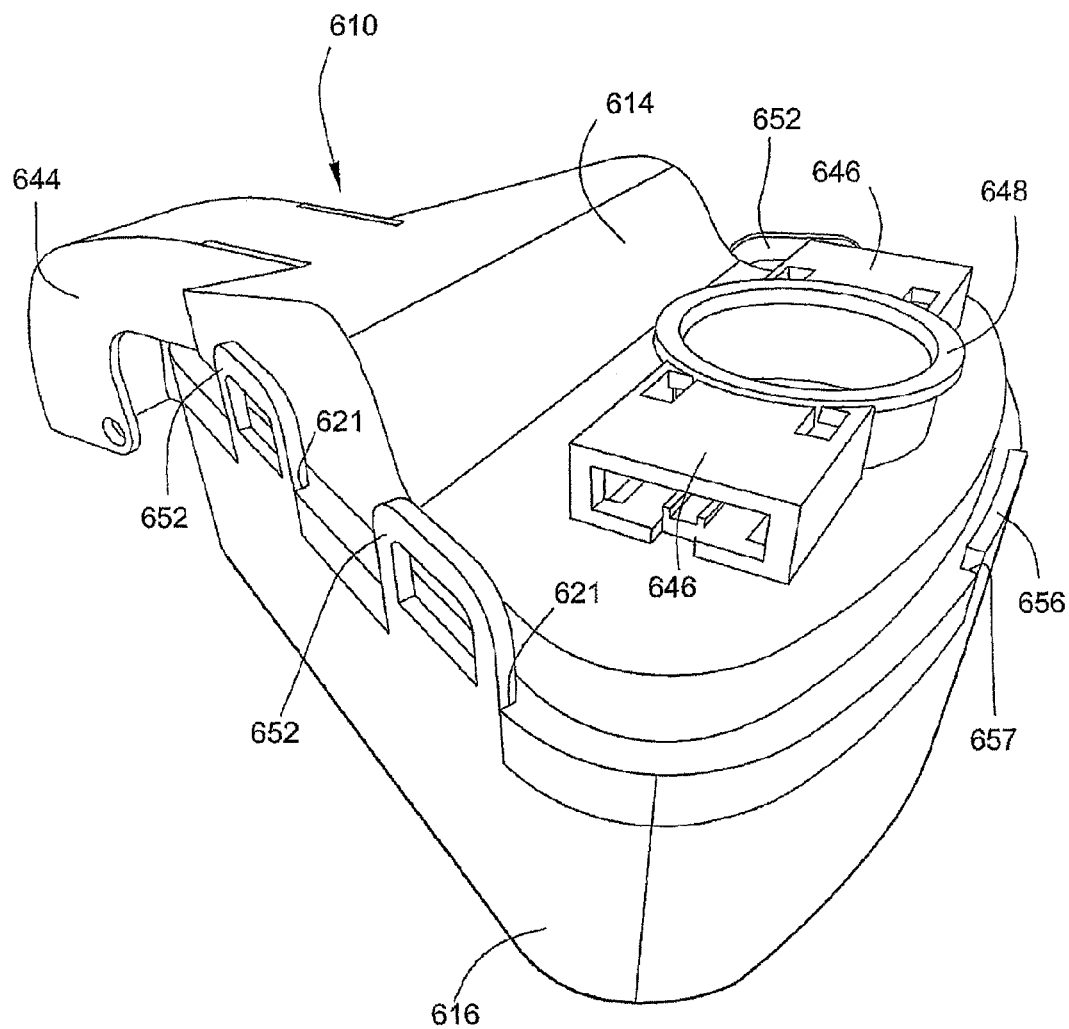
FIG. 11 is a top perspective view of the mask assembly shown in FIG. 10, the mask assembly in an assembled condition.

FIGS. 10-11 illustrate a mask assembly 610 including a cushion to frame assembly mechanism according to another embodiment of the present invention. In the illustrated embodiment, the cushion to frame assembly mechanism includes a cushion 616 with integrally molded hooks 652 that are adapted to removably interlock and/or engage with features molded onto the frame 614.

As shown in FIG. 10, the cushion 616 includes a side wall 624 and a face contacting portion 626 extending from the side wall 624. In an embodiment, the face contacting portion 626 has a double wall construction, e.g., membrane and underlying support cushion. Also, in an embodiment, the cushion 626 is constructed of liquid silicone rubber (LSR). However, other suitable materials may be used. As illustrated, interlocking members in the form of hooks 652 protrude from the side walls 624. In the illustrated embodiment, four hooks 652 are provided. However, the cushion 616 may include any suitable number of hooks 652.

The frame 614 includes an upper support member 644 adapted to support a forehead support, lower headgear clip receptacles 646 adapted to be engaged with clips provided to straps of a headgear assembly (not shown), and an annular elbow connection seal 648 adapted to engage an inlet conduit, e.g., elbow. Also, the frame side wall 620 includes a series of recesses 621 around the perimeter thereof. In the illustrated embodiment, the side wall 620 includes the same number of recesses 621 as hooks 652 on the cushion 616, e.g., four. In an embodiment, the frame 614 is molded in one-piece with polycarbonate and the recesses 651 are integrally molded into the frame 614.

As shown in FIG. 11, the cushion 616 is engaged with the frame 614 such that the hooks 652 interlock with respective recesses 621 provided around the perimeter of the frame 614, e.g., with a friction fit. In an embodiment, each recess 621 may provide a projection adapted to extend through a respective hook 652 to facilitate attachment of the cushion 616. Further, the cushion 616 includes an additional projection 656 that engages with an additional recess 657 provided on the frame 614. The additional projection 656/recess 657 may facilitate alignment and/or interlocking engagement between the cushion 616 and the frame 614.

Figure 12:
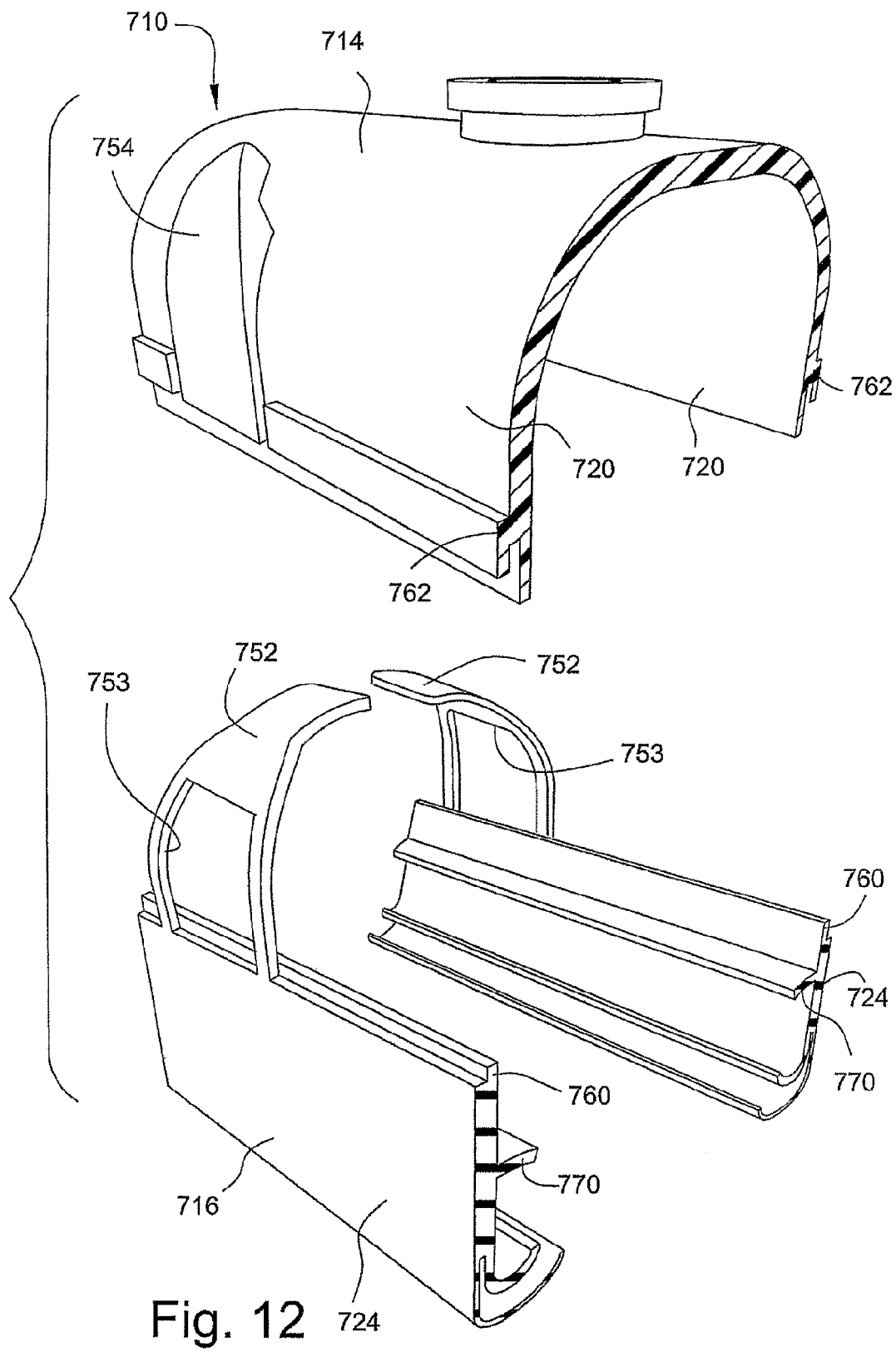
FIG. 12 is a side perspective view of a mask assembly including a cushion to frame assembly mechanism according to another embodiment of the present invention, the mask assembly in a pre-assembled condition.
Figure 13:
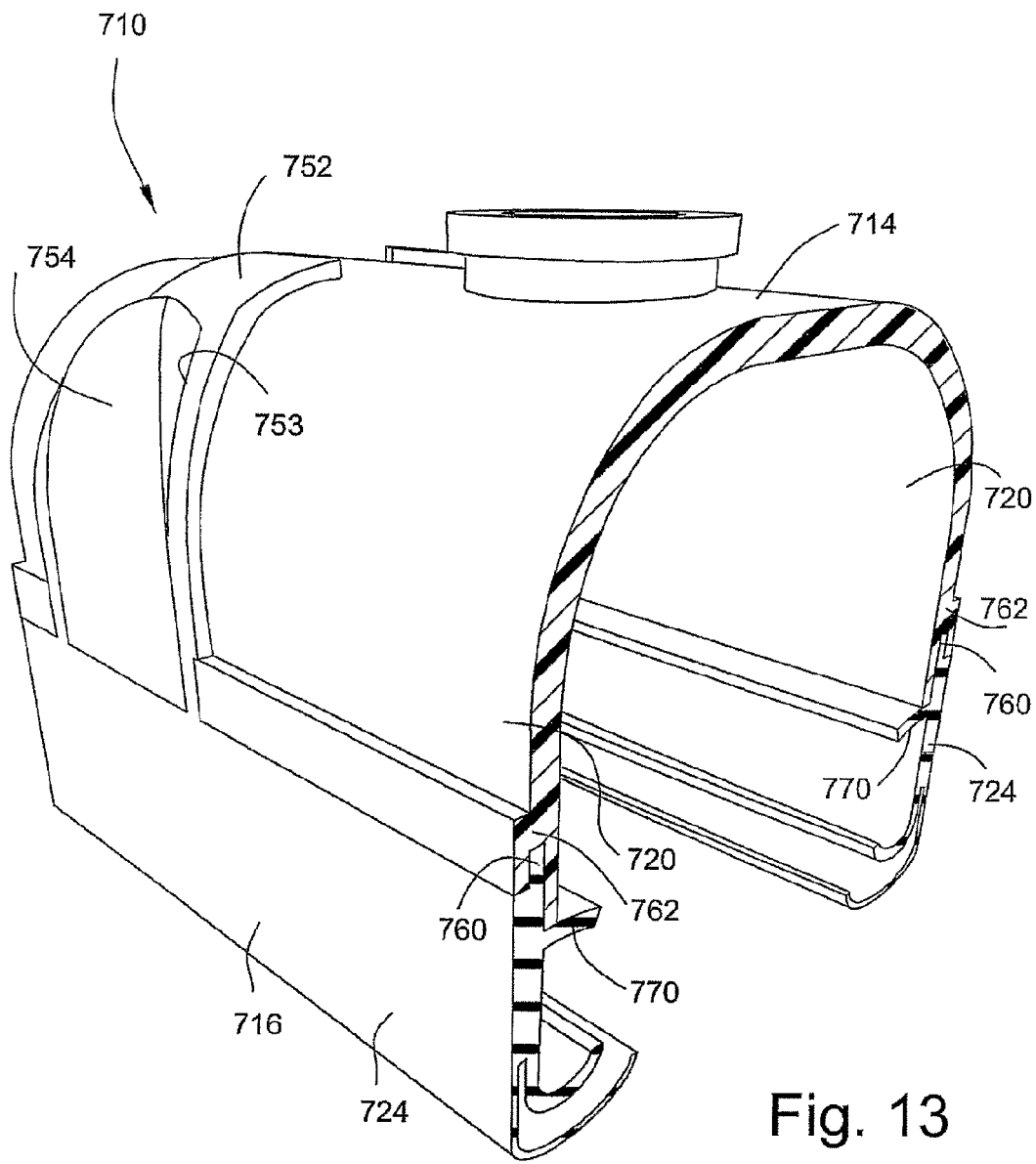
FIG. 13 is a side perspective view of the mask assembly shown in FIG. 12, the mask assembly in an assembled condition.

FIGS. 12 and 13 illustrate a mask assembly 710 including a cushion to frame assembly mechanism according to another embodiment of the present invention. Similar to the above embodiment, the cushion to frame assembly mechanism includes a cushion 716 with integrally molded tabs 752 that are adapted to removably interlock with locking features molded onto the frame 714.

As illustrated, each side wall 724 of the cushion 716 includes a protruding tab 752 that defines an opening 753. In addition, each side wall 724 includes a first locking member 760 that extends along the length thereof. The frame 714 includes a protrusion 754 on opposite side walls 720 thereof. In addition, the side walls 720 each include a second locking member 762 that extends along the length thereof.

As shown in FIG. 13, the cushion 716 is engaged with the frame 714 such that the tabs 752 interlock with respective protrusions 754 provided on the frame 714. Specifically, the tabs 752 are pulled over respective protrusions 754 until the protrusions 754 protrude through respective openings 753 in the tabs 752. In addition, the first locking member 760 interlocks with the second locking member 762 to further secure the cushion 716 to the frame 714 and provide a seal. As illustrated, the first locking member 760 includes an elongated resiliently flexible lip 770 is adapted to engage the lower edge of the frame 714. The lip 770 is resiliently flexible so that it provides a pressure assisted seal in use.

In an embodiment, the frame 614 could potentially be over-molded with the cushion 616, thereby negating the need for frame recesses 621 and respective cushion hooks 652. Also, the frame 714 could potentially be over-molded with the cushion 716, thereby negating the need for frame protrusions 754 and respective cushion protruding tabs 752.

5. Fifth Embodiment of Cushion to Frame Assembly Mechanism

FIGS. 14-17 illustrate a mask assembly 810 including a cushion to frame assembly mechanism according to another embodiment of the present invention. In the illustrated embodiment, the cushion to frame assembly mechanism includes a frame clip 812 and fold-over clips 852 that are adapted to removably connect the frame 814 to the cushion 816.

Figure 14:
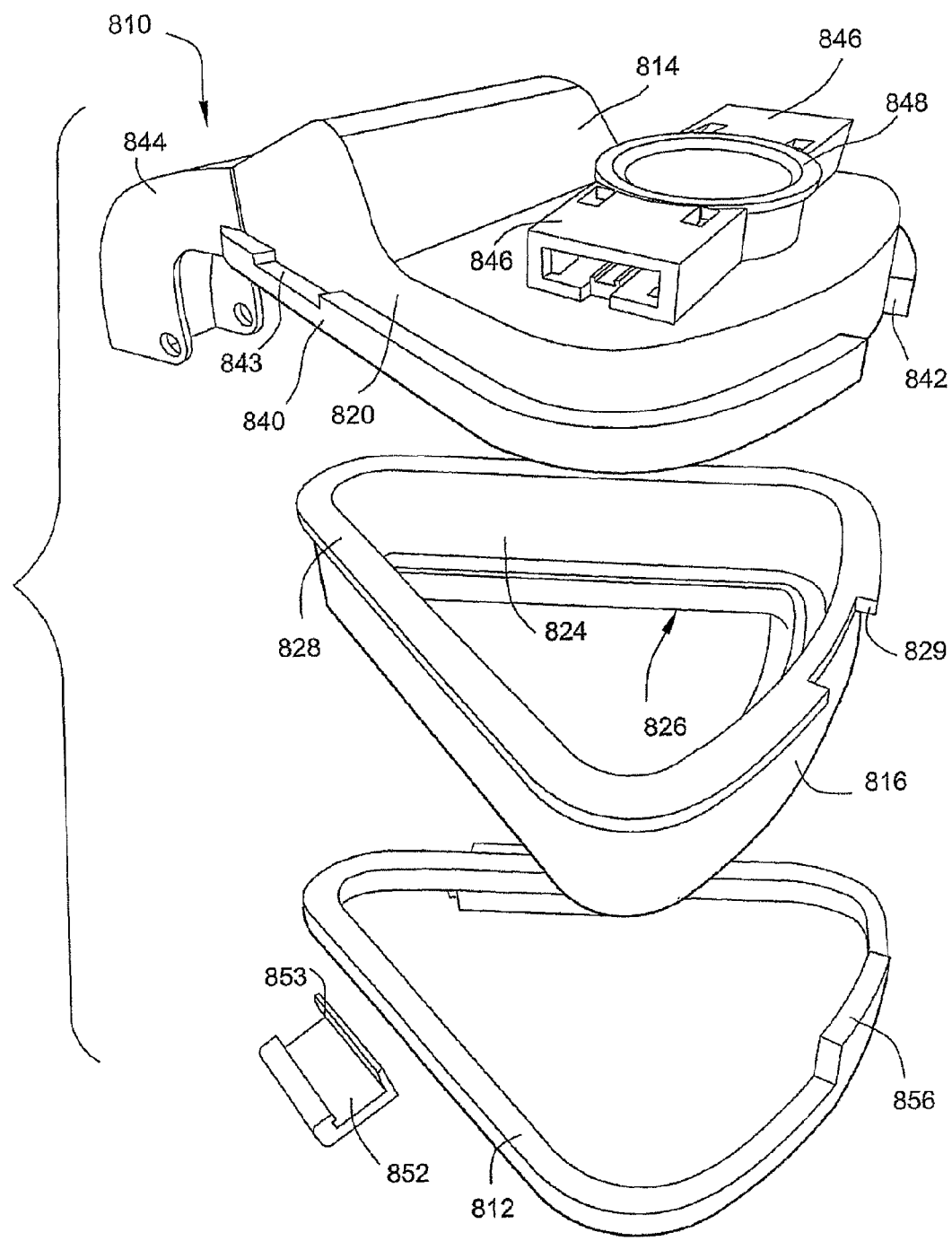
FIG. 14 is a top perspective view of a mask assembly including a cushion to frame assembly mechanism according to another embodiment of the present invention, the mask assembly in a pre-assembled condition.

As shown in FIG. 14, the cushion 816 includes a side wall 824 and a face contacting portion 826 extending from the side wall 824. In an embodiment, the face contacting portion 826 has a double wall construction, e.g., membrane and underlying support cushion. Also, in an embodiment, the cushion 816 is constructed of liquid silicone rubber (LSR). However, other suitable materials may be used. As illustrated, a flange 828 protrudes outwardly from the side wall 824 around the perimeter thereof. A recess 829 is provided in a portion of the flange 828.

The frame 814 includes an upper support member 844 adapted to support a forehead support, lower headgear clip receptacles 846 (FIG. 16) adapted to be engaged with clips provided to straps of a headgear assembly (not shown), and an annular elbow connection seal 848 adapted to engage an inlet conduit, e.g., elbow. Also, the frame side wall 820 includes a flange 840 around a portion of the perimeter thereof. A recess 842 is provided in a portion of the flange 840. Further, latching features 843, e.g., two recessed portions, are provided on the flange 840. In an embodiment, the frame 814 is molded in one-piece with polycarbonate and the latching features 843 are integrally molded into the frame 814.

The frame clip 812, e.g., molded of plastic, has a hoop-like configuration that generally corresponds in shape to the cushion 816 and frame 814, e.g., generally triangular. A projection 856 is provided in a portion of the frame clip 812.

Fold-over clips 852, e.g., molded of plastic, are provided to interconnect the frame clip 812, cushion 816, and frame 814. The fold-over clips 852 may be molded separately from the frame clip 812 and then assembled thereto. Alternatively, the fold-over clips 852 may be integrally molded onto the frame clip 812. As illustrated, two fold-over clips 852 are provided. However, other suitable numbers of fold-over clips may be used, e.g., more than two, to interconnect the frame clip 812, cushion 816, and frame 814.

Figure 15:
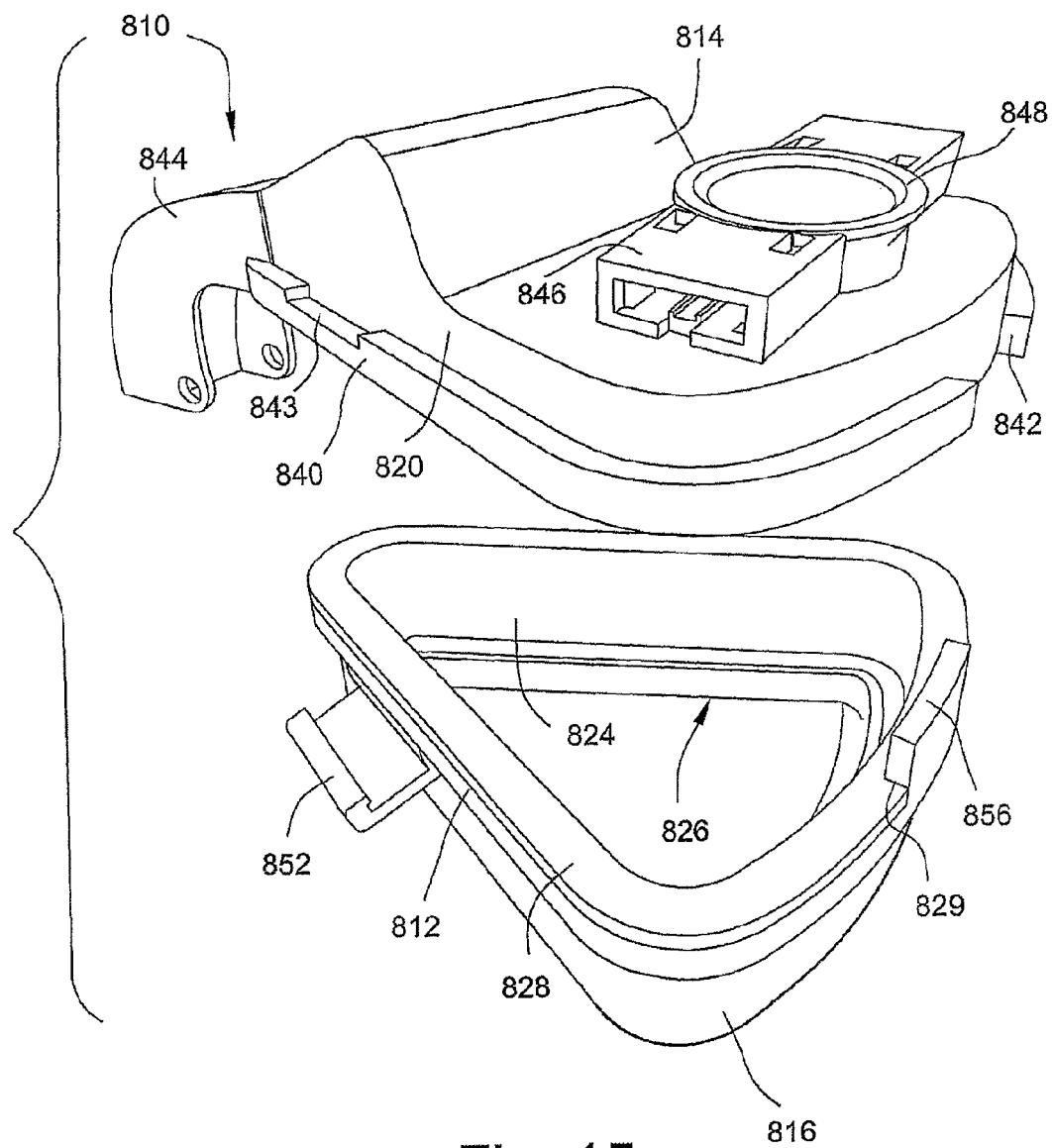
FIG. 15 is a top perspective view of the mask assembly shown in FIG. 14, the mask assembly in a first partial assembled condition.

As shown in FIG. 15, the frame clip 812 is engaged with the cushion 816 so that it extends around the cushion perimeter and abuts the flange 828. In addition, the projection 856 of the frame clip 812 extends through the recess 829 to facilitate alignment. Further, the fold-over clips 852 (if formed separately from the frame clip 812) each include a first latching end 853 (see FIG. 14) that is adapted to engage the frame clip 812 at a position that will align with a respective latching feature 843 of the frame 814.

Figure 16:
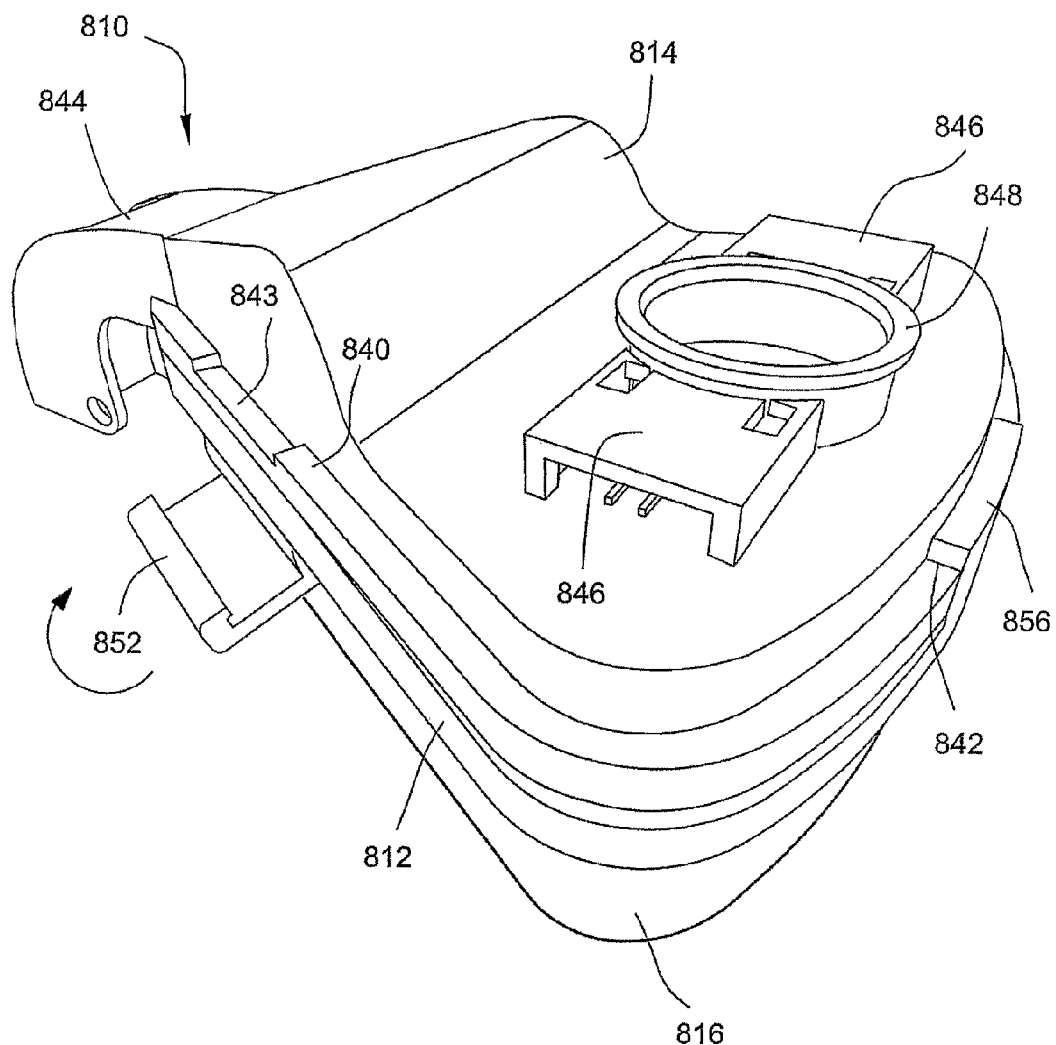
FIG. 16 is a top perspective view of the mask assembly shown in FIG. 14, the mask assembly in a second partial assembled condition.
Figure 17:
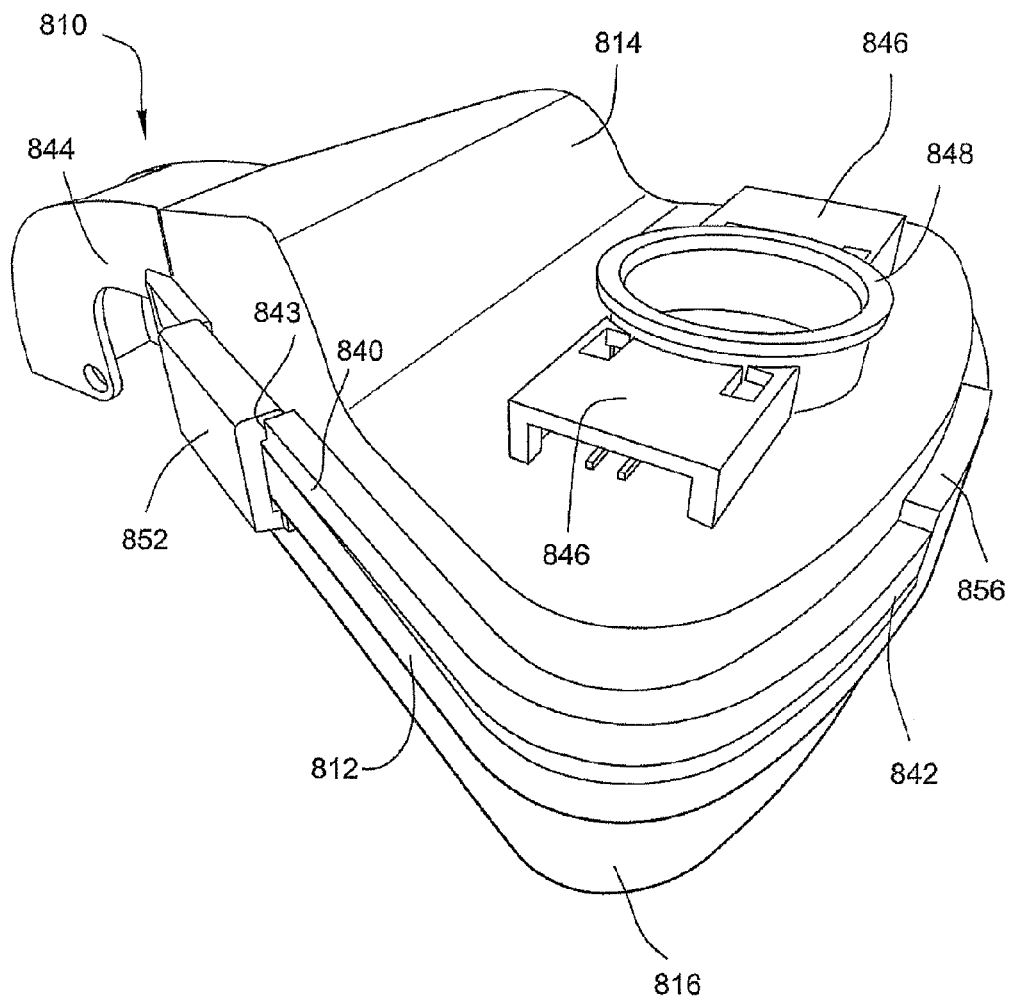
FIG. 17 is a top perspective view of the mask assembly shown in FIG. 14, the mask assembly in an assembled condition.

As shown in FIG. 16, the frame 814 is engaged with the cushion 816/frame clip 812/fold-over clip 852 sub-assembly such that the projection 856 of the frame clip 812 extends through the recess 842 in the frame 814. Then, the fold-over clips 852 are folded over so that they engage or latch onto respective latching features 843 provided on the frame 814. FIG. 17 illustrates the assembled mask assembly 810.

In the illustrated embodiment, the frame clip 812 is assembled from the bottom, e.g., cushion side, and the fold-over clips 852 latch onto latching features 843 molded onto the frame 814. In another embodiment, the frame clip 812 may be assembled from the top, e.g., frame side, and the fold-over clips 852 may latch onto latching features molded onto the cushion 816.

As described above, the cushion 816 may include a resiliently flexible lip that is adapted to engage the frame 814 to provide a pressure assisted seal in use.

In an embodiment, the frame clip 812 may be over-molded with the cushion 816. In another embodiment, the fold-over clips 852 may be integrally molded with the frame 814 (inverse configuration from that shown, i.e., the fold-over clips 852 would latch onto the cushion 816).

6. Sixth Embodiment of Cushion to Frame Assembly Mechanism

Figure 18:
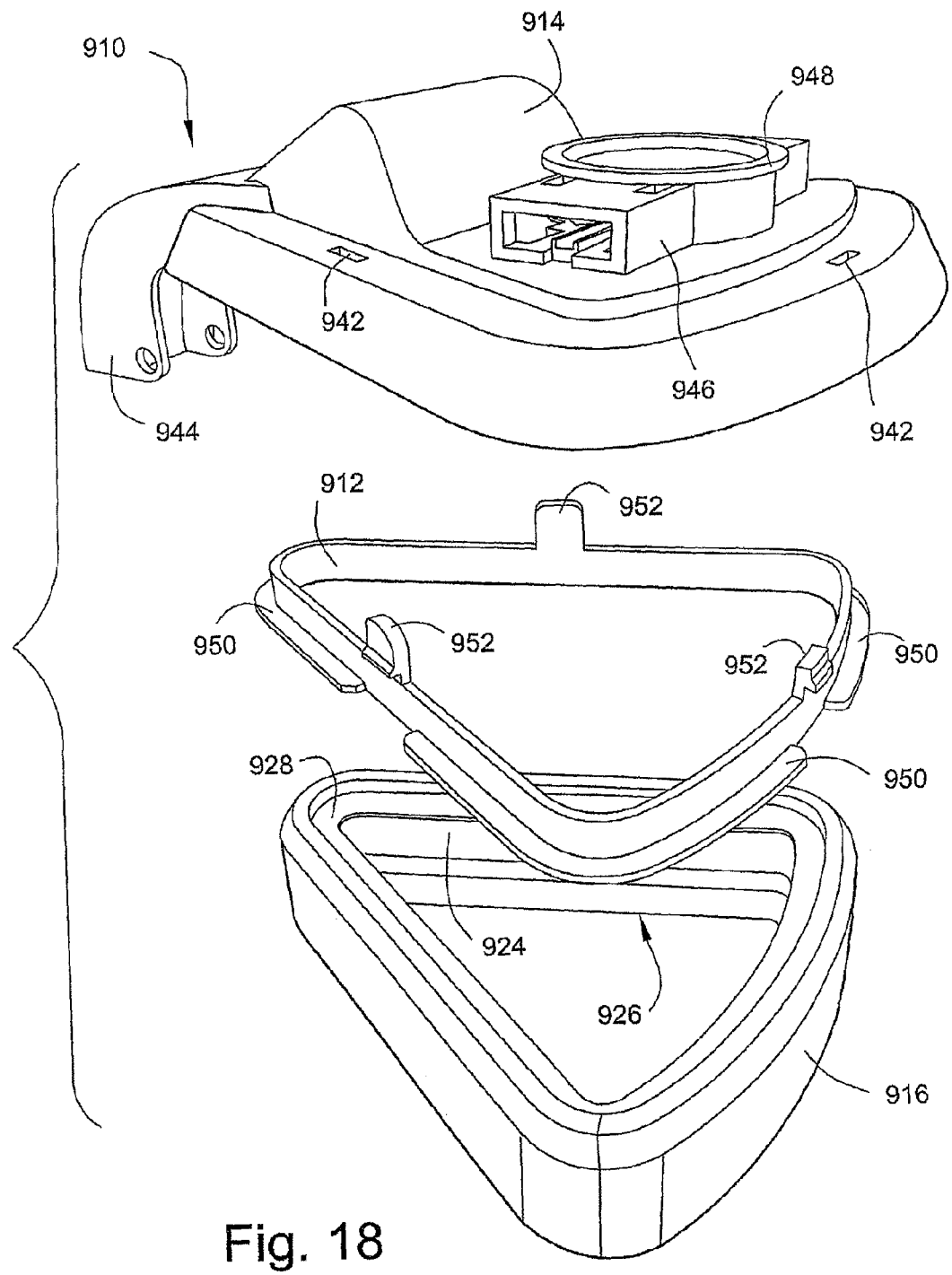
FIG. 18 is a top perspective view of a mask assembly including a cushion to frame assembly mechanism according to another embodiment of the present invention, the mask assembly in a pre-assembled condition.
Figure 19:
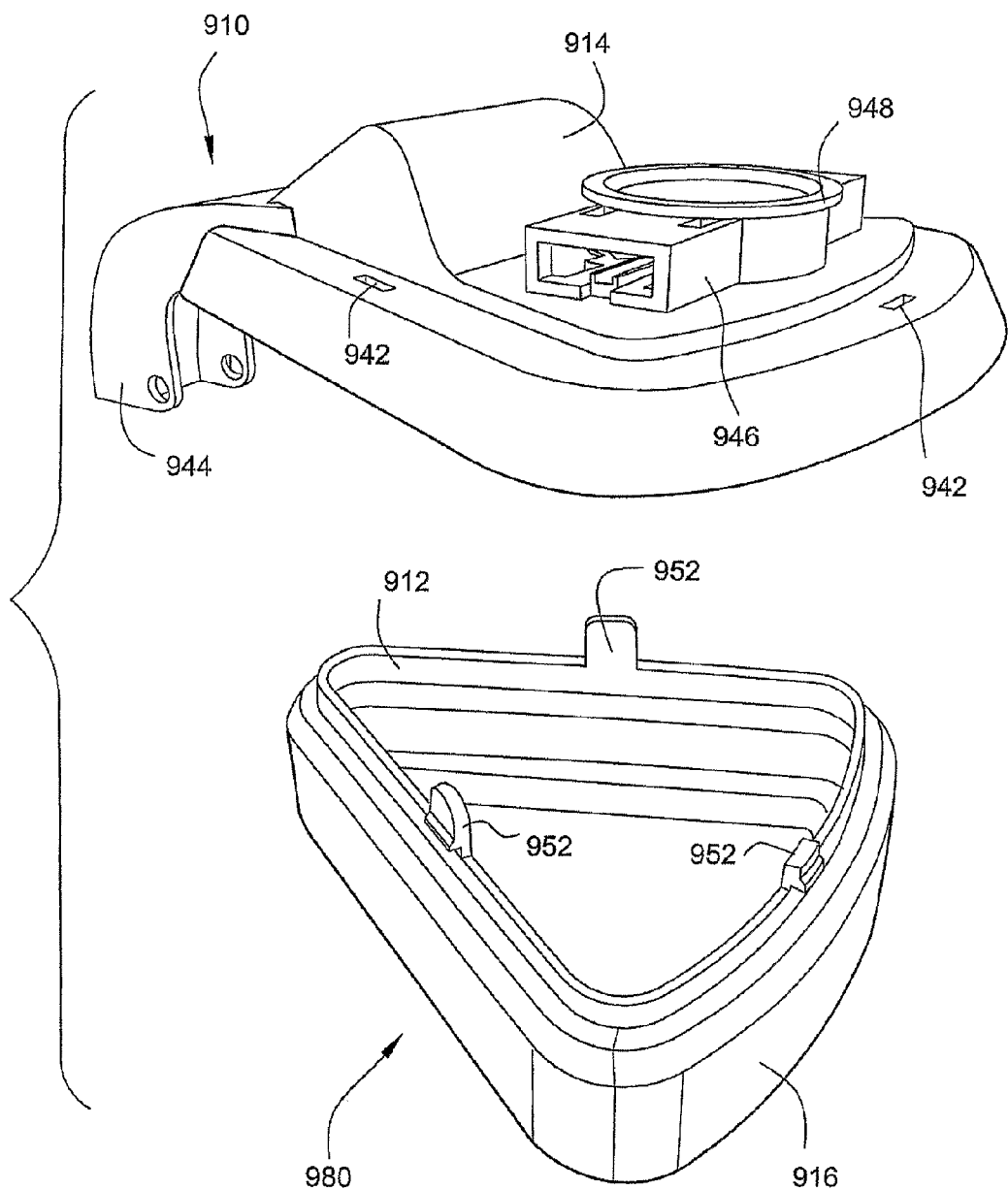
FIG. 19 is a top perspective view of the mask assembly shown in FIG. 18, the mask assembly in a partial assembled condition.
Figure 20:
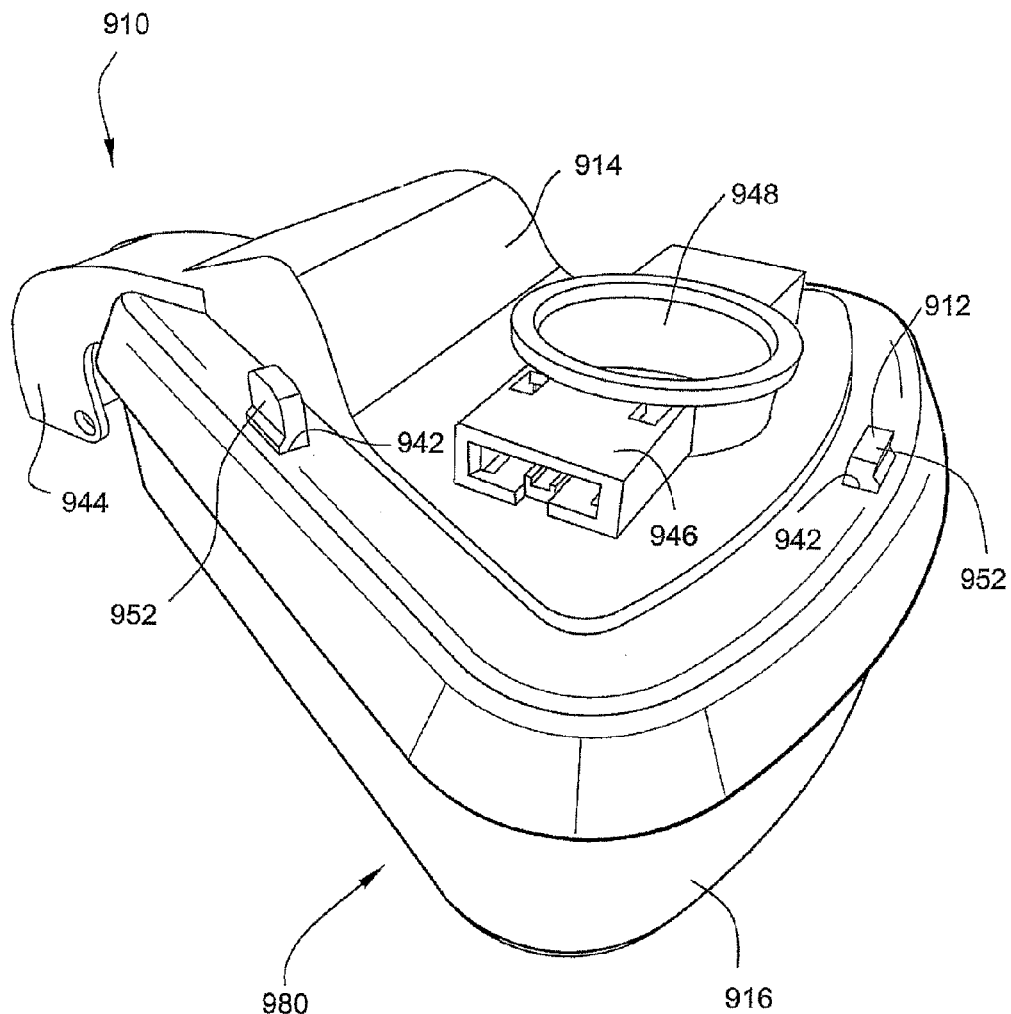
FIG. 20 is a top perspective view of the mask assembly shown in FIG. 18, the mask assembly in an assembled condition.

FIGS. 18-20 illustrate a mask assembly 910 including a cushion to frame assembly mechanism according to another embodiment of the present invention. In the illustrated embodiment, the cushion to frame assembly mechanism includes a cushion clip 912 that is adapted to removably connect the cushion 916 to the frame 914.

As shown in FIG. 18, the cushion 916 includes a side wall 924 and a face contacting portion 926 extending from the side wall 924. In an embodiment, the face contacting portion 926 has a double wall construction, e.g., membrane and underlying support cushion. Also, in an embodiment, the cushion 916 is constructed of liquid silicone rubber (LSR). However, other suitable materials may be used. As illustrated, a flange 928 protrudes inwardly from the side wall 924 around the perimeter thereof.

The frame 914 includes an upper support member 944 adapted to support a forehead support, lower headgear clip receptacles 946 adapted to be engaged with clips provided to straps of a headgear assembly (not shown), and an annular elbow connection seal 948 adapted to engage an inlet conduit, e.g., elbow. Also, the top wall of the frame 914 includes a plurality of slots 942 therethrough, e.g., three slots. In an embodiment, the frame 914 is molded in one-piece with polycarbonate, e.g., clear polycarbonate.

The cushion clip 912, e.g., molded of plastic, has a hoop-like configuration that generally corresponds in shape to the cushion 916 and frame 914, e.g., generally triangular. One or more flange portions 950 are provided around the perimeter of the cushion clip 912. Also, the cushion clip 912 includes a plurality of clip portions 952. As illustrated, the cushion clip 912 includes the same number of clip portions 952 as slots 942 on the frame 914, e.g., three clip portions.

As shown in FIG. 19, the cushion clip 912 is first assembled or interlocked with the cushion 916 to provide a cushion clip/cushion sub-assembly 980: Specifically, the cushion 916 is assembled around the cushion clip 912 by engaging the flange portions 950 of the cushion clip 912 with the flange 928 of the cushion 916. The cushion clip/cushion sub-assembly 980 is engaged with the frame 914 by inserting the clip portions 952 of the cushion clip 912 into respective slots 942 of the frame 914. The clip portions 952 are adapted to engage respective slots 942 with a snap-fit. FIG. 20 illustrates the assembled mask assembly 910 with the cushion clip/cushion sub-assembly 980 retained at three perimeter points on the frame 914.

As described above, the cushion 916 may include a resiliently flexible lip that is adapted to engage the frame 914 to provide a pressure assisted seal in use.

Figure 21:
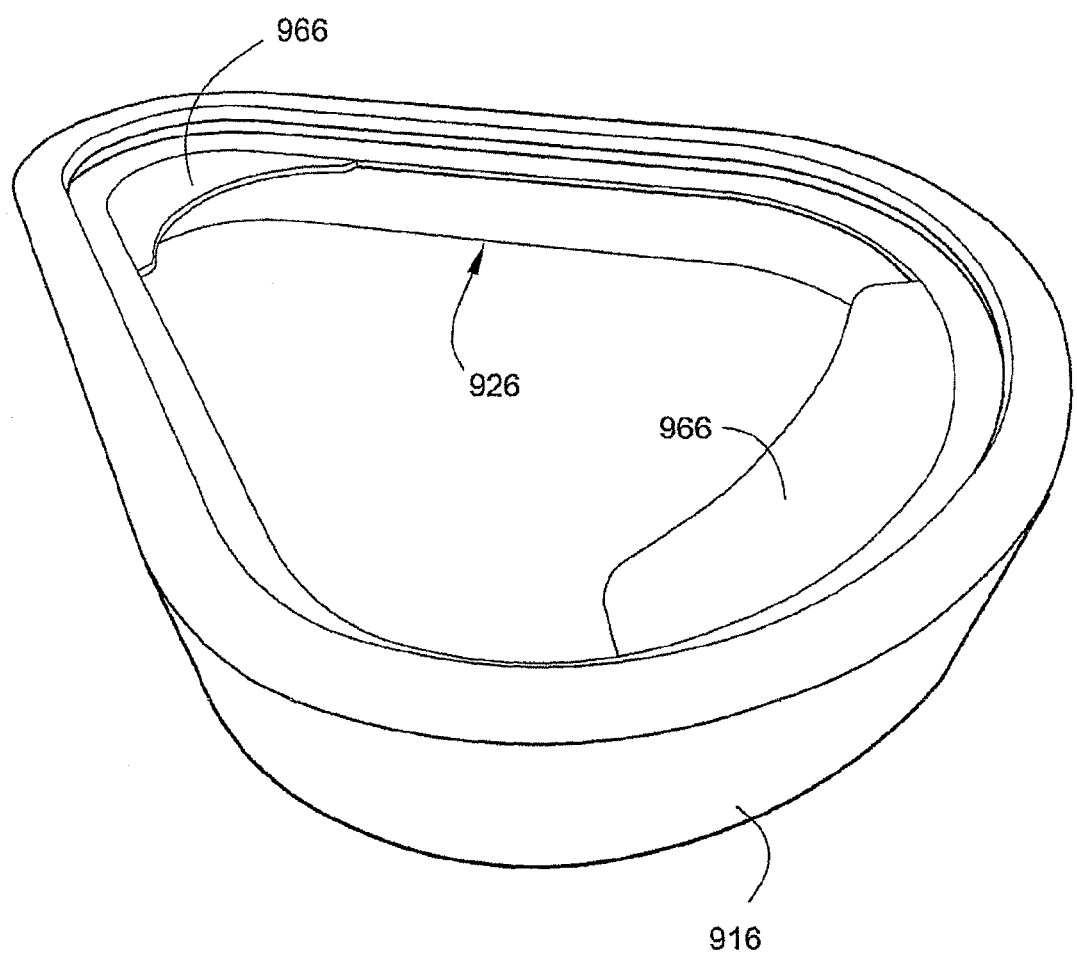
FIG. 21 is a top perspective view of a cushion according to another embodiment of the present invention.

Also, as shown in FIG. 21, the cushion 916 may have tab features 966 on a cushion lip thereof to facilitate easier assembly of the cushion clip 912.

In an embodiment, the cushion clip 912 may be over-molded with the cushion 916.

7. Seventh Embodiment of Cushion to Frame Assembly Mechanism

FIGS. 22-26 illustrate a mask assembly 1010 including a cushion to frame assembly mechanism according to another embodiment of the present invention. In the illustrated embodiment, the cushion to frame assembly mechanism includes a pressure assisted lip seal design.

Figure 22:
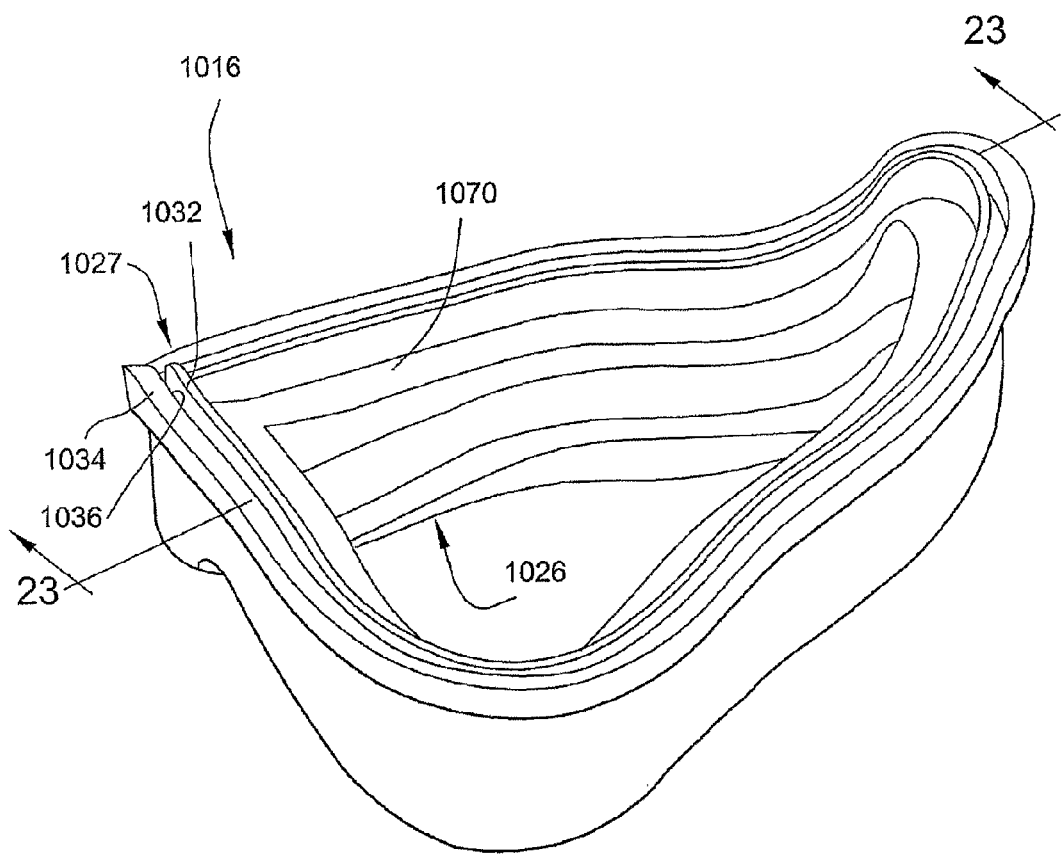
FIG. 22 is a top perspective view of a cushion including a cushion to frame assembly mechanism according to another embodiment of the present invention.
Figure 23:
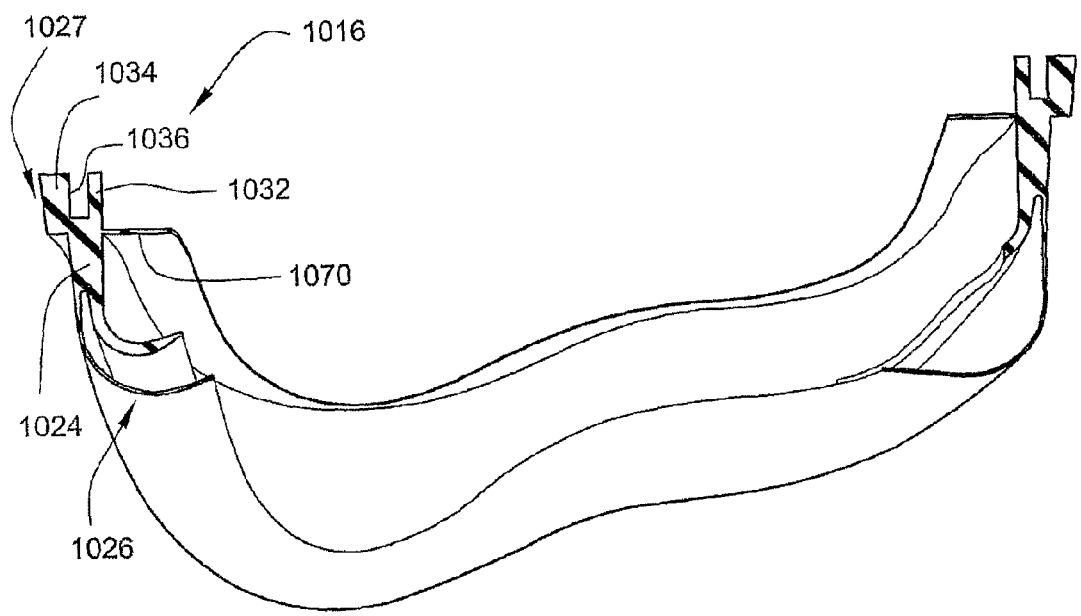
FIG. 23 is a cross-sectional view of the cushion shown in FIG. 22.

As best shown in FIGS. 22-23, the cushion 1016 includes a side wall 1024, a face-contacting portion 1026, and a non-face-contacting portion 1027. In the illustrated embodiment, the face-contacting portion 1026 has a double wall construction, e.g., membrane and underlying support cushion. The non-face-contacting portion 1027 provides a frame connection. Specifically, the non-face-contacting portion 1027 includes inner and outer 1032, 1034 that define a retaining recess 1036 around the perimeter of the cushion 1016. In addition, the non-face-contacting portion 1027 provides an elongated resiliently flexible lip 1070 that is adapted to engage the frame 1014 to provide a pressure assisted seal in use. As shown in FIG. 22, the lip 1070 has a non-planar trajectory or configuration. In an embodiment, the lip 1070 has a length of 4-12 mm, preferably 8 mm, and a width of 0.25-1.25, preferably 0.75 mm. However, other dimensions are possible depending on application. Also, in an embodiment, the cushion 1016 is constructed of liquid silicone rubber (LSR). However, other suitable materials may be used.

Figure 24:
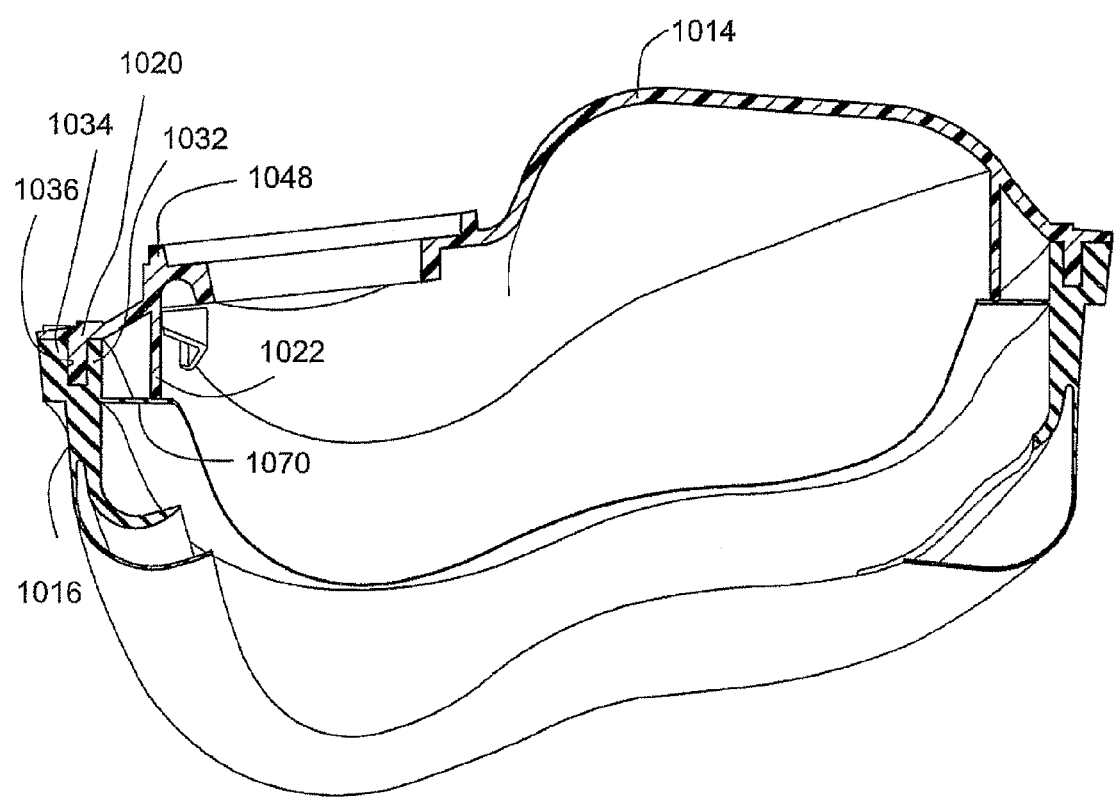
FIG. 24 is a cross-sectional view of the cushion shown in FIG. 22 engaged with a mask frame according to an embodiment of the present invention.
Figure 25:
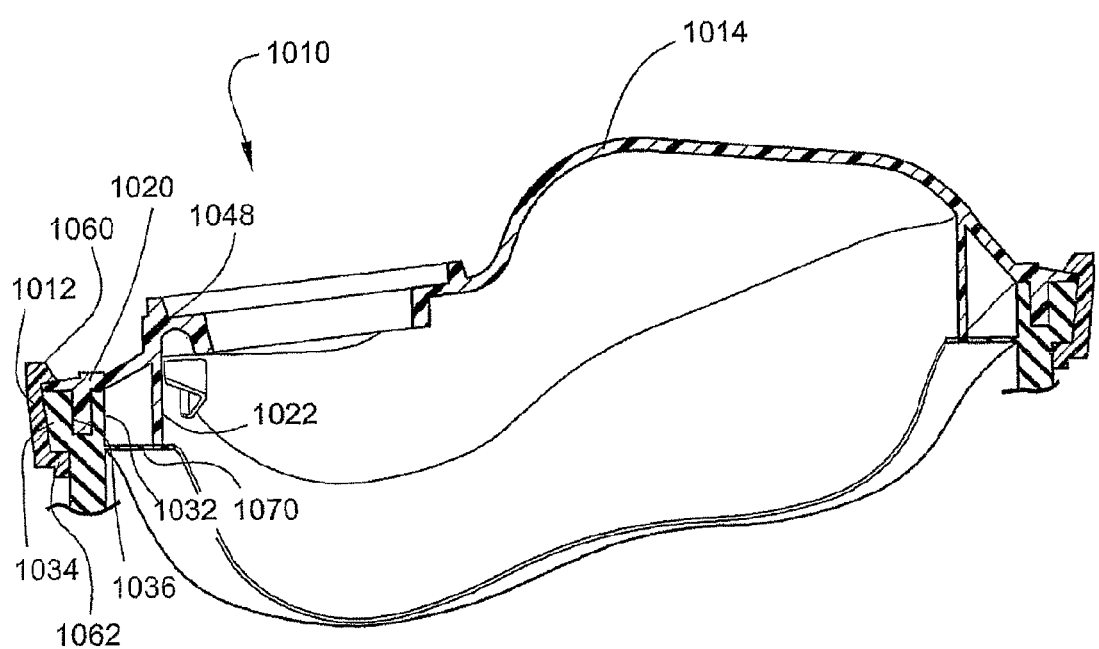
FIGS. 25-26 are cross-sectional views illustrating a cushion clip to maintain the engagement between the frame and the cushion shown in FIG. 24.
Figure 26:
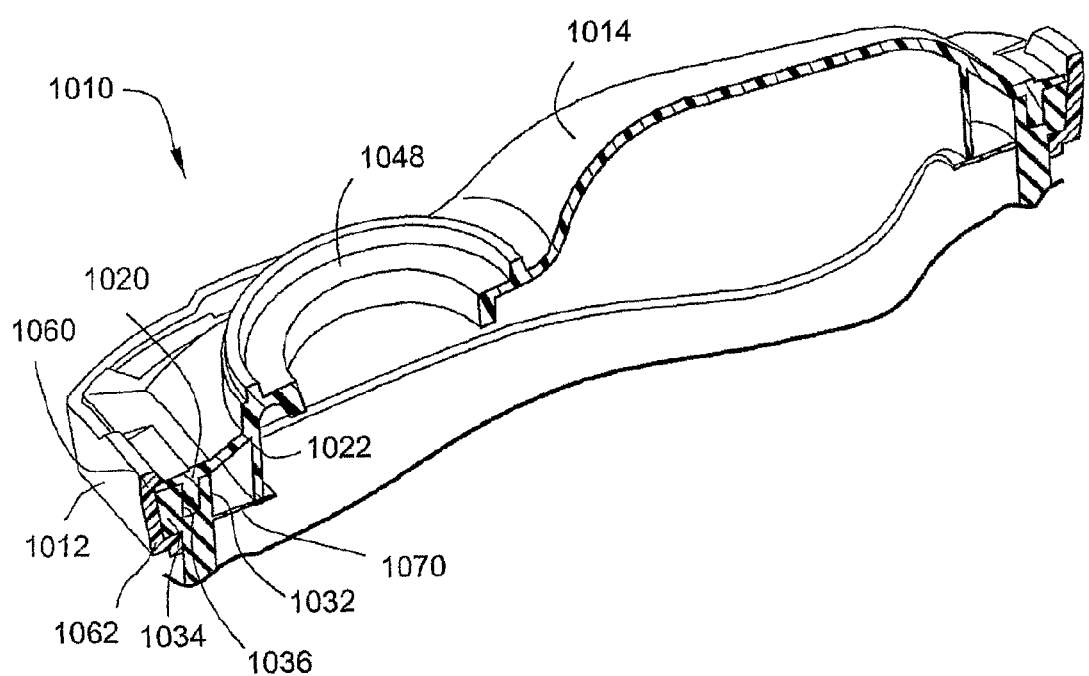

As shown in FIGS. 24-26, the frame 1014 includes an annular elbow connection seal 1048 adapted to engage an inlet conduit, e.g., elbow. Also, the frame 1014 provides a cushion connection including an outer wall 1020 and an inner wall 1022 that extend around the perimeter of the frame 1014. In an embodiment, the frame 1014 is molded in one-piece with polycarbonate.

As shown in FIG. 24, the cushion 1016 is engaged with the frame 1014 to provide a cushion/frame sub-assembly 1030. Specifically, the outer wall 1020 of the frame 1014 is inserted into the retaining recess 1036 of the cushion 1016, e.g., with a friction fit. In addition, the lip 1070 of the cushion 1016 resiliently engages the inner wall 1022 of the frame 1014 to provide a seal in use.

As shown in FIGS. 25 and 26, a cushion clip 1012, e.g., molded of plastic, is provided to maintain engagement between the frame 1014 and the cushion 1016. As illustrated, the cushion clip 1012 includes a first retaining portion 1060 that provides a shoulder for engaging the frame 1014 and a second retaining portion 1062 that provides a shoulder for engaging the cushion 1016. Thus, the cushion clip 1012 sandwiches the frame 1014 and the cushion 1016 to maintain their engagement.

In an embodiment, the frame clip 1012 may be over-molded with the cushion 1016. In another embodiment, the frame 1014 may be over-molded with the cushion 1016, thereby negating the need for the frame clip 1012.

Figure 27:
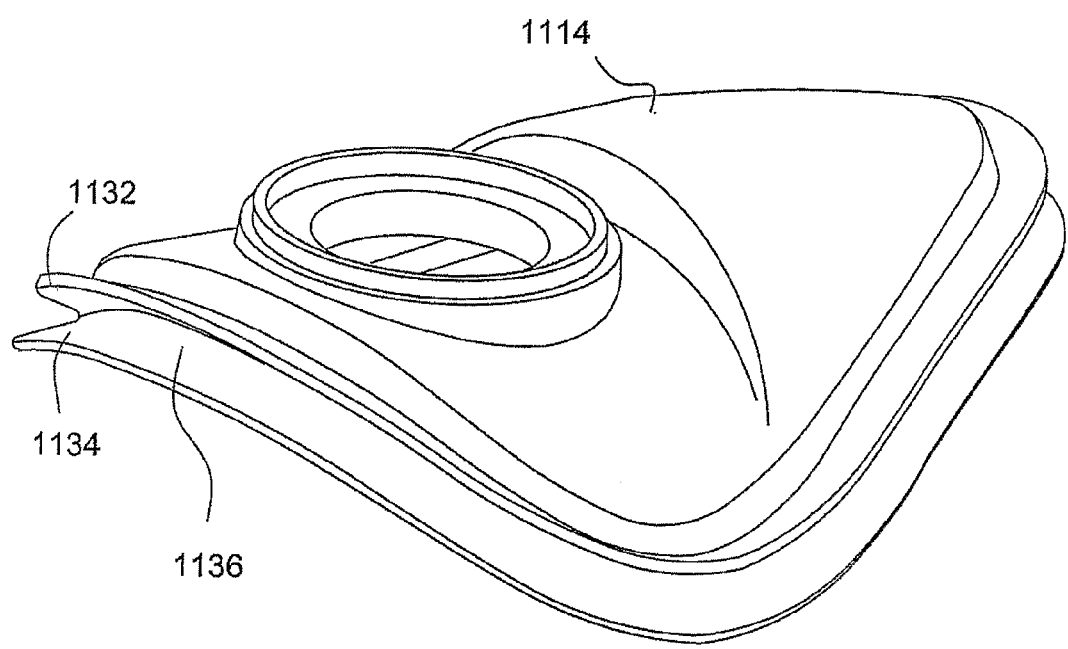
FIG. 27 is a perspective view of a mask frame according to another embodiment of the present invention.
Figure 28:
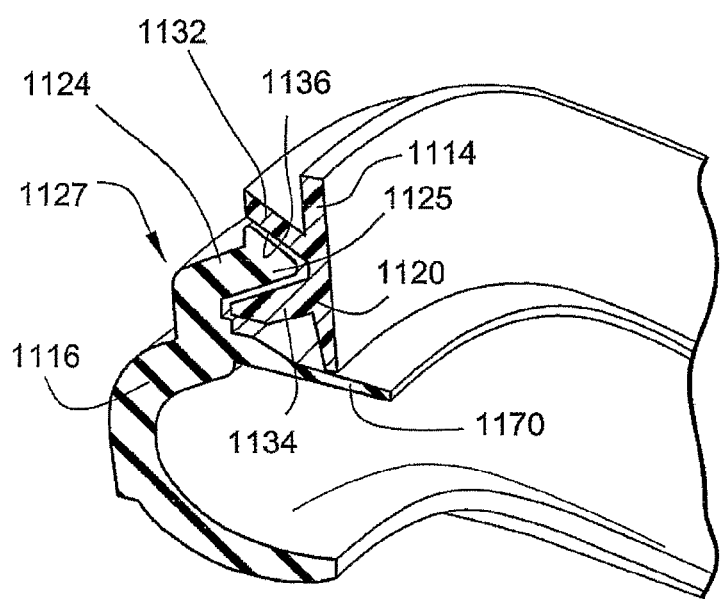
FIG. 28 is a cross-sectional view of the frame shown in FIG. 27 engaged with a mask cushion according to an embodiment of the present invention.
Figure 29:
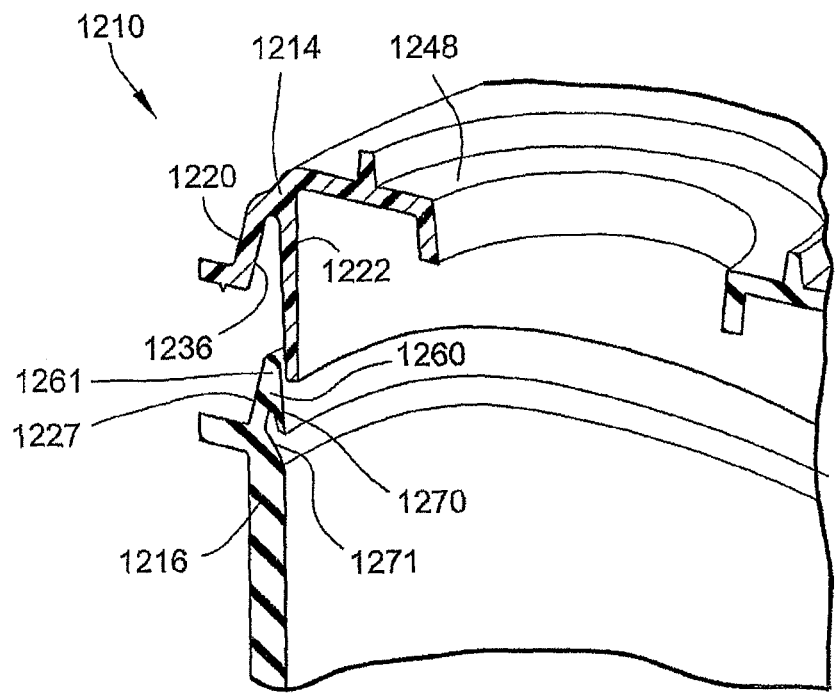
FIGS. 29-32 are cross-sectional views illustrating a cushion to frame assembly mechanism according to another embodiment of the present invention.

FIGS. 27 and 28 illustrate a cushion to frame assembly mechanism according to another embodiment of the present invention. As illustrated, the frame 1114 provides a cushion connection including a side wall 1120 and an upper wall 1132 and a lower wall 1134 that extend around the perimeter of the side wall 1120. In the illustrated embodiment, the upper and lower walls 1132, 1134 are inclined such that the walls 1120, 1132, 1134 define a generally k-shaped cross-sectional configuration.

As shown in FIG. 28, the non-face-contacting portion 1127 of the cushion 1116 includes a retaining wall 1124 that is inclined towards the cushion interior. As illustrated, the end 1125 of the retaining wall 1124 has an angled or pointed configuration. In addition, the non-face-contacting portion 1127 provides an elongated resiliently flexible lip 1170.

The cushion 1116 is engaged with the frame 1114 by stretching the cushion 1116 over the frame perimeter such that the retaining wall 1124 engages within the retaining recess 1136 defined between the upper and lower walls 1132, 1134. As illustrated, the angled or pointed end 1125 of the retaining wall 1124 conforms to the incline defined by the upper and lower walls 1132, 1134. In addition, the lip 1170 of the cushion 1116 resiliently engages the inner end of the frame side wall 1120 to provide a seal in use. A cushion clip (not shown) may be provided, e.g., around the cushion perimeter, to maintain engagement between the frame 1114 and the cushion 1116.

In an embodiment, the frame 1114 could potentially be over-molded with the cushion 1116, thereby negating need for a cushion clip.

8. Eighth Embodiment of Cushion to Frame Assembly Mechanism

FIGS. 29-32 illustrate a mask assembly 1210 including a cushion to frame assembly mechanism according to another embodiment of the present invention. In the illustrated embodiment, the cushion to frame assembly mechanism includes an integrated lip seal design.

As illustrated, the frame 1214 includes an annular elbow connection seal 1248 adapted to engage an inlet conduit, e.g., elbow. Also, the frame 1214 provides a cushion connection including an outer wall 1220 and an inner wall 1222 that extend around the perimeter of the frame 1214. The outer and inner walls 1220, 1222 define a retaining recess 1236 therebetween. In an embodiment, the frame 1214 is molded in one-piece with polycarbonate.

The non-face-contacting portion 1227 of the cushion 1216 includes a retaining portion 1260. As illustrated, the end 1261 of the retaining portion 1260 has an angled or pointed configuration. In addition, the non-face-contacting portion 1227 provides a resiliently flexible lip 1270. A space 1271 is provided behind the lip 1270 to provide the lip 1270 with a range of movement in use.

Figure 30:
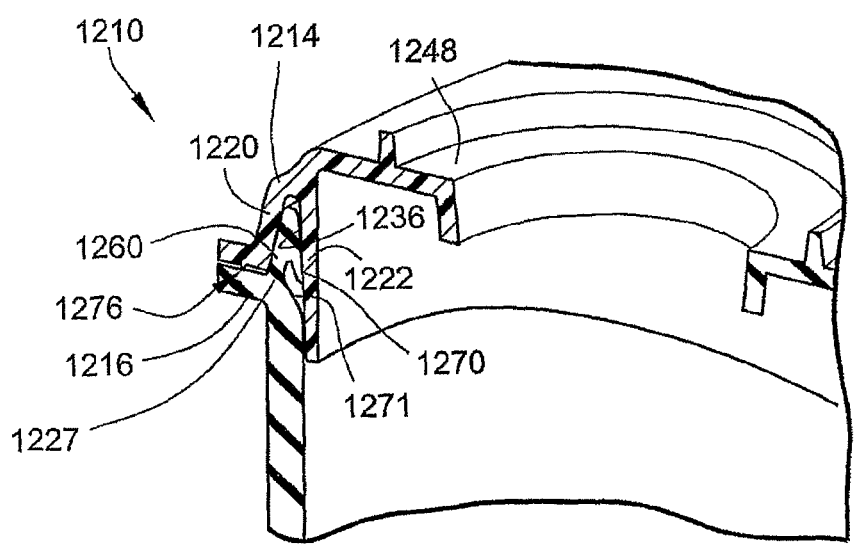
Figure 31:
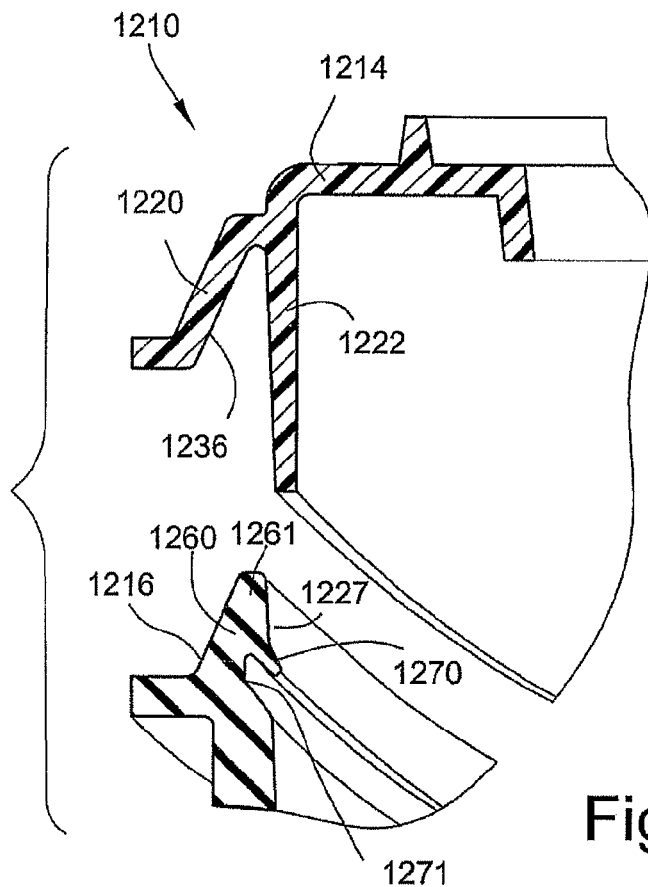
Figure 32:
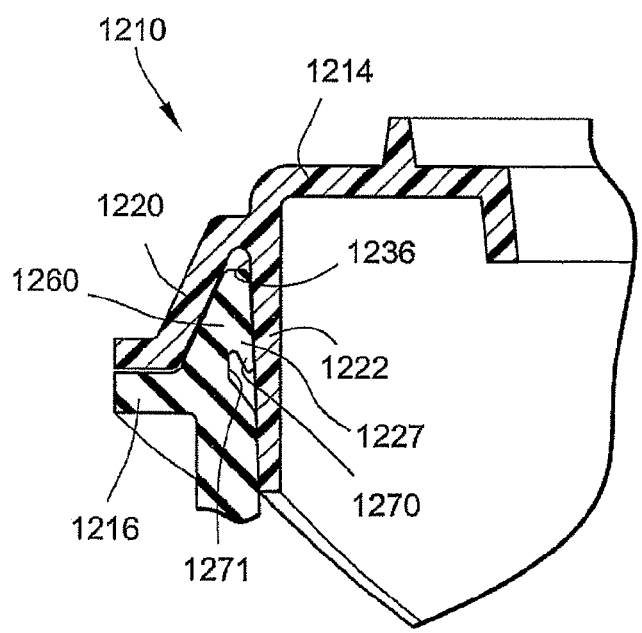

As shown in FIGS. 30 and 32, the frame 1214 is engaged with the cushion 1216 such that the retaining portion 1260 of the cushion 1216 engages within the retaining recess 1236 defined between the outer and inner walls 1220, 1222. As illustrated, the angled or pointed end 1261 of the retaining portion 1260 conforms to the incline defined by the outer and inner walls 1220, 1222. In addition, the lip 1270 of the cushion 1216 resiliently engages the inner wall 1222 of the frame 1214 to provide a seal in use. The lip 1270 may deflect inwardly into the space 1271, against resiliency thereof, to provide the seal. Also, as shown in FIG. 30, a pressure line 1276 may be incorporated into the flange perimeter of the frame 1214 and cushion 1216.

A frame clip may be provided to maintain engagement between the frame 1214 and the cushion 1216. The frame clip may be assembled from the bottom, e.g., cushion side, or the frame clip may be assembled from the top, e.g., frame side.

Figure 33:
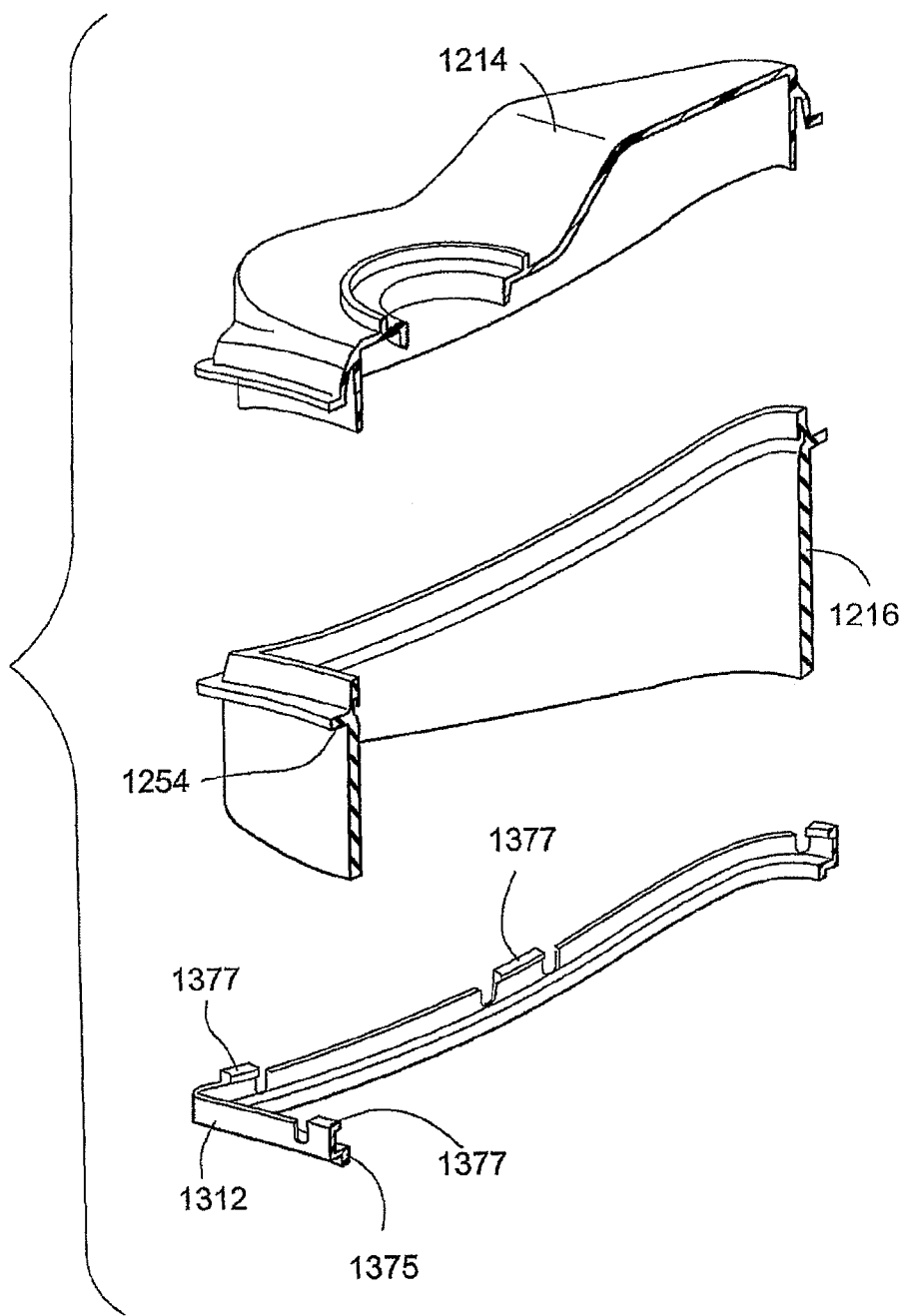
FIGS. 33-34 are cross-sectional views illustrating a bottom assembling frame clip to maintain the engagement between the frame and the cushion shown in FIGS. 29-32.
Figure 34:
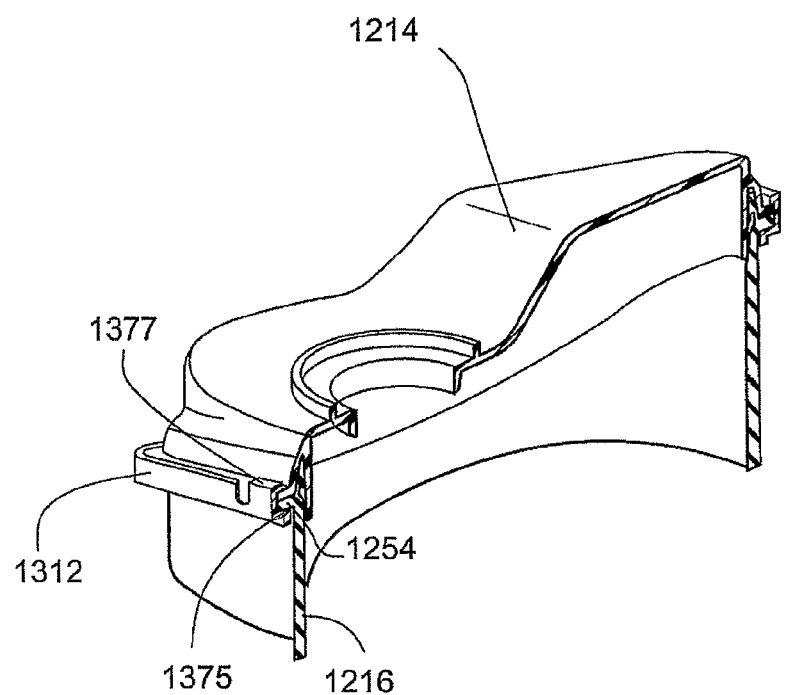
Figure 35:
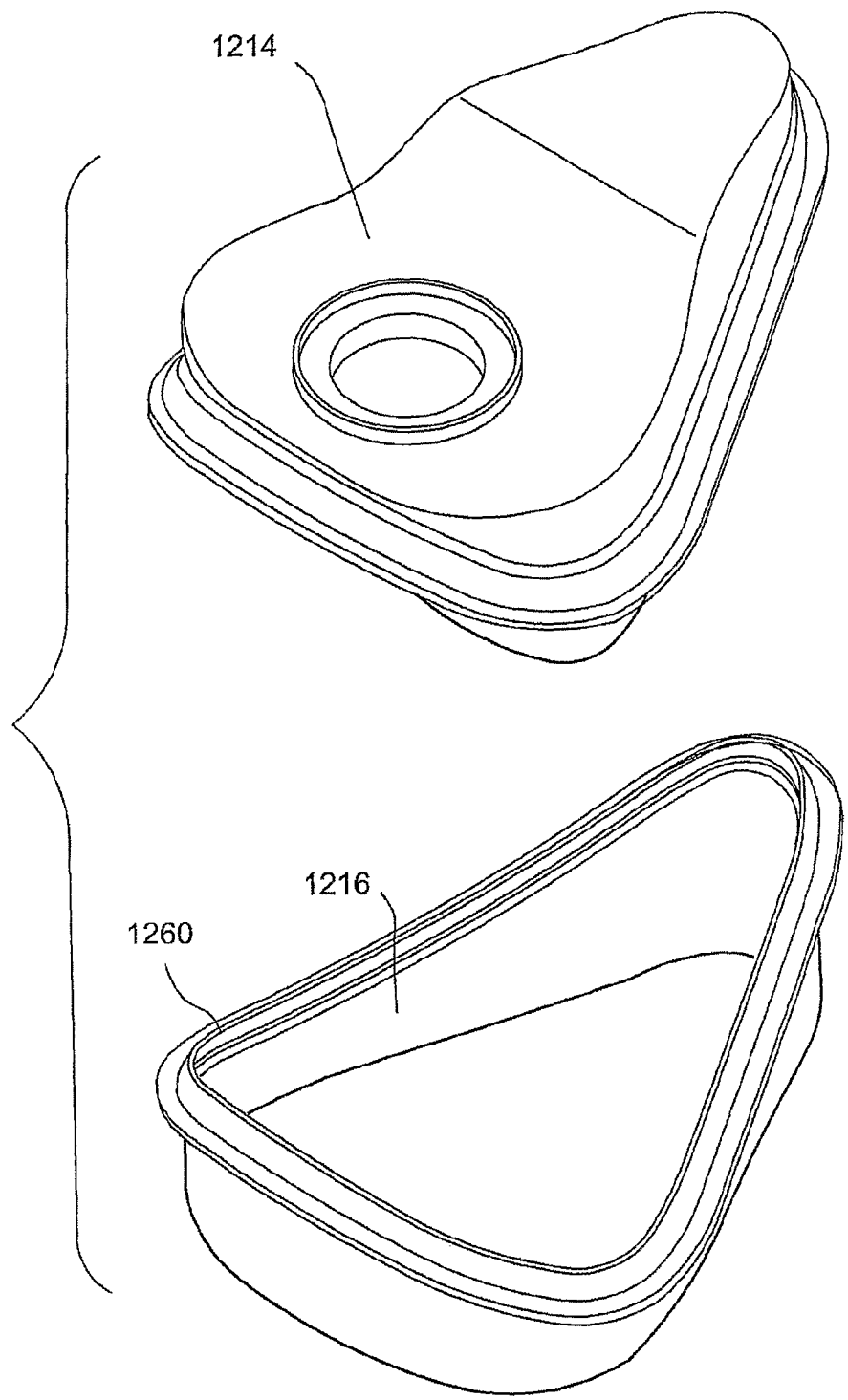
FIGS. 35-39 illustrate a top assembling frame clip to maintain the engagement between the frame and the cushion shown in FIGS. 29-32.

FIGS. 33-34 illustrate a bottom assembling frame clip 1312. As illustrated, the frame clip 1312, e.g., molded of plastic, is assembled over the cushion 1216 and includes a first retaining portion 1375 that provides a shoulder for engaging the cushion flange 1254 and a plurality of second retaining portions 1377 that provide a shoulder for engaging the frame 1214. Thus, the frame clip 1312 sandwiches the frame 1214 and the cushion 1216 to maintain their engagement.

In an embodiment, the frame clip 1312 may be over-molded with the cushion 1216. In another embodiment, the frame 1214 may be over-molded with the cushion 1216, thereby negating the need for the frame clip 1312.

Figure 36:
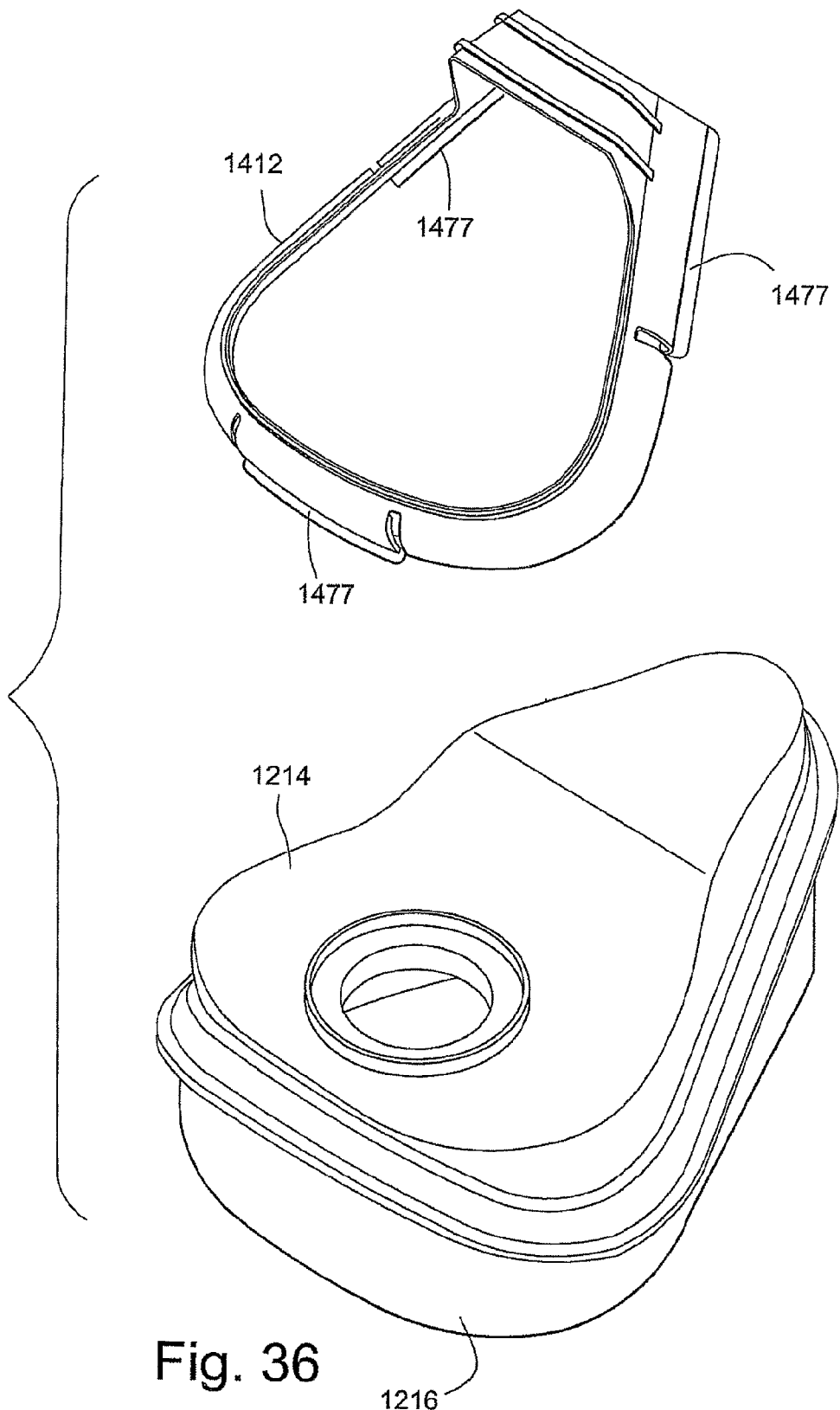
Figure 37:
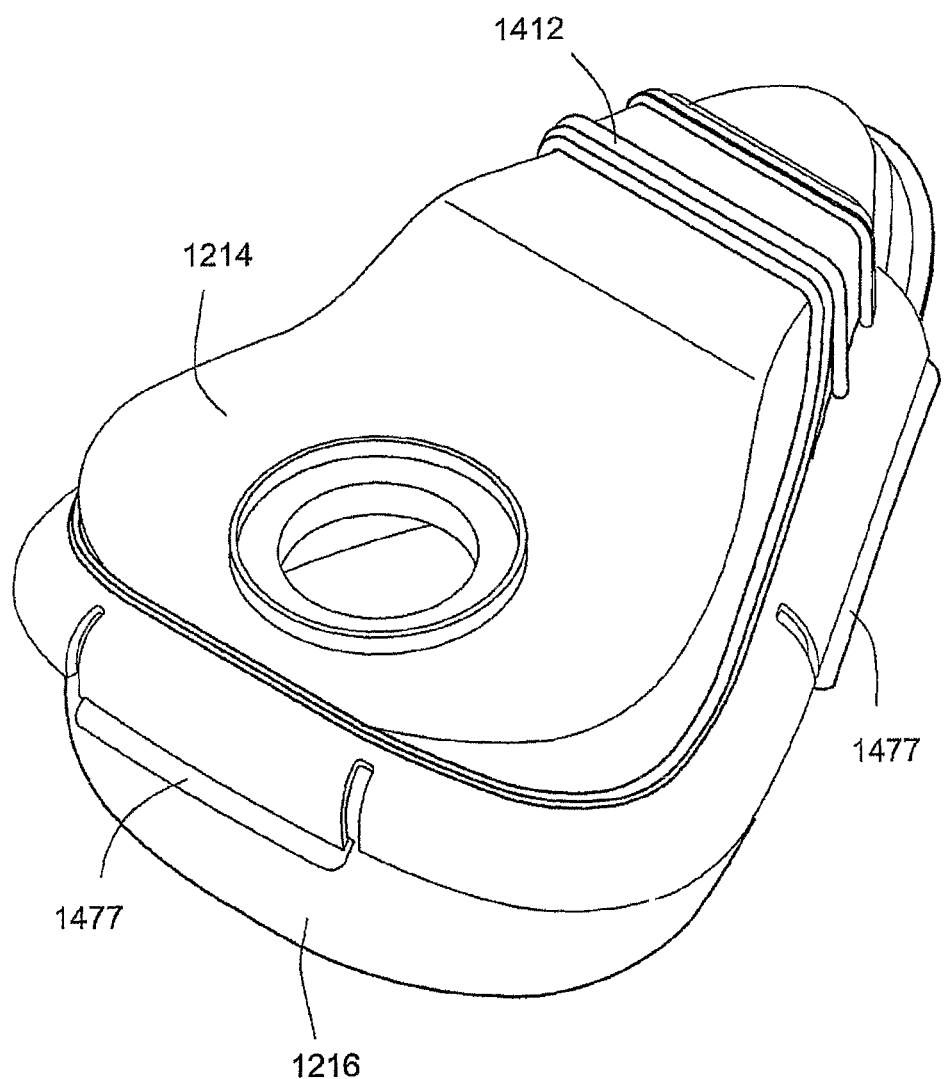
Figure 38:
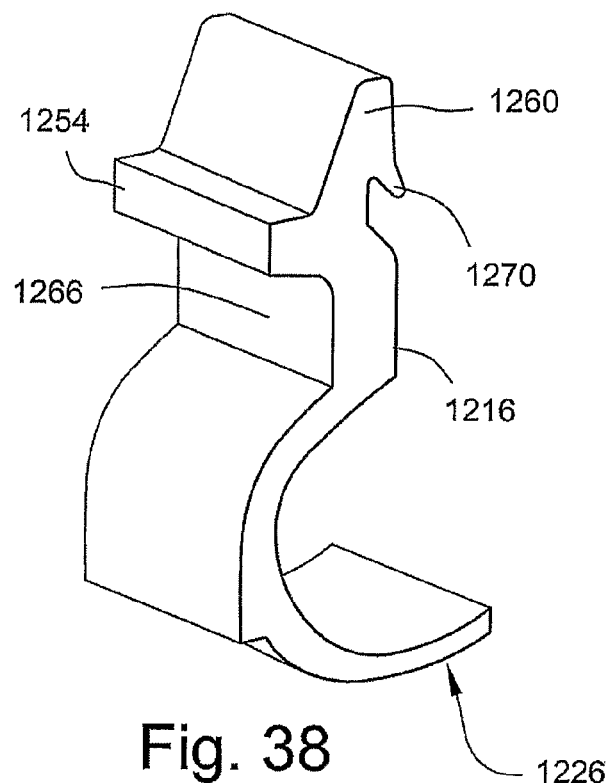

FIGS. 35-39 illustrate a top assembling frame clip 1412. Similar to the above, the frame 1214 is engaged with the cushion 1216 such that the retaining portion 1260 of the cushion 1216 engages within the retaining recess 1236 defined between the outer and inner walls 1220, 1222 (see FIGS. 35-36). FIG. 38 illustrates a portion of the cushion 1216 to show the retaining portion 1260, the lip 1270, and the face-contacting portion 1226 thereof. FIG. 38 also illustrates an undercut region 1266 in the cushion 1216 that defines the cushion flange 1254.

Figure 39:
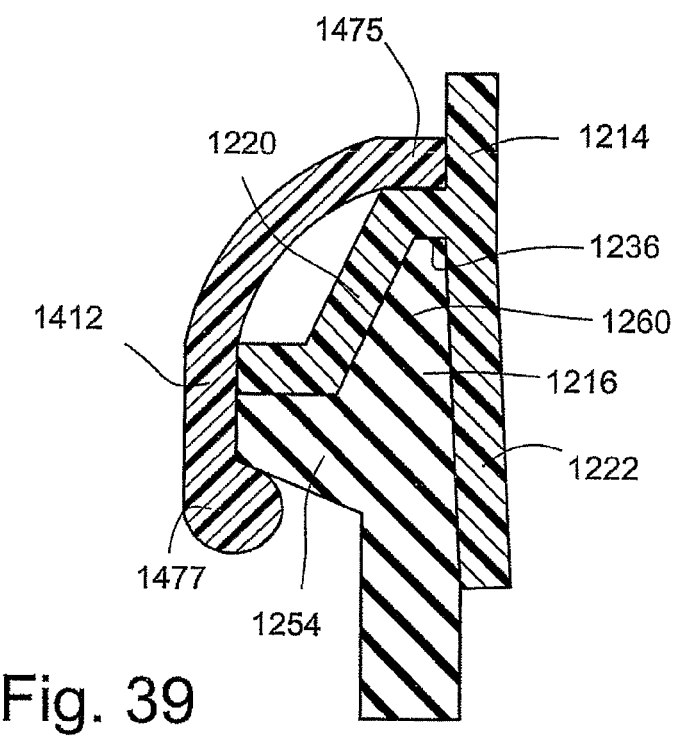

The frame clip 1412, e.g., molded of plastic, is assembled over the frame 1214 and includes a first retaining portion 1475 that provides a shoulder for engaging the frame 1214 and a plurality of second retaining portions 1477, e.g., three retaining portions, that provide a shoulder for engaging the cushion flange 1254, as shown in FIGS. 36, 37, and 39. Thus, the frame clip 1412 sandwiches the frame 1214 and the cushion 1216 to maintain their engagement as best shown in FIG. 39.

In an embodiment, the frame 1214 could potentially be over-molded with the cushion 1216, thereby negating the need for the frame clip 1412.

Figure 40:
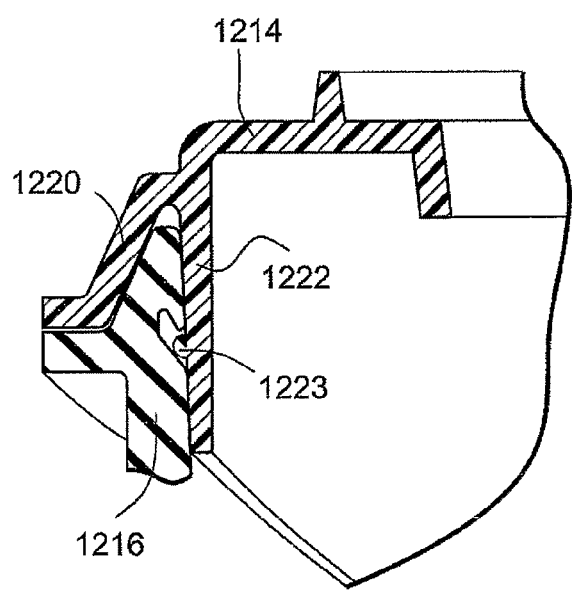
FIG. 40 illustrates a mask frame according to another embodiment of the present invention, the mask frame adapted for use with the cushion shown in FIGS. 29-32.
Figure 41:
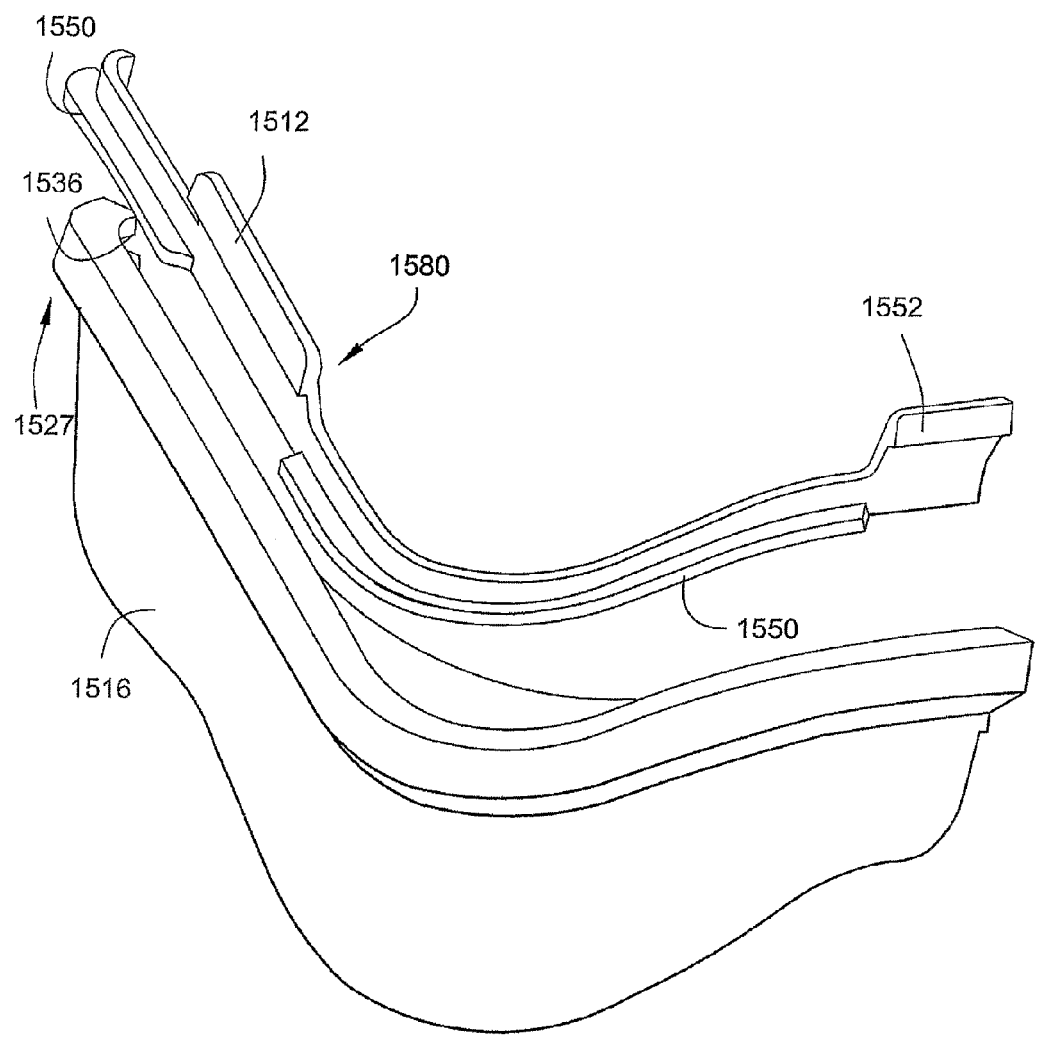
FIGS. 41-44 illustrate a cushion to frame assembly mechanism according to yet another embodiment of the present invention.
Figure 42:
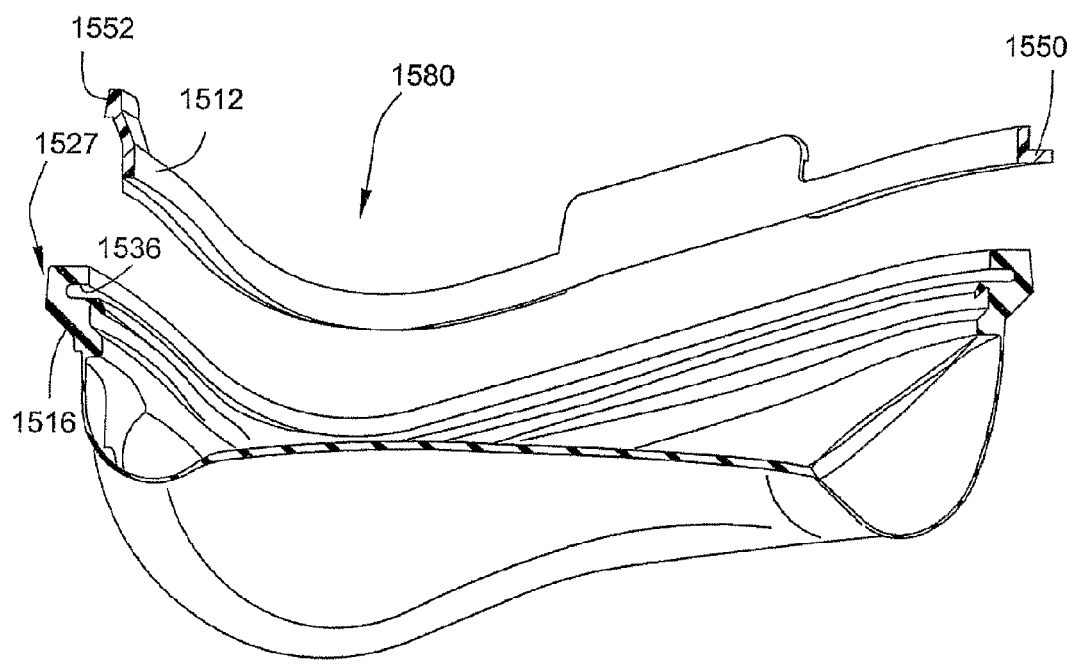
Figure 43:
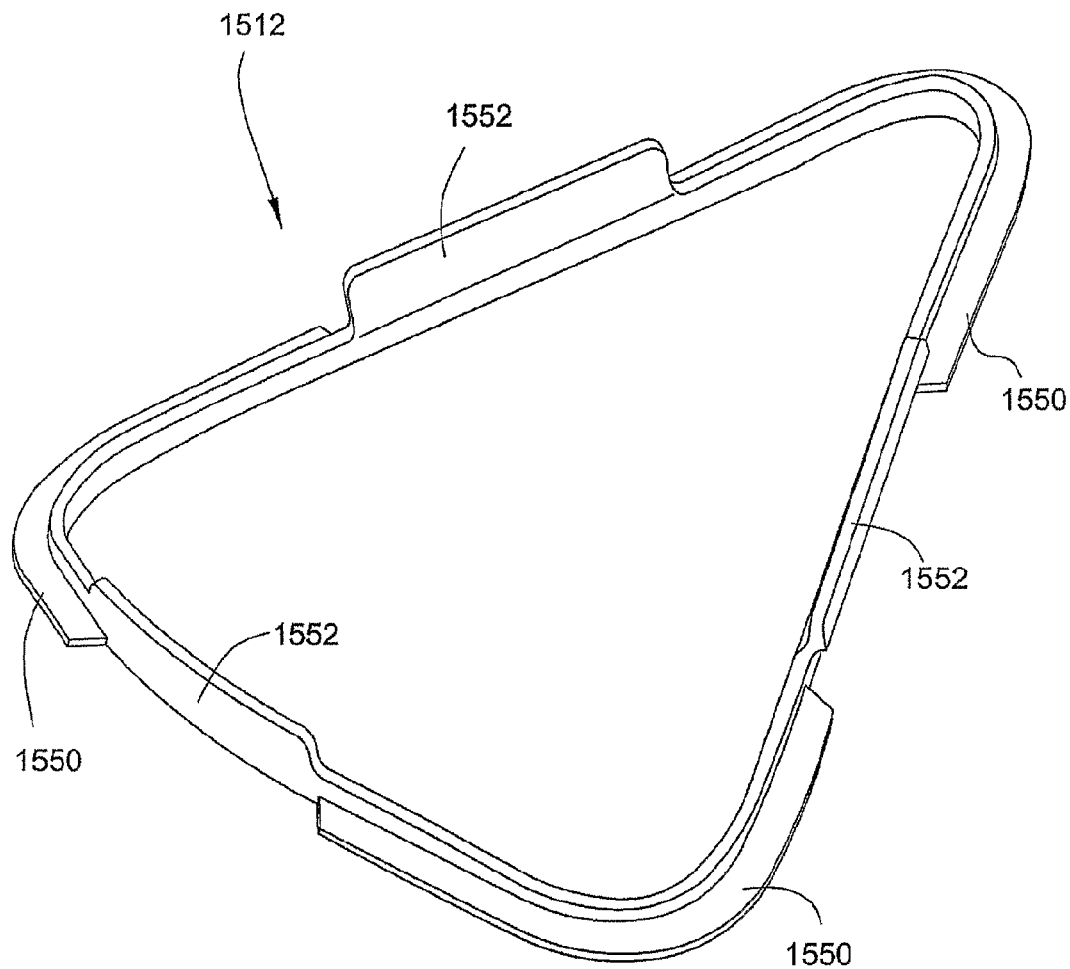

In an alternative embodiment, as shown in FIG. 40, the inner wall 1222 of the frame 1214 may include a protrusion 1223 along the perimeter thereof. The protrusion 1223 provides interference with the cushion 1216 in use, thereby preventing inadvertent removal of the cushion 1216 from the frame 1214. Moreover, the protrusion 1223 may provide sufficient interference to avoid the need for a frame clip.

FIGS. 41-44 illustrate another cushion to frame assembly mechanism including a cushion clip 1512 for use with a cushion 1516 having an integrated lip seal. As illustrated, the non-face-contacting portion 1527 of the cushion 1516 includes a retaining recess 1536 around the perimeter thereof that is adapted to engage the cushion clip 1512. Specifically, the cushion clip 1512, e.g., molded of plastic, includes one or more flange portions 1550 around the perimeter thereof that are engaged within the retaining recess 1536 of the cushion 1516 to provide a cushion clip/cushion sub-assembly 1580.

Figure 44:
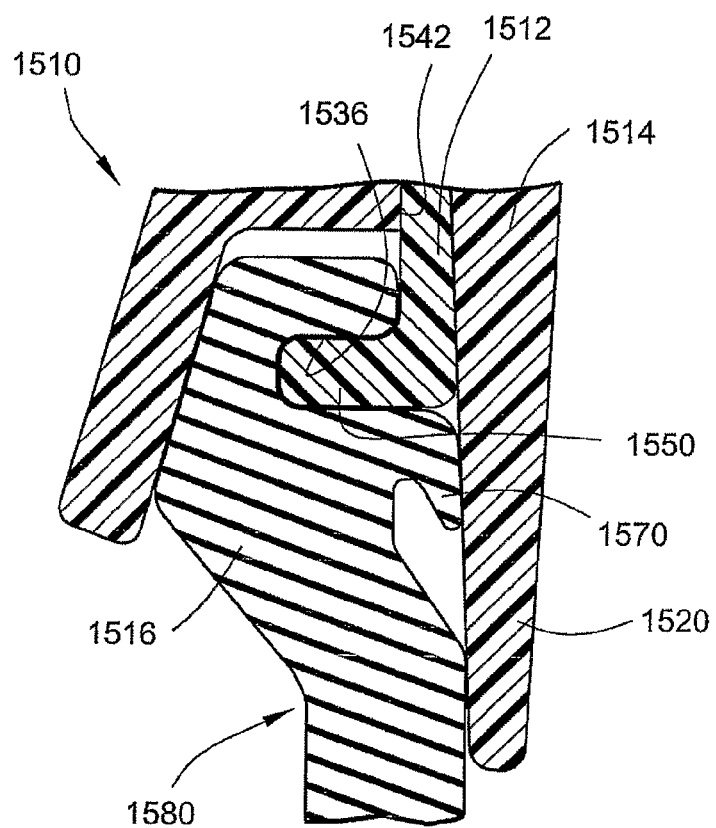

The cushion clip/cushion sub-assembly 1580 is then engaged with the frame 1514 by inserting the clip portions 1552, e.g., three clip portions, of the cushion clip 1512 into respective slots 1542 of the frame 1514. The clip portions 1552 are adapted to engage respective slots 1542 with a snap-fit. FIG. 44 illustrates the assembled mask assembly 1510 with the cushion clip/cushion sub-assembly 1580 retained on the frame 1514. As illustrated, the lip 1570 of the cushion 1516 resiliently engages the inner wall 1520 of the frame 1514 to provide a seal in use.

In an embodiment, the cushion clip 1512 could potentially be over-molded with the cushion 1516.

9. Ninth Embodiment of Cushion to Frame Assembly Mechanism

Figure 45:
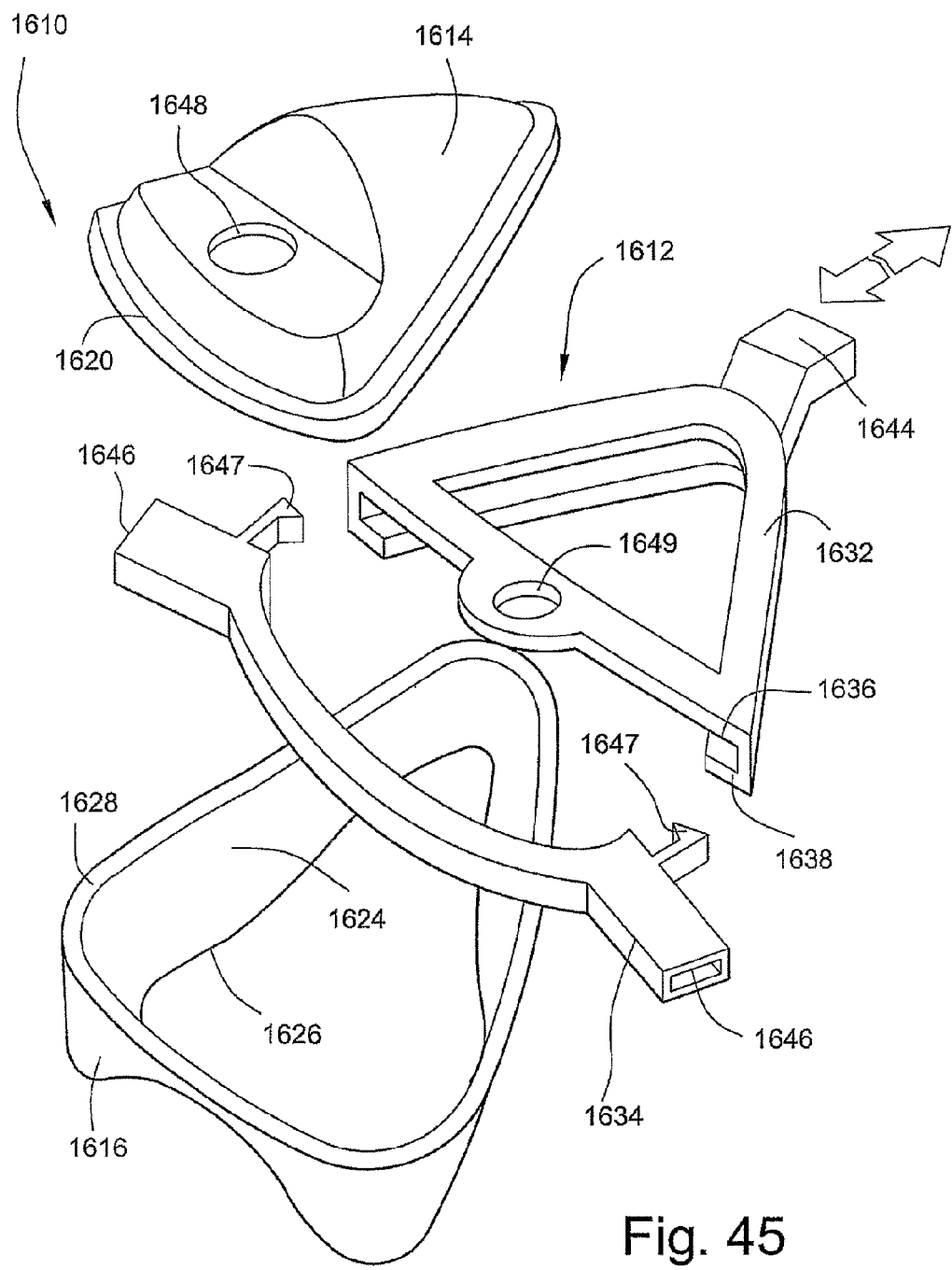
FIGS. 45-46 illustrate a cushion to frame assembly mechanism according to another embodiment of the present invention.
Figure 46:
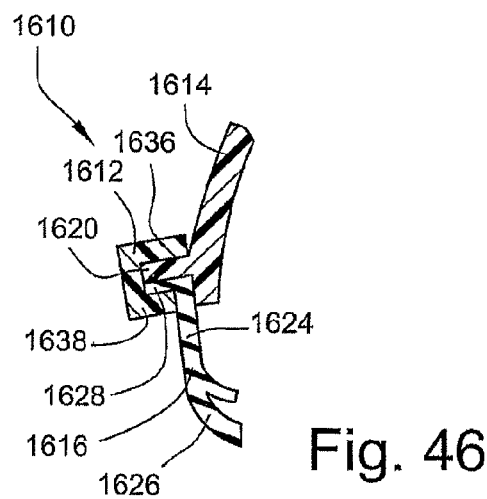

FIGS. 45 and 46 illustrate a mask assembly 1610 including a cushion to frame assembly mechanism according to another embodiment of the present invention. In the illustrated embodiment, the cushion to frame assembly mechanism includes a slide-on two-part frame clip 1612 that is adapted to removably connect the cushion 1616 to the frame 1614.

As shown in FIG. 45, the cushion 1616 includes a side wall 1624 and a face contacting portion 1626 extending from the side wall 1624. In an embodiment, the face contacting portion 1626 may have a double wall construction, e.g., membrane and underlying support cushion. Also, in an embodiment, the cushion 1616 is constructed of liquid silicone rubber (LSR). However, other suitable materials may be used. As illustrated, a flange 1628 protrudes inwardly from, the side wall 1624 around the perimeter thereof.

The frame 1614 includes an opening 1648 that is communicated with an inlet conduit. Also, the frame 1614 provides a flange 1620 that extends around the perimeter of the frame 1614. In an embodiment, the frame 1614 is molded in one-piece with polycarbonate.

The slide-on two-part frame clip 1612 includes a first part 1632 and a second part 1634 attachable to the first part 1632, e.g., with a snap-fit. The first part 1632 includes an upper support member 1644 adapted to support a forehead support and an annular elbow connection seal 1649 adapted to engage an inlet conduit, e.g., elbow. Also, the perimeter of the first part 1632 includes spaced apart upper and lower wall portions 1636, 1638. The second part 1634 includes lower headgear clip receptacles 1646 adapted to be engaged with clips provided to straps of a headgear assembly (not shown) and retaining members 1647 adapted to interlock with the first part 1632. Also, the perimeter of the second part 1634 includes spaced apart upper and lower wall portions (not shown). In an embodiment, the first and second parts 1632, 1634 of the frame clip 1612 are molded with polycarbonate.

The cushion 1616 is first engaged with the frame 1614 to provide a cushion/frame sub-assembly. Specifically, the side wall 1624 of the cushion 1616 is engaged with the side wall of the frame 1614, e.g., with a friction fit, such that the cushion flange 1628 engages against the frame flange 1620 (see FIG. 46).

Then, the first part 1632 of the frame clip 1612 is slid onto one side of the cushion/frame sub-assembly and the second part 1634 is slid onto the opposite side of the cushion/frame sub-assembly such that the upper and lower wall portions 1636, 1638 of the first and second parts 1632, 1634 sandwich the cushion flange 1628 and the frame flange 1620 therebetween (see FIG. 46). The first and second parts 1632, 1634 are slid towards one another until the retaining members 1647 of the second part 1634 interlock with the first part 1632, e.g., with a snap-fit. Thus, the first and second parts 1632, 1634 sandwich the frame 1614 and the cushion 1616 to maintain their engagement. The upper and lower wall portions 1636, 1638 of the first and second parts 1632, 1634 provide a compression seal in use.

Figure 47:
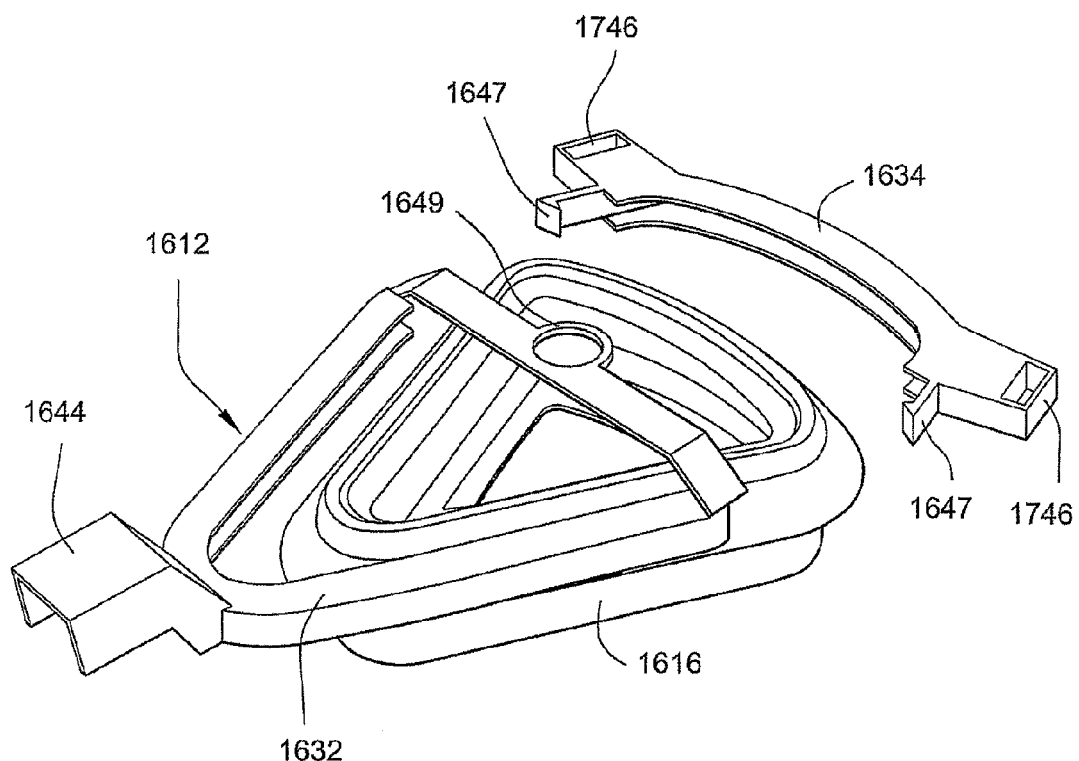
FIGS. 47-49 illustrate a cushion to frame assembly mechanism according to another embodiment of the present invention.
Figure 48:
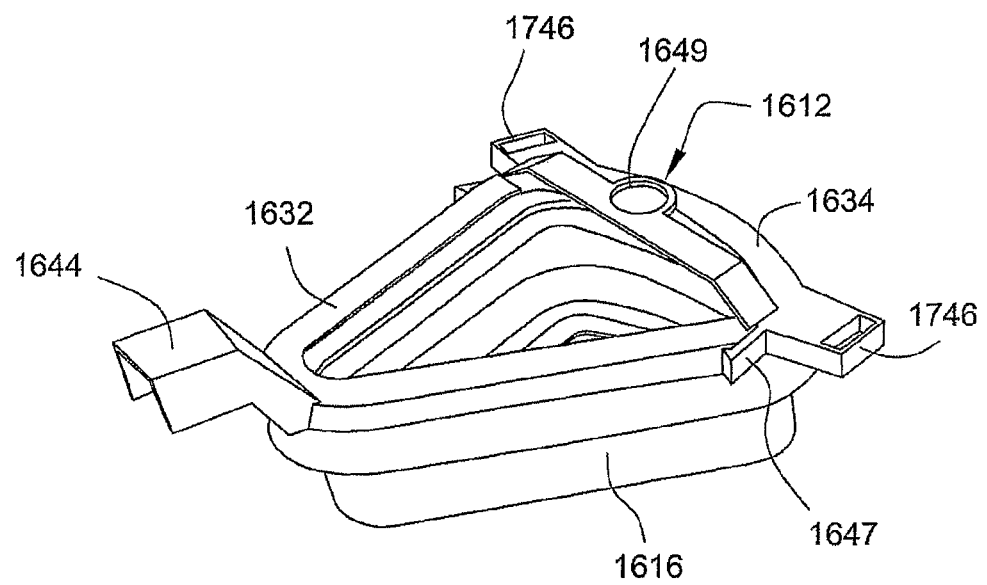
Figure 49:
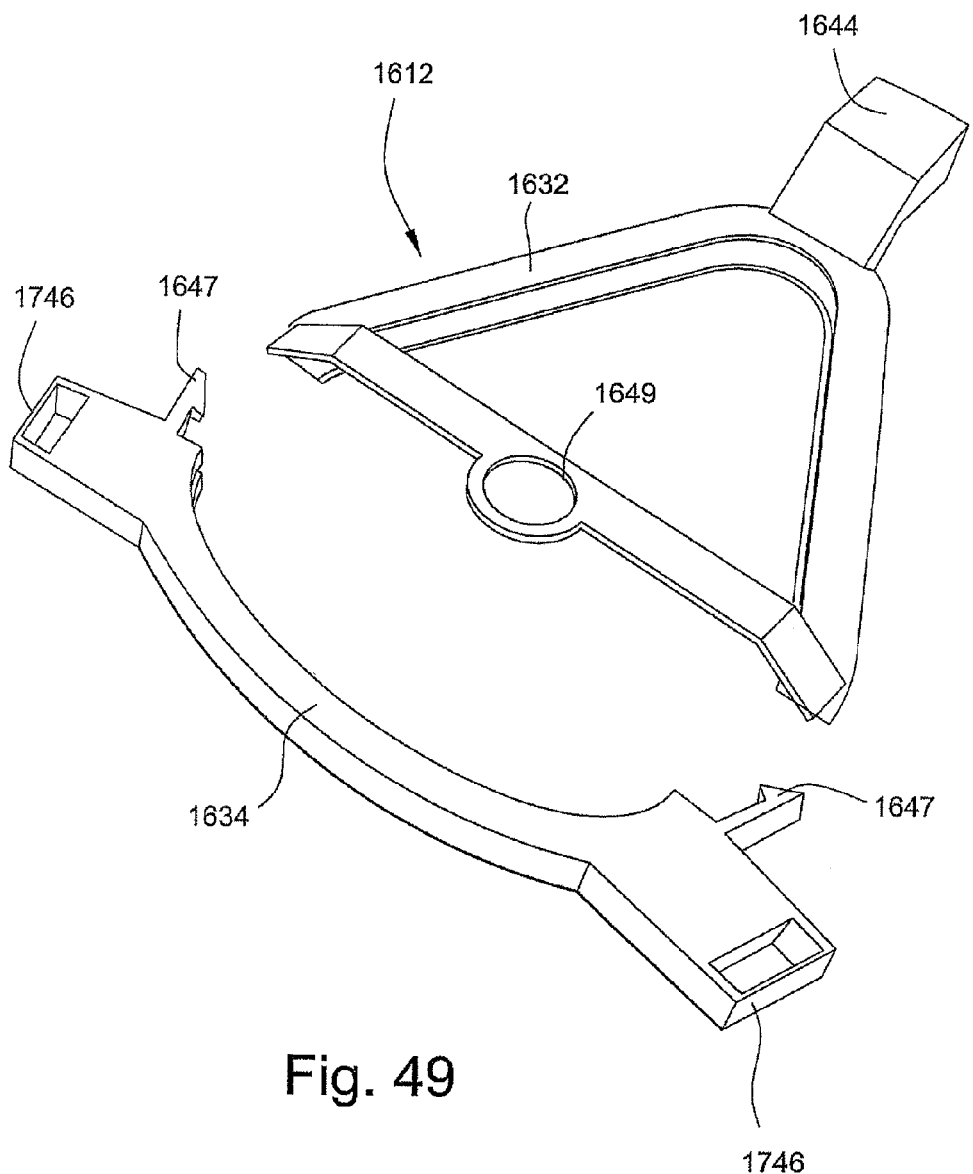

FIGS. 47-49 illustrate a mask assembly substantially similar to the mask assembly 1610 described above. Therefore, similar components are indicated with similar reference numerals. In contrast, the second part 1634 includes lower headgear cross-bars 1746 adapted to be engaged with straps of a headgear assembly (not shown). Also, an inner frame member provided between the cushion 1616 and frame clip 1612 is not shown.

In each embodiment, the cushion to frame assembly mechanism provides a flat or radial slide path.

In an embodiment, the frame 1614 and cushion 1616 may be integrally molded in one-piece, e.g., with LSR, to provide a one-piece cushion/frame sub-assembly.

Figure 50:
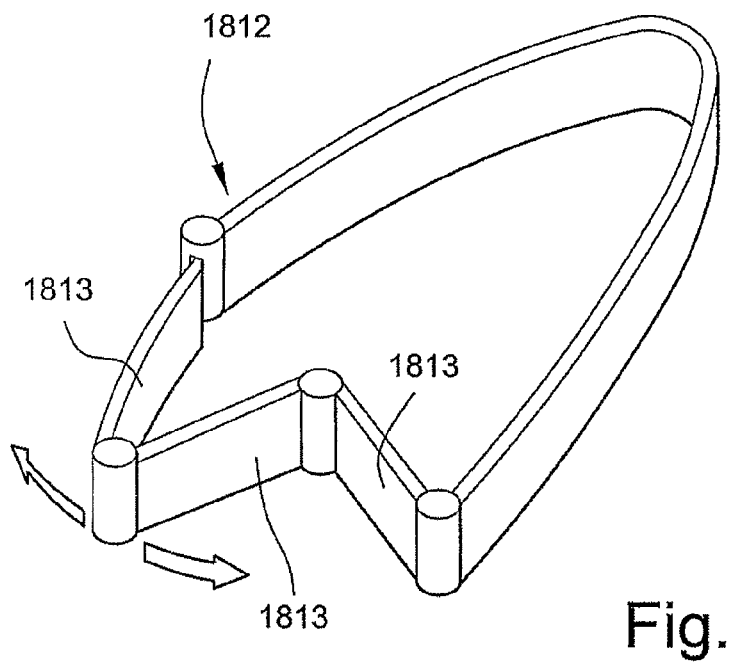
FIGS. 50-51 illustrate alternative frame clip designs.
Figure 51:
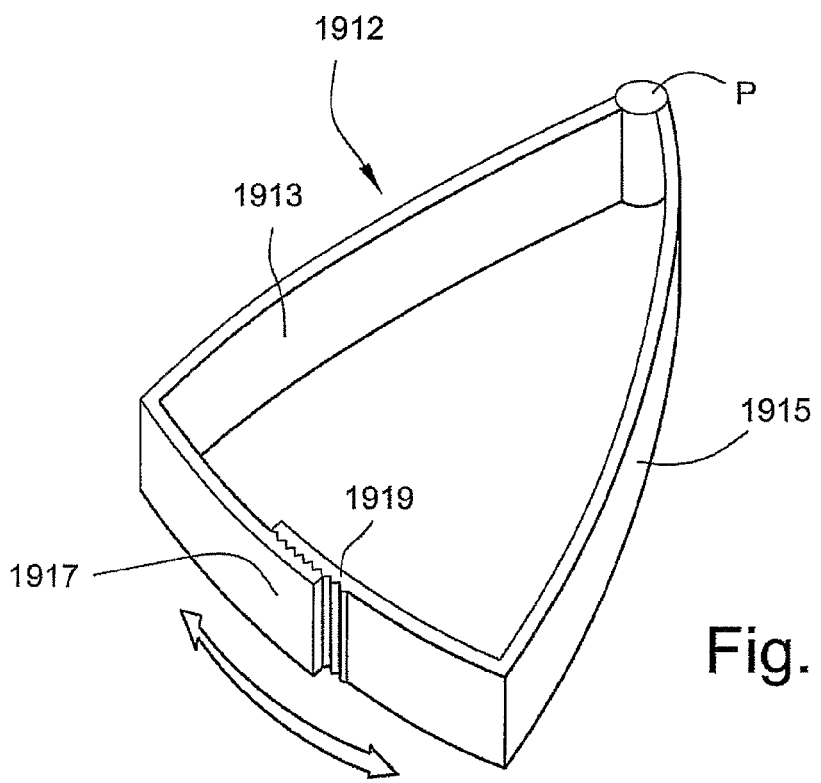
Figure 52:
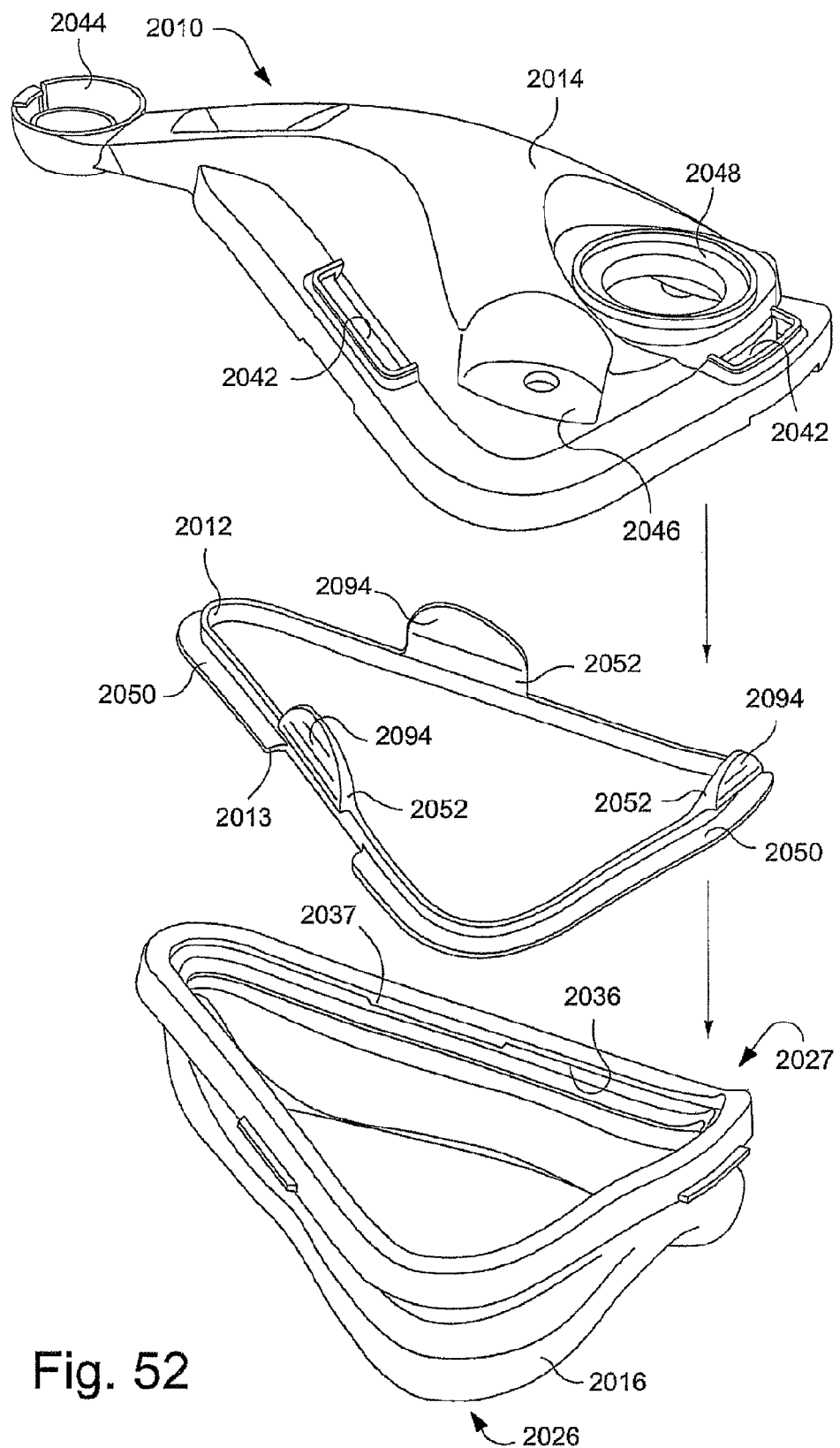
FIG. 52 is a top perspective view of a mask assembly including a cushion to frame assembly mechanism according to another embodiment of the present invention, the mask assembly in a pre-assembled condition.

FIGS. 50-51 illustrate alternative frame clip designs. FIG. 50 illustrates an over-center clip 1812 having a plurality of hinged links 1813, e.g., three links, that can be pivoted to secure the clip 1812 in place. FIG. 51 illustrates a ratchet clip 1912 having arms 1913, 1915 that are pivotable about hinge point P. The arms 1913, 1915 have toothed end portions 1917, 1919 that interlock to secure the clip 1912 in place.

10. Tenth Embodiment of Cushion to Frame Assembly Mechanism

FIGS. 52-71 illustrate a mask assembly 2010 including a cushion to frame assembly mechanism according to another embodiment of the present invention. In the illustrated embodiment, the cushion to frame assembly mechanism includes a cushion clip 2012 that is adapted to removably connect the cushion 2016 to the frame 2014.

As shown in FIGS. 52-55 and 62-66, the cushion 2016 includes a face-contacting portion 2026 and a non-face-contacting portion 2027. In an embodiment, the face contacting portion 2026 has a double wall construction, e.g., membrane and underlying support cushion. Also, in an embodiment, the cushion 2016 is constructed of liquid silicone rubber (LSR). However, other suitable materials may be used. As illustrated, the non-face-contacting portion 2027 of the cushion 2016 includes a retaining recess 2036 around the perimeter thereof that is adapted to engage the cushion clip 2012.

As shown in FIGS. 52-61, the frame 2014 includes an upper support member 2044 adapted to support a forehead support, lower headgear clip receptacles 2046 adapted to be engaged with clips provided to straps of a headgear assembly (not shown), and an annular elbow connection seal 2048 adapted to engage an inlet conduit, e.g., elbow. Also, the top wall of the frame 2014 includes a plurality of slots 2042 therethrough, e.g., three slots. In an embodiment, the frame 2014 is molded in one-piece with polycarbonate.

As shown in FIGS. 52-56 and 67-71, the cushion clip 2012, e.g., molded of plastic, has a hoop-like configuration that generally corresponds in shape to the cushion 2016 and frame 2014, e.g., generally triangular. In addition, the cushion clip 2012 is contoured to match the contour of the frame 2014 and cushion 2016. One or more flange portions 2050 are provided around the perimeter of the cushion clip 2012. Also, the cushion clip 2012 includes a plurality of clip portions 2052. As illustrated, the cushion clip 2012 includes the same number of clip portions 2052 as slots 2042 on the frame 2014, e.g., three clip portions.

Figure 53:
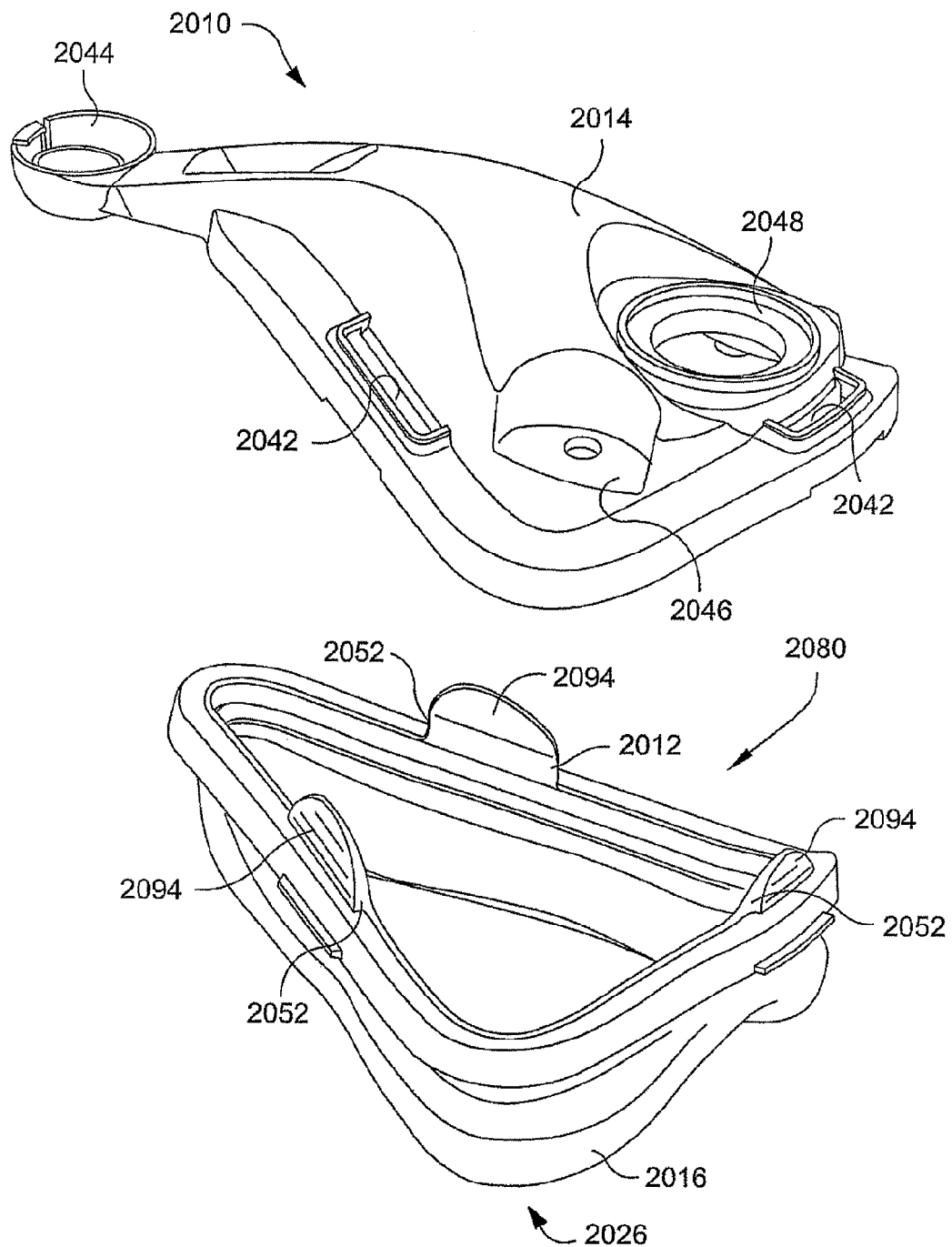
FIG. 53 is a top perspective view of the mask assembly shown in FIG. 52, the mask assembly in a partial assembled condition.
Figure 54:
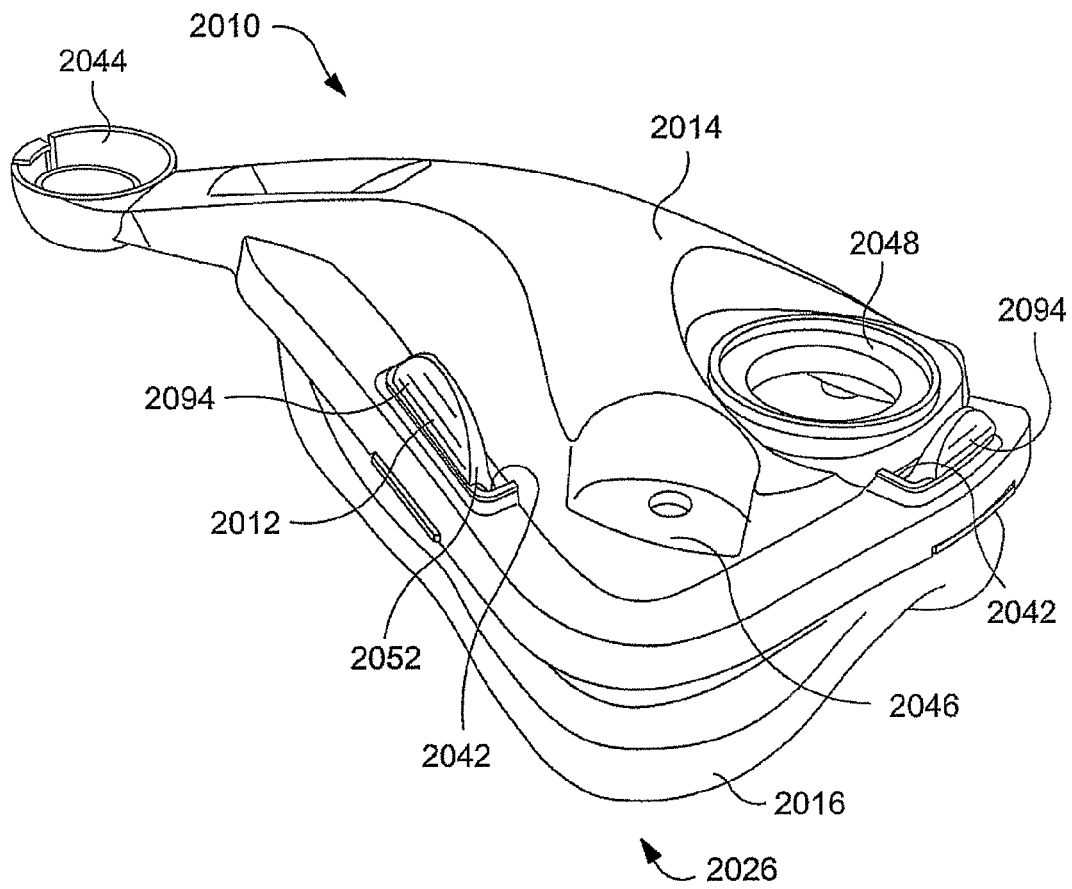
FIG. 54 is a top perspective view of the mask assembly shown in FIG. 52, the mask assembly in an assembled condition.
Figure 55:
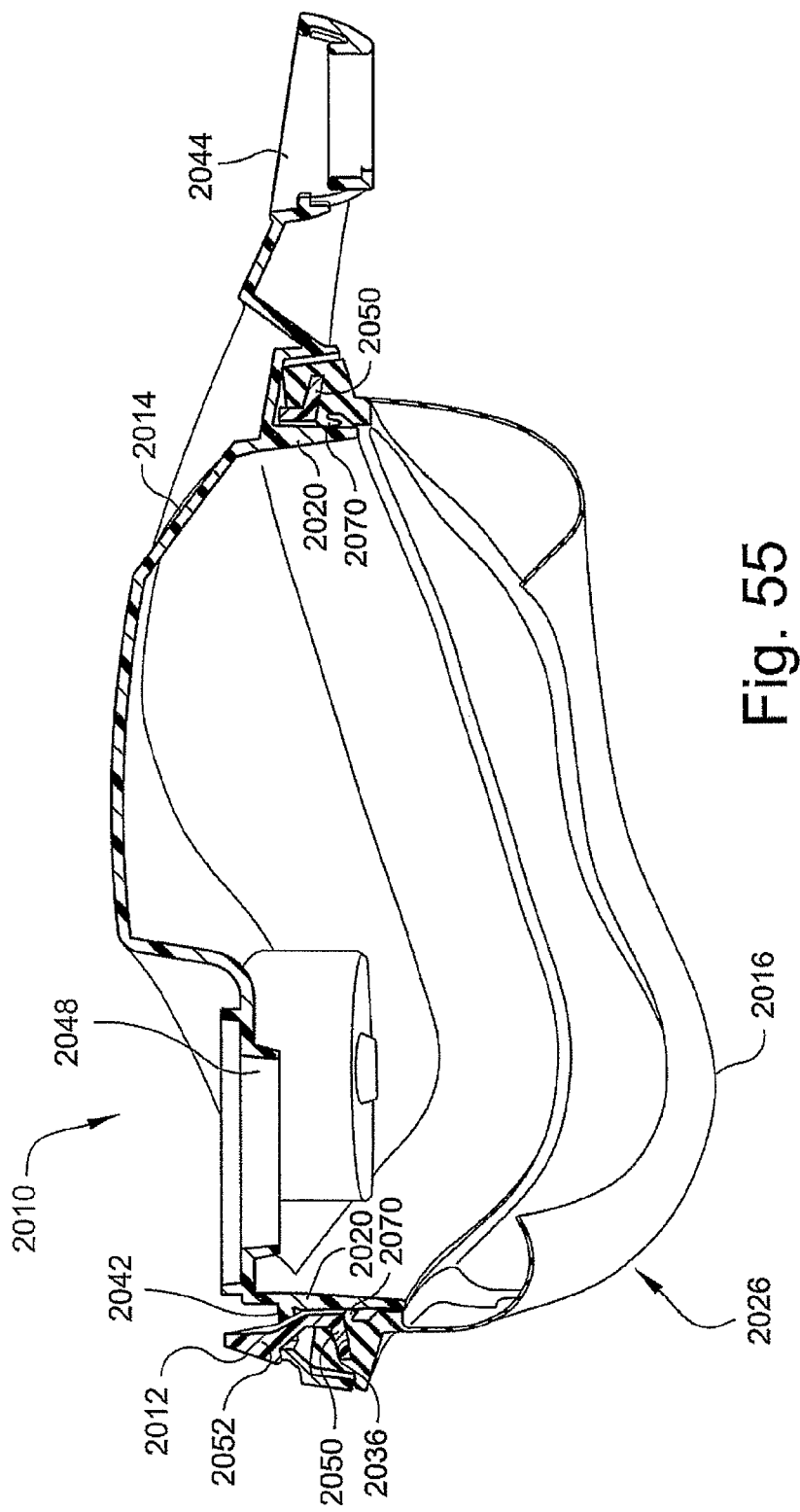
FIG. 55 is a cross-sectional view of the mask assembly shown in FIG. 52.
Figure 56:
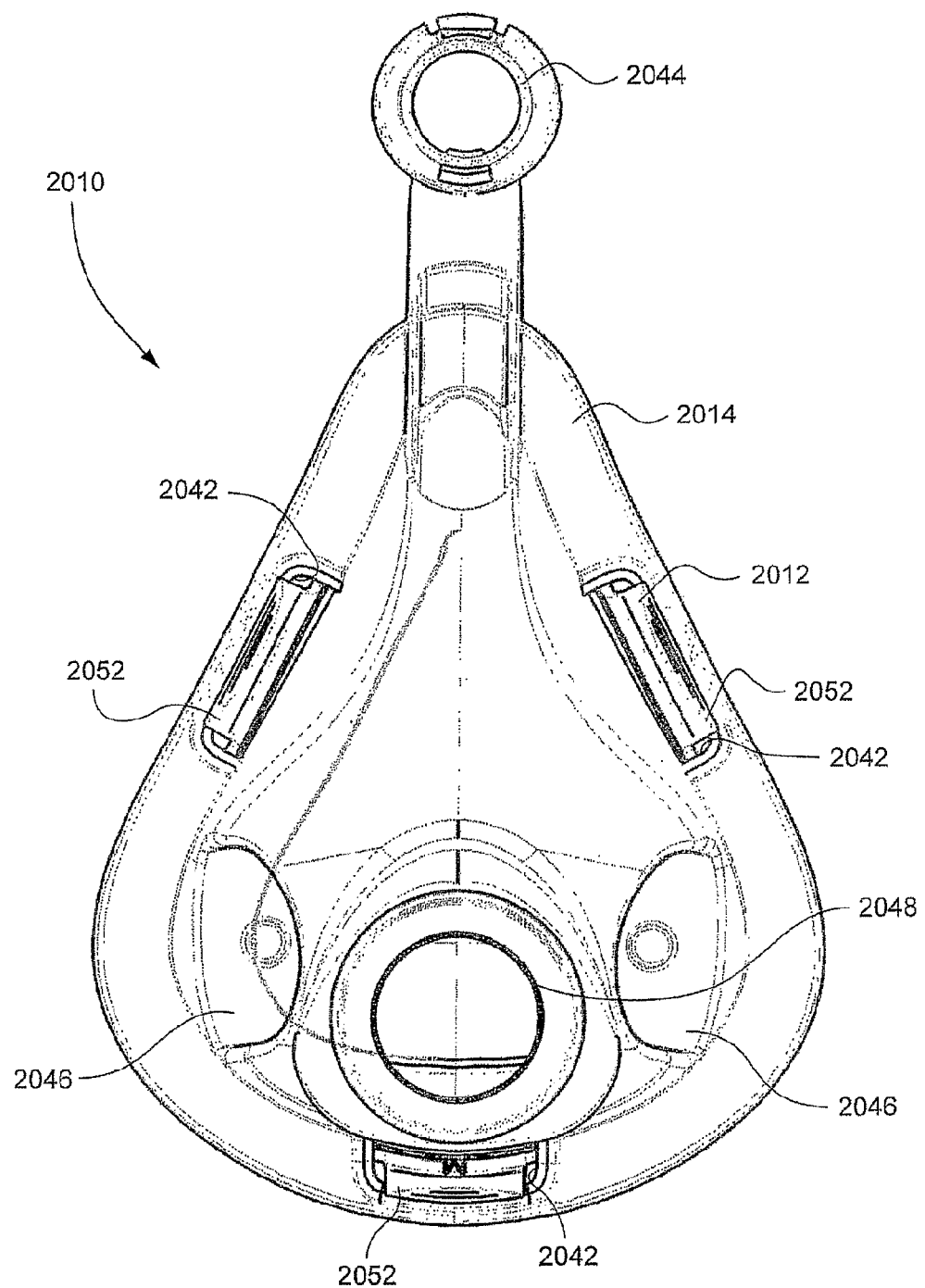
FIG. 56 is a top view of the mask assembly shown in FIG. 52.
Figure 57:
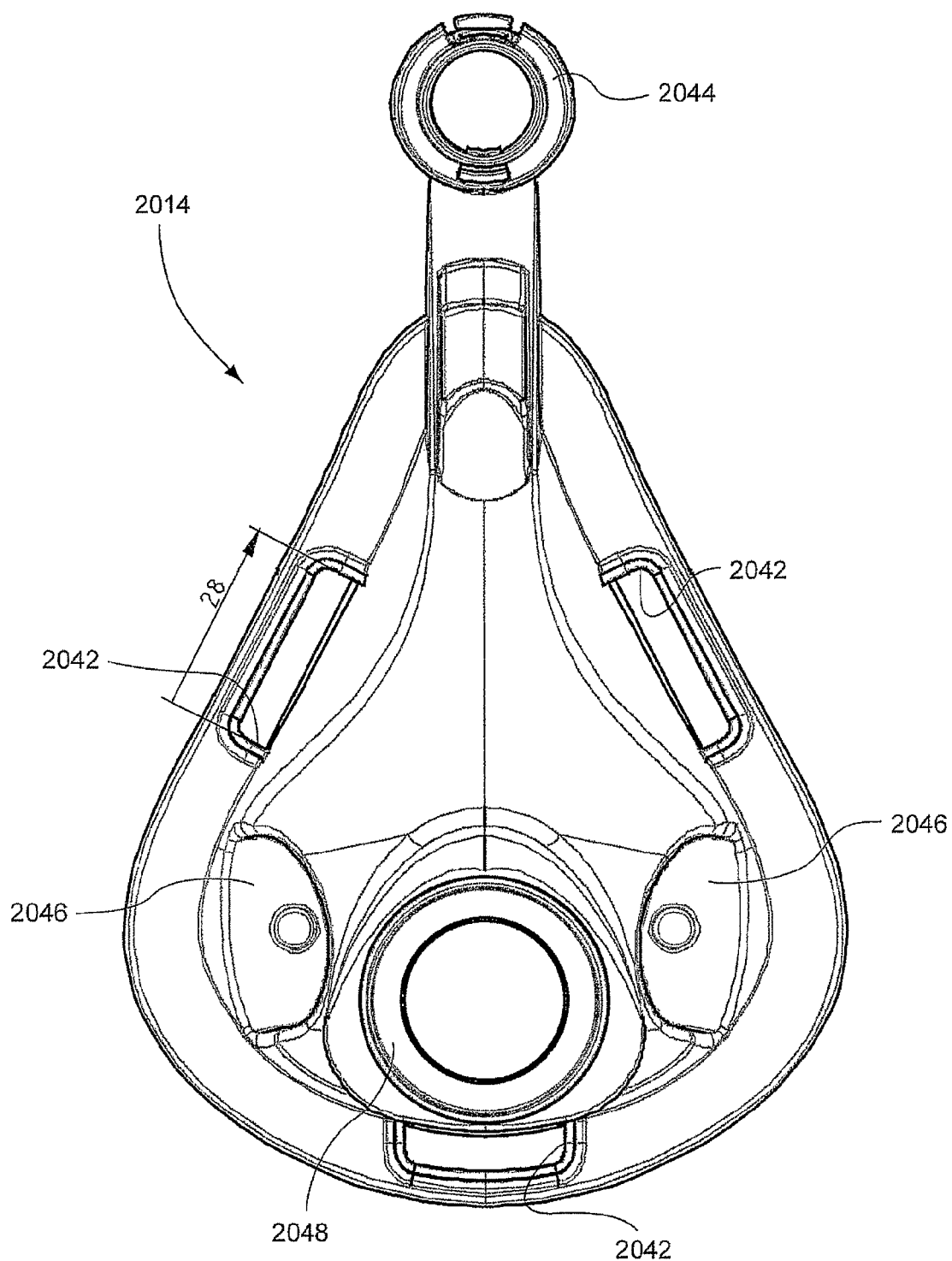
FIGS. 57-61 are various views of the frame of the mask assembly shown in FIG. 52 and showing exemplary dimensions of an embodiment.
Figure 58:
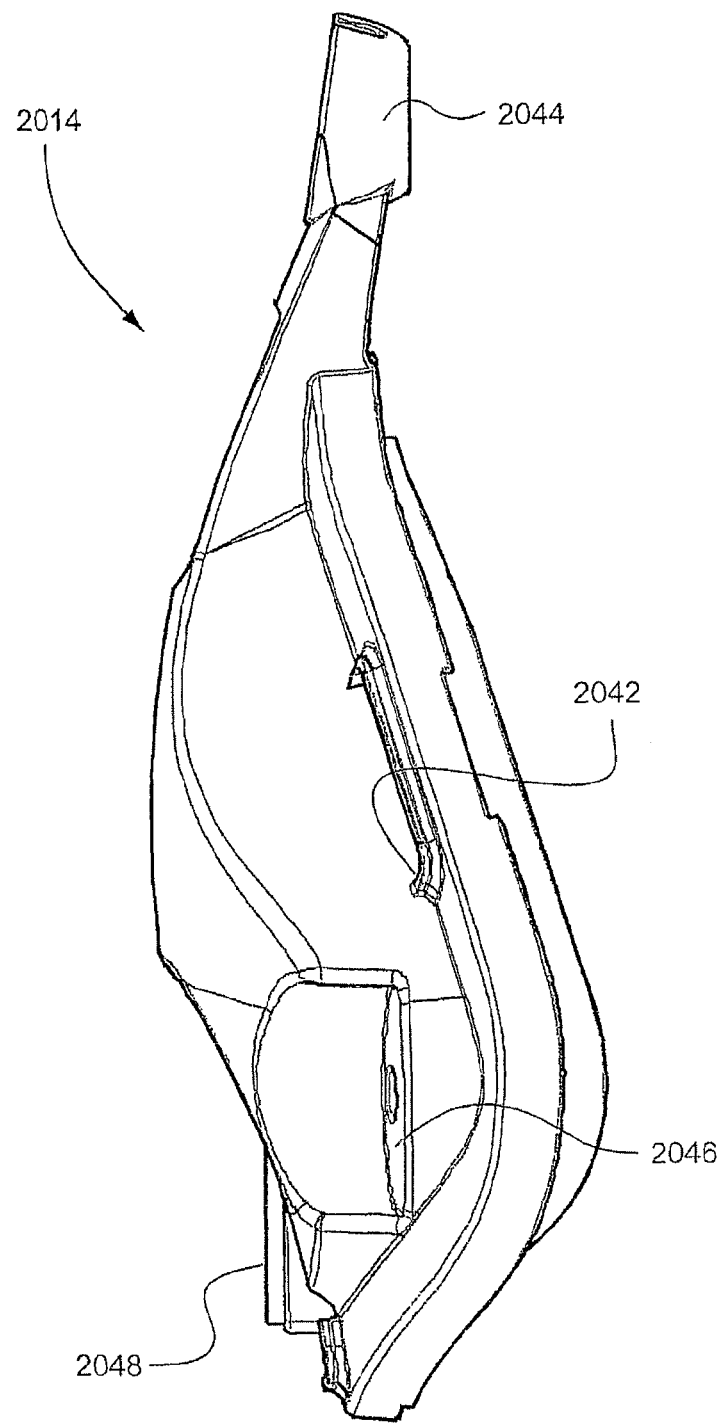
Figure 59:
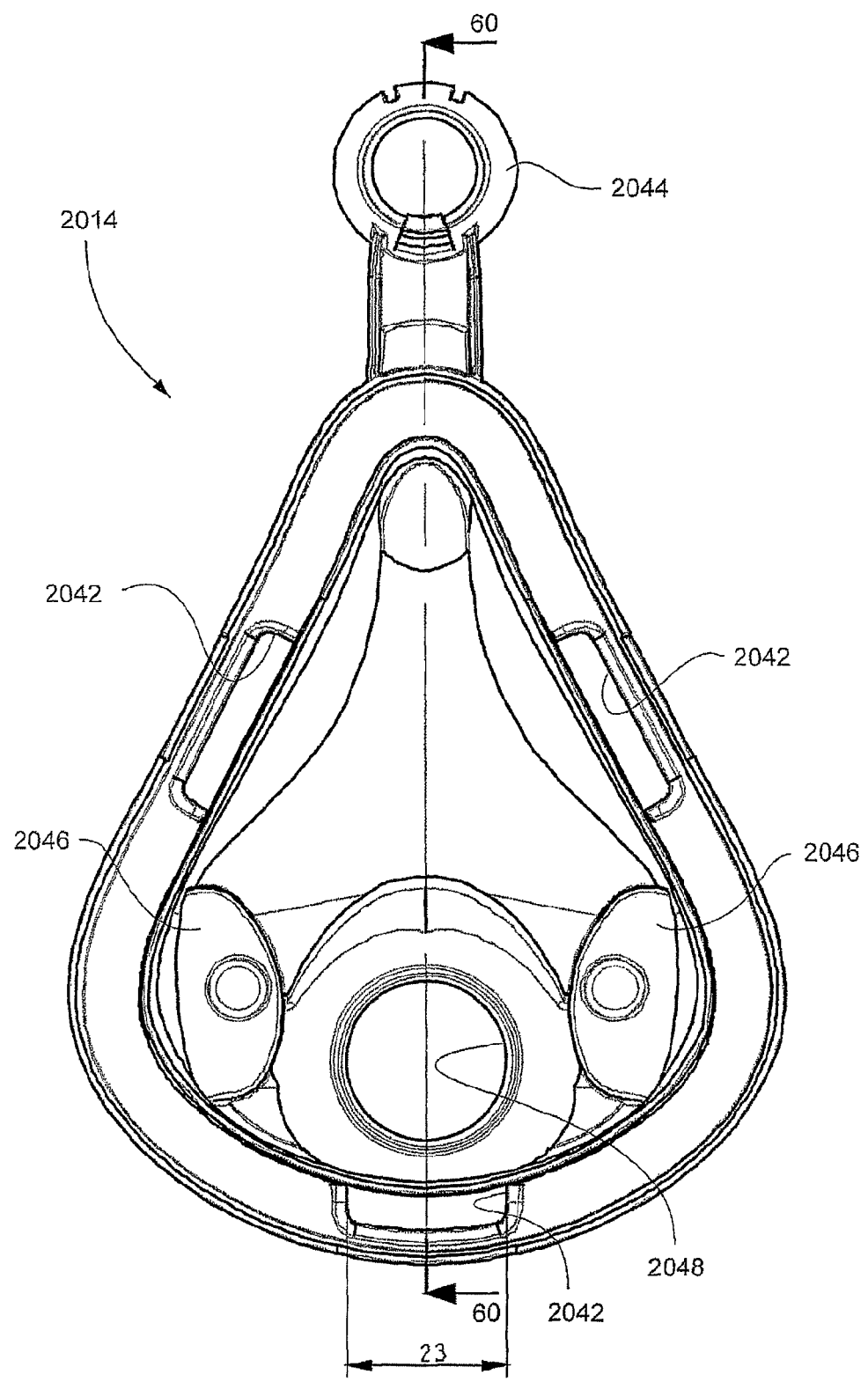
Figure 60:
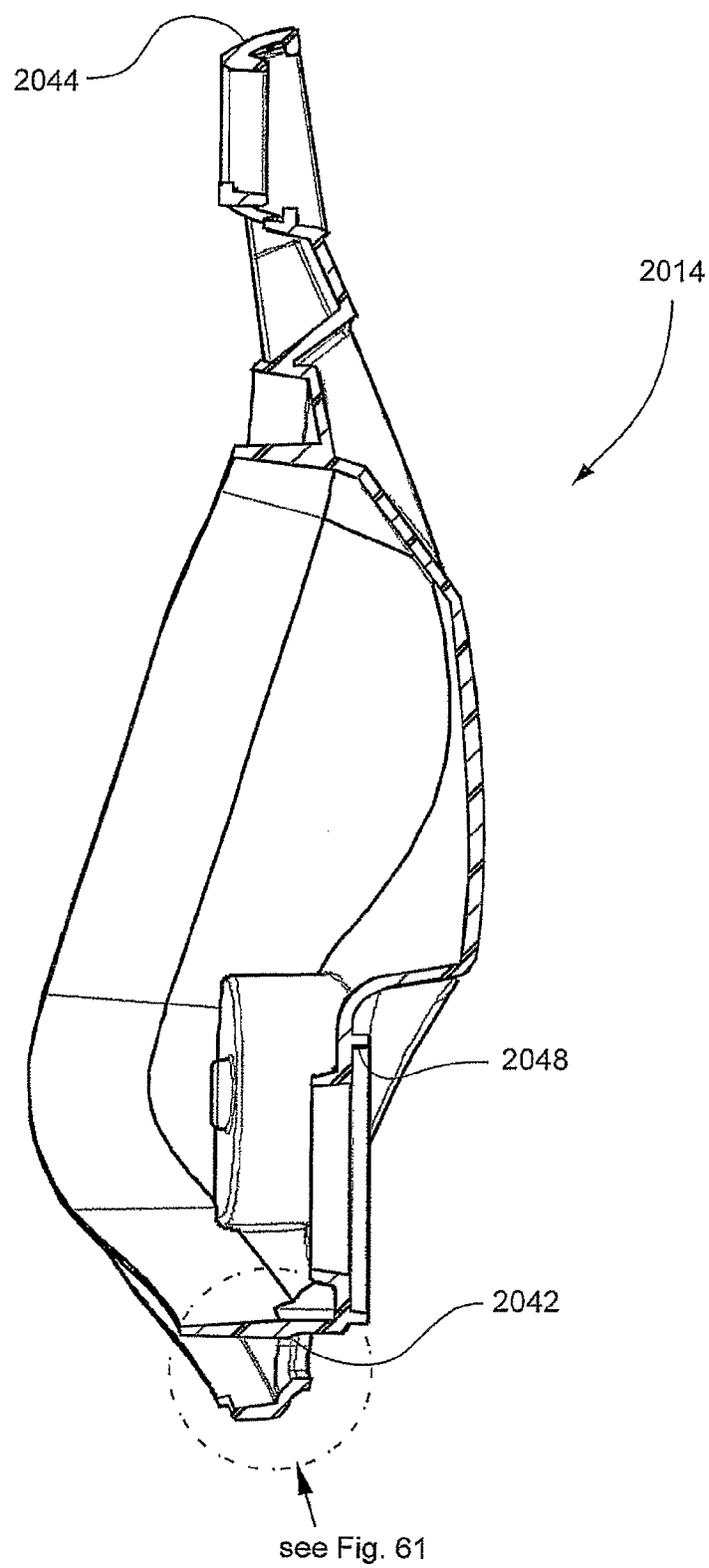
Figure 61:
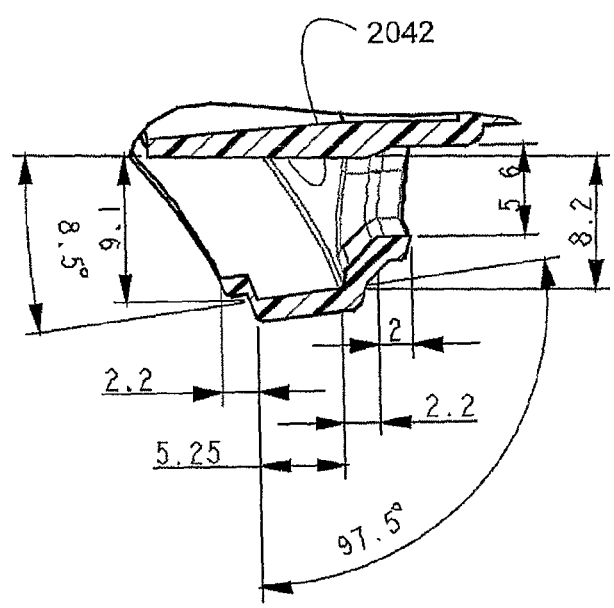
Figure 62:
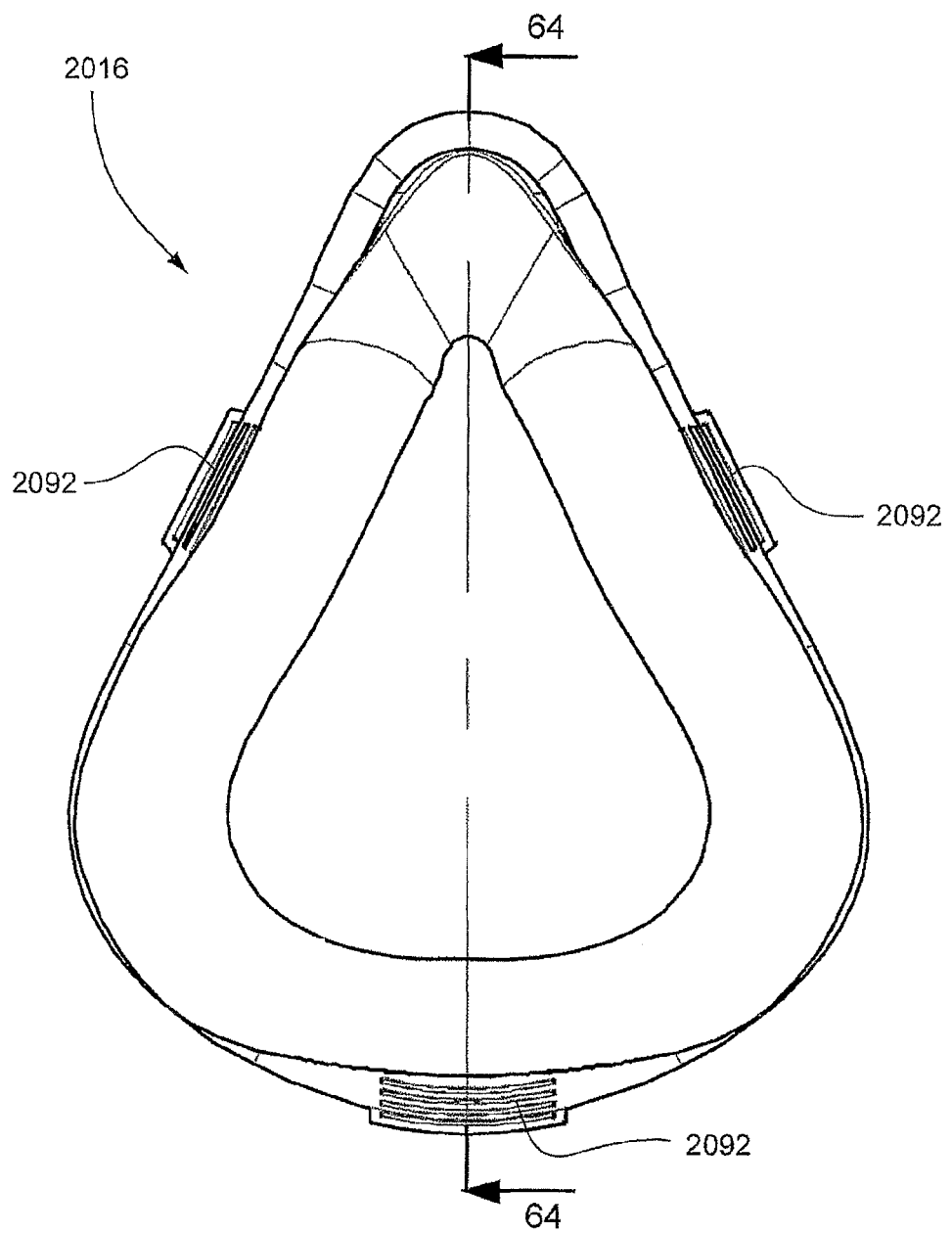
FIGS. 62-66 are various views of the cushion of the mask assembly shown in FIG. 52 and showing exemplary dimensions of an embodiment.
Figure 63:
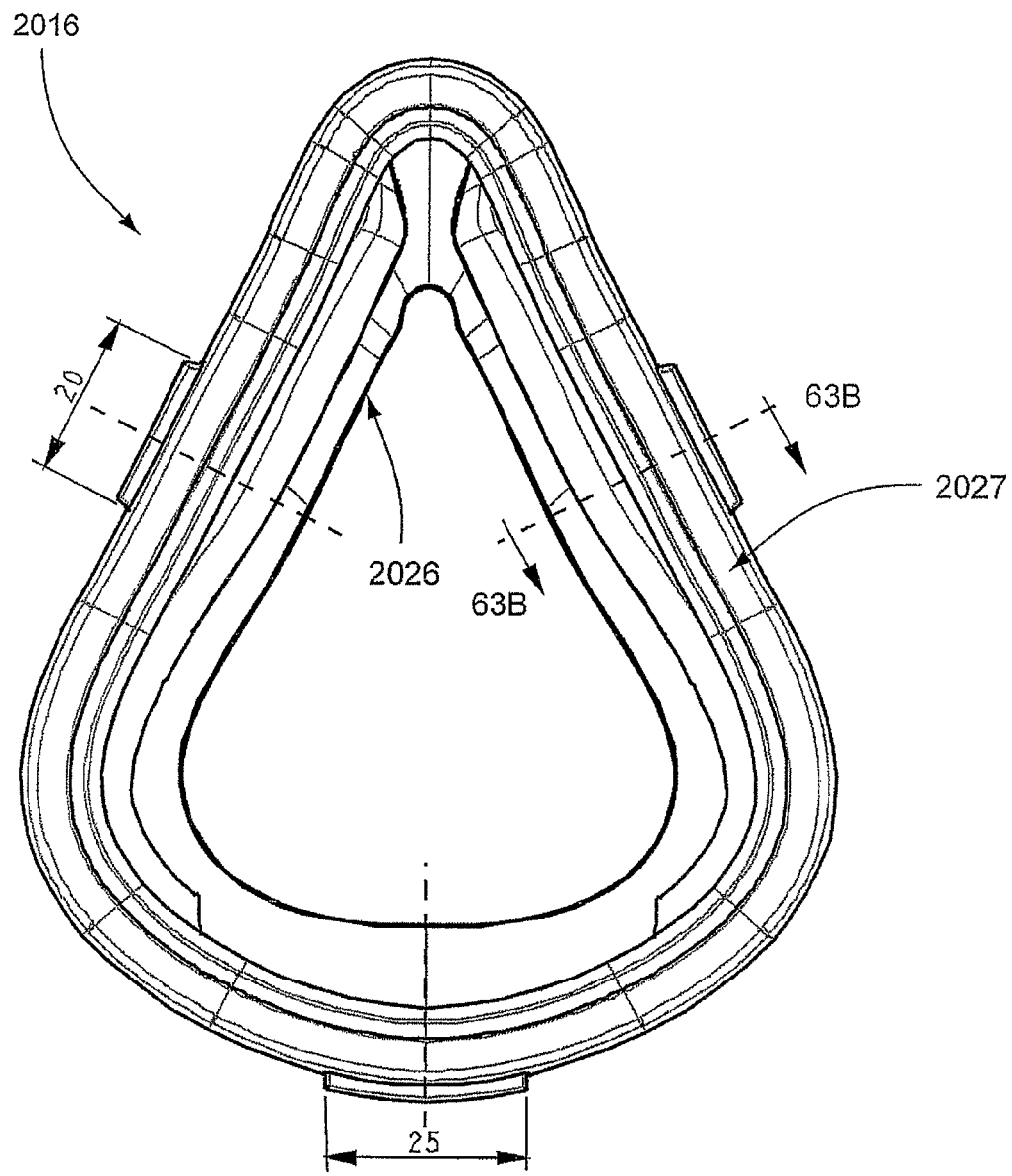
Figure 63B:
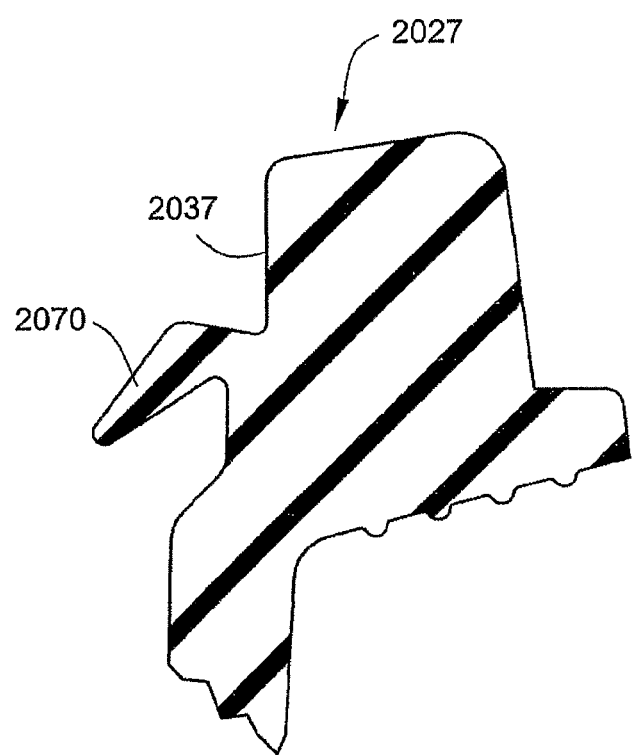
Figure 64:
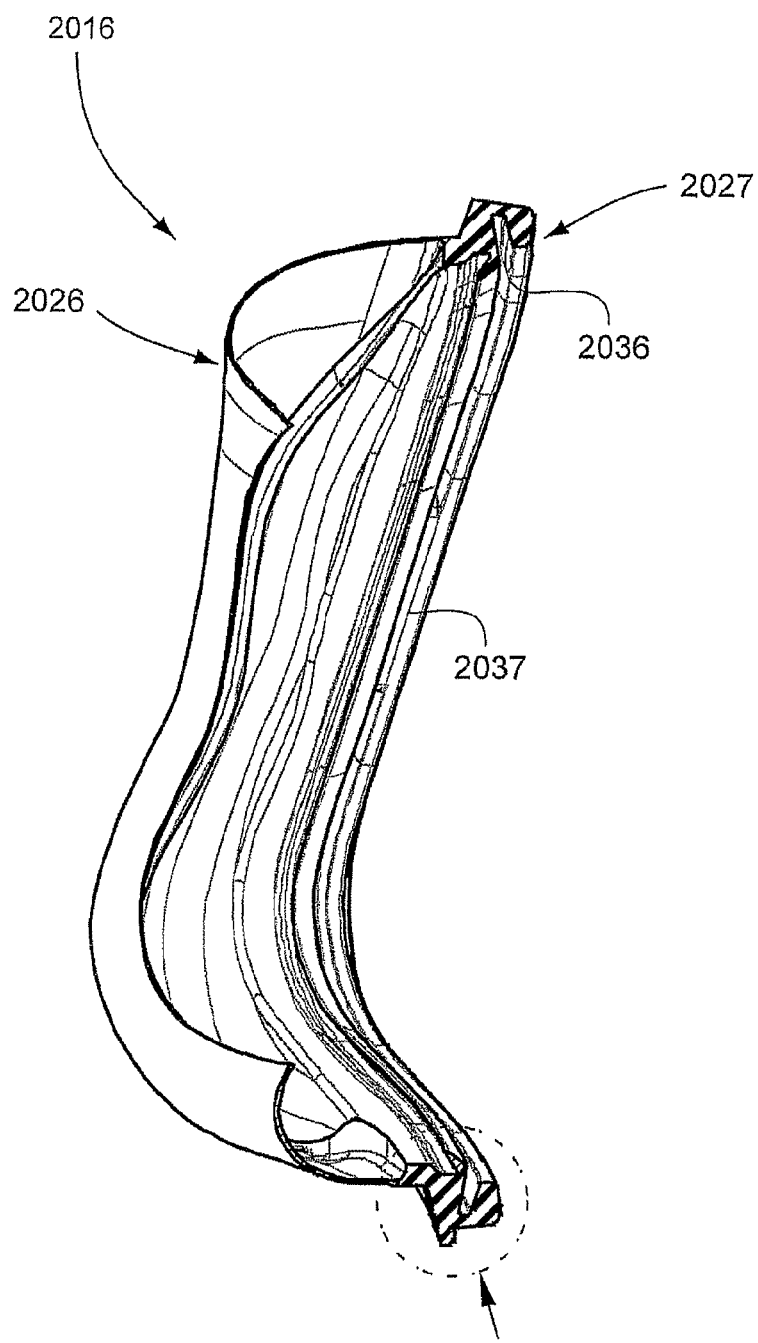
Figure 65:
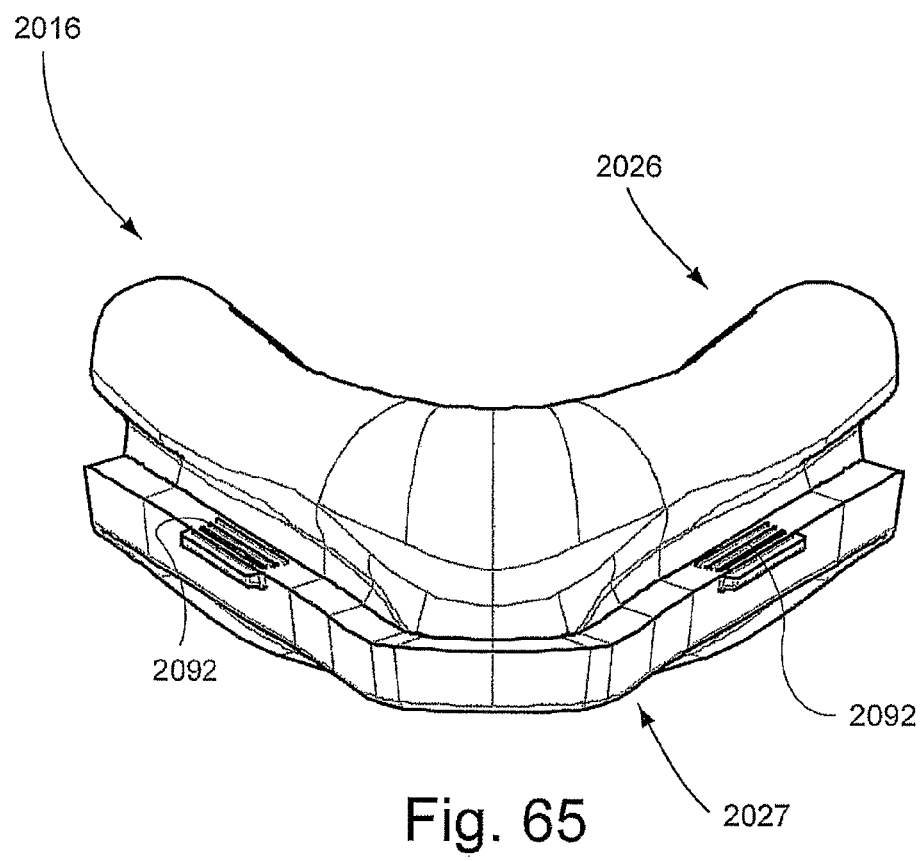

As shown in FIG. 53, the cushion clip 2012 is first assembled or interlocked with the cushion 2016 to provide a cushion clip/cushion sub-assembly 2080. Specifically, the cushion 2016 is assembled around the cushion clip 2012 by engaging the flange portions 2050 of the cushion clip 2012 within the retaining recess 2036 of the cushion 2016. The cushion clip/cushion sub-assembly 2080 is then engaged with the frame 2014 by inserting the clip portions 2052 of the cushion clip 2012 into respective slots 2042 of the frame 2014. The clip portions 2052 are adapted to engage respective slots 2042 with a snap-fit. FIG. 54-56 illustrate the assembled mask assembly 2010 with the cushion clip/cushion sub-assembly 2080 retained at three perimeter points on the frame 2014.

As best shown in FIGS. 52, 63B, 64, and 70, the cushion clip 2012 includes slots 2013 on opposing sides thereof, i.e., created by breaks in the flange portions 2050, that interlock or engage with respective solid sections 2037 provided in the retaining recess 2036 on opposing sides of the cushion 2016. The two solid sections 2037 assist with the correct orientation or alignment of the cushion clip 2012 onto the cushion 2016.

Figure 66:
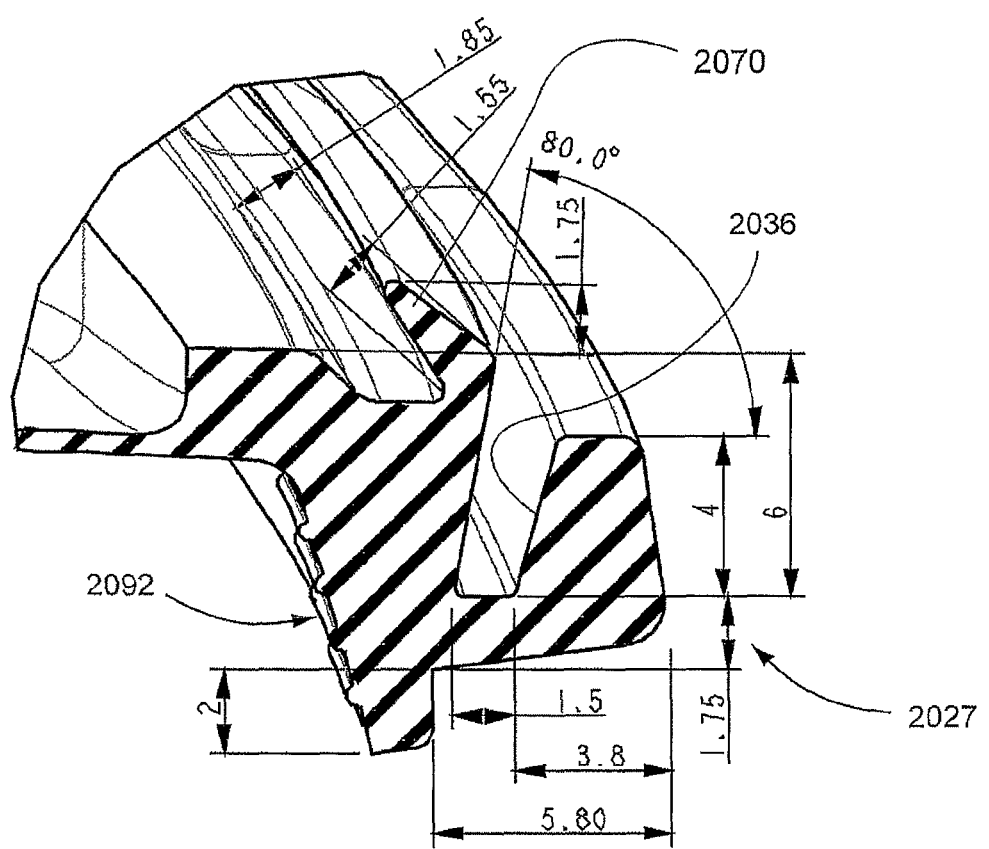
Figure 67:
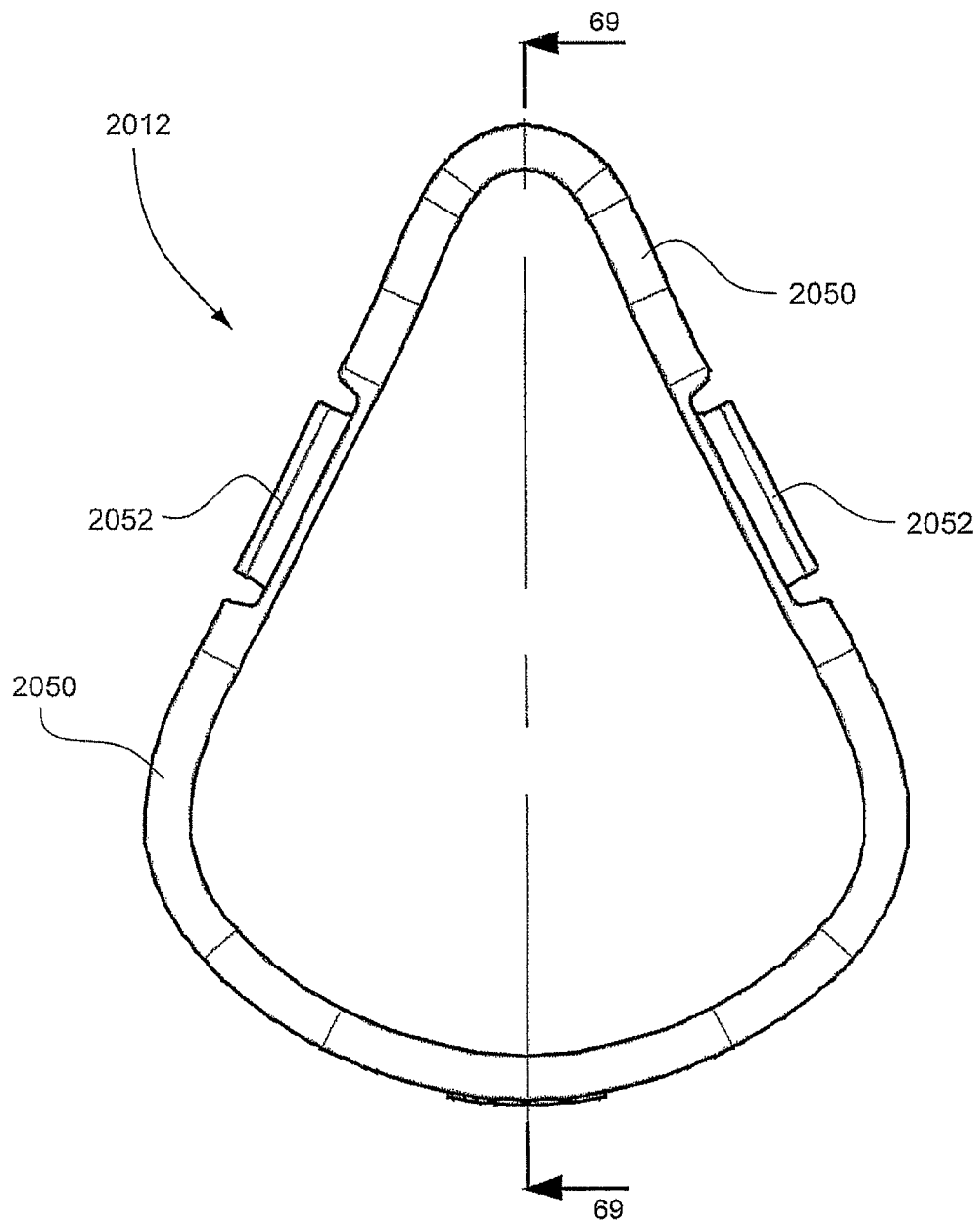
Figure 70:
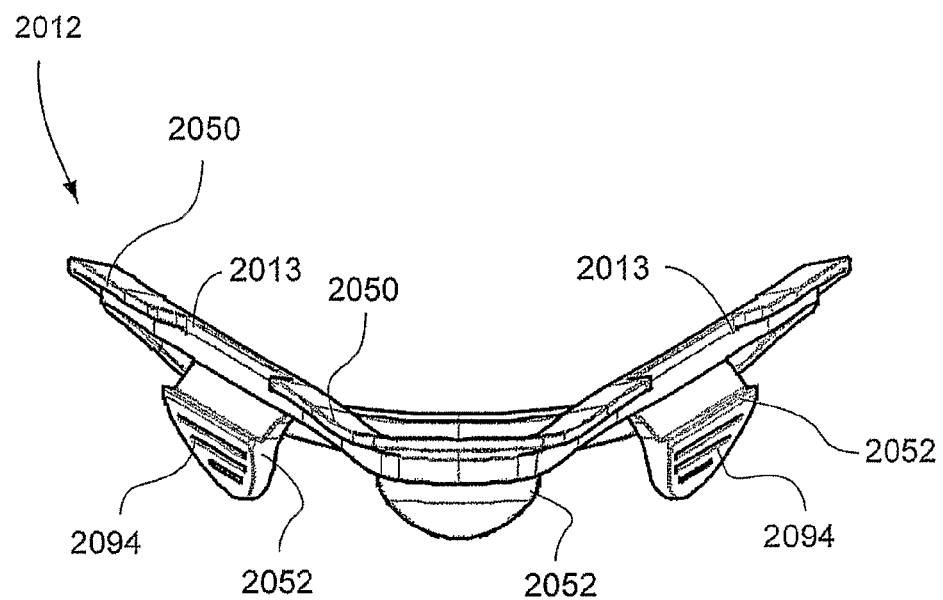
Figure 71:
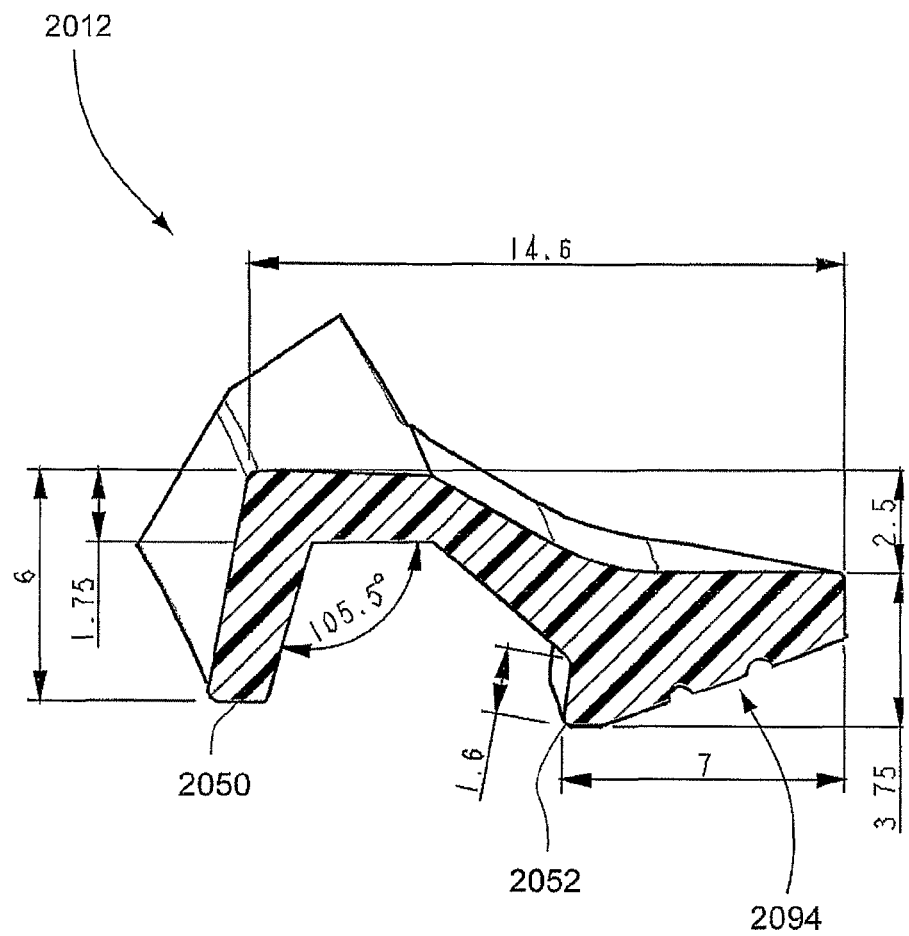
Figure 72:
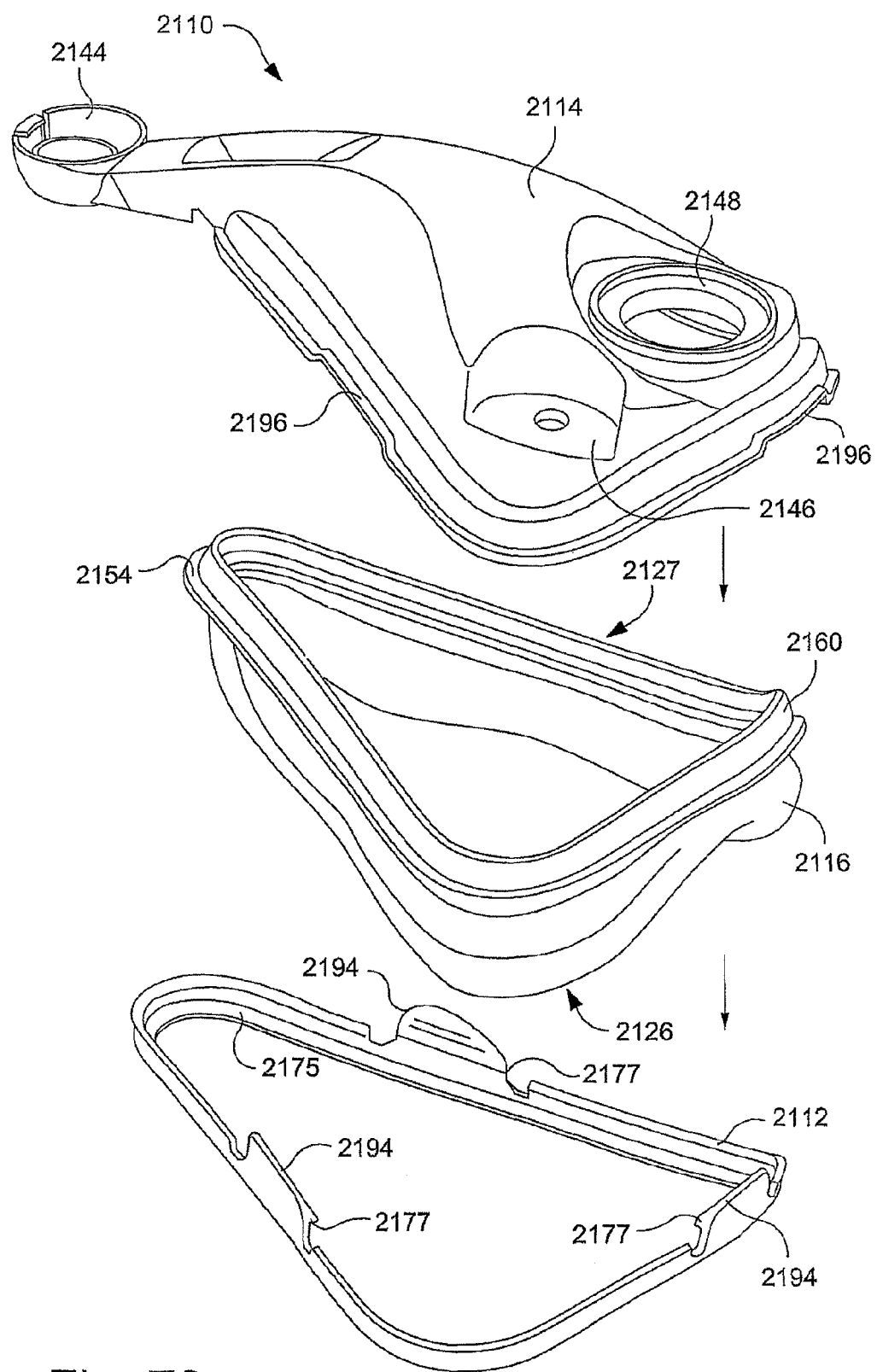
FIG. 72 is a top perspective view of a mask assembly including a cushion to frame assembly mechanism according to another embodiment of the present invention, the mask assembly in a pre-assembled condition.

As best shown in FIGS. 55 and 66, the cushion 2016 includes a resiliently flexible lip 2070 that resiliently engages the inner wall 2020 of the frame 2014 to provide a seal in use. Also, the cushion 2016 includes finger grips 2092 on a flange portion thereof to facilitate assembly (e.g., see FIGS. 62, 65, and 66).

The clip portions 2052 of the cushion clip 2012 include contoured finger grips 2094 to facilitate assembly. As illustrated, the finger grips 2094 are relatively thick for ease of finding and use.

FIGS. 92-105 illustrate a mask assembly substantially similar to the mask assembly 2010 described above. Therefore, similar components are indicated with similar reference numerals. In contrast, the cushion clip 2012 of FIGS. 92-105 includes a continuous flange 2050 that extends or runs around the entire perimeter of the cushion clip 2012. Thus, the cushion clip 2012 of FIGS. 92-105 does not include any slots along the flange 2050, and the two solid sections in the cushion retaining recess of the cushion shown in FIGS. 52-71 may be removed. Removal of the interlocking feature, i.e., slot of clip interlocked with solid section of cushion, provides more support to the cushion 2016 to prevent leak between the cushion and the frame. The continuous flange 2050 of FIGS. 92-105 also makes the cushion clip 2012 stiffer.

Figure 95:
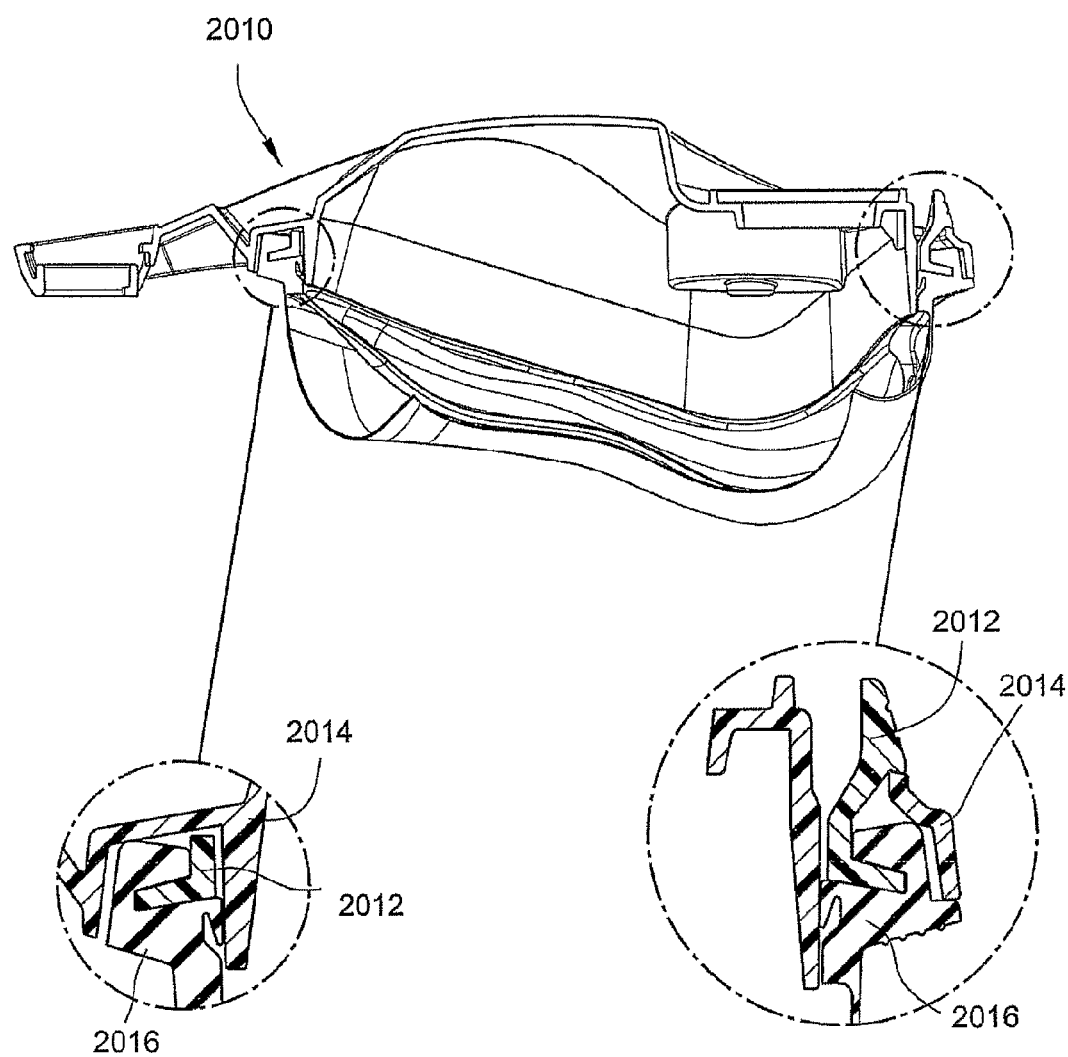
FIG. 95 are cross-sectional views of the assembled mask assembly shown in FIG. 94.
Figure 96:
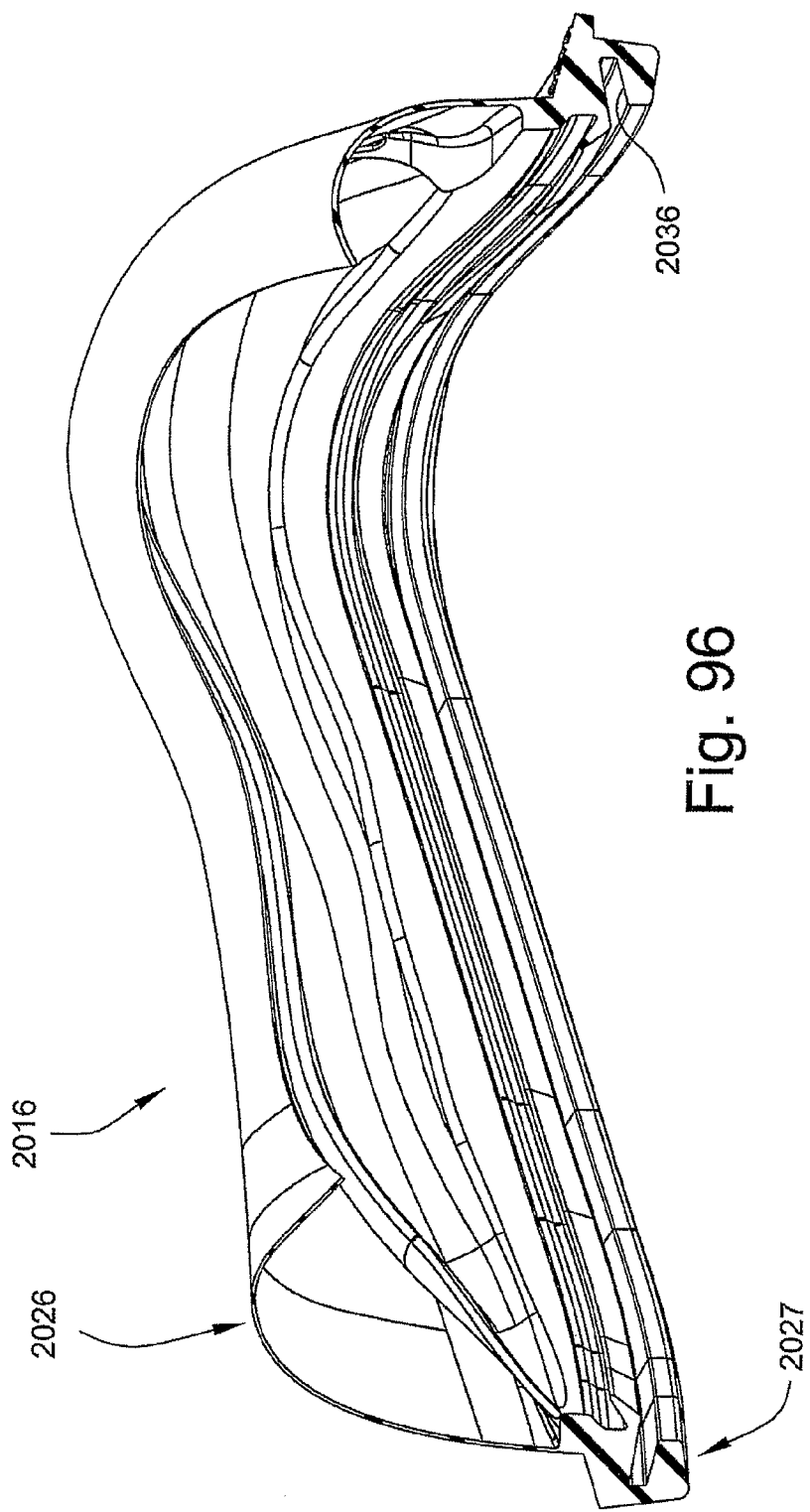
FIG. 96 is a cross-sectional view of the cushion of the mask assembly shown in FIG. 92.
Figure 97:
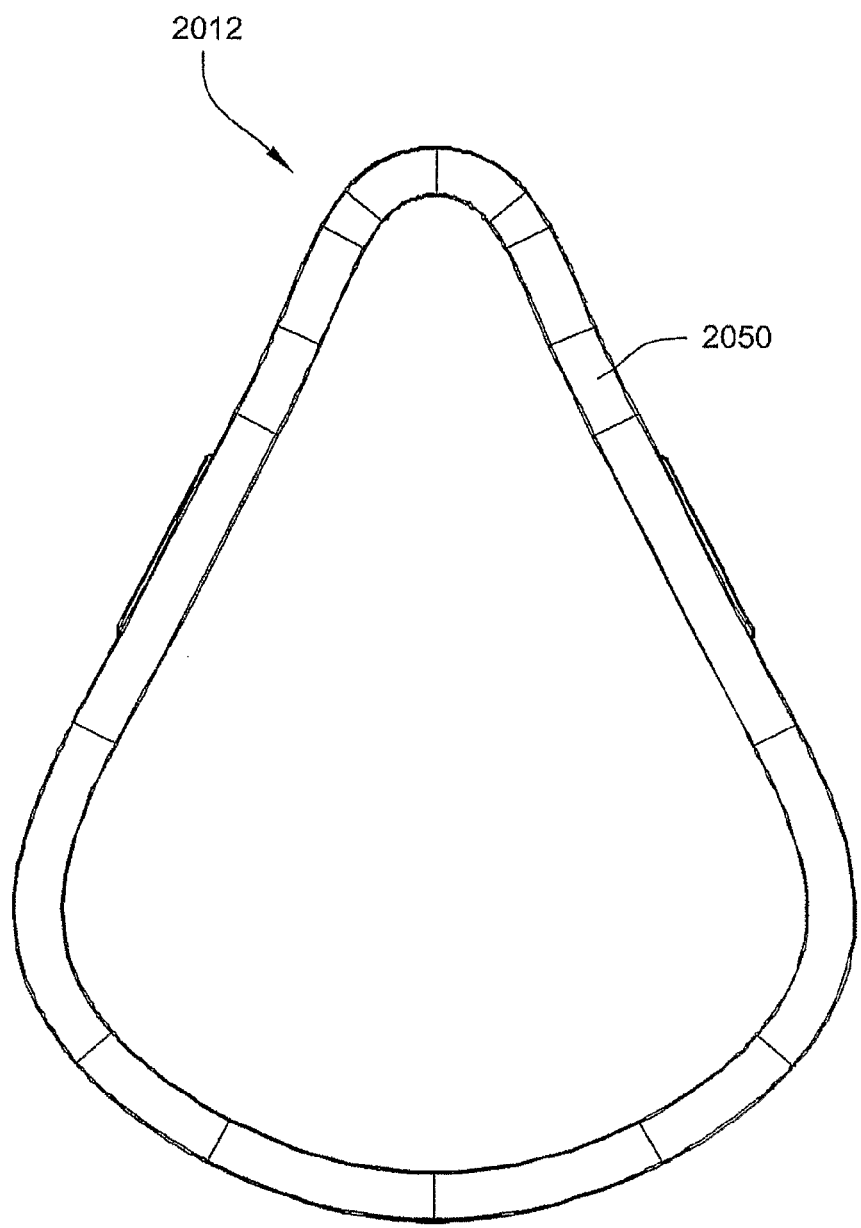
FIGS. 97-105 are various views of the cushion clip of the mask assembly shown in FIG. 92 and showing exemplary dimensions of an embodiment.
Figure 98:
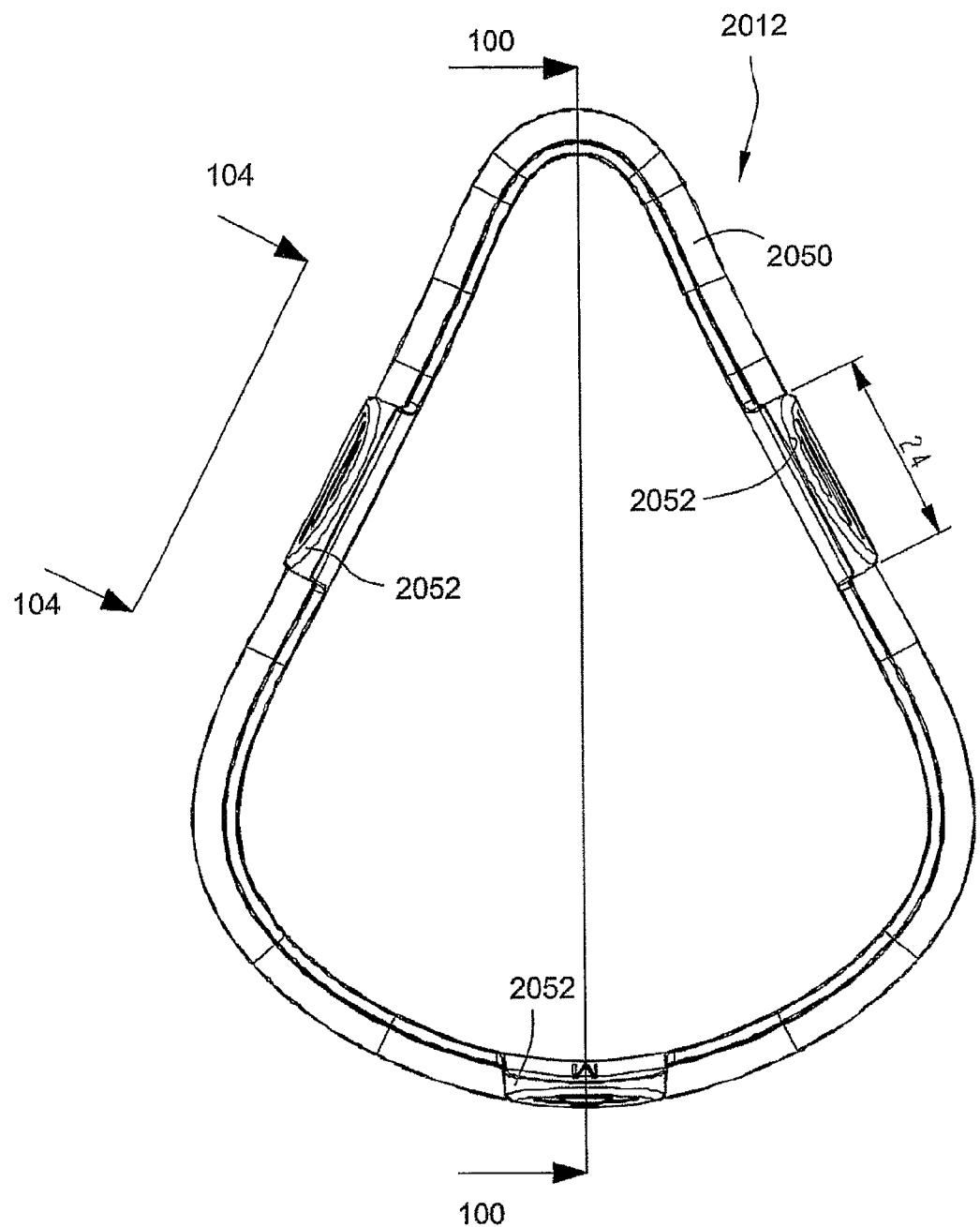
Figure 99:
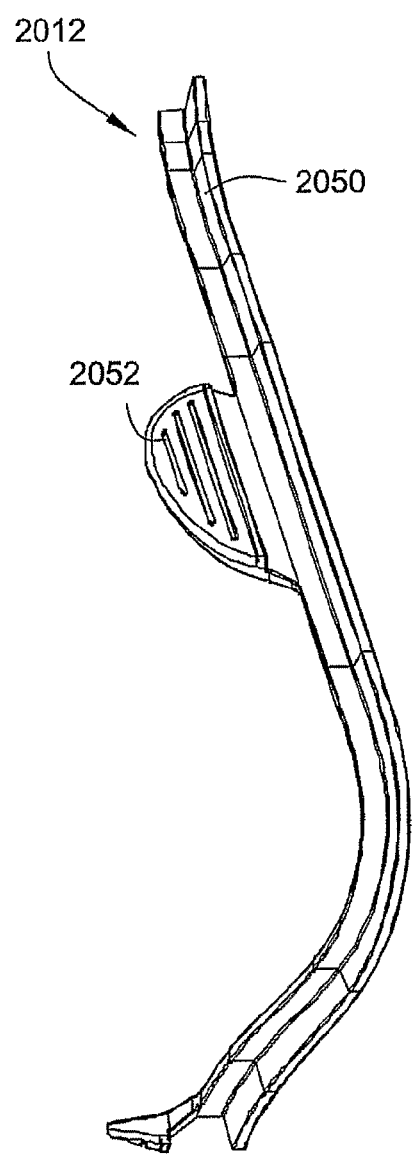
Figure 100:
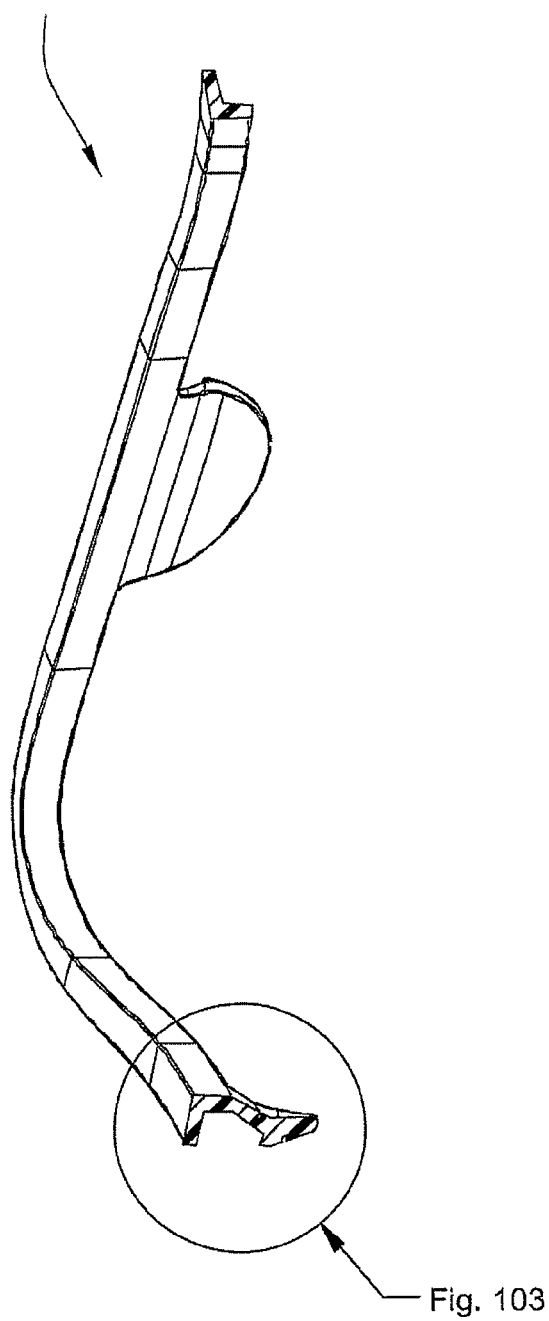
Figure 101:
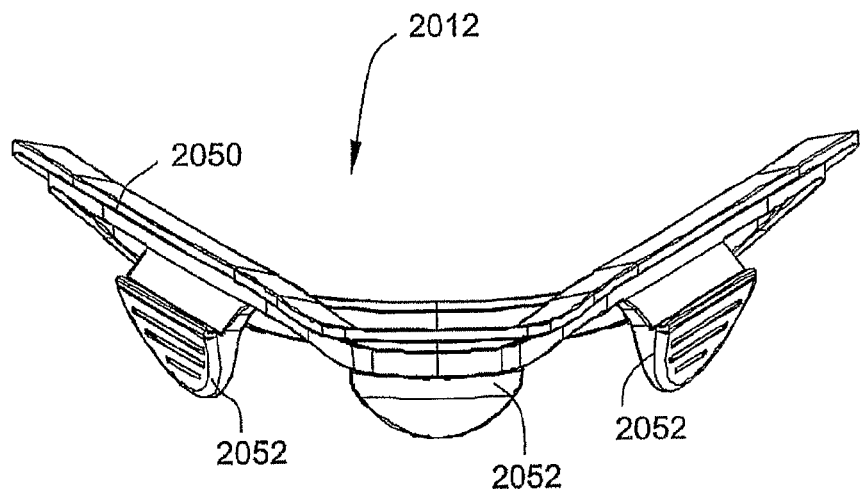
Figure 102:
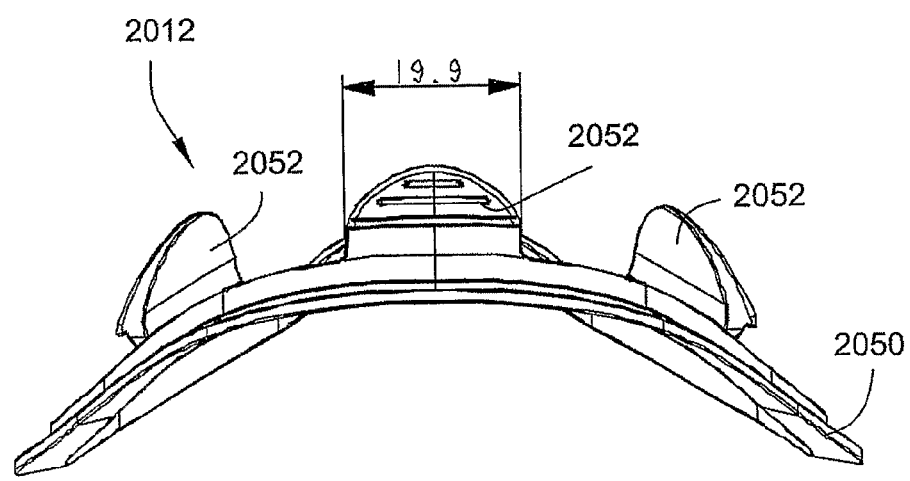
Figure 103:
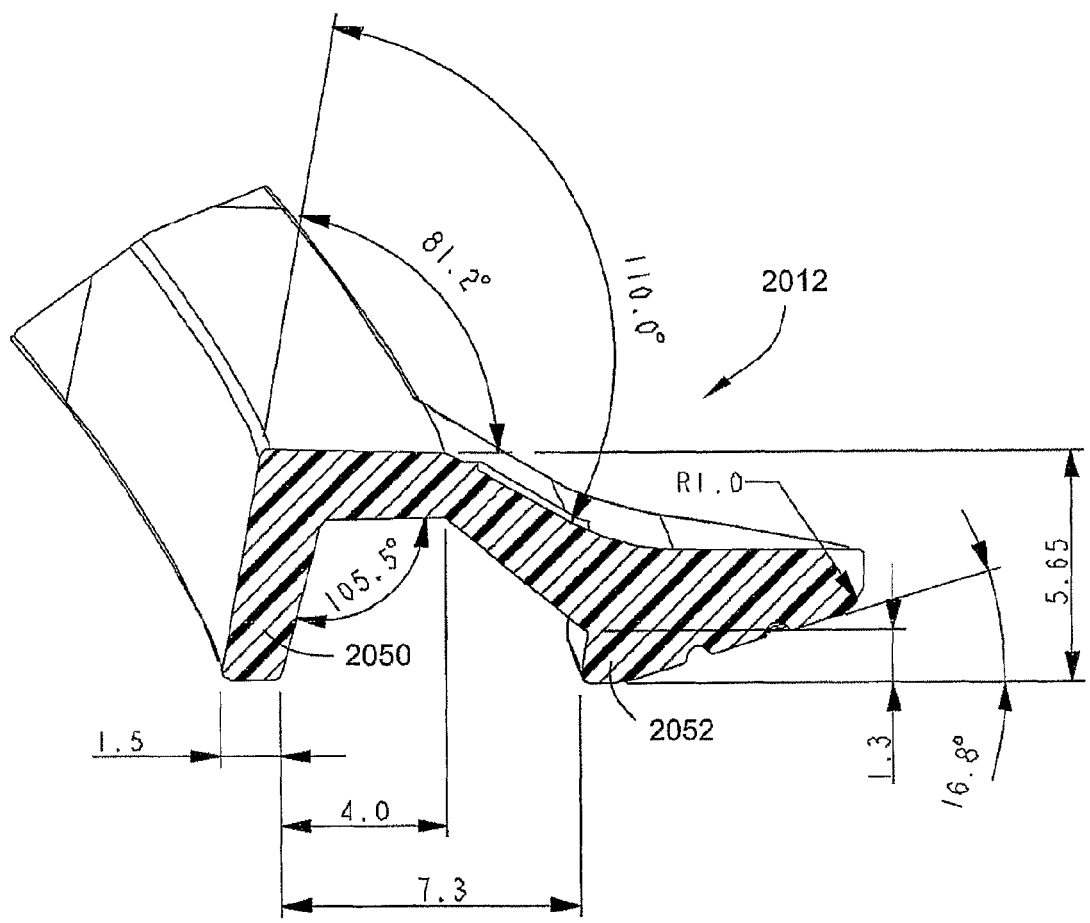
Figure 104:
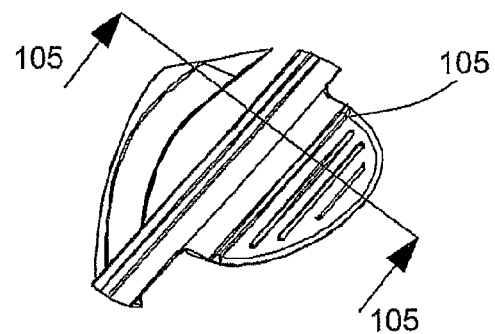
Figure 105:
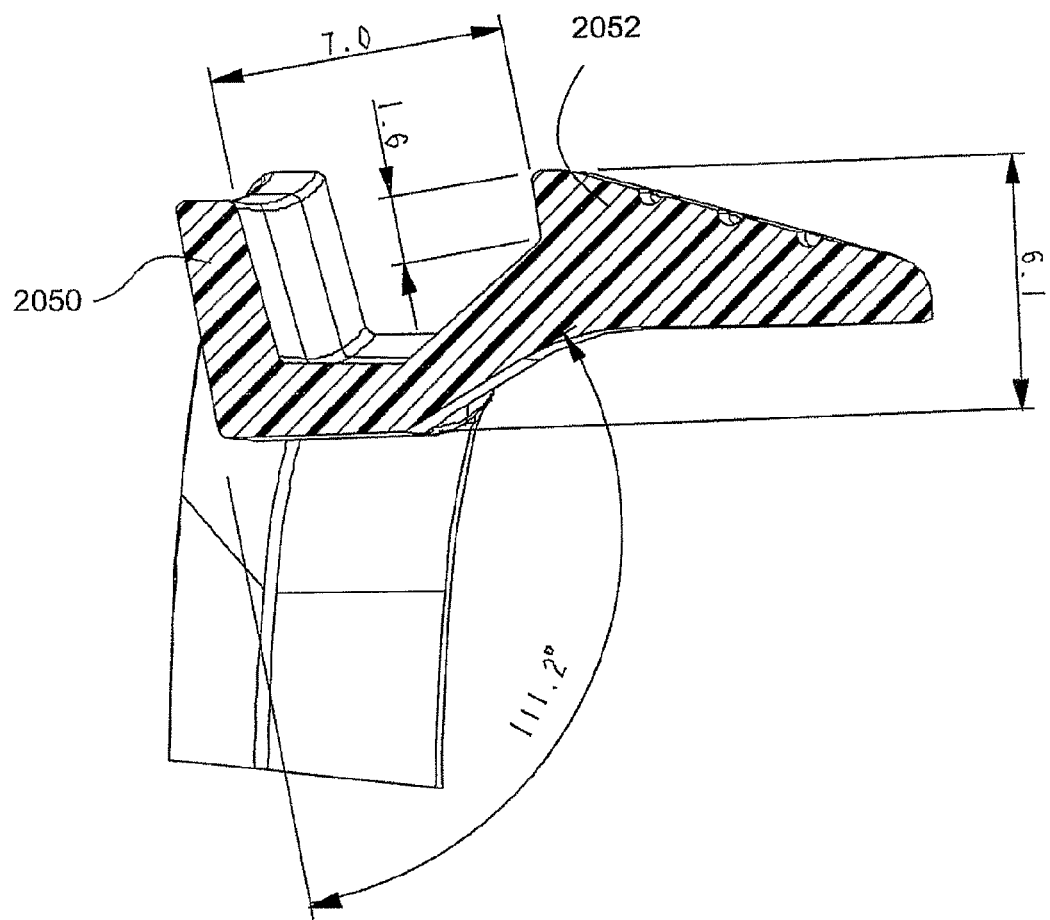
Figure 106:
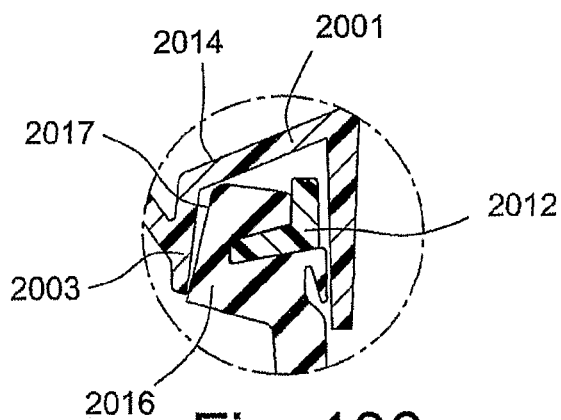
FIGS. 106-107 are cross-sectional views at top and bottom portions of a mask assembly according to another embodiment of the present invention.
Figure 107:
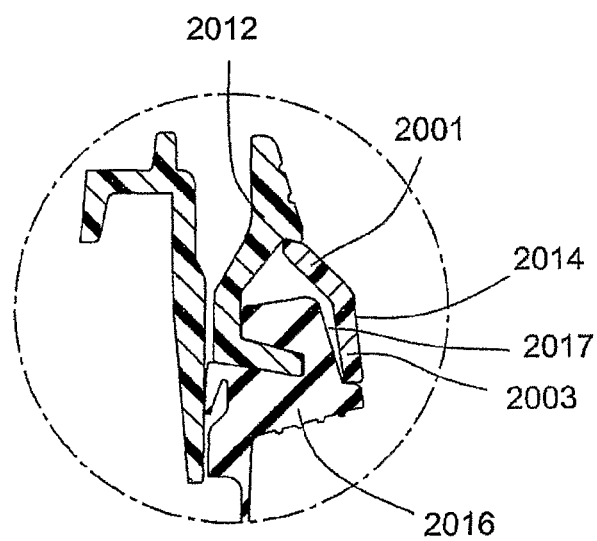

FIGS. 55 and 95 illustrate the assembled cushion 2016, cushion clip 2012, and frame 2014 at top and bottom portions of the mask assembly. FIGS. 106 and 107 illustrate an alternative embodiment at top and bottom portions of the mask assembly. For example, the top wall 2001 of the frame 2014 at top and bottom portions thereof may have a steeper angle or incline for styling or aesthetics purposes. Also, the exterior or outer surface 2017 of the cushion 2016 may be angled or inclined. The inclined outer surface 2017 varies the gap or distance between the outer surface 2017 and the inner surface of the frame side wall 2003. This may facilitate reduction of the possible movement range between the cushion 2016 and the frame wall 2003, which in turn reduces system leakage under side loading.

In each of the embodiments, the cushion clip 2012 could potentially be over-molded with the cushion 2016.

11. Eleventh Embodiment of Cushion to Frame Assembly Mechanism

FIGS. 72-91 illustrate a mask assembly 2110 including a cushion to frame assembly mechanism according to another embodiment of the present invention. In the illustrated embodiment, the cushion to frame assembly mechanism includes an integrated lip seal design and a frame clip 2112 that is adapted to removably connect the cushion 2116 to the frame 2114.

As shown in FIGS. 72-81, the frame 2114 includes an upper support member 2144 adapted to support a forehead support, lower headgear clip receptacles 2146 adapted to be engaged with clips provided to straps of a headgear assembly (not shown), and an annular elbow connection seal 2148 adapted to engage an inlet conduit, e.g., elbow. Also, the frame 2114 provides a cushion connection including an outer wall 2120 and an inner wall 2122 that extend around the perimeter of the frame 2114. The outer and inner walls 2120, 2122 define a retaining recess 2136 therebetween. In an embodiment, the frame 2114 is molded in one-piece with polycarbonate.

As shown in FIGS. 72-75 and 82-86, the cushion 2116 includes a face-contacting portion 2126 and a non-face-contacting portion 2127. In an embodiment, the face contacting portion 2126 has a double wall construction, e.g., membrane and underlying support cushion. Also, in an embodiment, the cushion 2116 is constructed of liquid silicone rubber (LSR). However, other suitable materials may be used. The non-face-contacting portion 2127 of the cushion 2116 includes a retaining portion 2160. As illustrated, the end 2161 of the retaining portion 2160 has an angled or pointed configuration. In addition, the non-face-contacting portion 2127 provides a resiliently flexible lip 2170. A space 2171 is provided behind the lip 2170 to provide the lip 2170 with a range of movement in use.

Figure 73:
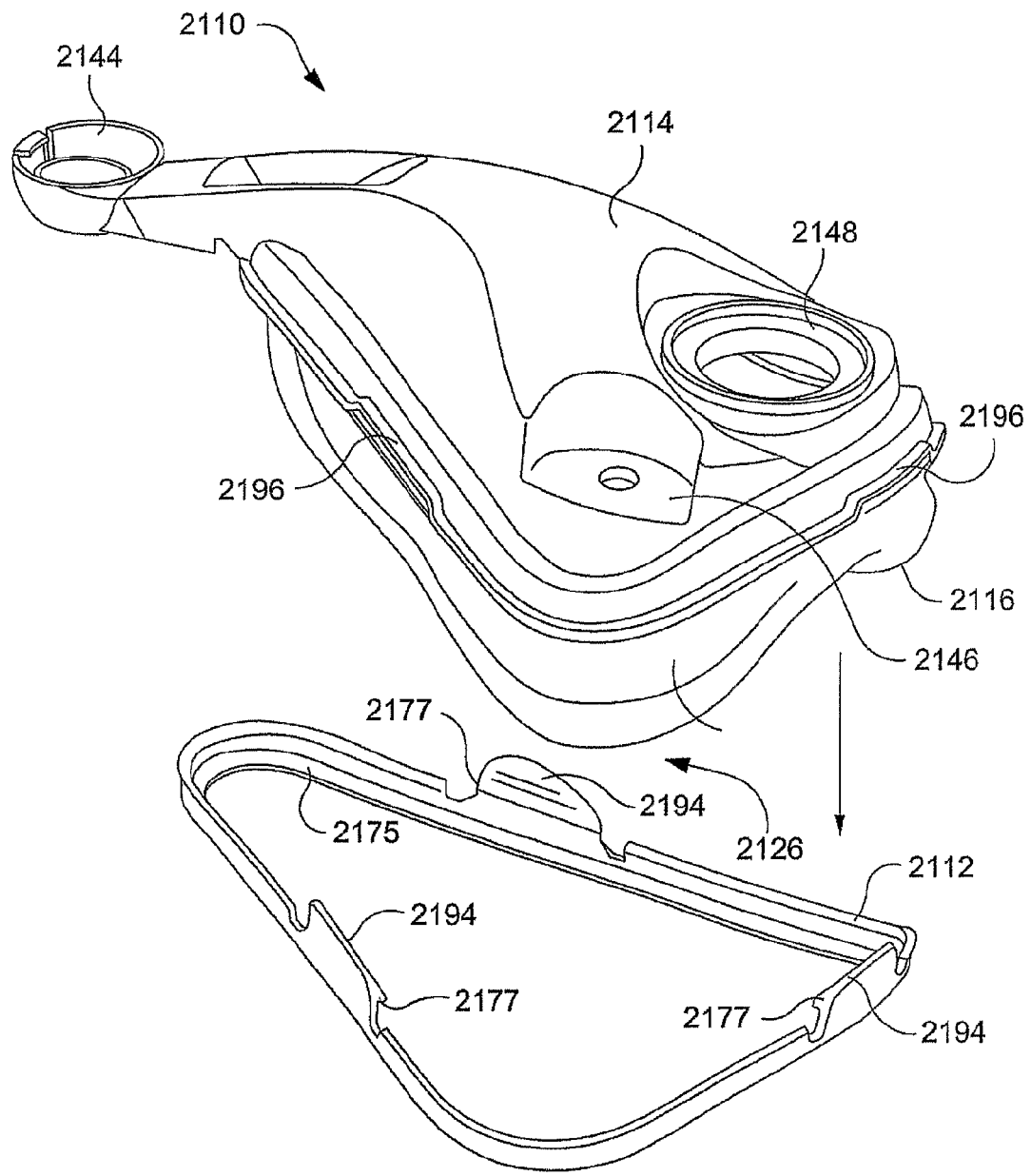
FIG. 73 is a top perspective view of the mask assembly shown in FIG. 72, the mask assembly in a partial assembled condition.
Figure 75:
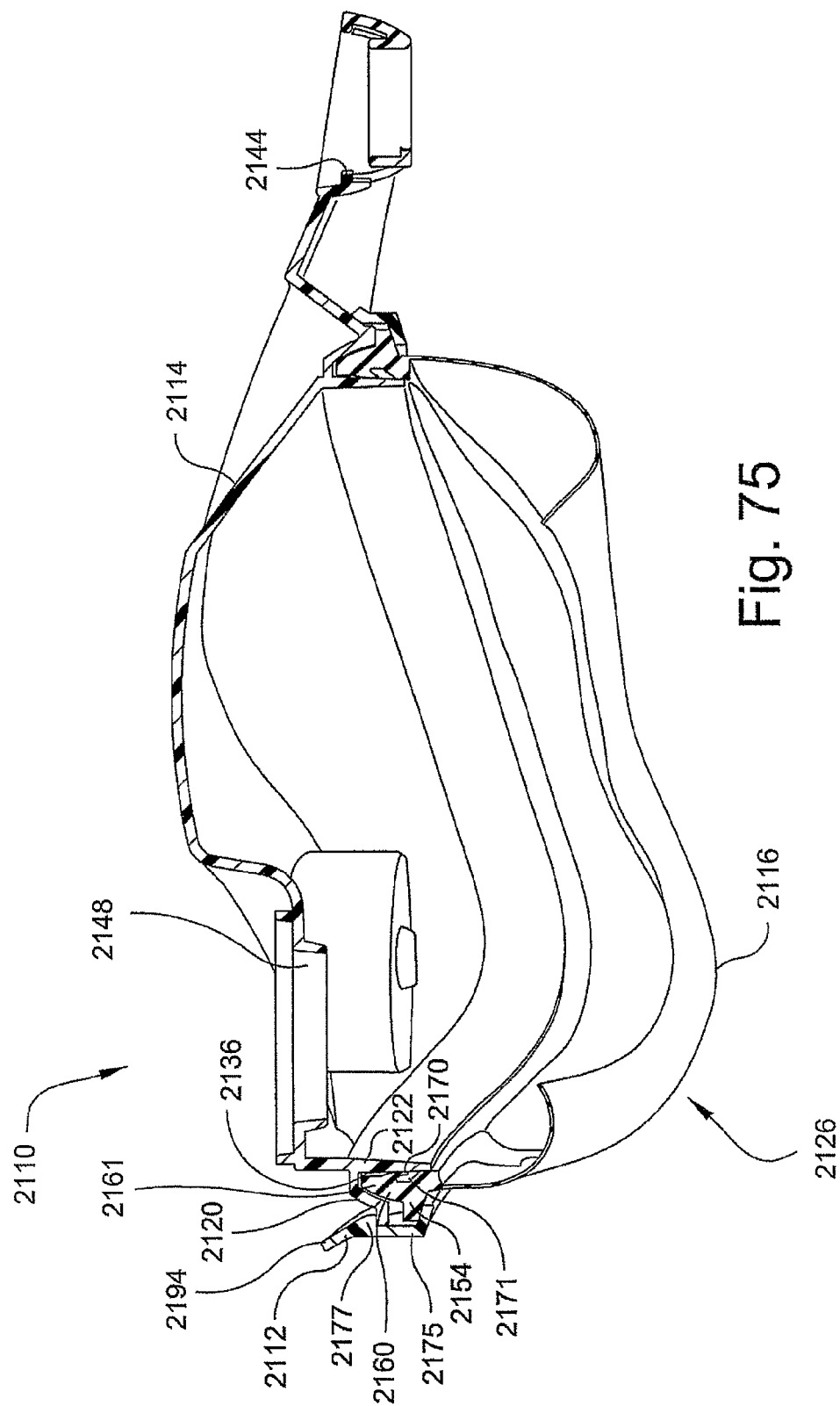
FIG. 75 is a cross-sectional view of the mask assembly shown in FIG. 72.

As shown in FIGS. 73 and 75, the frame 2114 is engaged with the cushion 2116 such that the retaining portion 2160 of the cushion 2116 engages within the retaining recess 2136 defined between the outer and inner walls 2120, 2122. As illustrated, the angled or pointed end 2161 of the retaining portion 2160 conforms to the incline defined by the outer and inner walls 2120, 2122. In addition, the lip 2170 of the cushion 2116 resiliently engages the inner wall 2122 of the frame 2114 to provide a seal in use. The lip 2170 may deflect inwardly into the space 2171, against resiliency thereof, to provide the seal.

Figure 74:
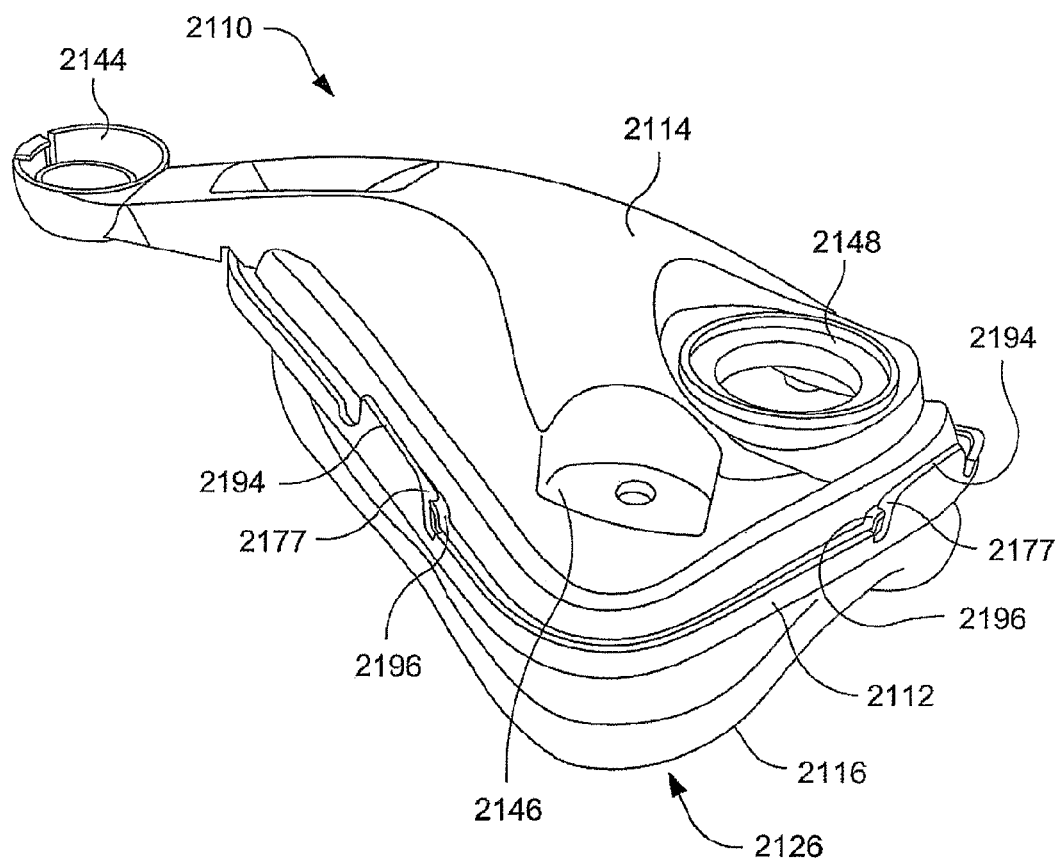
FIG. 74 is a top perspective view of the mask assembly shown in FIG. 72, the mask assembly in an assembled condition.
Figure 76:
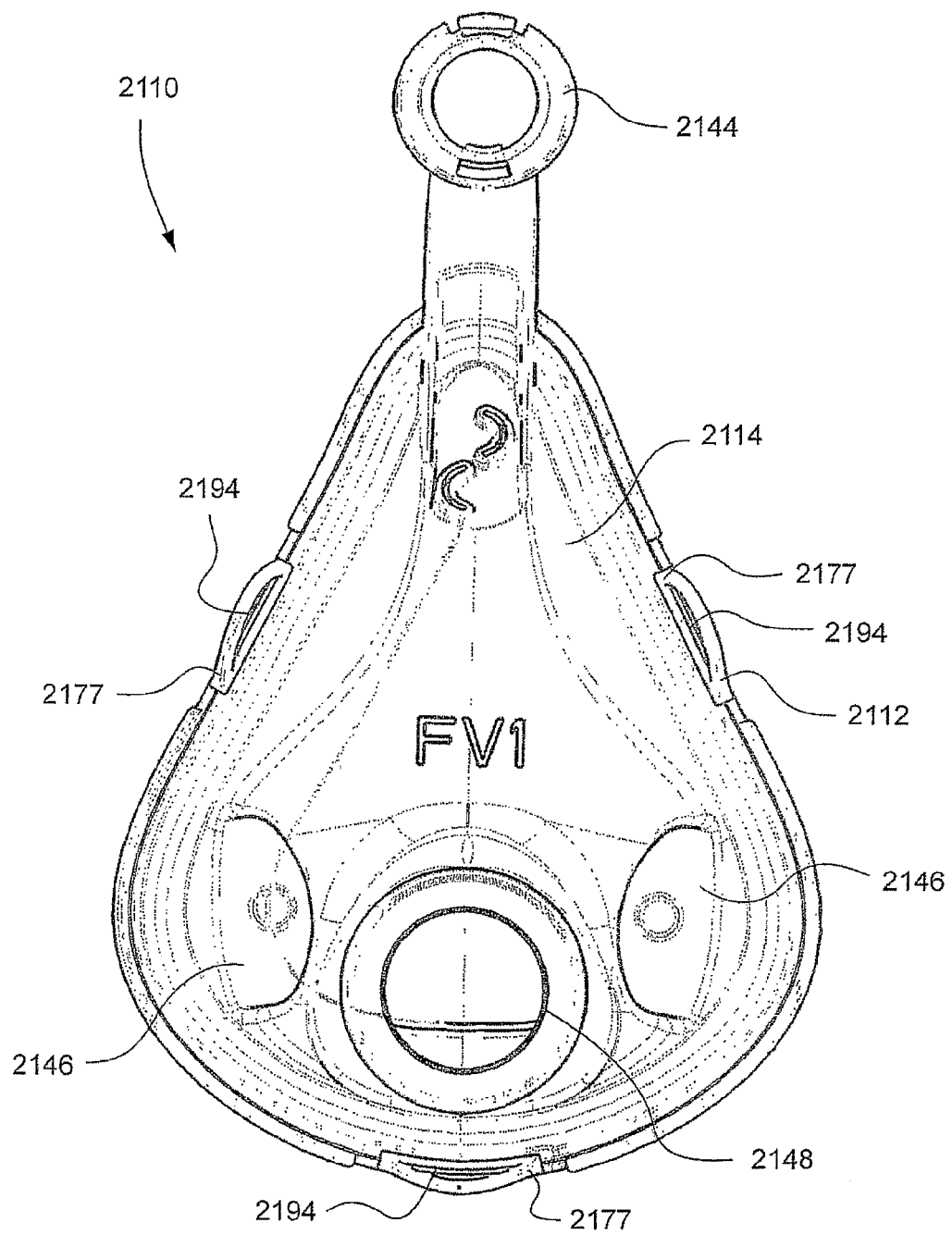
FIG. 76 is a top view of the mask assembly shown in FIG. 72.
Figure 77:
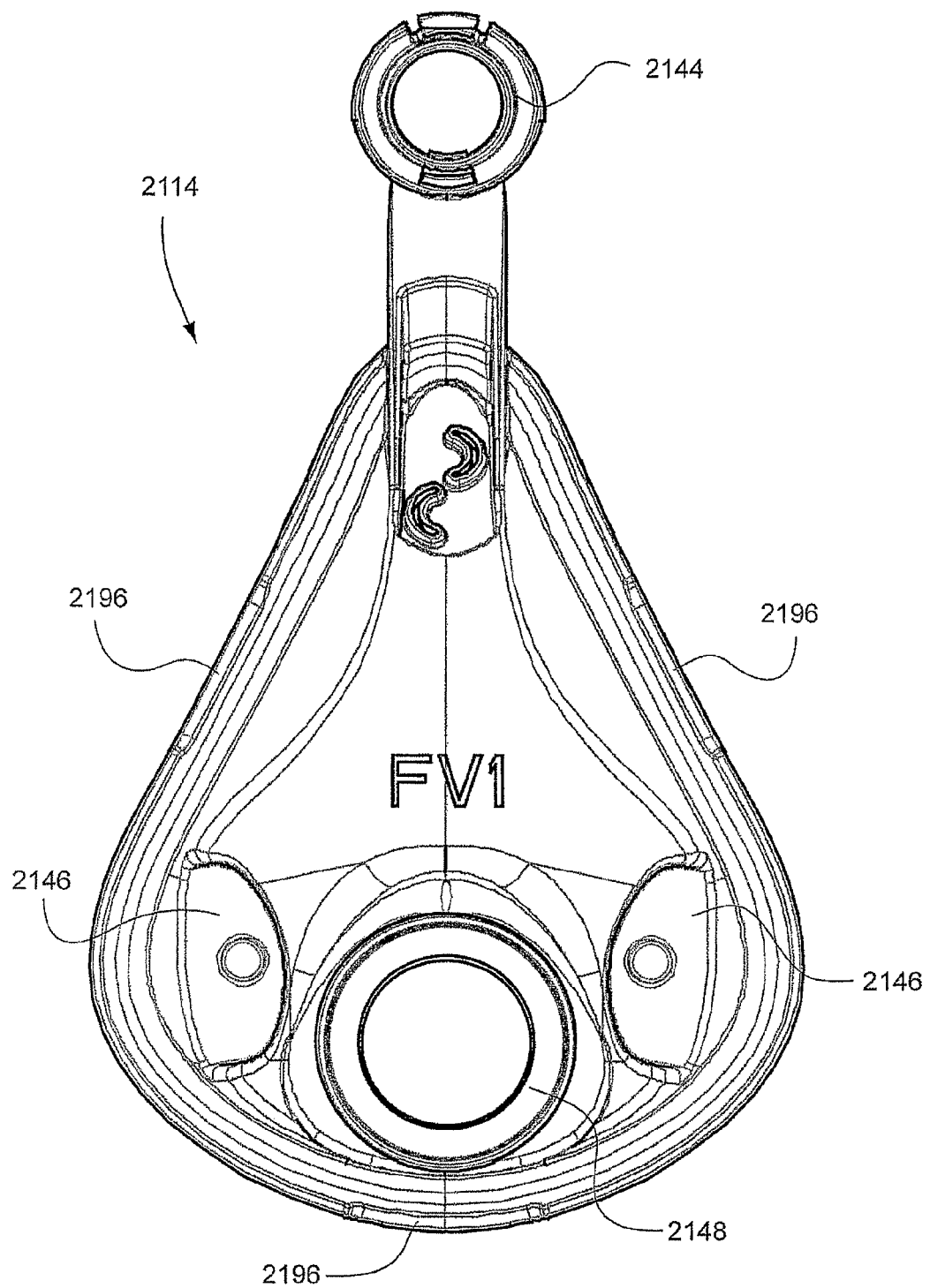
FIGS. 77-81 are various views of the frame of the mask assembly shown in FIG. 72 and showing exemplary dimensions of an embodiment.
Figure 78:
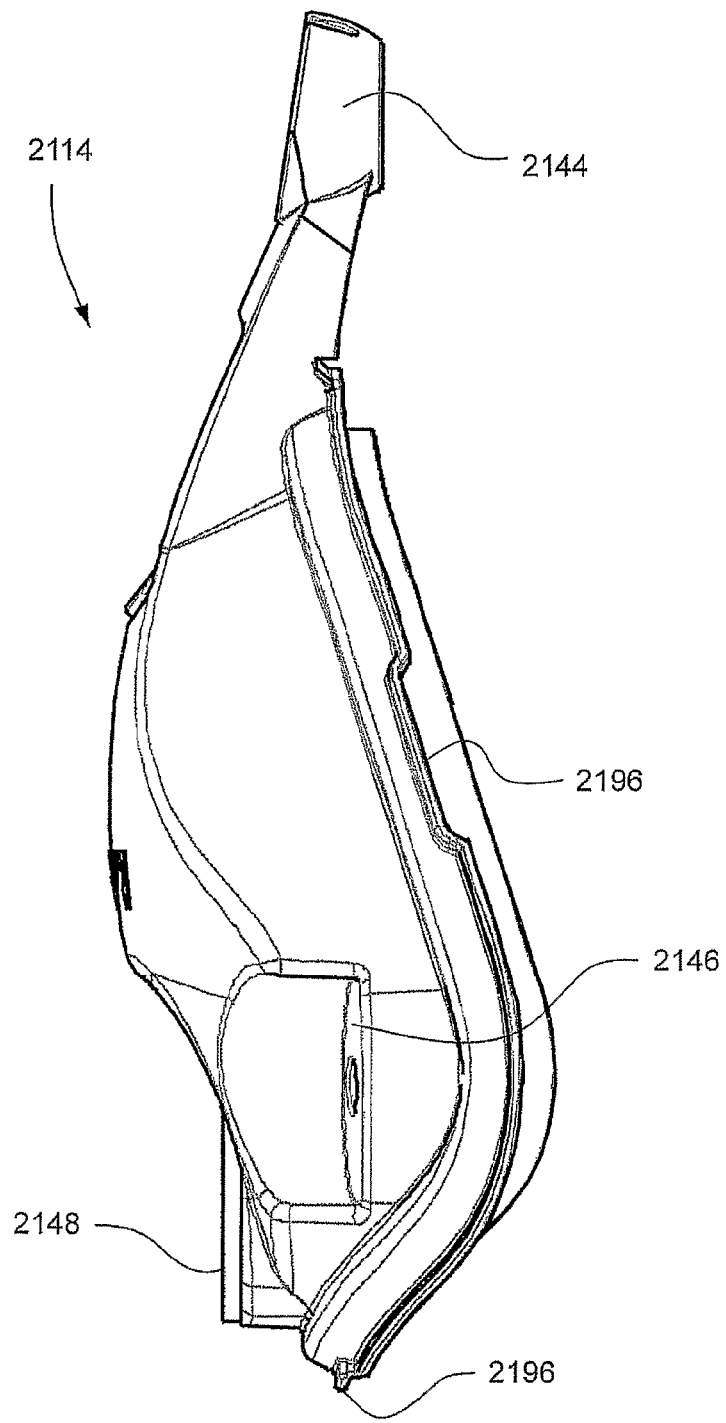
Figure 79:
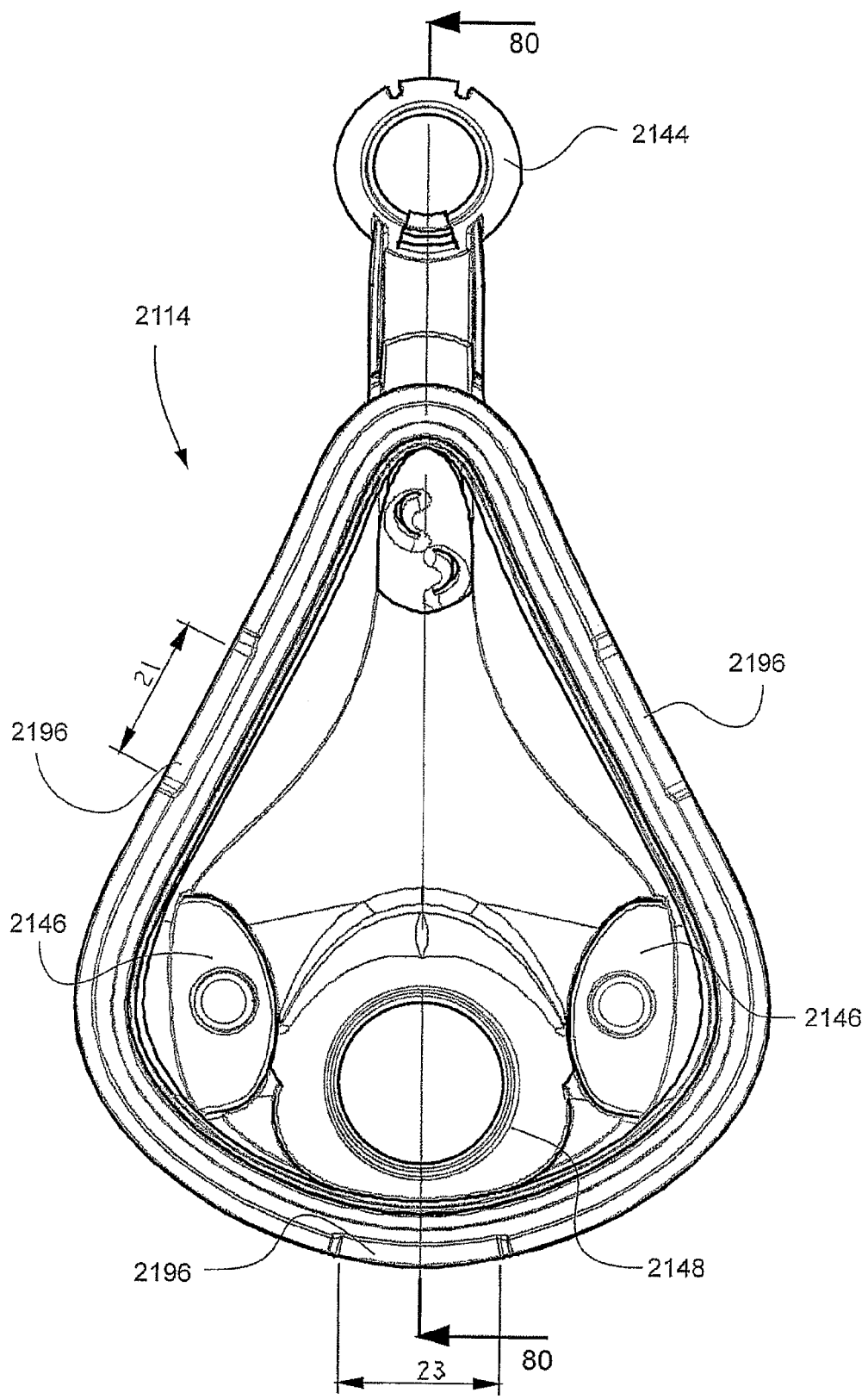
Figure 80:
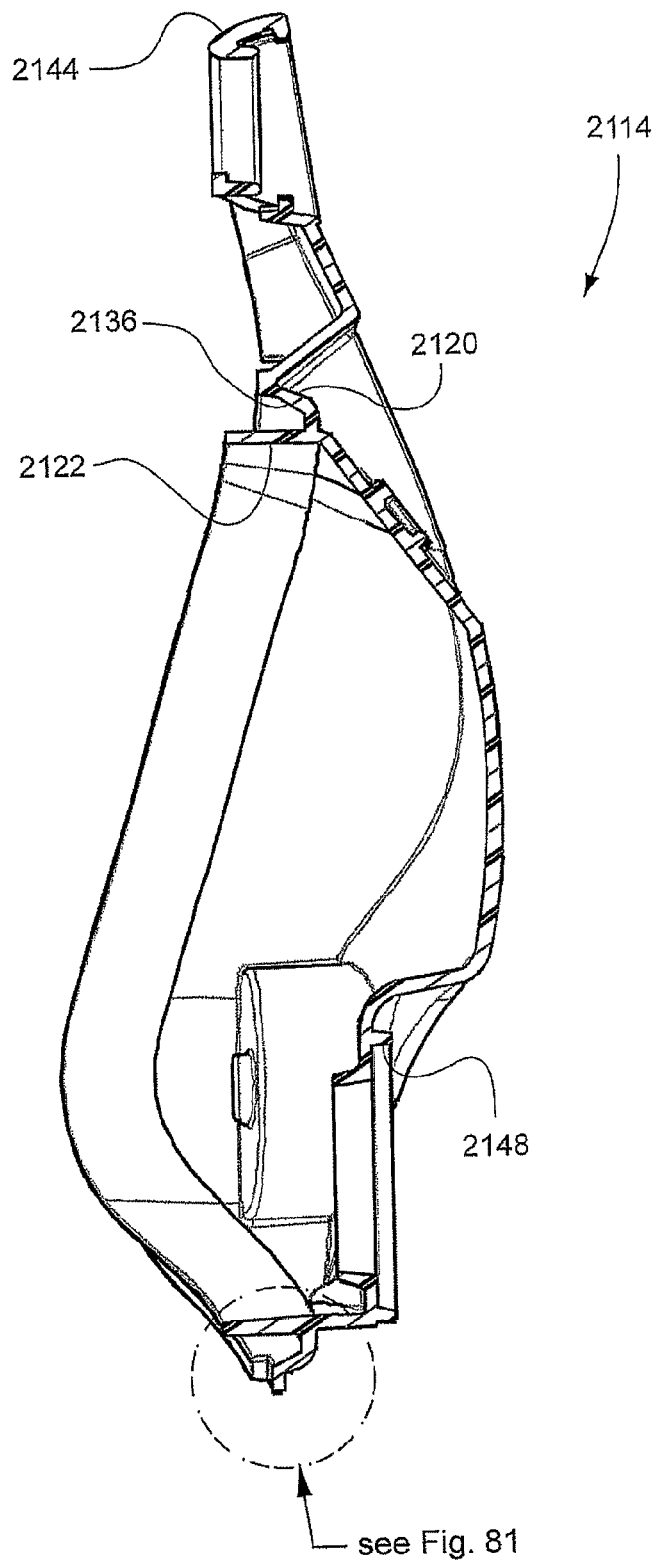
Figure 81:
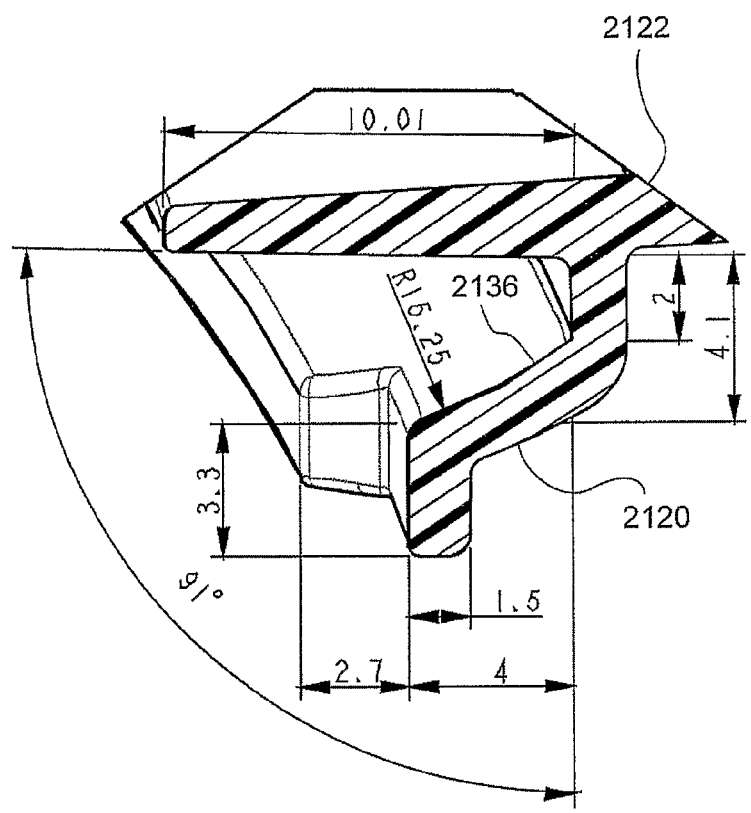
Figure 82:
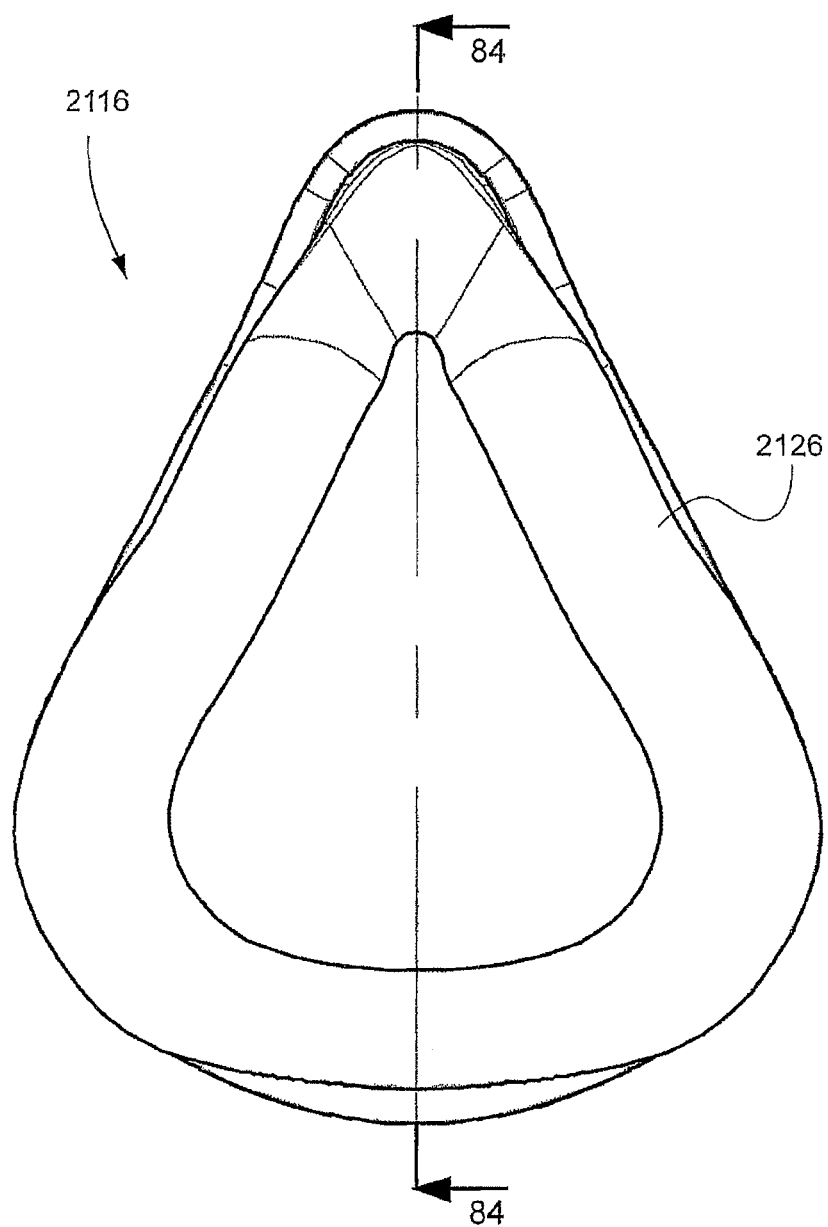
FIGS. 82-86 are various views of the cushion of the mask assembly shown in FIG. 72 and showing exemplary dimensions of an embodiment.
Figure 83:
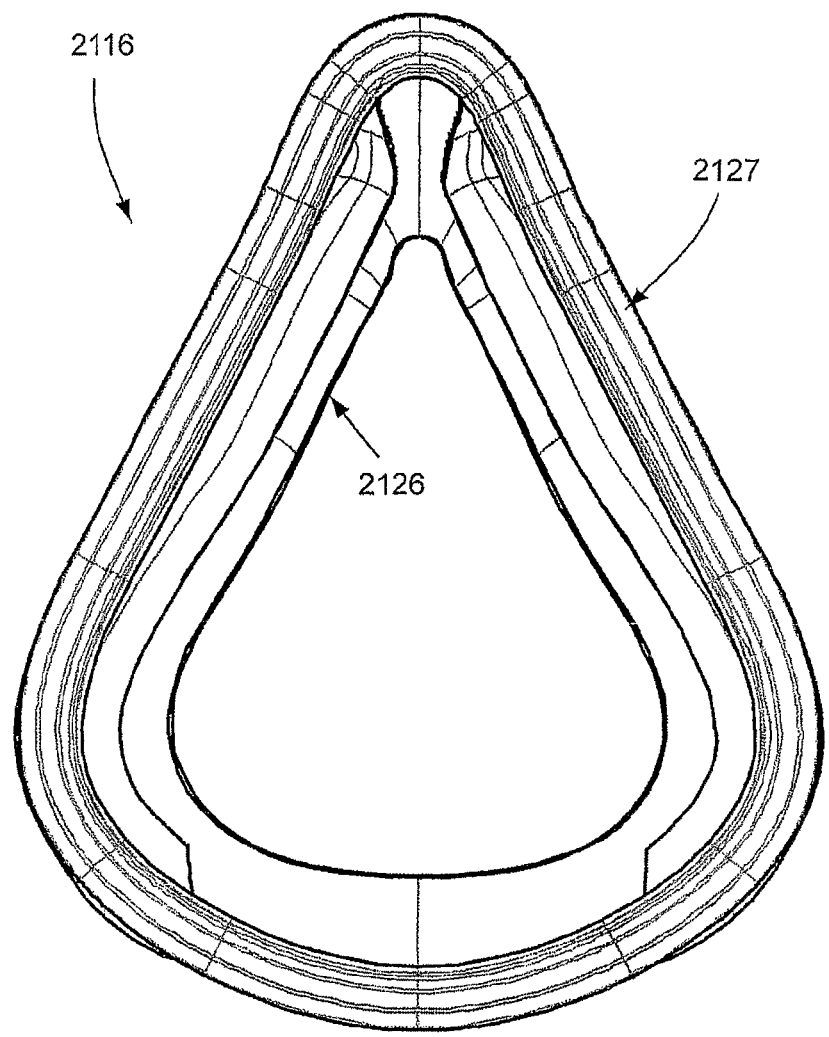
Figure 84:
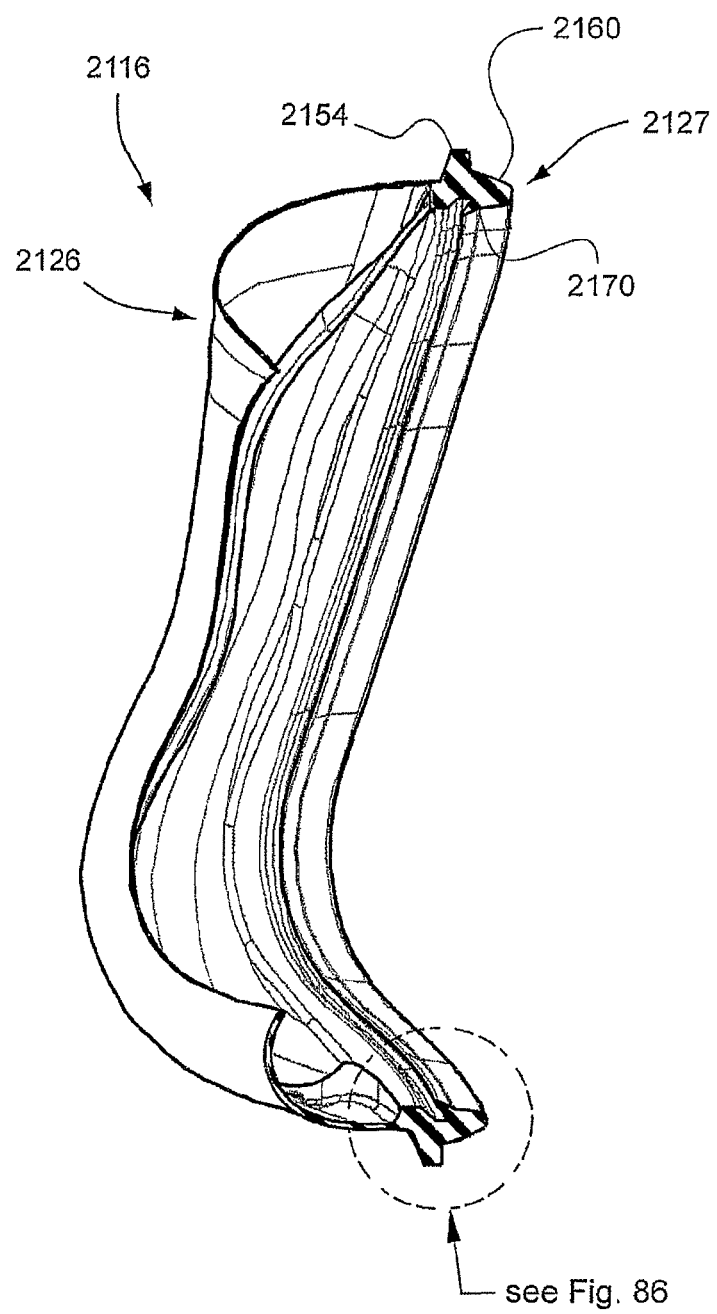
Figure 85:
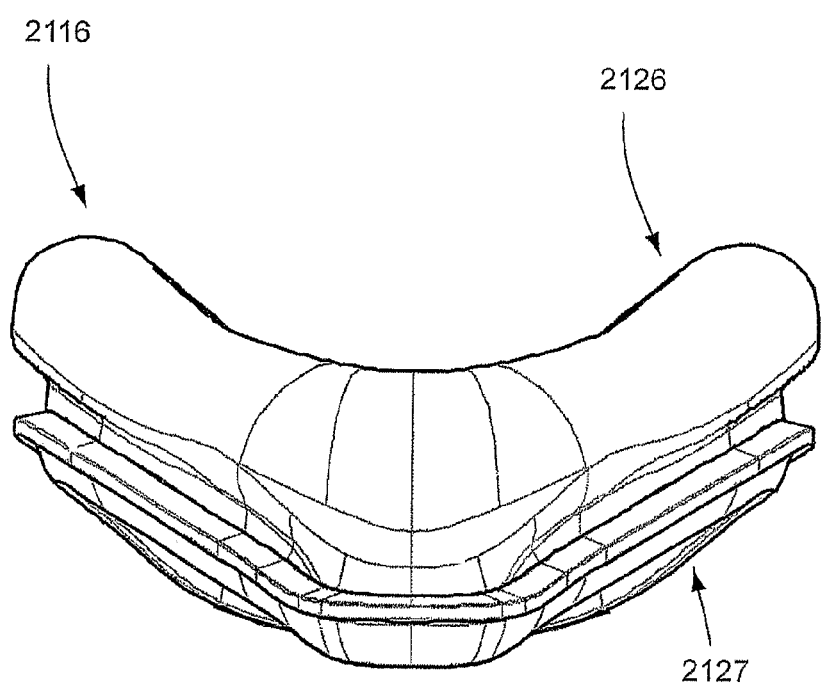
Figure 86:
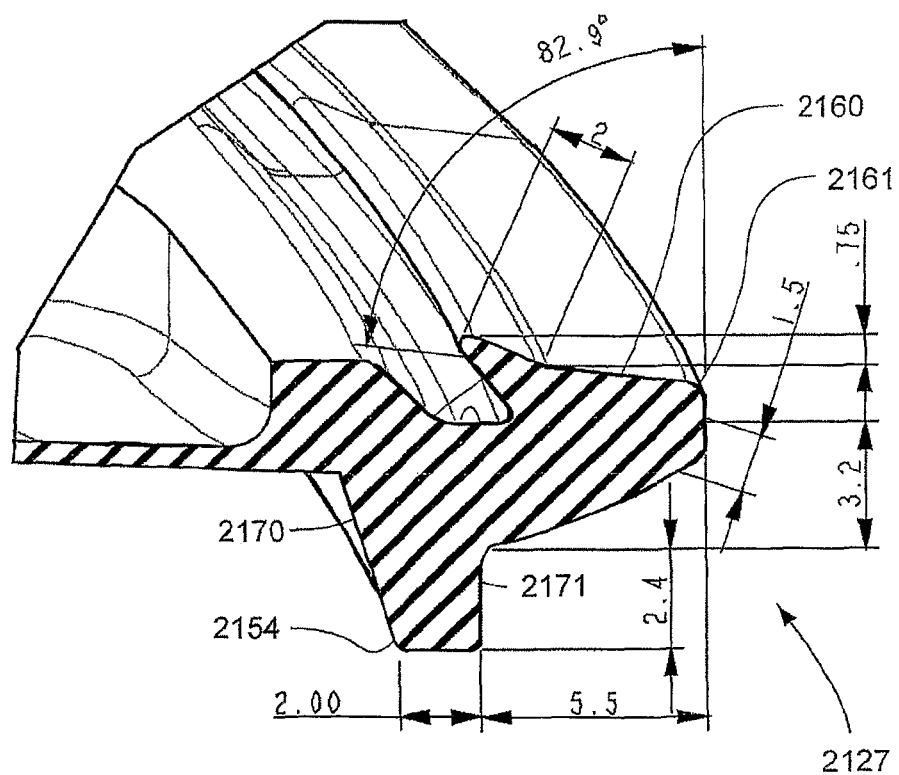
Figure 87:
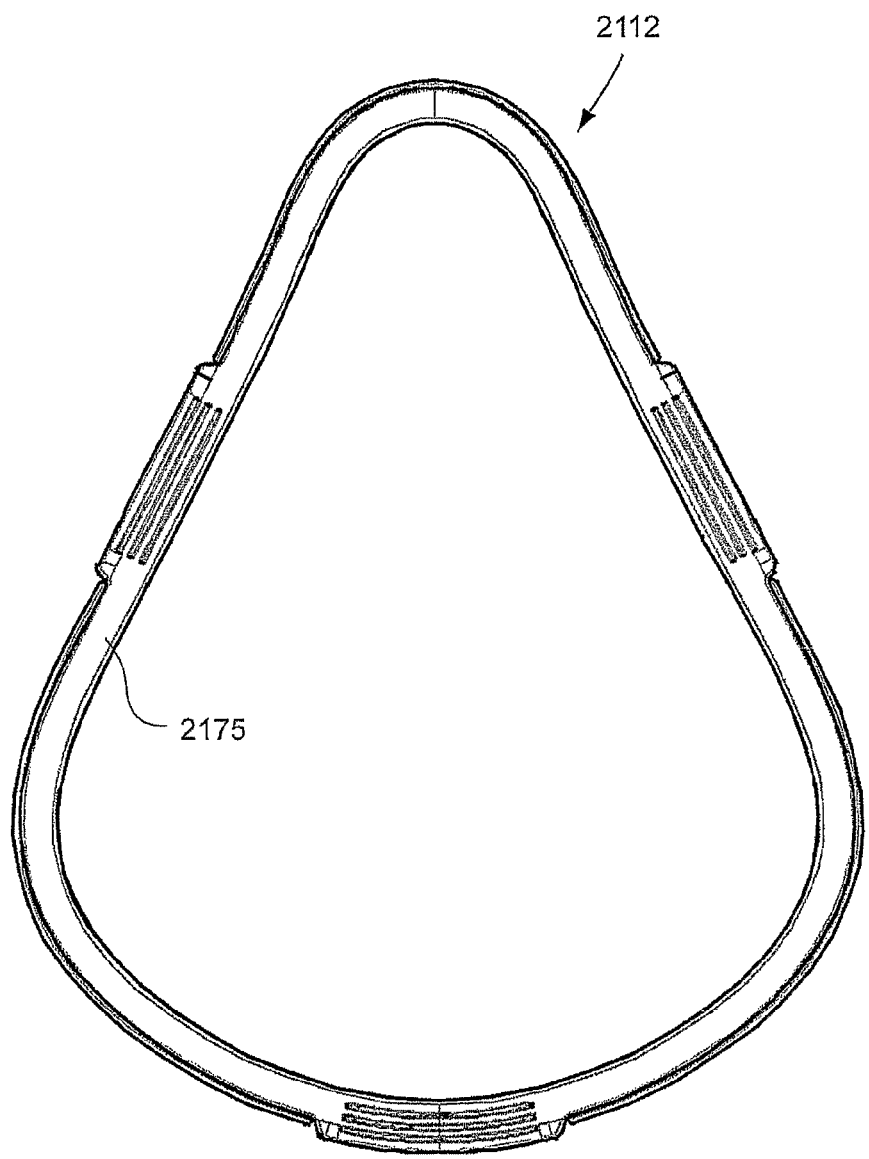
FIGS. 87-91 are various views of the frame clip of the mask assembly shown in FIG. 72 and showing exemplary dimensions of an embodiment.
Figure 88:
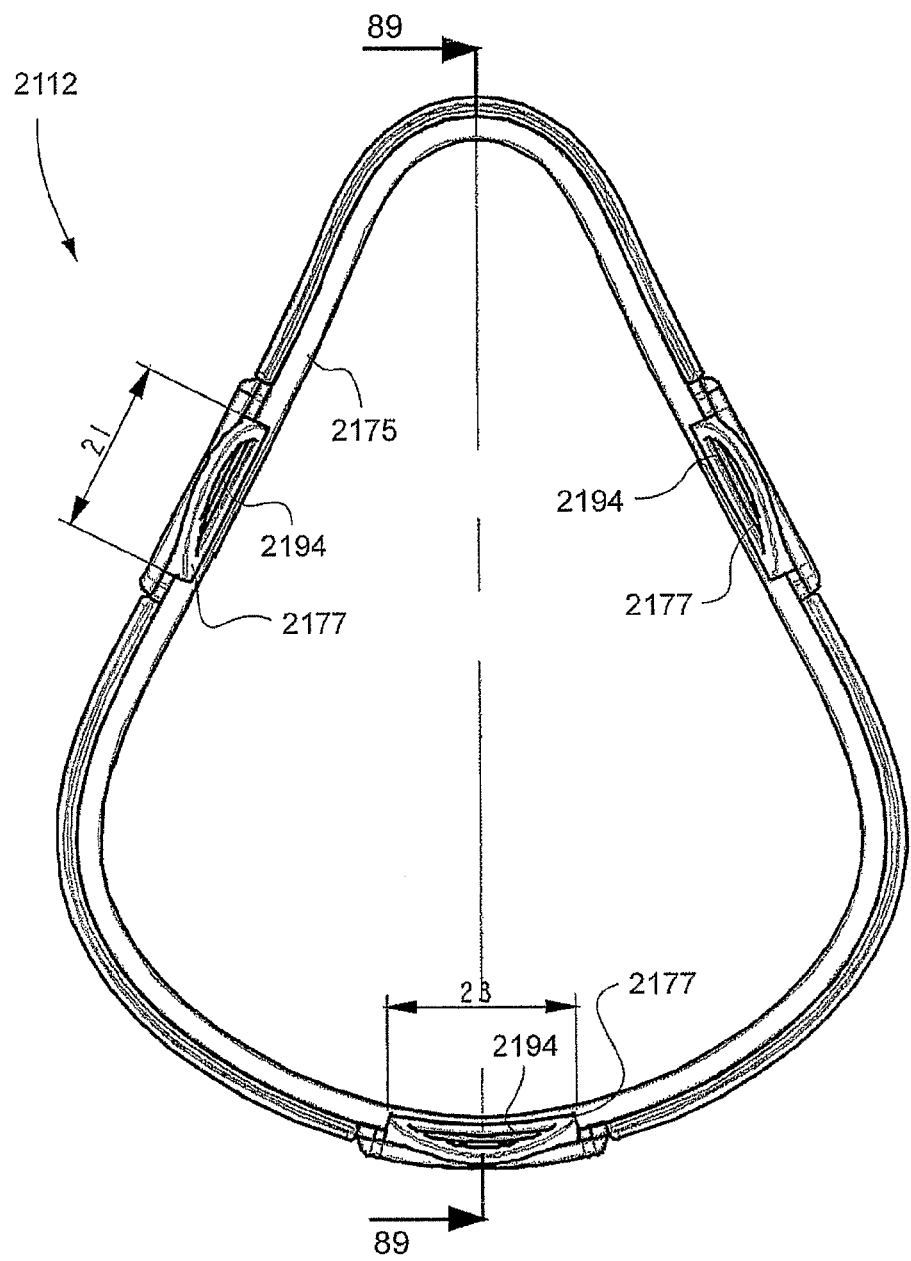
Figure 89:
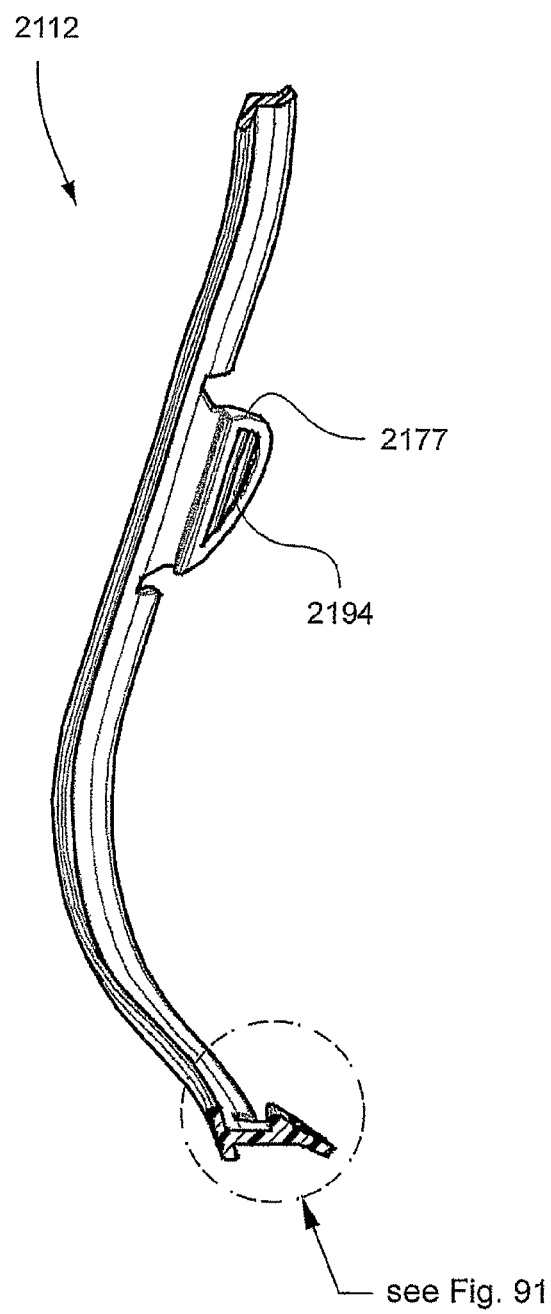
Figure 90:
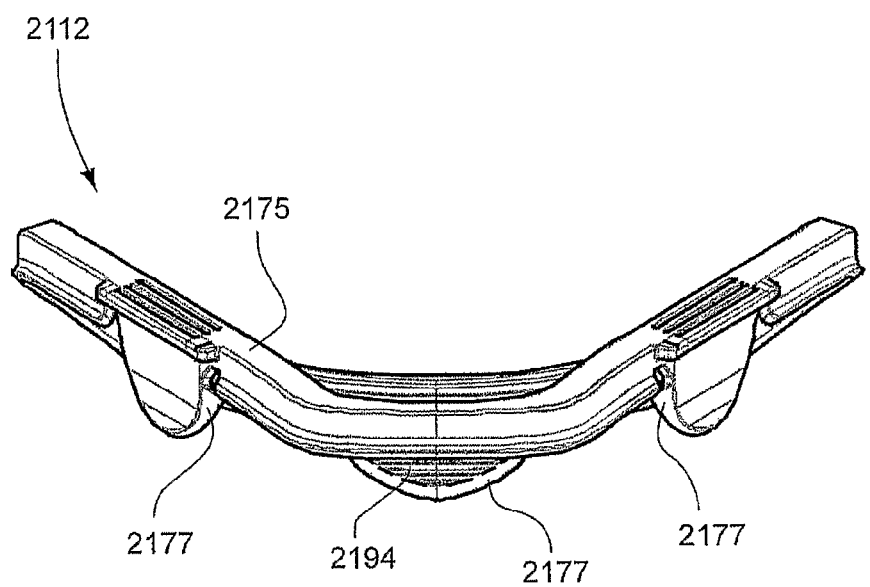
Figure 91:
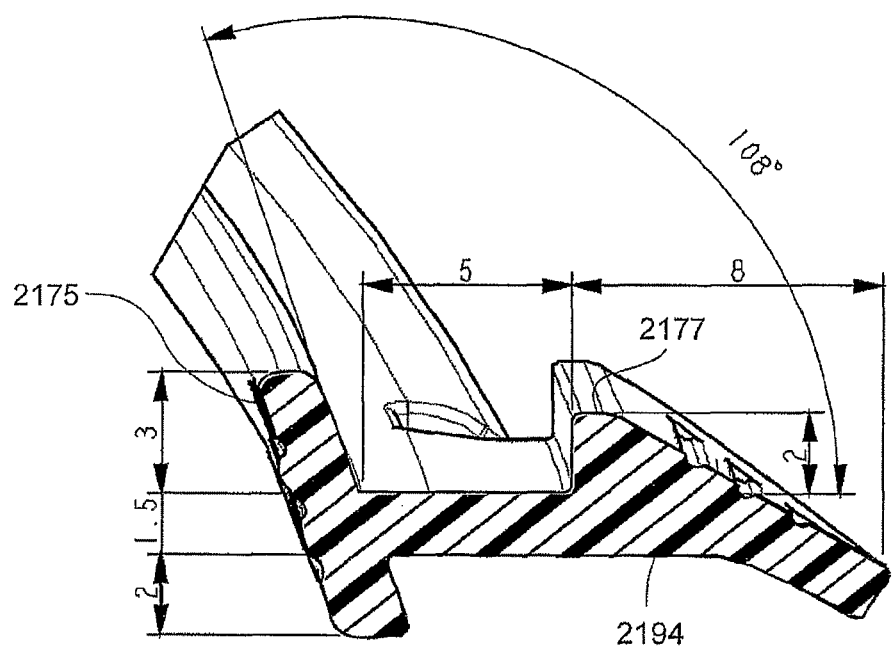
Figure 92:
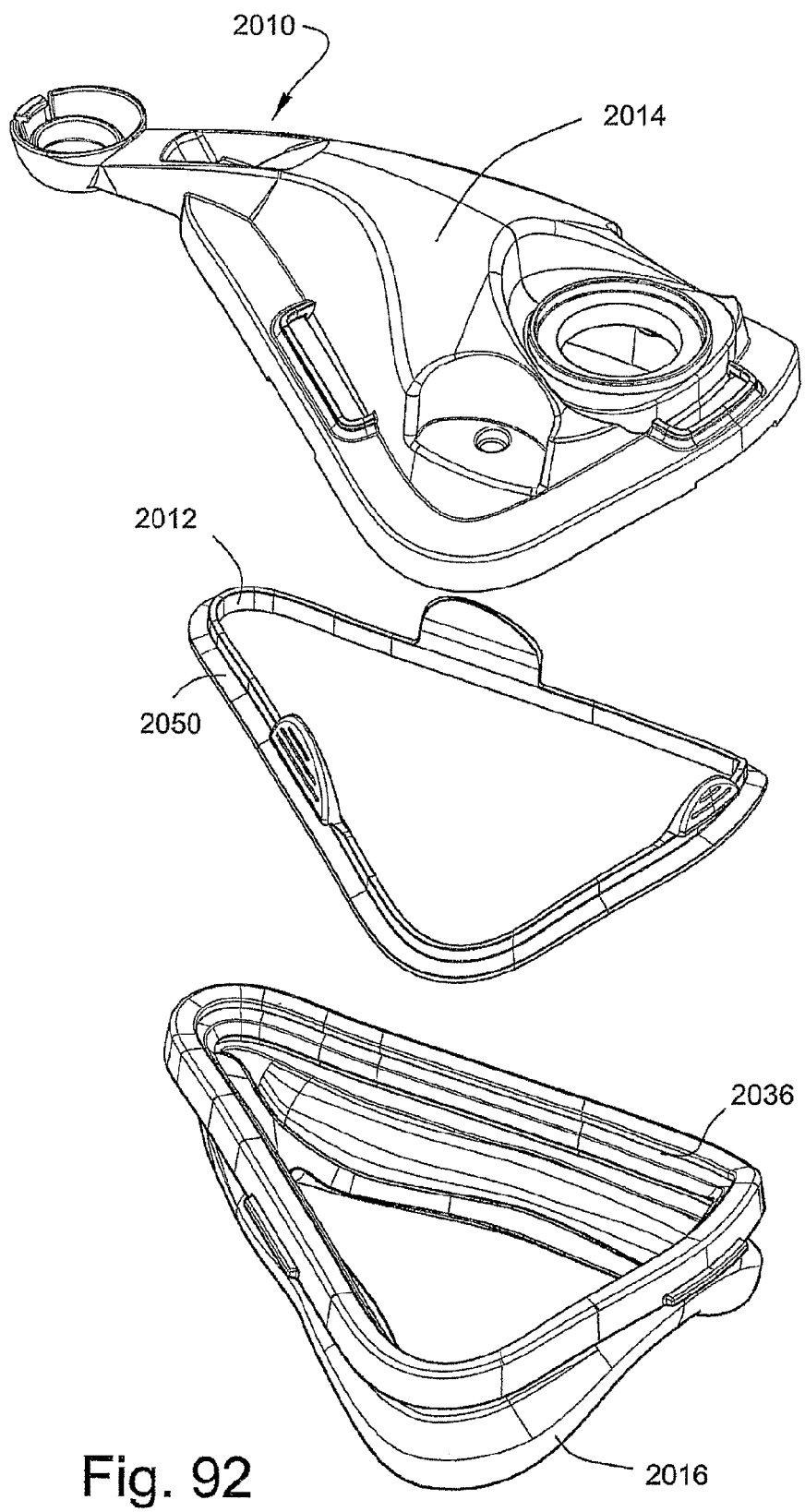
FIG. 92 is an exploded top perspective view of a mask assembly including a cushion to frame assembly mechanism according to another embodiment of the present invention, the mask assembly being in a pre-assembled condition.
Figure 93:
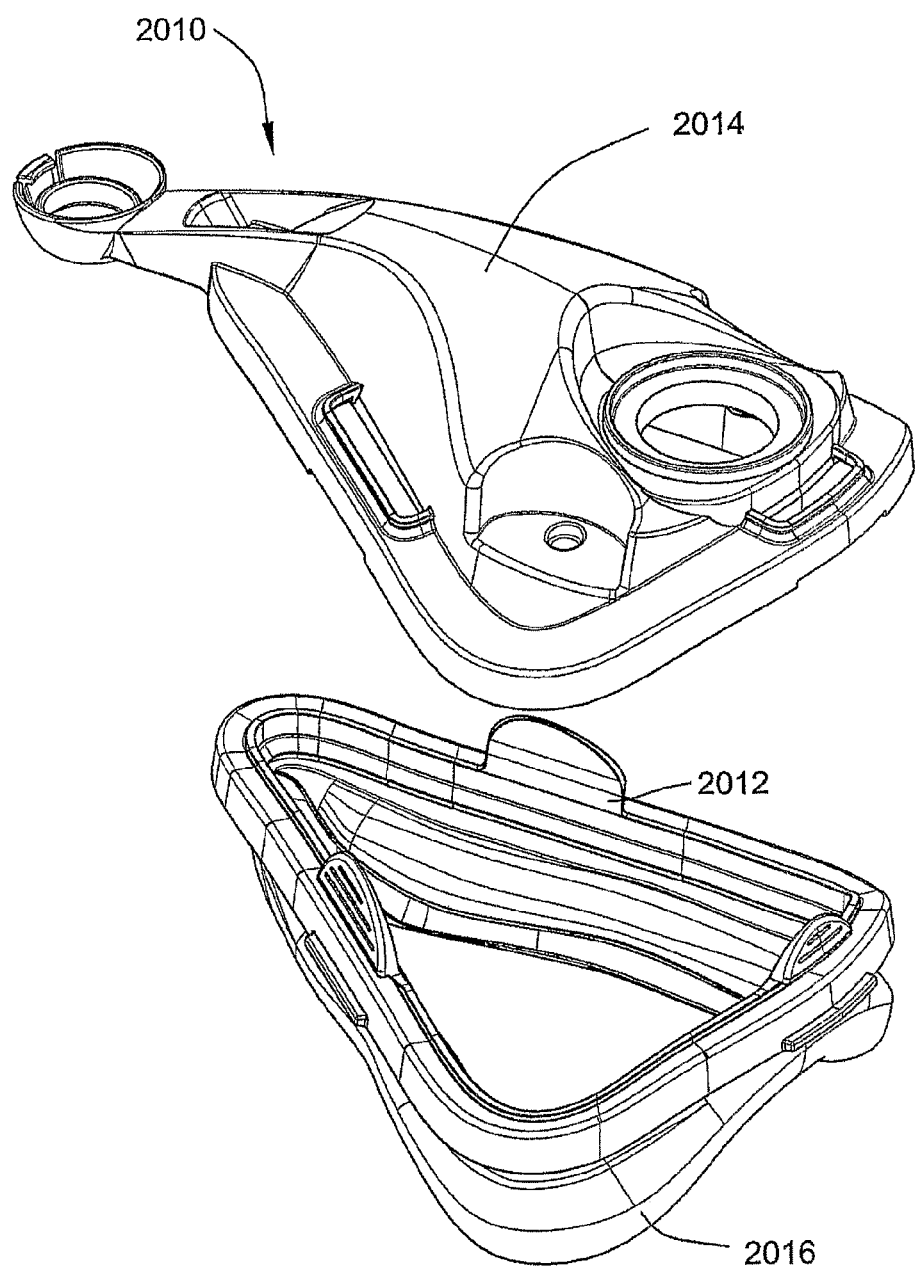
FIG. 93 is a top perspective view of the mask assembly shown in FIG. 92, the mask assembly being in a partial assembled condition.
Figure 94:
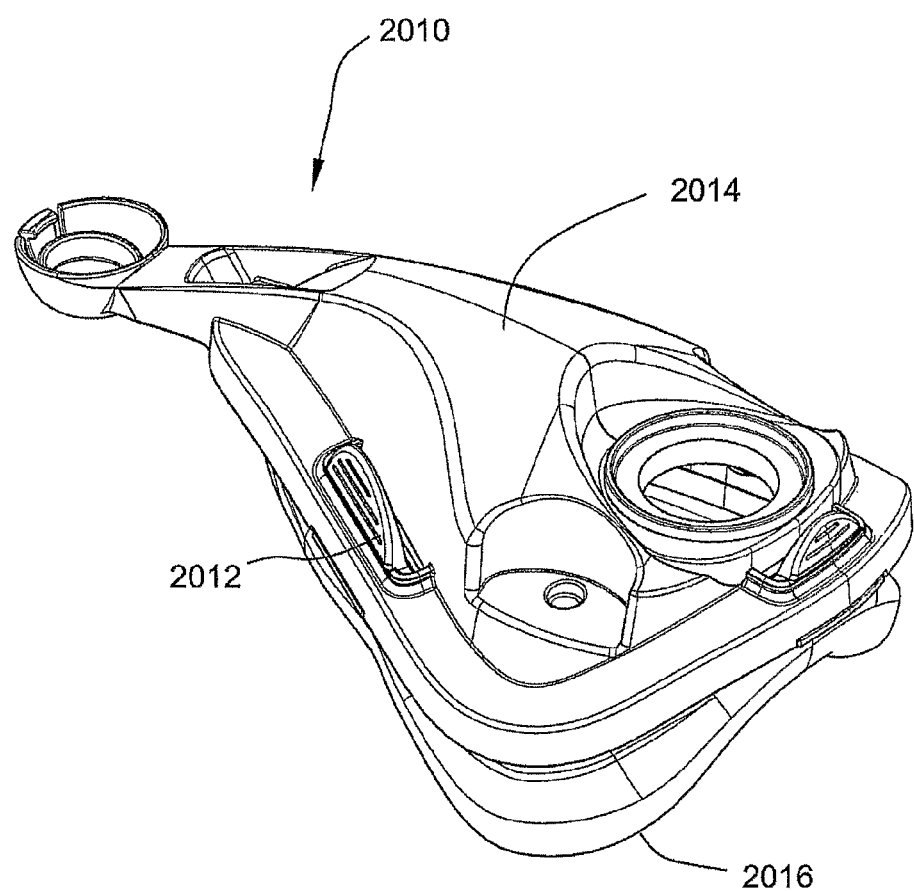
FIG. 94 is a top perspective view of the mask assembly shown in FIG. 92, the mask assembly being in an assembled condition.

As shown in FIGS. 72-76 and 87-91, a bottom assembling frame clip 2112 is provided to maintain engagement between the frame 2114 and the cushion 2116. The frame clip 2112 is contoured to match the contour of the frame 2114 and cushion 2116. As illustrated, the frame clip 2112, e.g., molded of polycarbonate, is assembled over the cushion 2116 and includes a first retaining portion 2175 that provides a shoulder for engaging the cushion flange 2154 and a plurality of second retaining portions 2177, e.g., three retaining portions 2177, that provide a shoulder for engaging the frame 2114. Thus, the frame clip 2112 sandwiches the frame 2114 and the cushion 2116 to maintain their engagement as shown in FIGS. 74-76.

The retaining portions 2177 of the frame clip 2112 include contoured finger grips 2194 to facilitate assembly. As illustrated, the finger grips 2194 are relatively thick for ease of finding and use.

In the illustrated embodiment, the cushion to frame assembly mechanism includes three retention points, e.g., three retaining portions 2177. Three retention points makes assembly time quicker and reduces the perceived (aesthetic) and actual (physical) assembly task complexity. Also, because the cushion 2116 includes the lip seal 2170, a high compression force between the frame 2114, cushion 2116, and frame clip 2112 is not required and three retaining portions 2177 are sufficient for sealing/retaining purposes.

Also, the frame 2114 includes top hat sections 2196 that engage respective retaining portions 2177 of the frame clip 2112 in use (e.g., see FIGS. 72, 73, and 77-79). The top hat sections 2196 provide a visual cue or indication as to where the frame clip 2112 clips onto the frame 2114, aid with alignment of the 2116 cushion onto the frame 2114 (e.g., cushion 2116 may have integrally molded protruding sections that align with the top hat sections 2196 of the frame 2194), provide guide or alignment points for possible automated assembly, and provide aesthetic interest or feature to the frame 2114.

In an embodiment, the frame clip 2112 may be over-molded with the cushion 2116. In another embodiment, the frame 2114 may be over-molded with the cushion 2116, thereby negating the need for the frame clip 2112.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A mask assembly for treatment of sleep disorder breathing by delivering a flow of pressurized gas to a patient, the mask assembly comprising:
   a cushion adapted to form a seal by abutting a patient's face around the patient's nose and mouth, the cushion comprising a face contacting portion with a membrane that contacts the patient's face around the patient's nose and mouth and a support cushion underlying at least a portion of the membrane;
   a frame integrally molded to the cushion, the frame comprising an annular wall surrounding an opening that allows fluid communication of the pressurized gas to an interior of the frame and a second wall surrounding the annular wall and connected to the cushion; and
   a skeleton frame removably attached to the frame, the skeleton frame comprising an upper support member adapted to receive a forehead support, a lower frame member comprising headgear attachment locations adapted to receive clips for straps of a headgear assembly, an annular hole adapted to align with the opening, and two frame members interconnecting the upper support member and the lower frame member and forming a substantially triangular open space between the two frame members and the lower frame member, wherein the frame is at least partially accessible through the substantially triangular space.

2. The mask assembly according to claim 1, wherein two headgear attachment locations of the headgear attachment locations are disposed adjacent to and on substantially opposite lateral sides of the opening.

3. The mask assembly according to claim 2, wherein the two headgear attachment locations of the headgear attachment locations are disposed substantially diametrically opposite to one another with respect to the opening.

4. The mask assembly according to claim 1, wherein the frame protrudes at least partially through the triangular space.

5. The mask assembly according to claim 1, wherein the skeleton frame and the frame are adapted to engage at the opening while an inlet elbow is engaged with the mask assembly.

6. The mask assembly according to claim 1, wherein the skeleton frame and the frame have mutual contact points to prevent relative rotation of the frame about the opening.

7. The mask assembly according to claim 1, wherein the headgear attachment locations are adapted to engage with clips attached to the straps of the headgear assembly.

8. The mask assembly according to claim 1, wherein two headgear attachment locations of the headgear attachment locations are disposed adjacent to and on substantially opposite lateral sides of the opening; the frame protrudes at least partially through the triangular space; the skeleton frame and the frame are adapted to engage at the opening while an inlet elbow is engaged with the mask assembly; the skeleton frame and the frame have mutual contact points to prevent relative rotation of the frame about the opening; and the two headgear attachment locations are adapted to engage with clips attached to the straps of the headgear assembly.

9. A mask assembly for treatment of sleep disorder breathing by delivering a flow of pressurized gas to a patient, the mask assembly comprising:
   a cushion adapted to form a seal by abutting a patient's face around the patient's nose and mouth, the cushion comprising a face contacting portion with a membrane that contacts the patient's face around the patient's nose and mouth and a support cushion underlying at least a portion of the membrane;
   a frame integrally molded to the cushion, the frame comprising an annular wall surrounding an opening that is adapted to allow fluid communication of the pressurized gas to an interior of the frame and a second wall surrounding the annular wall and connected to the cushion;
   an inlet elbow to contact the frame and to communicate the pressurized gas to the interior of the frame; and
   a skeleton frame adapted to be removably engageable with the frame, the skeleton frame comprising an upper support member adapted to receive a forehead support, a lower frame member comprising headgear attachment locations adapted to engage with clips for straps of a headgear assembly, two frame members interconnecting the upper support member and the lower frame member and forming an open space between the two frame members and the lower frame member, wherein
   the skeleton frame and the frame are adapted to be releasably engageable to one another at the opening, and
   the frame is at least partially accessible through the open space.

10. The mask assembly according to claim 9, wherein two headgear attachment locations of the headgear attachment locations are disposed adjacent to and on substantially opposite lateral sides of the opening.

11. The mask assembly according to claim 10, wherein the two headgear attachment locations of the headgear attachment locations are disposed substantially diametrically opposite to one another with respect to the opening.

12. The mask assembly according to claim 9, wherein the frame protrudes at least partially through the open space.

13. The mask assembly according to claim 9, wherein the skeleton frame and the frame are adapted to engage at the opening while the inlet elbow is engaged with the mask assembly.

14. The mask assembly according to claim 9, wherein the skeleton frame and the frame have mutual contact points to prevent relative rotation of the frame about the opening.

15. The mask assembly according to claim 9, wherein the headgear attachment locations are adapted to engage with clips attached to the straps of the headgear assembly.

16. The mask assembly according to claim 9, wherein two headgear attachment locations of the headgear attachment locations are disposed adjacent to and on substantially opposite lateral sides of the opening; the frame protrudes at least partially through the open space; the skeleton frame and the frame are adapted to engage at the opening while the inlet elbow is engaged with the mask assembly; the skeleton frame and the frame have mutual contact points to prevent relative rotation of the frame about the opening; and the two headgear attachment locations are adapted to engage with clips attached to the straps of the headgear assembly.

17. A mask assembly for treatment of sleep disorder breathing by delivering a flow of pressurized gas to a patient, the mask assembly comprising:
   a first frame made of first material;
   a cushion connected to the first frame, the cushion being adapted to form a seal around a patient's nose and mouth and being made from a second material that is more flexible than the first material; and
   a second frame adapted to constrain the first frame, the second frame comprising an upper support member that supports a forehead support, two lower headgear clip attachments engaged with clips provided to straps of a headgear assembly, an annular connection adapted to engage an elbow of an inlet conduit and an opening located between the annular connection and the upper support member, the opening providing access to the first frame.

18. The mask assembly according to claim 17, wherein the first frame and the cushion are integrally molded in one piece to provide a cushion-frame sub-assembly.

19. The mask assembly according to claim 17, wherein the upper support member comprises an annular opening adapted to receive the forehead support.

20. The mask assembly according to claim 17, wherein the first frame is contoured to fit over the patient's nose and mouth.

21. The mask assembly according to claim 17, wherein the first frame comprises an opening that provides a flow path adapted to communicate with the inlet conduit.

22. The mask assembly according to claim 17, wherein the second frame includes contact points to prevent rotation of the first frame with respect to the second frame.

23. The mask assembly according to claim 17, wherein the first frame and the cushion together form a breathing chamber around the patient's nose and mouth.

24. The mask assembly according to claim 17, wherein the cushion comprises a face contacting portion with a membrane that contacts a patient's face and a support cushion underlying at least a portion of the membrane.

25. The mask assembly according to claim 24, wherein the support cushion is omitted at a location corresponding to a patient's chin.

26. The mask assembly according to claim 17, wherein the second frame comprises two connecting members that connect a lower portion of the second frame to the upper support member and the opening is located between the two connecting members.

27. The mask assembly according to claim 17, wherein the opening is substantially triangular.

28. The mask assembly according to claim 17, wherein the two lower headgear clip attachments are adjacent to and on opposite lateral sides of the annular connection.

29. The mask assembly according to claim 17, wherein the first frame is releasably secured to the second frame by way of an interlocking and/or frictional fit.

30. The mask assembly according to claim 17, wherein the first frame and the second frame have complementary shapes.

31. The mask assembly according to claim 17, wherein the first frame and the cushion are integrally molded in one piece to provide a cushion-frame assembly,
the upper support member comprises an annular opening adapted to receive the forehead support,
the cushion is contoured to fit the patient's nose and mouth,
the first frame comprises an opening that provides a flow path adapted to communicate with the inlet conduit,
the second frame includes contact points that prevent rotation of the first frame with respect to the second frame,
the first frame and the cushion together form a breathing chamber around the patient's nose and mouth,
the cushion comprises a face contacting portion with a membrane that contacts a patient's face and a support cushion underlying at least a portion of the membrane,
the support cushion is omitted at a location corresponding to a patient's chin,
the second frame comprises two connecting members that connect a lower portion of the second frame to the upper support member and the opening is located between the two connecting members,
the opening is substantially triangular,
the two lower headgear clip attachments are adjacent to and on opposite lateral sides of the annular connection,
the first frame is releasably secured to the second frame by way of an interlocking and/or frictional fit, and
the first frame and the second frame have complementary shapes.

32. A mask assembly for treatment of sleep disorder breathing by delivering a flow of pressurized gas to a patient, the mask assembly comprising:
a first frame made of first material;
a cushion connected to the first frame, the cushion being adapted to form a seal around a patient's nose and mouth and being made from a second material that is more flexible than the first material, the first frame and the cushion together forming a breathing chamber; and
a second frame adapted to constrain the first frame, the second frame comprising an upper support member adapted to assist with forehead support, two lower headgear clip attachments engaged with clips provided to straps of a headgear assembly, an annular opening adapted to allow an elbow to provide pressurized gas to the patient, and a separate opening located between the annular opening and the upper support member, the separate opening providing access to the first frame while the mask assembly is fully assembled.

33. The mask assembly according to claim 32, wherein the first frame and the cushion are integrally molded in one piece to provide a cushion-frame sub-assembly.

34. The mask assembly according to claim 32, wherein the upper support member comprises a second annular opening adapted to receive a forehead support.

35. The mask assembly according to claim 32, wherein the first frame is contoured to fit over the patient's nose and mouth.

36. The mask assembly according to claim 32, wherein the first frame comprises a frame-opening that provides a flow path adapted to communicate with the elbow.

37. The mask assembly according to claim 32, wherein the second frame includes contact points contacting the first frame to prevent rotation of the first frame with respect to the second frame.

38. The mask assembly according to claim 32, wherein the first frame and the cushion together form the breathing chamber around the patient's nose and mouth.

39. The mask assembly according to claim 32, wherein the cushion comprises a face contacting portion with a membrane that contacts a patient's face and a support cushion underlying at least a portion of the membrane.

40. The mask assembly according to claim 39, wherein the support cushion is omitted at a location corresponding to a patient's chin.

41. The mask assembly according to claim 32, wherein the second frame comprises two connecting members that connect a lower portion of the second frame to the upper support member, and the separate opening is located between the two connecting members.

42. The mask assembly according to claim 32, wherein the separate opening is substantially triangular.

43. The mask assembly according to claim 32, wherein the two lower headgear clip attachments are adjacent to and on opposite lateral sides of the annular opening.

44. The mask assembly according to claim 32, wherein the first frame is releasably secured to the second frame by way of an interlocking and/or frictional fit.

45. The mask assembly according to claim 32, wherein the first frame and the second frame have complementary shapes.

46. The mask assembly according to claim 32, wherein the annular opening and the elbow are sealingly connected.

47. The mask assembly according to claim 32, wherein the first frame and the cushion are integrally molded in one piece to provide a cushion-frame sub-assembly,
the upper support member comprises a second annular opening adapted to receive a forehead support,
the cushion is contoured to fit the patient's nose and mouth,
the first frame comprises a frame-opening that allows for a flow path adapted to communicate with the elbow,
the second frame includes contact points that prevent rotation of the first frame with respect to the second frame,
the first frame and the cushion together form the breathing chamber around the patient's nose and mouth,
the cushion comprises a face contacting portion with a membrane that contacts a patient's face and a support cushion underlying at least a portion of the membrane,
the support cushion is omitted at a location corresponding to a patient's chin,
the second frame comprises two connecting members that connect a lower portion of the second frame to the upper support member and the separate opening is located between the two connecting members,
the separate opening is substantially triangular,
the two lower headgear clip attachments are adjacent to and on opposite lateral sides of the annular opening,
the first frame is releasably secured to the second frame by way of an interlocking and/or frictional fit,
the annular opening and the elbow are sealingly connected, and
the first frame and the second frame have complementary shapes.

48. The mask assembly according to claim 32, wherein the first frame and the cushion are integrally molded in one piece to provide a cushion-frame sub-assembly,
the cushion is contoured to fit the patient's nose and mouth,
the first frame comprises a frame-opening that allows for a flow path to communicate the elbow with an interior of the first frame,
the second frame includes contact points that prevent rotation of the first frame with respect to the second frame,
the first frame and the cushion together form the breathing chamber around the patient's nose and mouth,
the cushion comprises a face contacting portion that contacts a patient's face,
the second frame comprises two connecting members that connect a lower portion of the second frame to the upper support member and the separate opening is located between the two connecting members,
the two lower headgear clip attachments are adjacent to and on opposite lateral sides of the annular opening,
the annular opening and the elbow are sealingly connected, and
the first frame is releasably secured to the second frame by way of an interlocking and/or frictional fit.

49. The mask assembly according to claim 48, wherein the separate opening is substantially triangular and the first frame and the second frame have complementary shapes.

50. The mask assembly according to claim 48, wherein the elbow engages the second frame.

51. A mask assembly for treatment of sleep disorder breathing by delivering a flow of pressurized gas to a patient, the mask assembly comprising:
a first frame with a first opening adapted to fluidly communicate an interior of the first frame with an inlet conduit, the first frame being made of a first material;
a cushion with a side wall and a face contacting portion extending from the side wall, wherein the cushion is over-molded to the first frame to form a cushion/frame sub-assembly and the cushion is adapted to form a seal around a patient's nose and mouth, the cushion being made of a second material that is less rigid than the first material; and
a second frame adapted to removably interlock with the cushion/frame sub-assembly, the second frame including
an upper member configured to provide forehead support;
lower portion with a second opening aligned with the first opening so that the inlet conduit fluidly communicates with a breathing chamber formed by the cushion and the first frame, and with headgear attachment structures on opposed lateral sides of the second opening, the headgear attachment structures being adapted to engage with headgear attachments;
two elongate frame members that interconnect the upper member and lower portion; and
an open space bounded at least in part by the two elongate frame members and the lower portion;
wherein the first frame protrudes at least partially through the open space.

52. The mask assembly according to claim 51, wherein the first opening is surrounded by an annular wall.

53. The mask assembly according to claim 51, wherein the headgear attachments are clips provided to straps of a headgear assembly.

54. The mask assembly according to claim 51, wherein the first frame and the second frame interlock at the second opening.

55. The mask assembly according to claim 51, wherein the elongate frame members engage with the cushion/frame sub-assembly to prevent rotation of the cushion/frame sub-assembly about the second opening.

56. The mask assembly according to claim 51, wherein the inlet conduit comprises an inlet elbow.

57. The mask assembly according to claim 51, wherein the first opening is surrounded by an annular wall, the headgear attachments are clips provided to straps of a headgear assembly, the first frame and the second frame interlock at the second opening, the elongate frame members engage with the cushion/frame sub-assembly to prevent rotation of the cushion/frame sub-assembly about the second opening, and the inlet conduit comprises an inlet elbow.

58. A mask assembly for treatment of sleep disorder breathing by delivering a flow of pressurized gas to a patient, the mask assembly comprising:
a cushion adapted to form a seal by abutting a patient's face around the patient's nose and mouth, the cushion comprising a face contacting portion with a sealing portion that contacts the patient's face around the patient's nose and mouth, the cushion being made of a first material;
a frame integrally molded to the cushion, the frame comprising an annular wall surrounding a frame-opening that allows fluid communication of the pressurized gas to an interior of the frame and a second wall connected to the cushion, the frame being made of a second material more rigid than the first material; and a skeleton frame removably attached to the frame, the skeleton frame comprising an upper support member adapted to receive a forehead contacting portion, a lower frame member comprising headgear attachment locations adapted to receive clips for straps of a headgear assembly, an annular hole adapted to align with the frame-opening, and two frame members interconnecting the upper support member and the lower frame member and forming an open space between the two frame members and the lower frame member, wherein the frame is at least partially accessible through the open space.

59. The mask assembly according to claim 58, wherein two of the headgear attachment locations are disposed adjacent to and on substantially opposite lateral sides of the annular hole.

60. The mask assembly according to claim 59, wherein the two headgear attachment locations are disposed substantially diametrically opposite to one another with respect to the annular hole.

61. The mask assembly according to claim 58, wherein the frame protrudes at least partially through the open space.

62. The mask assembly according to claim 58, wherein the skeleton frame and the frame are adapted to engage at the frame-opening.

63. The mask assembly according to claim 58, wherein the skeleton frame and the frame have mutual contact points to prevent relative rotation of the frame about the frame-opening.

64. The mask assembly according to claim 58, wherein two of the headgear attachment locations are disposed adjacent to and on substantially opposite lateral sides of the annular hole; the frame protrudes at least partially through the open space; the skeleton frame and the frame are adapted to engage at the frame-opening; and the skeleton frame and the frame have mutual contact points to prevent relative rotation of the frame about the frame-opening.

65. A mask assembly for treatment of sleep disorder breathing by delivering a flow of pressurized gas to a patient, the mask assembly comprising:

a cushion adapted to form a seal by abutting a patient's face around the patient's nose and mouth, the cushion comprising a face contacting portion with a sealing portion that contacts the patient's face around the patient's nose and mouth and comprising a first material;

a frame integrally molded to the cushion, the frame comprising an annular wall surrounding an opening that is adapted to allow fluid communication of the pressurized gas to an interior of the frame and a second wall surrounding the annular wall and connected to the cushion and comprising a second material that is more rigid than the first material;

an inlet conduit in fluid communication with the frame to communicate the pressurized gas to the interior of the frame; and a skeleton frame adapted to be removably engageable with the frame, the skeleton frame comprising an upper support member adapted to receive a forehead contacting portion, a lower frame member comprising attachment locations adapted to engage with clips for straps, two frame members interconnecting the upper support member and the lower frame member and forming an open space between the two frame members and the lower frame member, wherein the skeleton frame and the frame are adapted to be releasably engageable to one another at the opening, and the frame is at least partially accessible through the open space.

66. The mask assembly according to claim 65, wherein two of the attachment locations are disposed adjacent to and on substantially opposite lateral sides of the opening.

67. The mask assembly according to claim 66, wherein the two attachment locations are disposed substantially diametrically opposite to one another with respect to the opening.

68. The mask assembly according to claim 65, wherein the frame protrudes at least partially through the open space.

69. The mask assembly according to claim 65, wherein the skeleton frame and the frame are engaged at the opening and the inlet conduit is engaged with the mask assembly at the opening.

70. The mask assembly according to claim 65, wherein the skeleton frame and the frame have mutual contact points to prevent relative rotation of the frame about the opening.

71. The mask assembly according to claim 65, wherein the inlet conduit comprises an inlet elbow.

72. The mask assembly according to claim 65, wherein two of the attachment locations are disposed adjacent to and on substantially opposite lateral sides of the opening; the frame protrudes at least partially through the open space; the skeleton frame and the frame are engaged at the opening; the inlet conduit comprises an inlet elbow that is engaged with the mask assembly at the opening; and the skeleton frame and the frame have mutual contact points to prevent relative rotation of the frame about the opening.

73. The mask assembly according to claim 72, wherein the inlet elbow engages the skeleton frame.

74. A mask assembly for treatment of sleep disorder breathing by delivering a flow of pressurized gas to a patient, the mask assembly comprising:

a first frame with a first opening surrounded by a first cylindrical wall and adapted to fluidly communicate an interior of the first frame with an inlet conduit, the first frame being made of a first material;

a cushion with a face contacting portion, wherein the cushion is over-molded to the first frame to form a cushion/frame sub-assembly and the cushion is adapted to form a seal around a patient's nose and mouth, the cushion being made of a second material that is less rigid than the first material; and a second frame adapted to removably interlock with the cushion/frame sub-assembly, the second frame including:

an upper member configured to support a forehead contacting portion, a lower member with a second opening surrounded by a second cylindrical wall and aligned with the first opening so that the first cylindrical wall and the second cylindrical wall at least partially overlap when the first frame and the second frame are assembled, two elongate frame members that interconnect the upper member and lower portion; and an open space bounded at least in part by the two elongate frame members and the lower member;

wherein the first frame is accessible through the open space after the first frame is assembled to the second frame.

75. The mask assembly according to claim 74, wherein the second frame includes headgear attachment points on opposed lateral sides of the second opening.

76. The mask assembly according to claim 74, wherein the first frame and the second frame interlock at the second opening.

77. The mask assembly according to claim 74, wherein the elongate frame members engage with the cushion/frame sub-assembly to prevent rotation of the cushion/frame sub-assembly about the second opening.

78. The mask assembly according to claim 74, wherein the inlet conduit comprises an inlet elbow.

79. The mask assembly according to claim 74, wherein the second frame includes headgear attachment points on opposed lateral sides of the second opening, the first frame and the second frame interlock at the second opening, the elongate frame members engage with the cushion/frame sub-assembly to prevent rotation of the cushion/frame sub-assembly about the second opening, and the inlet conduit comprises an inlet elbow.

80. The mask assembly according to claim 79, wherein the inlet elbow engages the second frame.

81. A mask assembly for treatment of sleep disorder breathing by delivering a flow of pressurized gas to a patient, the mask assembly comprising:
- a first frame made of first material;
- a cushion connected to the first frame, the cushion being adapted to form a seal around a patient's nose and mouth and being made from a second material that is more flexible than the first material, the first frame and the cushion together forming a breathing chamber; and
- a second frame adapted to constrain the first frame, the second frame comprising an upper member, a lower member with an annular opening adapted to allow an inlet conduit to provide pressurized gas to the patient, and a separate opening located between the annular opening and the upper member, the separate opening providing access to the first frame when the mask assembly is fully assembled,
- wherein the first frame and the second frame snap-fit together.

82. The mask assembly according to claim 81, further comprising two elongate frame members connecting the upper member and lower member and at least partially bounding the separate opening.

83. The mask assembly according to claim 82, wherein the elongate frame members include contact points with the first frame to prevent rotation of the first frame with respect to the second frame.

84. The mask assembly according to claim 81, wherein the first frame and the cushion are integrally molded in one piece to provide a cushion-frame sub-assembly.

85. The mask assembly according to claim 81, wherein the first frame is contoured to fit over the patient's nose and mouth.

86. The mask assembly according to claim 81, wherein the separate opening is substantially triangular.

87. The mask assembly according to claim 81, further comprising two headgear clip attachments adjacent to and on opposite lateral sides of the annular opening.

88. The mask assembly according to claim 81, wherein the inlet conduit comprises an inlet elbow.

89. The mask assembly according to claim 81, further comprising two headgear clip attachments adjacent to and on opposite lateral sides of the annular opening; and
- two elongate frame members connecting the upper member and lower member and at least partially bounding the separate opening, wherein
- the elongate frame members include contact points with the first frame to prevent rotation of the first frame with respect to the second frame,
- the first frame and the cushion are integrally molded in one piece to provide a cushion- frame sub-assembly,
- the first frame is contoured to fit over the patient's nose and mouth, and
- the inlet conduit comprises an inlet elbow.

90. The mask assembly according to claim 89, wherein separate opening is substantially triangular.

91. The mask assembly according to claim 89, wherein the inlet elbow engages the second frame.

* * * * *